United States Patent
Ott et al.

(10) Patent No.: US 6,740,649 B2
(45) Date of Patent: May 25, 2004

(54) CYCLIC HYDROXAMIC ACIDS AS INHIBITORS OF MATRIX METALLOPROTEINASES AND/OR TNF-α CONVERTING ENZYME (TACE)

(75) Inventors: Gregory R. Ott, Media, PA (US); Xiao-Tao Chen, Newark, DE (US); Jingwu Duan, Newark, DE (US); Zhonghui Lu, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/244,626

(22) Filed: Sep. 16, 2002

(65) Prior Publication Data

US 2003/0139388 A1 Jul. 24, 2003

Related U.S. Application Data

(60) Provisional application No. 60/322,630, filed on Sep. 17, 2001.

(51) Int. Cl.[7] .............................................. A61K 31/54
(52) U.S. Cl. .................... 514/224.2; 514/300; 514/303; 514/311; 514/314; 514/322; 514/326; 514/393; 514/412; 514/414; 514/459; 514/469; 544/52; 544/102; 544/105; 544/128; 546/79; 546/89; 546/104; 546/118; 546/121; 546/165; 546/175; 546/196; 546/199; 546/201; 546/202; 548/306.1; 548/309.7; 548/452; 548/467; 548/525; 549/414; 549/471
(58) Field of Search ........................ 544/52, 102, 105, 544/128; 546/79, 118, 121, 89, 104, 165, 175, 196, 199, 201, 202; 548/306.1, 309.7, 452, 467, 525; 549/414; 514/224.2, 300, 303, 311, 314, 322, 326, 393, 412, 414, 459, 469

(56) References Cited

U.S. PATENT DOCUMENTS

| | | |
|---|---|---|
| 5,210,079 A | 5/1993 | Carini et al. |
| 5,236,943 A | 8/1993 | Heitsch et al. |
| 5,663,186 A | 9/1997 | Nelson et al. |
| 5,663,187 A | 9/1997 | Nelson et al. |

FOREIGN PATENT DOCUMENTS

| | | |
|---|---|---|
| WO | WO01/70673 | 9/2001 |
| WO | WO 02/074738 | 9/2002 |

OTHER PUBLICATIONS

Database CA on STN, Chemical Abstracts, (Columbus, Ohio, USA), No. 137:262960, Ott, G.R. et al. "Preparation of spiro-cyclic .beta.-amino acid derivates as inhibitors of matrix metalloproteinases and TNF-.alpha. converting enzyme (TACE)," abstract, WO 2002074738, Sep. 2002.

*Primary Examiner*—Bernard Dentz
(74) *Attorney, Agent, or Firm*—Jing S. Belfield

(57) ABSTRACT

The present application describes novel cyclic hydroxamic acids of formula I:

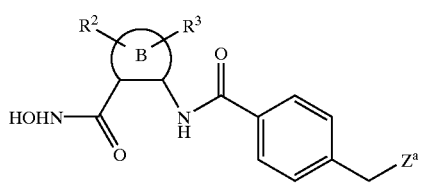

I or pharmaceutically acceptable salt forms thereof, wherein ring B is a 5–7 membered cyclic system containing from 0–2 heteroatoms selected from O, N, $NR^1$, and $S(O)_p$, and 0–1 carbonyl groups and the other variables are defined in the present specification, which are useful as inhibitors of matrix metalloproteinases (MMP), TNF-α converting enzyme (TACE), aggrecanase or a combination thereof, pharmaceutical compositions containing the same, and methods of using the same.

49 Claims, No Drawings

CYCLIC HYDROXAMIC ACIDS AS INHIBITORS OF MATRIX METALLOPROTEINASES AND/OR TNF-α CONVERTING ENZYME (TACE)

CROSS-REFERENCE TO RELATED APPLICATIONS

This application claims the priority benefit of U.S. Provisional Application No. 60/322,630, filed Sep. 17, 2001, the disclosure of which is incorporated herein by reference in its entirety.

FIELD OF THE INVENTION

This invention relates generally to novel cyclic hydroxamic acids as inhibitors of matrix metalloproteinases (MMP), TNF-α converting enzyme (TACE), aggrecanase or a combination thereof, pharmaceutical compositions containing the same, and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis; corneal, epidermal, or gastric ulceration; tumor metastasis or invasion; periodontal disease; and, bone disease.

Tumor necrosis factor-α (TNF-α) has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis. Compounds which inhibit the production of TNF-α are of therapeutic importance for the treatment of inflammatory disorders.

This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV, and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

WO01/70673 describes matrix metalloproteases and TNF-α inhibitors of the following formula:

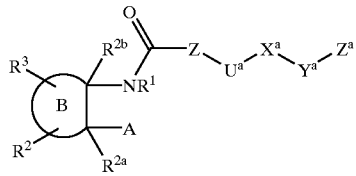

wherein ring B is a 3–13 membered non-aromatic carbocyclic or heterocyclic ring; A is a variety of groups including hydroxamic acid; Z is absent, a $C_{3-13}$ carbocycle or a 5–14 membered heterocycle; $Z^a$ is H, a $C_{3-13}$ carbocycle or a 5–14 membered heterocycle; $U^a$, $X^a$ and $Y^a$ are linkers; and, $R^1$, $R^2$, $R^{2a}$, $R^{2b}$, and $R^3$ are a variety of groups. Compounds specifically described in WO01/70673 are not considered to be part of the present invention.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases (e.g., specificity for one MMP versus another). It is also desirable and preferable to find compounds with advantageous and improved characteristics in one or more of the following categories, but are not limited to: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding and volume of distribution); (e) factors that decrease the liability for clinical drug—drug interactions (e.g., cytochrome P450 enzyme inhibition or induction); (f) factors that decrease the potential for adverse side-effects (e.g., potential chemical or metabolic reactivity and limited CNS penetration); and, (g) factors that improve manufacturing costs or feasibility (e.g., difficulty of synthesis, number of chiral centers, chemical stability, and ease of handling).

The compounds of the present invention act as inhibitors of MPs, in particular TACE, MMPs, and/or aggrecanase. These novel molecules are provided as anti-inflammatory compounds and cartilage protecting therapeutics. The inhibition of aggrecanase, TACE, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel cyclic hydroxamic acids useful as MMP, TACE and/or aggrecanase inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory disorders, comprising: administering to a host, in need of such treatment, a therapeutically effective amount of at least one of the compounds of the present invention or a pharmaceutically acceptable salt or prodrug form thereof.

The present invention provides a method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt or prodrug form thereof.

The present invention provides a method comprising: administering a compound of the present invention or a pharmaceutically acceptable salt or prodrug form thereof in an amount effective to treat a condition or disease mediated by MMPs, TACE, aggrecanase, or a combination thereof.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides novel compounds of the present invention for use in therapy.

The present invention provides the use of novel compounds of the present invention for the manufacture of a medicament for the treatment of a condition or disease mediated by MMPs, TNF, aggrecanase, or a combination thereof.

These and other objects, which will become apparent during the following detailed description, have been achieved by the inventors' discovery that compounds of formula (I):

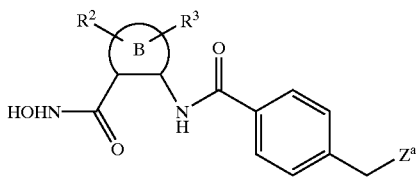

or a stereoisomer or pharmaceutically acceptable salt or prodrug form thereof, wherein B, $R^2$, $R^3$ and $Z^a$ are defined below, are effective as MMP, TACE, and/or aggrecanase inhibitors.

DETAILED DESCRIPTION OF PREFERRED EMBODIMENTS

[1] Thus, in an embodiment, the present invention provides a novel compound of formula (I):

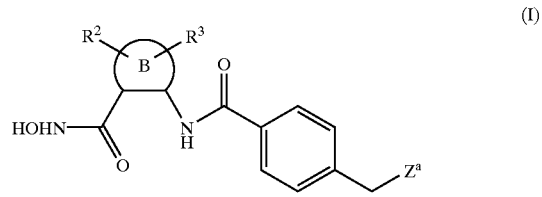

or a stereoisomer or pharmaceutically acceptable salt form thereof, wherein;

ring B is a 4–7 membered non-aromatic carbocyclic or heterocyclic ring consisting of: carbon atoms, 0–3 carbonyl groups, 0–3 double bonds, and 0–2 ring heteroatoms selected from O, N, $NR^1$, and $S(O)_p$, provided that ring B contains other than a S—S, O—O, or S—O bond;

$R^1$ is selected from Q, $C_{1-6}$ alkylene-Q, $C_{2-6}$ alkenylene-Q, $C_{2-6}$ alkynylene-Q, $(CR^aR^{a1})_qO(CR^aR^{a1})_s$-Q, $(CR^aR^{a1})_q NR^a(CR^aR^{a1})_s$-Q, $(CR^aR^{a1})_rC(O)(CR^aR^{a1})_s$-Q, $(CR^aR^{a1})_rC(O)$—$C_{2-6}$ alkenylene-Q, $(CR^aR^{a1})_rC(O)O(CR^aR^{a1})_s$-Q, $(CR^aR^{a1})_qOC(O)(CR^aR^{a1})_s$-Q, $(CR^aR^{a1})_q OC(O)O(CR^aR^{a1})_s$-Q, $(CR^aR^{a1})_q OC(O)NR^a(CR^aR^{a1})_s$-Q, $(CR^aR^{a1})_rC(O)NR^aR^{a1}$, $(CR^aR^{a1})_rC(O)NR^a(CR^aR^{a1})_s$-Q, $(CR^aR^{a1})_q NR^aC(O)(CR^aR^{a1})_s$-Q, $(CR^aR^{a1})_q NR^aC(O)O(CR^aR^{a1})_s$-Q, $(CR^aR^{a1})_q NR^aC(O)NR^a(CR^aR^{a1})_s$-Q, $(CR^aR^{a1})_rS(O)_p(CR^aR^{a1})_s$-Q, $(CR^aR^{a1})_q NR^aSO_2(CR^aR^{a1})_s$-Q, and $(CR^aR^{a1})_rSO_2NR^a(CR^aR^{a1})_s$-Q;

$R^2$ is selected from Q, $C_{1-6}$ alkylene-Q, $C_{2-6}$ alkenylene-Q, $C_{2-6}$ alkynylene-Q, $(CR^aR^{a1})_rO(CR^aR^{a1})_s$-Q, $(CR^aR^{a1})_r NR^a(CR^aR^{a1})_s$-Q, $(CR^aR^{a1})_rC(O)(CR^aR^{a1})_s$-Q, $(CR^aR^{a1})_rC(O)$—$C_{2-6}$ alkenylene-Q, $(CR^aR^{a1})_rC(O)O(CR^aR^{a1})_s$-Q, $(CR^aR^{a1})_rC(O)NR^aR^{a1}$, $(CR^aR^{a1})_rC(O)NR^a(CR^aR^{a1})_s$-Q, $(CR^aR^{a1})_rNR^aC(O)(CR^aR^{a1})_s$-Q, $(CR^aR^{a1})_rNR^aC(O)O(CR^aR^{a1})_s$-Q, $(CR^aR^{a1})_rNR^aC(O)NR^a(CR^aR^{a1})_s$-Q, $(CR^aR^{a1})_rS(O)_p(CR^aR^{a1})_s$-Q, and $(CR^aR^{a1})_rSO_2NR^a(CR^aR^{a1})_s$-Q;

Q is selected from H, a $C_{3-6}$ carbocycle substituted with 0–3 $R^d$, and a 5–10 membered heterocycle consisting of: carbon atoms and 1–4 heteroatoms selected from the group consisting of N, O, and $S(O)_p$, and substituted with 0–3 $R^d$;

$R^3$ is selected from $Q^1$, Cl, F, $C_{1-6}$ alkylene-$Q^1$, $C_{2-6}$ alkenylene-$Q^1$, $C_{2-6}$ alkynylene-$Q^1$, $(CR^aR^{a1})_rO(CR^aR^{a1})_s$-$Q^1$, $(CR^aR^{a1})_rNR^a(CR^aR^{a1})_s$-$Q^1$, $(CR^aR^{a1})_r NR^aC(O)(CR^aR^{a1})_s$-$Q^1$, $(CR^aR^{a1})_rC(O)NR^a(CR^aR^{a1})_s$-$Q^1$, $(CR^aR^{a1})_rC(O)(CR^aR^{a1})_s$-$Q^1$, $(CR^aR^{a1})_rC(O)O(CR^aR^{a1})_s$-$Q^1$, $(CR^aR^{a1}_2)_rS(O)_p(CR^aR^{a1})_s$-$Q^1$, and $(CR^aR^{a1})_rSO_2NR^a(CR^aR^{a1})_s$-$Q^1$;

$Q^1$ is selected from H, phenyl substituted with 0–3 $R^d$, naphthyl substituted with 0–3 $R^d$ and a 5–10 membered heterocycle consisting of: carbon atoms and 1–4 heteroatoms selected from the group consisting of N, O, and $S(O)_p$, and substituted with 0–3 $R^d$;

$Z^a$ is selected from the group:

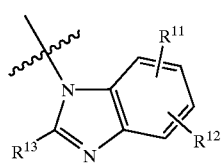 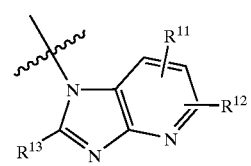

-continued

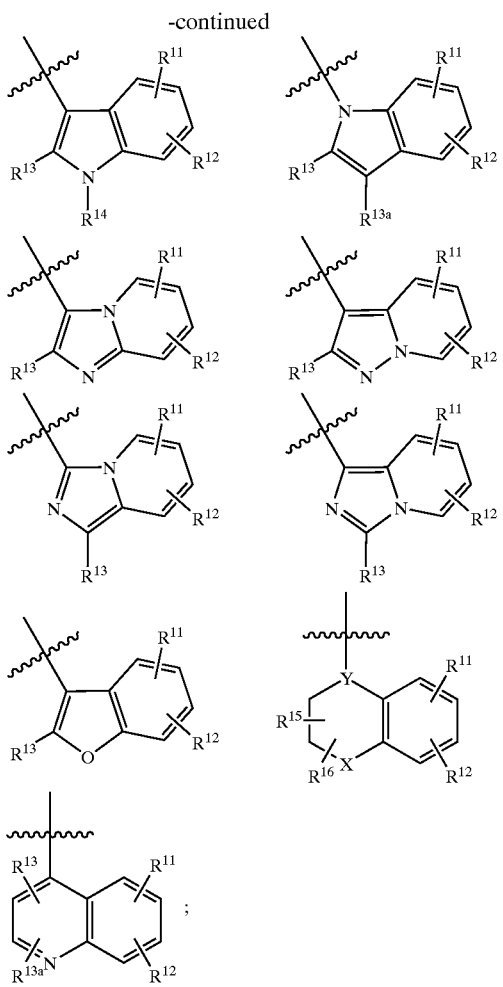

X is S, SO, SO$_2$, O, or NR$^{14}$;
Y is N or CR$^{17}$;
R$^{11}$ and R$^{12}$, at each occurrence, are independently selected from H, R$^c$, C$_{1-6}$ alkyl substituted with 0–3 R$^{c1}$, C$_{3-10}$ carbocycle substituted with 0–3 R$^{c1}$, and a 5–14 membered heterocycle consisting of: carbon atoms and 1–4 heteroatoms selected from the group consisting of N, O, and S(O)$_p$, and substituted with 0–3 R$^{c1}$;

R$^{13}$ and R$^{13a}$, at each occurrence, are independently selected from H, R$^c$, C$_{1-6}$ alkyl substituted with 0–3 R$^{c1}$, C$_{3-10}$ carbocycle substituted with 0–3 R$^{c1}$; and a 5–14 membered heterocycle consisting of: carbon atoms and 1–4 heteroatoms selected from the group consisting of N, O, and S(O)$_p$, and substituted with 0–3 R$^{c1}$;

alternatively, when R$^{13}$ and R$^{13a}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, and 0–2 heteroatoms selected from the group consisting of N, O, and S(O)$_p$, and substituted with 0–2 R$^{c1}$;

R$^{14}$, at each occurrence, is independently selected from H, C$_{1-4}$ alkyl, phenyl, and benzyl;

R$^{15}$ and R$^{16}$, at each occurrence, are independently selected from H, R$^{c1}$, C$_{1-6}$ alkyl substituted with 0–3 R$^{c1}$, C$_{3-10}$ carbocycle substituted with 0–3 R$^{c1}$, and a 5–14 membered heterocycle consisting of: carbon atoms and 1–4 heteroatoms selected from the group consisting of N, O, and S(O)$_p$, and substituted with 0–3 R$^{c1}$;

alternatively, when R$^{15}$ and R$^{16}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, 0–2 heteroatoms selected from the group consisting of N, O, and S(O)$_p$, and substituted with 0–2 R$^{c1}$;

alternatively, when R$^{15}$ and R$^{16}$ are attached to the same carbon atom, together with the carbon atom to which they are attached, they form a 3–7 membered carbocyclic or heterocyclic ring consisting of: carbon atoms, 0–2 carbonyl groups, 0–3 double bonds, and 0–2 heteroatoms selected from the group consisting of N, O, and S(O)$_p$, and substituted with 0–2 R$^{c1}$;

R$^{17}$ is selected from H, Cl, F, and C$_{1-4}$ alkyl;

R$^a$, at each occurrence, is independently selected from H, C$_{1-4}$ alkyl, phenyl, and benzyl;

R$^{a1}$, at each occurrence, is independently selected from H and C$_{1-4}$ alkyl;

R$^{a2}$, at each occurrence, is independently selected from C$_{1-4}$ alkyl, phenyl, and benzyl;

R$^c$, at each occurrence, is independently selected from C$_{1-6}$ alkyl, OR$^a$, Cl, F, Br, I, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O) NR$^a$R$^{a1}$, R$^a$NC(O)OR$^a$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, CH$_2$F, and CHF$_2$;

R$^{c1}$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)OR$^a$, S(O)$_2$NR$^a$R$^{a1}$, NR$^a$S(O)$_2$ R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, CH$_2$F, and CHF$_2$;

R$^d$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$ R$^{a2}$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, C$_{3-10}$ carbocycle, and a 5–14 membered heterocycle consisting of: carbon atoms and 1–4 heteroatoms selected from the group consisting of N, O, and S(O)$_p$;

p, at each occurrence, is selected from 0, 1, and 2;
q, at each occurrence, is selected from 1, 2, 3, and 4;
r, at each occurrence, is selected from 0, 1, 2, 3, and 4; and,
s, at each occurrence, is selected from 0, 1, 2, 3, and 4.

[2] In a preferred embodiment, the present invention provides a novel compound of formula (I), wherein;

ring B is a 5–6 membered non-aromatic carbocyclic or heterocyclic ring consisting of: carbon atoms, 0–1 carbonyl groups, 0–2 double bonds, and 0–2 ring heteroatoms selected from O, N, and NR$^1$, provided that ring B contains other than a O—O bond;

R$^1$ is selected from Q, C$_{1-6}$ alkylene-Q, C$_{2-6}$ alkenylene-Q, C$_{2-6}$ alkynylene-Q, C(O)(CR$^a$R$^{a1}$)$_s$-Q, C(O)—C$_{2-6}$ alkenylene-Q, C(O)O(CR$^a$R$^{a1}$)$_s$-Q, C(O)NR$^a$R$^{a1}$, C(O) NR$^a$(CR$^a$R$^{a1}$)$_s$-Q, and S(O)$_p$(CR$^a$R$^{a1}$)$_s$-Q;

R$^2$ is selected from Q, C$_{1-6}$ alkylene-Q, C$_{2-6}$ alkenylene-Q, C$_{2-6}$ alkynylene-Q, C(O)(CR$^a$R$^{a1}$)$_s$-Q, C(O)—C$_{2-6}$ alkenylene-Q, C(O)O(CR$^a$R$^{a1}$)$_s$-Q, C(O)NR$^a$(CR$^a$R$^{a1}$)$_s$-Q, and S(O)$_p$(CR$^a$R$^{a1}$)$_s$-Q;

Q is selected from H, cyclopropyl substituted with 0–1 R$^d$, cyclobutyl substituted with 0–1 R$^d$, cyclopentyl substituted with 0–1 R$^d$, cyclohexyl substituted with 0–1 R$^d$, phenyl substituted with 0–3 R$^d$, and a heterocycle substituted with 0–2 R$^d$, wherein the heterocycle is selected from pyridyl, quinolinyl, thiazolyl, furanyl, tetrahydrofuranyl, imidazolyl, isoxazolyl, pyranyl, tetrahydro-2H-pyranyl, morpholinyl, piperidinyl, piperazinyl, and pyrrolidinyl;

$R^3$ is selected from $Q^1$, Cl, F, $C_{1-4}$ alkylene-$Q^1$, $C_{2-4}$ alkenylene-$Q^1$, and $C_{2-4}$ alkynylene-$Q^1$;

$Q^1$ is selected from H and phenyl;

$R^{11}$ and $R^{12}$, at each occurrence, are independently selected from H, $R^c$, $C_{1-4}$ alkyl substituted with 0–3 $R^{c1}$, and phenyl substituted with 0–3 $R^{c1}$;

$R^{13}$ and $R^{13a}$, at each occurrence, are independently selected from H, $R^c$, $C_{1-4}$ alkyl substituted with 0–3 $R^{c1}$, $C_{3-6}$ cycloalkyl substituted with 0–2 $R^{c1}$, phenyl substituted with 0–3 $R^{c1}$, and a 5–6 membered heterocycle consisting of: carbon atoms and 1–4 heteroatoms selected from the group consisting of N, O, and $S(O)_p$ and substituted with 0–3 $R^{c1}$;

alternatively, when $R^{13}$ and $R^{13a}$ are attached to adjacent carbon atoms, together with the carbon atoms to which they are attached they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$;

$R^{14}$, at each occurrence, is independently selected from H, $C_{1-4}$ alkyl, and benzyl;

$R^{15}$ and $R^{16}$, at each occurrence, are independently selected from H, $R^{c1}$, $C_{1-4}$ alkyl substituted with 0–3 $R^{c1}$, and phenyl substituted with 0–3 $R^{c1}$;

alternatively, when $R^{15}$ and $R^{16}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$;

alternatively, when $R^{15}$ and $R^{16}$ are attached to the same carbon atom, together with the carbon atom to which they are attached, they form a 3–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–1 $R^{c1}$;

$R^a$, at each occurrence, is independently selected from H, $C_{1-4}$ alkyl, and benzyl;

$R^{a2}$, at each occurrence, is independently selected from $C_{1-4}$ alkyl, and benzyl;

$R^c$, at each occurrence, is independently selected from $C_{1-6}$ alkyl, $OR^a$, Cl, F, Br, $NR^aR^{a1}$, $C(O)R^a$, $C(O)NR^aR^{a1}$, $S(O)_2NR^aR^{a1}$, $S(O)_pR^{a2}$, $CF_3$, $OCF_3$, $CF_2CF_3$, $CH_2F$, and $CHF_2$;

$R^{c1}$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, $OCF_3$, $CF_2CF_3$, $CH_2F$, and $CHF_2$; and, $R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl.

[3] In another preferred embodiment, the present invention provides a novel compound of formula (I), wherein;

ring B is a 5–6 membered non-aromatic carbocyclic or heterocyclic ring consisting of: carbon atoms, 0–1 carbonyl groups, 0–1 double bonds, and 0–1 ring heteroatoms selected from O, N, and $NR^1$;

$R^1$ is selected from Q, $C_{1-6}$ alkylene-Q, $C_{2-4}$ alkenylene-Q, $C_{2-4}$ alkynylene-Q, $C(O)(CR^aR^{a1})_s$-Q, $C(O)$—$C_{2-6}$ alkenyl, $C(O)O(CR^aR^{a1})_s$-Q, $C(O)NR^a$-Q, and $S(O)_p(CR^aR^{a1})_s$-Q;

$R^2$ is selected from Q, $C_{1-4}$ alkylene-Q, $C_{2-4}$ alkenylene-Q, $C_{2-4}$ alkynylene-Q, $C(O)$-Q, $C(O)$—$C_{2-6}$ alkenyl, $C(O)O$-Q, $C(O)NR^a$-Q, and $S(O)_p$-Q;

Q is selected from H, cyclopropyl, cyclobutyl, cyclopentyl, cyclohexyl, tetrahydro-2H-pyran-4-yl, and phenyl substituted with 0–2 $R^d$;

$R^3$ is H;

X is S, SO, $SO_2$ or O;

Y is N;

$R^{11}$ and $R^{12}$, at each occurrence, are independently selected from H, $R^c$, and $C_{1-4}$ alkyl substituted with 0–3 $R^{c1}$;

$R^{13}$ and $R^{13a}$, at each occurrence, are independently selected from H, $R^c$, $C_{1-4}$ alkyl substituted with 0–3 $R^{c1}$, $C_{3-6}$ cycloalkyl substituted with 0–2 $R^{c1}$, phenyl substituted with 0–3 $R^{c1}$, and a 5–6 membered heterocycle consisting of: carbon atoms and 1–2 heteroatoms selected from the group consisting of N, O, and $S(O)_p$;

alternatively, when $R^{13}$ and $R^{13a}$ are attached to adjacent carbon atoms, together with the carbon atoms to which they are attached, they form a 5–6 membered carbocyclic or heterocyclic ring consisting of: carbon atoms, 0–2 double bonds, and 0–1 heteroatoms selected from the group consisting of N, O, and $S(O)_p$, and substituted with 0–2 $R^{c1}$;

$R^{15}$ and $R^{16}$, at each occurrence, are independently selected from H, $R^{c1}$, and $C_{1-4}$ alkyl substituted with 0–3 $R^{c1}$;

alternatively, when $R^{15}$ and $R^{16}$ are attached to adjacent carbon atoms, together with the carbon atoms to which they are attached, they form a 6 membered aromatic ring substituted with 0–2 $R^{c1}$;

alternatively, when $R^{15}$ and $R^{16}$ are attached to the same carbon atom, together with the carbon atom to which they are attached, they form a 3–6 membered cycloalkyl;

$R^a$, at each occurrence, is independently selected from H, $CH_3$, and $CH_2CH_3$;

$R^{a1}$, at each occurrence, is independently selected from H, $CH_3$, and $CH_2CH_3$; and, $R^{a2}$, at each occurrence, is independently selected from $CH_3$, and $CH_2CH_3$.

[4] In another preferred embodiment, the present invention provides a novel compound of formula (II):

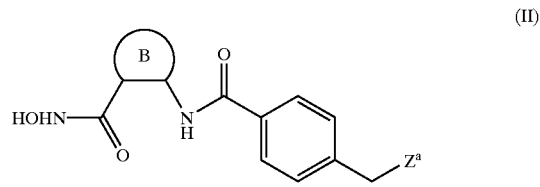

(II)

or a stereoisomer or pharmaceutically acceptable salt form thereof, wherein;

ring B is selected from the group:

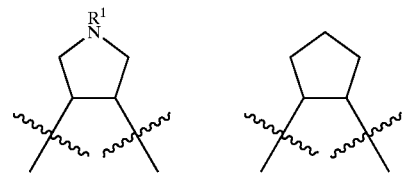

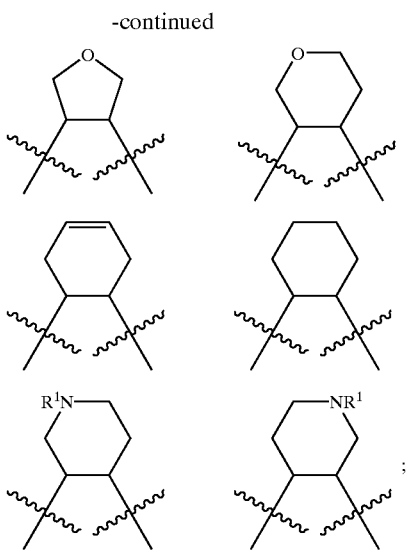

R[1] is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

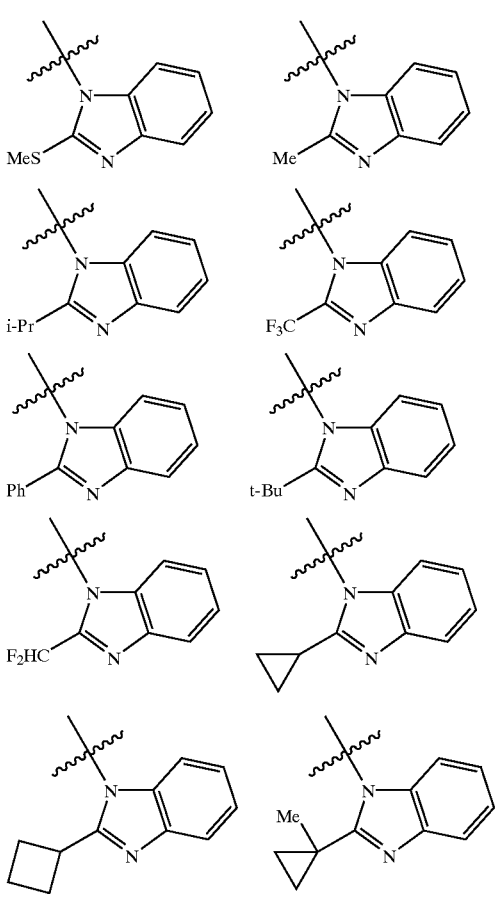

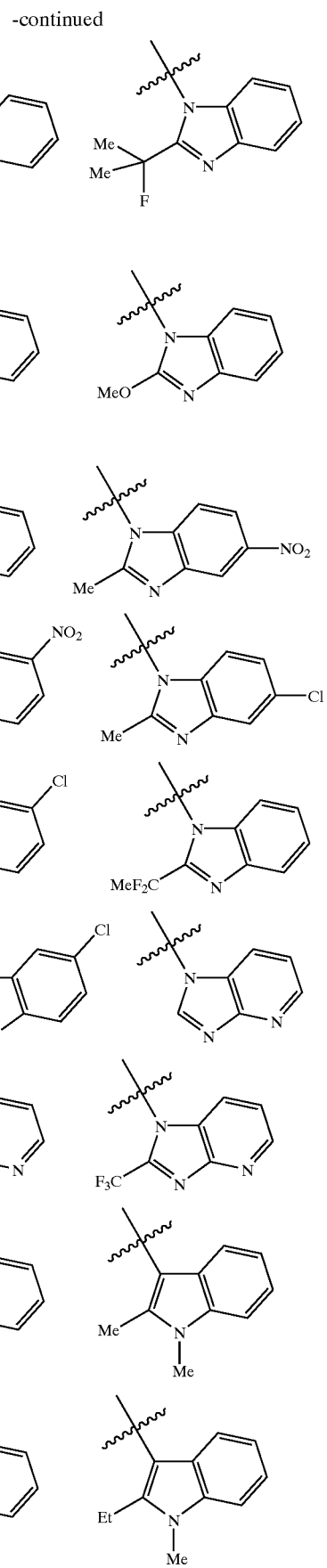

-continued
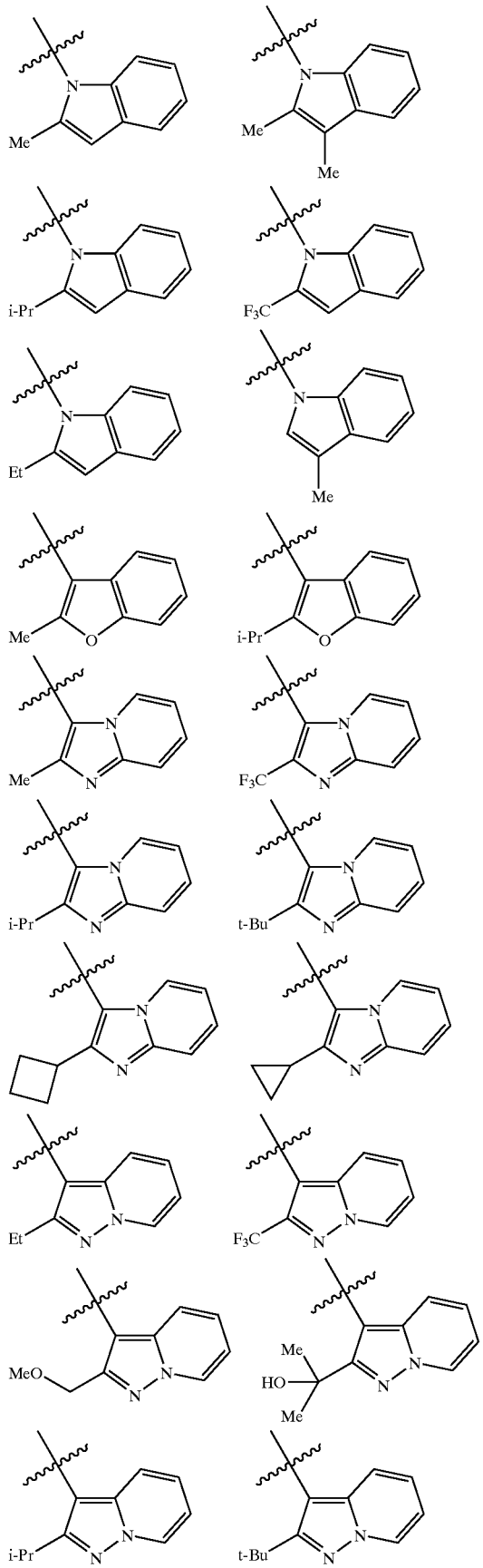
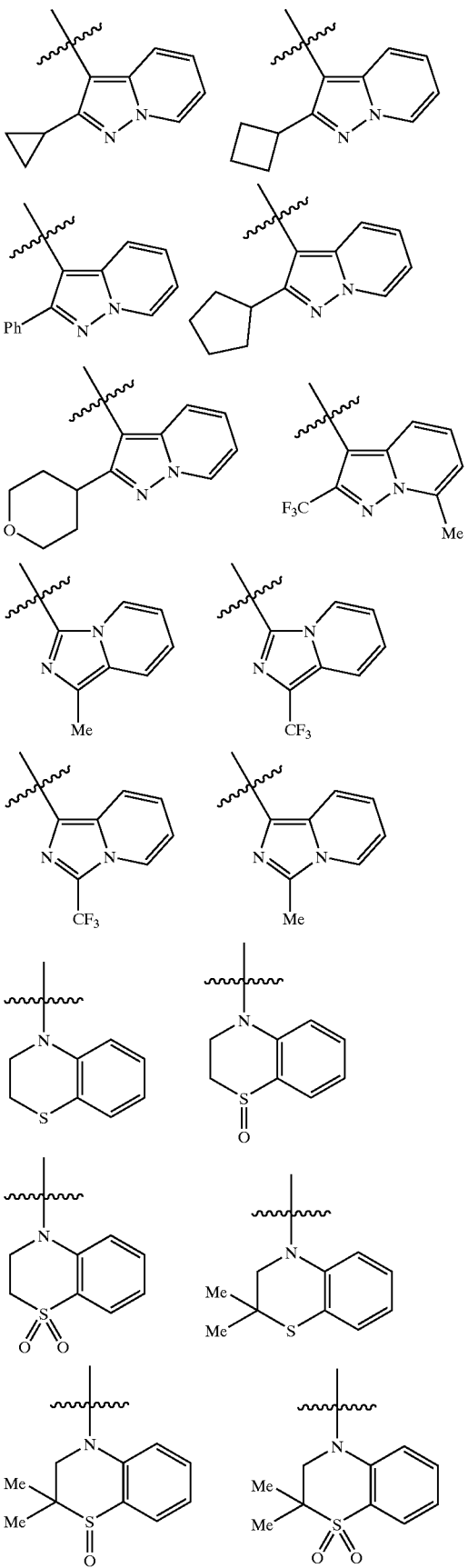

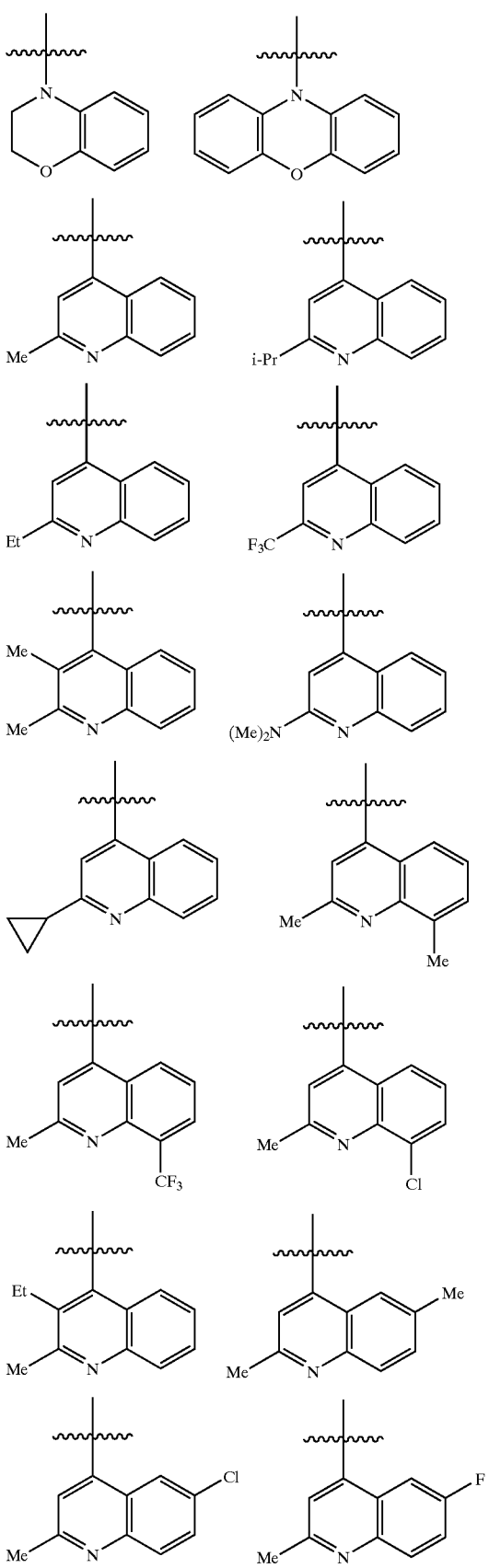
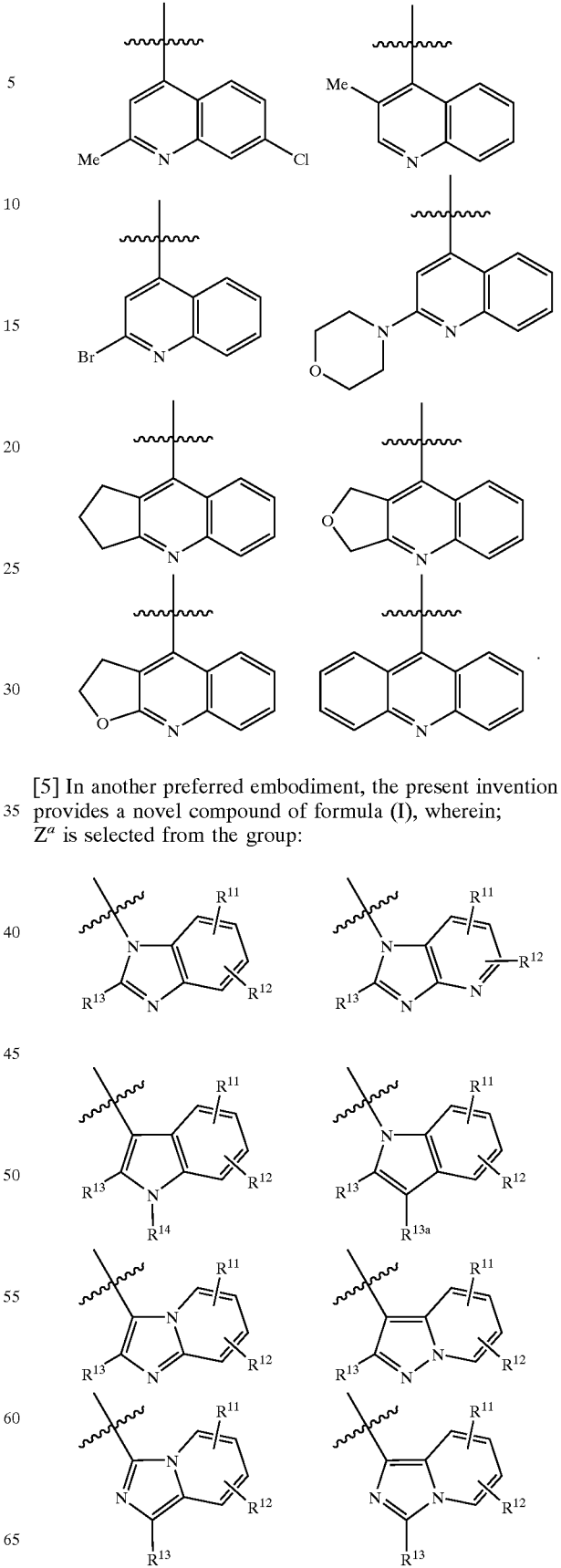
[5] In another preferred embodiment, the present invention provides a novel compound of formula (I), wherein;
$Z^a$ is selected from the group:

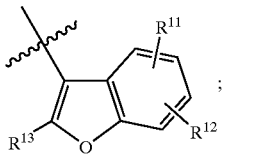

$R^{11}$ and $R^{12}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5-14 membered heterocycle consisting of: carbon atoms and 1–4 heteroatoms selected from the group consisting of N, O, and $S(O)_p$, and substituted with 0–3 $R^{c1}$;

$R^{13}$ and $R^{13a}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5-14 membered heterocycle consisting of: carbon atoms and 1–4 heteroatoms selected from the group consisting of N, O, and $S(O)_p$, and substituted with 0–3 $R^{c1}$; and, $R^{14}$, at each occurrence, is independently selected from H, $C_{1-4}$ alkyl, phenyl, and benzyl.

[6] In a preferred embodiment, the present invention provides a novel compound of formula (I), wherein; $Z^a$ is selected from the group:

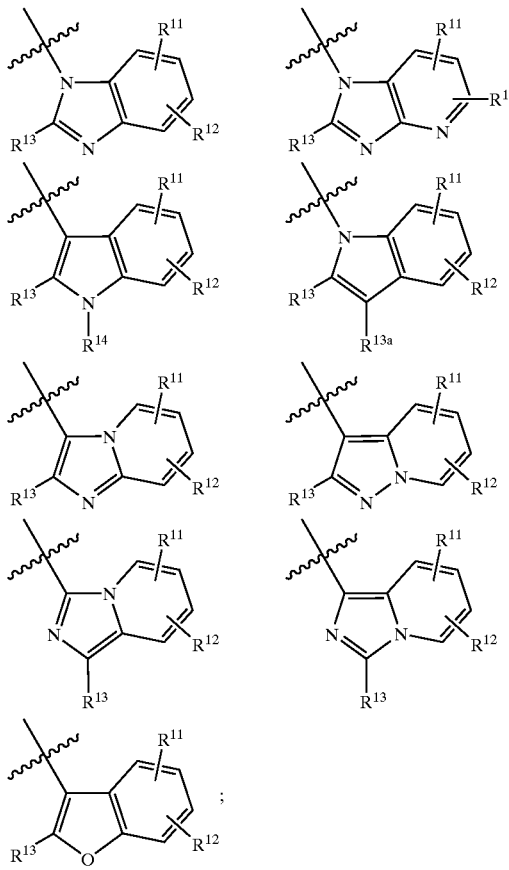

$R^{11}$ and $R^{12}$, at each occurrence, are independently selected from H, $R^c$, $C_{1-4}$ alkyl substituted with 0–3 $R^{c1}$, and phenyl substituted with 0–3 $R^{c1}$;

$R^{13}$ and $R^{13a}$, at each occurrence, are independently selected from H, $R^c$, $C_{1-4}$ alkyl substituted with 0–3 $R^{c1}$, $C_{3-6}$ cycloalkyl substituted with 0–2 $R^{c1}$, phenyl substituted with 0–3 $R^{c1}$, and a 5–6 membered heterocycle consisting of: carbon atoms and 1–4 heteroatoms selected from the group consisting of N, O, and $S(O)_p$, and substituted with 0–3 $R^{c1}$; and, $R^{14}$, at each occurrence, is independently selected from H, $C_{1-4}$ alkyl, and benzyl.

[7] In another preferred embodiment, the present invention provides a novel compound of formula (II), wherein;

ring B is selected from the group:

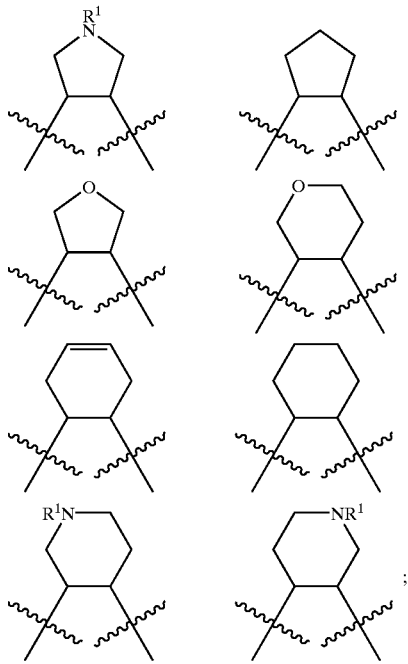

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

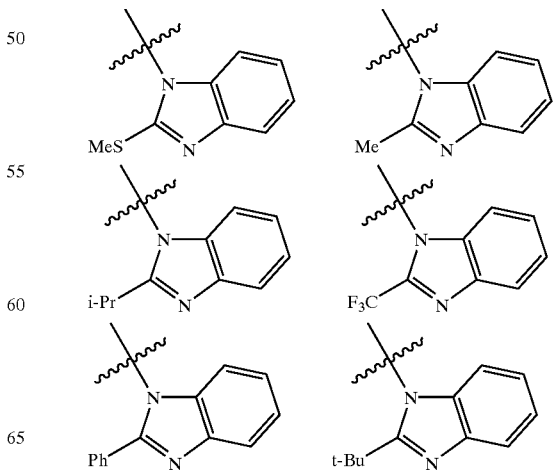

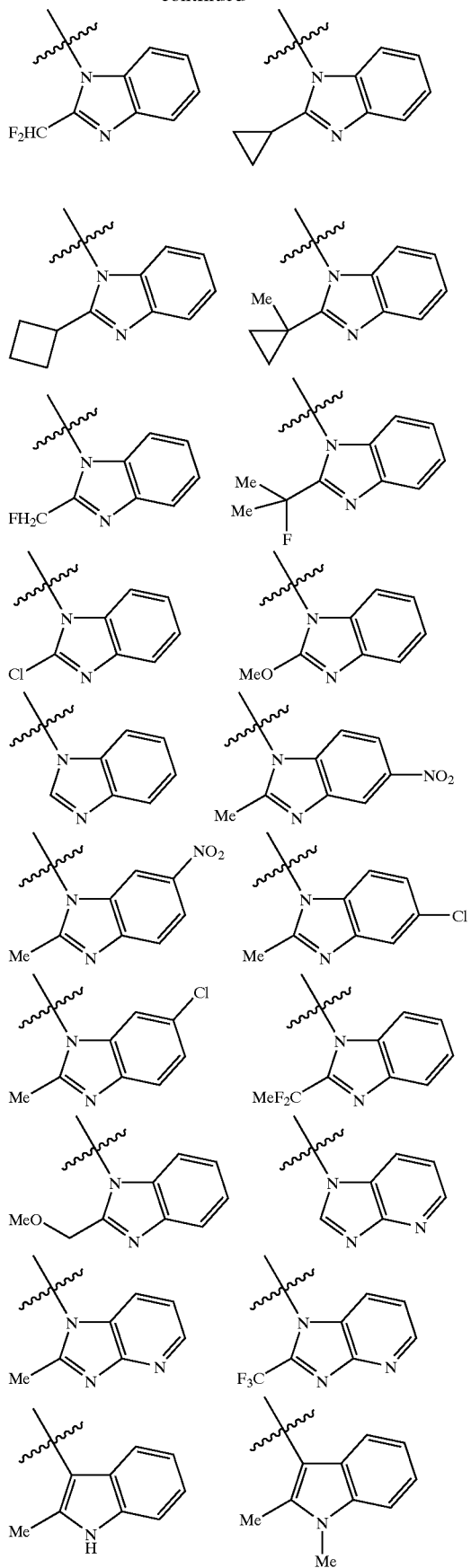
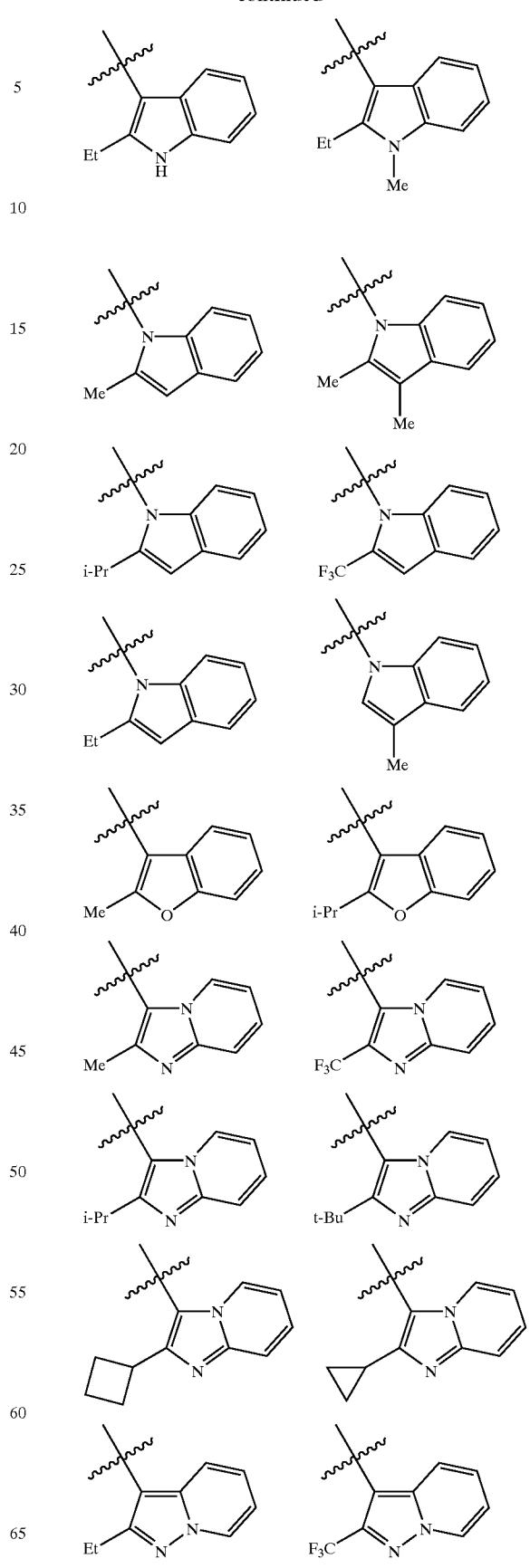

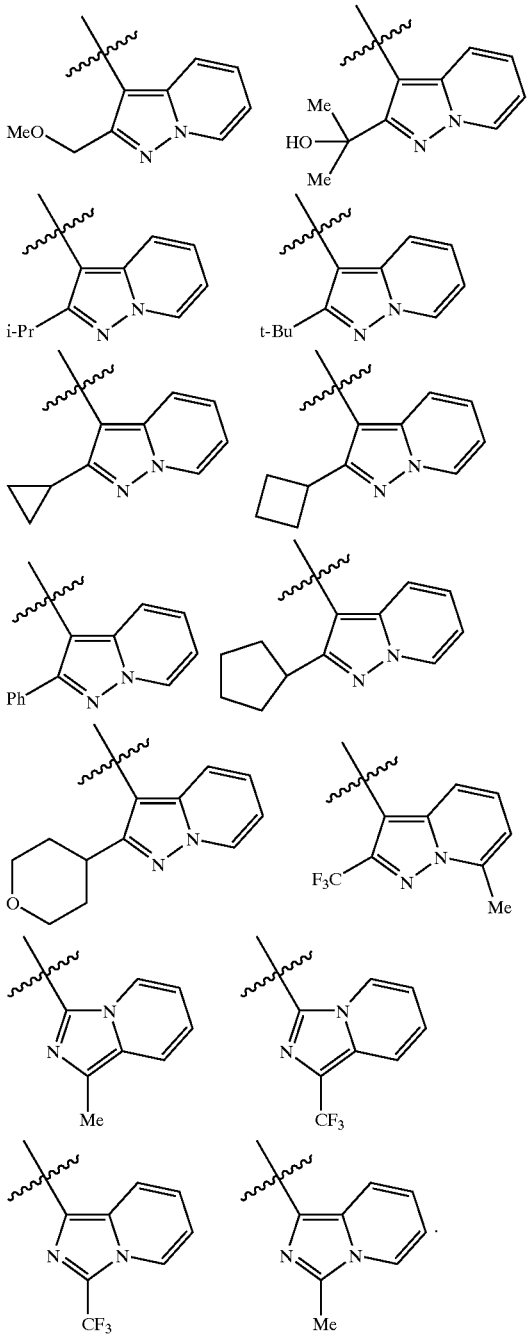

[8] In another preferred embodiment, the present invention provides a compound selected from the group:

tert-butyl (3S,4S)-3-[(hydroxyamino)carbonyl]-4-[(4-{[2-(methylthio)-1H-benzimidazol-1-yl]methyl}benzoyl)amino]-1-pyrrolidinecarboxylate;
(3S,4S)-N-hydroxy-4-[(4-{[2-(methylthio)-1H-benzimidazol-1-yl]methyl}benzoyl)amino]-3-pyrrolidinecarboxamide;
(3S,4S)-N-hydroxy-1-(methylsulfonyl)-4-[(4-{[2-(methylthio)-1H-benzimidazol-1-yl]methyl}benzoyl)amino]-3-pyrrolidinecarboxamide;
(3S,4S)-N-hydroxy-4-[(4-{[2-(methylthio)-1H-benzimidazol-1-yl]methyl}benzoyl)amino]-1-(2-propynyl)-3-pyrrolidinecarboxamide;
(3S,4S)-N-hydroxy-1-methyl-4-[(4-{[2-(methylthio)-1H-benzimidazol-1-yl]methyl}benzoyl)amino]-3-pyrrolidinecarboxamide;
(3S,4S)-N-hydroxy-1-isopropyl-4-[(4-{[2-(methylthio)-1H-benzimidazol-1-yl]methyl}benzoyl)amino]-3-pyrrolidinecarboxamide;
(3S,4S)-1-acetyl-N-hydroxy-4-[(4-{[2-(methylthio)-1H-benzimidazol-1-yl]methyl}benzoyl)amino]-3-pyrrolidinecarboxamide;
(3S,4S)-N-hydroxy-4-[(4-{[2-(methylthio)-1H-benzimidazol-1-yl]methyl}benzoyl)amino]-1-(propylsulfonyl)-3-pyrrolidinecarboxamide;
(3S,4S)-N-hydroxy-1-(isopropylsulfonyl)-4-[(4-{[2-(methylthio)-1H-benzimidazol-1-yl]methyl}benzoyl)amino]-3-pyrrolidinecarboxamide;
tert-butyl (3S,4S)-3-[(hydroxyamino)carbonyl]-4-({4-[(2-methyl-1H-benzimidazol-1-yl)methyl]benzoyl}amino)-1-pyrrolidinecarboxylate;
(3S,4S)-N-hydroxy-4-({4-[(2-methyl-1H-benzimidazol-1-yl)methyl]benzoyl}amino)-3-pyrrolidinecarboxamide;
(3S,4S)-N-hydroxy-4-({4-[(2-methyl-1H-benzimidazol-1-yl)methyl]benzoyl}amino)-1-(2-propynyl)-3-pyrrolidinecarboxamide;
(3S,4S)-1-(2-butynyl)-N-hydroxy-4-({4-[(2-methyl-1H-benzimidazol-1-yl)methyl]benzoyl}amino)-3-pyrrolidinecarboxamide;
(3S,4S)-1-(3-butenyl)-N-hydroxy-4-({4-[(2-methyl-1H-benzimidazol-1-yl)methyl]benzoyl}amino)-3-pyrrolidinecarboxamide;
N-{(1R,2S)-2-[(hydroxyamino)carbonyl]cyclopentyl}-4-[(2-methyl-1H-benzimidazol-1-yl)methyl]benzamide;
(3S,4S)-N-hydroxy-1-isopropyl-4-({4-[(2-methyl-1H-benzimidazol-1-yl)methyl]benzoyl}amino)-3-pyrrolidinecarboxamide;
(3S,4S)-N-hydroxy-4-({4-[(2-methyl-1H-benzimidazol-1-yl)methyl]benzoyl}amino)-1-neopentyl-3-pyrrolidinecarboxamide;
tert-butyl (3S,4S)-3-[(hydroxyamino)carbonyl]-4-({4-[(2-isopropyl-1H-benzimidazol-1-yl)methyl]benzoyl}amino)-1-pyrrolidinecarboxylate;
(3S,4S)-N-hydroxy-4-({4-[(2-isopropyl-1H-benzimidazol-1-yl)methyl]benzoyl}amino)-3-pyrrolidinecarboxamide;
(3S,4S)-N-hydroxy-4-({4-[(2-isopropyl-1H-benzimidazol-1-yl)methyl]benzoyl}amino)-1-methyl-3-pyrrolidinecarboxamide;
(3S,4S)-N-hydroxy-4-({4-[(2-isopropyl-1H-benzimidazol-1-yl)methyl]benzoyl}amino)-1-propyl-3-pyrrolidinecarboxamide;
(3S,4S)-N-hydroxy-1-isopropyl-4-({4-[(2-isopropyl-1H-benzimidazol-1-yl)methyl]benzoyl}amino)-3-pyrrolidinecarboxamide;
(3S,4S)-N-hydroxy-4-({4-[(2-isopropyl-1H-benzimidazol-1-yl)methyl]benzoyl}amino)-1-(2-propynyl)-3-pyrrolidinecarboxamide;
(3S,4S)-1-(3-butenyl)-N-hydroxy-4-({4-[(2-isopropyl-1H-benzimidazol-1-yl)methyl]benzoyl}amino)-3-pyrrolidinecarboxamide;
(3S,4S)-1-(2-butynyl)-N-hydroxy-4-({4-[(2-isopropyl-1H-benzimidazol-1-yl)methyl]benzoyl}amino)-3-pyrrolidinecarboxamide;
(3S,4S)-N-hydroxy-4-({4-[(2-isopropyl-1H-benzimidazol-1-yl)methyl]benzoyl}amino)-1-(propylsulfonyl)-3-pyrrolidinecarboxamide;
(3S,4S)-1-(butylsulfonyl)-N-hydroxy-4-({4-[(2-isopropyl-1H-benzimidazol-1-yl)methyl]benzoyl}amino)-3-pyrrolidinecarboxamide;
(3S,4S)-N-hydroxy-4-({4-[(2-isopropyl-1H-benzimidazol-1-yl)methyl]benzoyl}amino)-1-(isopropylsulfonyl)-3-pyrrolidinecarboxamide;

N-{(1R,2S)-2-[(hydroxyamino)carbonyl]cyclopentyl}-4-[(2-isopropyl-1H-benzimidazol-1-yl)methyl]benzamide;

(3S,4S)-N-hydroxy-1-isobutyl-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-neopentyl-3-pyrrolidinecarboxamide;

tert-butyl (3S,4S)-3-[(hydroxyamino)carbonyl]-4-[(4-{[2-(trifluoromethyl)-1H-benzimidazol-1-yl]methyl}benzoyl)amino]-1-pyrrolidinecarboxylate;

(3S,4S)-N-hydroxy-4-[(4-{[2-(trifluoromethyl)-1H-benzimidazol-1-yl]methyl}benzoyl)amino]-3-pyrrolidinecarboxamide;

(3S,4S)-N-hydroxy-1-isopropyl-4-[(4-{[2-(trifluoromethyl)-1H-benzimidazol-1-yl]methyl}benzoyl)amino]-3-pyrrolidinecarboxamide;

(3S,4S)-N-hydroxy-1-(2-propynyl)-4-[(4-{[2-(trifluoromethyl)-1H-benzimidazol-1-yl]methyl}benzoyl)amino]-3-pyrrolidinecarboxamide;

(3S,4S)-1-(2-butynyl)-N-hydroxy-4-[(4-{[2-(trifluoromethyl)-1H-benzimidazol-1-yl]methyl}benzoyl)amino]-3-pyrrolidinecarboxamide;

(3S,4S)-1-(3-butenyl)-N-hydroxy-4-[(4-{[2-(trifluoromethyl)-1H-benzimidazol-1-yl]methyl}benzoyl)amino]-3-pyrrolidinecarboxamide;

(3R,4R)-N-hydroxy-4-({4-[(2-isopropyl-1H-benzimidazol-1-yl)methyl]benzoyl}amino)tetrahydro-2H-pyran-3-carboxamide;

(3R,4R)-N-hydroxy-4-[(4-{[2-(trifluoromethyl)-1H-benzimidazol-1-yl]methyl}benzoyl)amino]tetrahydro-2H-pyran-3-carboxamide;

(3S,4S)-N-hydroxy-1-(propylsulfonyl)-4-[(4-{[2-(trifluoromethyl)-1H-benzimidazol-1-yl]methyl}benzoyl)amino]-3-pyrrolidinecarboxamide;

(3S,4S)-N-hydroxy-1-(isopropylsulfonyl)-4-[(4-{[2-(trifluoromethyl)-1H-benzimidazol-1-yl]methyl}benzoyl)amino]-3-pyrrolidinecarboxamide;

(3S,4S)-1-(butylsulfonyl)-N-hydroxy-4-[(4-{[2-(trifluoromethyl)-1H-benzimidazol-1-yl]methyl}benzoyl)amino]-3-pyrrolidinecarboxamide;

(3S,4S)-1-acetyl-N-hydroxy-4-[(4-{[2-(trifluoromethyl)-1H-benzimidazol-1-yl]methyl}benzoyl)amino]-3-pyrrolidinecarboxamide;

(3S,4S)-N-hydroxy-1-(4-pentenoyl)-4-[(4-{[2-(trifluoromethyl)-1H-benzimidazol-1-yl]methyl}benzoyl)amino]-3-pyrrolidinecarboxamide;

(3S,4S)-N-hydroxy-1-isobutyl-4-[(4-{[2-(trifluoromethyl)-1H-benzimidazol-1-yl]methyl}benzoyl)amino]-3-pyrrolidinecarboxamide;

(3S,4S)-N-hydroxy-1-neopentyl-4-[(4-{[2-(trifluoromethyl)-1H-benzimidazol-1-yl]methyl}benzoyl)amino]-3-pyrrolidinecarboxamide;

cis-N-{-2-[(hydroxyamino)carbonyl]cyclopentyl}-4-{[2-(trifluoromethyl)-1H-benzimidazol-1-yl]methyl}benzamide;

(3R,4S)-N-hydroxy-4-[(4-{[2-(trifluoromethyl)-1H-benzimidazol-1-yl]methyl}benzoyl)amino]tetrahydro-3-furancarboxamide;

tert-butyl (3S,4S)-3-[(hydroxyamino)carbonyl]-4-({4-[(2-phenyl-1H-benzimidazol-1-yl)methyl]benzoyl}amino)-1-pyrrolidinecarboxylate;

(3S,4S)-N-hydroxy-4-({4-[(2-phenyl-1H-benzimidazol-1-yl)methyl]benzoyl}amino)-3-pyrrolidinecarboxamide;

tert-butyl (3S,4S)-3-({4-[(2-tert-butyl-1H-benzimidazol-1-yl)methyl]benzoyl}amino)-4-[(hydroxyamino)carbonyl]-1-pyrrolidinecarboxylate;

(3S,4S)-4-({4-[(2-tert-butyl-1H-benzimidazol-1-yl)methyl]benzoyl}amino)-N-hydroxy-3-pyrrolidinecarboxamide;

(3S,4S)-4-({4-[(2-tert-butyl-1H-benzimidazol-1-yl)methyl]benzoyl}amino)-N-hydroxy-1-(2-propynyl)-3-pyrrolidinecarboxamide;

(3S,4S)-4-({4-[(2-tert-butyl-1H-benzimidazol-1-yl)methyl]benzoyl}amino)-1-(2-butynyl)-N-hydroxy-3-pyrrolidinecarboxamide;

(3S,4S)-4-({4-[(2-tert-butyl-1H-benzimidazol-1-yl)methyl]benzoyl}amino)-N-hydroxy-1-isopropyl-3-pyrrolidinecarboxamide;

cis-4-[(2-tert-butyl-1H-benzimidazol-1-yl)methyl]-N-{2-[(hydroxyamino)carbonyl]cyclopentyl}benzamide;

(3R,4R)-4-({4-[(2-tert-butyl-1H-benzimidazol-1-yl)methyl]benzoyl}amino)-N-hydroxytetrahydro-2H-pyran-3-carboxamide;

(3R,4S)-4-({4-[(2-tert-butyl-1H-benzimidazol-1-yl)methyl]benzoyl}amino)-N-hydroxytetrahydro-3-furancarboxamide;

tert-butyl (3S,4S)-3-[(4-{[2-(difluoromethyl)-1H-benzimidazol-1-yl]methyl}benzoyl)amino]-4-[(hydroxyamino)carbonyl]-1-pyrrolidinecarboxylate;

(3S,4S)-4-[(4-{[2-(difluoromethyl)-1H-benzimidazol-1-yl]methyl}benzoyl)amino]-N-hydroxy-3-pyrrolidinecarboxamide;

(3S,4S)-4-[(4-{[2-(difluoromethyl)-1H-benzimidazol-1-yl]methyl}benzoyl)amino]-N-hydroxy-1-isopropyl-3-pyrrolidinecarboxamide;

(3S,4S)-4-[(4-{[2-(difluoromethyl)-1H-benzimidazol-1-yl]methyl}benzoyl)amino]-N-hydroxy-1-(2-propynyl)-3-pyrrolidinecarboxamide;

(3S,4S)-4-[(4-{[2-(difluoromethyl)-1H-benzimidazol-1-yl]methyl}benzoyl)amino]-N-hydroxy-1-isobutyl-3-pyrrolidinecarboxamide;

(3S,4S)-4-[(4-{[2-(difluoromethyl)-1H-benzimidazol-1-yl]methyl}benzoyl)amino]-N-hydroxy-1-neopentyl-3-pyrrolidinecarboxamide;

4-{[2-(difluoromethyl)-1H-benzimidazol-1-yl]methyl}-N-cis-2-[(hydroxyamino)carbonyl]cyclopentyl}benzamide;

(3R,4R)-4-[(4-{[2-(difluoromethyl)-1H-benzimidazol-1-yl]methyl}benzoyl)amino]-N-hydroxytetrahydro-2H-pyran-3-carboxamide;

(3R,4S)-4-[(4-{[2-(difluoromethyl)-1H-benzimidazol-1-yl]methyl}benzoyl)amino]-N-hydroxytetrahydro-3-furancarboxamide;

4-[(2-cyclopropyl-1H-benzimidazol-1-yl)methyl]-N-{(1R,2S)-2-[(hydroxyamino)carbonyl]cyclopentyl}benzamide;

(3R,4R)-4-({4-[(2-cyclopropyl-1H-benzimidazol-1-yl)methyl]benzoyl}amino)-N-hydroxytetrahydro-2H-pyran-3-carboxamide;

(3R,4S)-4-({4-[(2-cyclopropyl-1H-benzimidazol-1-yl)methyl]benzoyl}amino)-N-hydroxytetrahydro-3-furancarboxamide;

4-[(2-cyclobutyl-1H-benzimidazol-1-yl)methyl]-N-{(1R,2S)-2-[(hydroxyamino)carbonyl]cyclopentyl}benzamide;

(3R,4R)-4-({4-[(2-cyclobutyl-1H-benzimidazol-1-yl)methyl]benzoyl}amino)-N-hydroxytetrahydro-2H-pyran-3-carboxamide;

(3R,4R)-N-hydroxy-4-[(4-{[2-(1-methylcyclopropyl)-1H-benzimidazol-1-yl]methyl}benzoyl)amino]tetrahydro-2H-pyran-3-carboxamide;

N-{(1R,2S)-2-[(hydroxyamino)carbonyl]cyclopentyl}-4-{[2-(1-methylcyclopropyl)-1H-benzimidazol-1-yl]methyl}benzamide;

(3R,4R)-4-[(4-{[2-(fluoromethyl)-1H-benzimidazol-1-yl]methyl}benzoyl)amino]-N-hydroxytetrahydro-2H-pyran-3-carboxamide;

4-{[2-(fluoromethyl)-1H-benzimidazol-1-yl]methyl}-N-{(1R,2S)-2-[(hydroxyamino)carbonyl]cyclopentyl}benzamide;

(3R,4R)-4-[(4-{[2-(1-fluoro-1-methylethyl)-1H-benzimidazol-1-yl]methyl}benzoyl)amino]-N-hydroxytetrahydro-2H-pyran-3-carboxamide;

4-{[2-(1-fluoro-1-methylethyl)-1H-benzimidazol-1-yl]methyl}-N-{(1R,2S)-2-[(hydroxyamino)carbonyl]cyclopentyl}benzamide;

(3S,4R)-N-hydroxy-4-({4-[(2-isopropyl-1H-benzimidazol-1-yl)methyl]benzoyl}amino)tetrahydro-2H-pyran-3-carboxamide;

(3R,4S)-N-hydroxy-4-({4-[(2-isopropyl-1H-benzimidazol-1-yl)methyl]benzoyl}amino)tetrahydro-2H-pyran-3-carboxamide;

tert-butyl (3S,4S)-3-({4-[(2-chloro-1H-benzimidazol-1-yl)methyl]benzoyl}amino)-4-[(hydroxyamino)carbonyl]-1-pyrrolidinecarboxylate;

tert-butyl (3S,4S)-3-[(hydroxyamino)carbonyl]-4-({4-[(2-methoxy-1H-benzimidazol-1-yl)methyl]benzoyl}amino)-1-pyrrolidinecarboxylate;

tert-butyl (3S,4S)-3-[(hydroxyamino)carbonyl]-4-({4-[(2-methyl-1H-imidazo[4,5-b]pyridin-1-yl)methyl]benzoyl}amino)-1-pyrrolidinecarboxylate;

tert-butyl (3S,4S)-3-[(hydroxyamino)carbonyl]-4-{[4-(1H-imidazo[4,5-b]pyridin-1-ylmethyl)benzoyl]amino}-1-pyrrolidinecarboxylate;

(3R,4R)-4-({4-[(2-chloro-1H-benzimidazol-1-yl)methyl]benzoyl}amino)-N-hydroxy-3-pyrrolidinecarboxamide;

(3S,4S)-N-hydroxy-4-{[4-(1H-imidazo[4,5-b]pyridin-1-ylmethyl)benzoyl]amino}-3-pyrrolidinecarboxamide;

(3S,4S)-N-hydroxy-4-({4-[(2-methyl-1H-imidazo[4,5-b]pyridin-1-yl)methyl]benzoyl}amino)-3-pyrrolidinecarboxamide;

tert-butyl (3S,4S)-3-[(hydroxyamino)carbonyl]-4-({4-[(2-methyl-5-nitro-1H-benzimidazol-1-yl)methyl]benzoyl}amino)-1-pyrrolidinecarboxylate;

tert-butyl (3S,4S)-3-[(hydroxyamino)carbonyl]-4-({4-[(2-methyl-6-nitro-1H-benzimidazol-1-yl)methyl]benzoyl}amino)-1-pyrrolidinecarboxylate;

tert-butyl (3S,4S)-3-({4-[(5-chloro-2-methyl-1H-benzimidazol-1-yl)methyl]benzoyl}amino)-4-[(hydroxyamino)carbonyl]-1-pyrrolidinecarboxylate;

tert-butyl (3S,4S)-3-({4-[(6-chloro-2-methyl-1H-benzimidazol-1-yl)methyl]benzoyl}amino)-4-[(hydroxyamino)carbonyl]-1-pyrrolidinecarboxylate;

4-[(2-cyclopropyl-1H-benzimidazol-1-yl)methyl]-N-{(1R,6S)-6-[(hydroxyamino)carbonyl]-3-cyclohexen-1-yl}benzamide;

4-[(2-cyclobutyl-1H-benzimidazol-1-yl)methyl]-N-{(1R,6S)-6-[(hydroxyamino)carbonyl]-3-cyclohexen-1-yl}benzamide;

N-{(1R,6S)-6-[(hydroxyamino)carbonyl]-3-cyclohexen-1-yl}-4-[(2-isopropyl-1H-benzimidazol-1-yl)methyl]benzamide;

N-{(1R,2S)-2-[(hydroxyamino)carbonyl]cyclohexyl}-4-[(2-isopropyl-1H-benzimidazol-1-yl)methyl]benzamide;

4-[(2-cyclopropyl-1H-benzimidazol-1-yl)methyl]-N-{(1R,2S)-2-[(hydroxyamino)carbonyl]cyclohexyl}benzamide;

4-[(2-cyclobutyl-1H-benzimidazol-1-yl)methyl]-N-{(1R,2S)-2-[(hydroxyamino)carbonyl]cyclohexyl}benzamide;

N-{(1R,2S)-2-[(hydroxyamino)carbonyl]cyclohexyl}-4-{[2-(trifluoromethyl)-1H-benzimidazol-1-yl]methyl}benzamide;

4-[(2-tert-butyl-1H-benzimidazol-1-yl)methyl]-N-{(1R,2S)-2-[(hydroxyamino)carbonyl]cyclohexyl}benzamide;

tert-butyl (3S,4R)-3-[(hydroxyamino)carbonyl]-4-[(4-{[2-(1-methylcyclopropyl)-1H-benzimidazol-1-yl]methyl}benzoyl)amino]-1-piperidinecarboxylate;

(3S,4R)-N-hydroxy-4-[(4-{[2-(1-methylcyclopropyl)-1H-benzimidazol-1-yl]methyl}benzoyl)amino]-3-piperidinecarboxamide;

tert-butyl (3S,4S)-4-[(hydroxyamino)carbonyl]-3-[(4-{[2-(trifluoromethyl)-1H-benzimidazol-1-yl]methyl}benzoyl)amino]-1-piperidinecarboxylate;

(3S,4S)-N-hydroxy-3-[(4-{[2-(trifluoromethyl)-1H-benzimidazol-1-yl]methyl}benzoyl)amino]-4-piperidinecarboxamide;

(3R,4R)-4-({4-[(2-(1,1-difluoro-ethyl)-1H-benzimidazol-1-yl)methyl]benzoyl}amino)-N-hydroxytetrahydro-2H-pyran-3-carboxamide;

(3R,4R)-N-hydroxy-4-[(4-{[2-(trifluoromethyl)-1H-imidazo[4,5-b]pyridin-1-yl]methyl}benzoyl)amino]tetrahydro-2H-pyran-3-carboxamide;

(3R,4R)-N-hydroxy-4-[(4-{[2-(methoxymethyl)-1H-benzimidazol-1-yl]methyl}benzoyl)amino]tetrahydro-2H-pyran-3-carboxamide;

tert-butyl (3S,4S)-3-[(hydroxyamino)carbonyl]-4-({4-[(2-methyl-1H-indol-3-yl)methyl]benzoyl}amino)-1-pyrrolidinecarboxylate;

tert-butyl (3S,4S)-3-({4-[(1,2-dimethyl-1H-1indol-3-yl)methyl]benzoyl}amino)-4-[(hydroxyamino)carbonyl]-1-pyrrolidinecarboxylate;

(3S,4S)-N-hydroxy-4-({4-[(2-methyl-1H-indol-3-yl)methyl]benzoyl}amino)-3-pyrrolidinecarboxamide;

(3S,4S)-4-({4-[(1,2-dimethyl-1H-indol-3-yl)methyl]benzoyl}amino)-N-hydroxy-3-pyrrolidinecarboxamide;

(3S,4S)-N-hydroxy-1-isopropyl-4-({4-[(2-methyl-1H-indol-3-yl)methyl]benzoyl}amino)-3-pyrrolidinecarboxamide;

(3S,4S)-N-hydroxy-4-({4-[(2-methyl-1H-indol-3-yl)methyl]benzoyl}amino)-1-(2-propynyl)-3-pyrrolidinecarboxamide;

(3R,4R)-N-hydroxy-4-({4-[(2-methyl-1H-indol-3-yl)methyl]benzoyl}amino)tetrahydro-2H-pyran-3-carboxamide;

(3R,4R)-N-hydroxy-4-({4-[(2-methyl-1H-indol-1-yl)methyl]benzoyl}amino)tetrahydro-2H-pyran-3-carboxamide;

N-{(1R,2S)-2-[(hydroxyamino)carbonyl]cyclopentyl}-4-[(2-methyl-1H-indol-1-yl)methyl]benzamide;

tert-butyl (3S,4S)-3-({4-[(2,3-dimethyl-1H-indol-1-yl)methyl]benzoyl}amino)-4-[(hydroxyamino)carbonyl]-1-pyrrolidinecarboxylate;

tert-butyl (3S,4S)-3-[(hydroxyamino)carbonyl]-4-({4-[(2-isopropyl-1H-indol-1-yl)methyl]benzoyl}amino)-1-pyrrolidinecarboxylate;

(3S,4S)-N-hydroxy-4-({4-[(2-isopropyl-1H-indol-1-yl)methyl]benzoyl}amino)-3-pyrrolidinecarboxamide;

(3S,4S)-4-({4-[(2,3-dimethyl-1H-indol-1-yl)methyl]benzoyl}amino)-N-hydroxy-3-pyrrolidinecarboxamide;

(3R,4R)-4-({4-[(2,3-dimethyl-1H-indol-1-yl)methyl]benzoyl}amino)-N-hydroxytetrahydro-2H-pyran-3-carboxamide;

(3R,4R)-N-hydroxy-4-[(4-{[2-(trifluoromethyl)-1H-indol-1-yl]methyl}benzoyl)amino]tetrahydro-2H-pyran-3-carboxamide;

(3R,4R)-4-({4-[(2-ethyl-1H-indol-1-yl)methyl]benzoyl}amino)-N-hydroxytetrahydro-2H-pyran-3-carboxamide;

(3R,4S)-4-({4-[(2-ethyl-1H-indol-1-yl)methyl]benzoyl}amino)-N-hydroxytetrahydrofuran-3-carboxamide;

(3R,4S)-4-({4-[(2,3-dimethyl-1H-indol-1-yl)methyl]benzoyl}amino)-N-hydroxytetrahydrofuran-3-carboxamide;

(3R,4R)-4-({4-[(2-ethyl-1H-indol-3-yl)methyl]benzoyl}amino)-N-hydroxytetrahydro-2H-pyran-3-carboxamide;

(3R,4S)-4-({4-[(2-ethyl-1H-indol-3-yl)methyl]benzoyl}amino)-N-hydroxytetrahydrofuran-3-carboxamide;

(3R,4S)-N-hydroxy-4 [(4-{[2-(trifluoromethyl)-1H-indol-1-yl]methyl}benzoyl)amino]tetrahydrofuran-3-carboxamide;

(3R,4R)-N-hydroxy-4-({4-[(3-methyl-1H-indol-1-yl)methyl]benzoyl}amino)tetrahydro-2H-pyran-3-carboxamide;

(3R,4S)-N-hydroxy-4-({4-[(3-methyl-1H-indol-1-yl)methyl]benzoyl}amino)tetrahydrofuran-3-carboxamide;

(3R,4R)-4-({4-[(1,2-dimethyl-1H-indol-3-yl)methyl]benzoyl}amino)-N-hydroxytetrahydro-2H-pyran-3-carboxamide;

N-cis-2-[(hydroxyamino)carbonyl]cyclopentyl}-4-[(3-methyl-1H-indol-1-yl)methyl]benzamide;

(3R,4S)-4-({4-[(1,2-dimethyl-1H-indol-3-yl)methyl]benzoyl}amino)-N-hydroxytetrahydrofuran-3-carboxamide;

(3R,4S)-4-({4-[(2-ethyl-1-methyl-1H-indol-3-yl)methyl]benzoyl}amino)-N-hydroxytetrahydrofuran-3-carboxamide;

(3R,4R)-4-({4-[(2-ethyl-1-methyl-1H-indol-3-yl)methyl]benzoyl}amino)-N-hydroxytetrahydro-2H-pyran-3-carboxamide;

(3R,4R)-N-hydroxy-4-({4-[(2-methyl-1-benzofuran-3-yl)methyl]benzoyl}amino)tetrahydro-2H-pyran-3-carboxamide;

tert-butyl (3S,4S)-3-[(hydroxyamino)carbonyl]-4-({4-[(2-methyl-1-benzofuran-3-yl)methyl]benzoyl}amino)pyrrolidine-1-carboxylate;

(3S,4S)-N-hydroxy-4-({4-[(2-methyl-1-benzofuran-3-yl)methyl]benzoyl}amino)pyrrolidine-3-carboxamide;

(3R,4R)-N-hydroxy-4-({4-[(2-isopropyl-1-benzofuran-3-yl)methyl]benzoyl}amino)tetrahydro-2H-pyran-3-carboxamide;

tert-butyl (3S,4S)-3-[(hydroxyamino)carbonyl]-4-({4-[(2-isopropyl-1-benzofuran-3-yl)methyl]benzoyl}amino)pyrrolidine-1-carboxylate;

(3S,4S)-N-hydroxy-4-({4-[(2-isopropyl-1-benzofuran-3-yl)methyl]benzoyl}amino)pyrrolidine-3-carboxamide;

(3R,4R)-N-hydroxy-4-({4-[(2-methylimidazo[1,2-a]pyridin-3-yl)methyl]benzoyl}amino)tetrahydro-2H-pyran-3-carboxamide;

(3R,4R)-N-hydroxy-4-[(4-{[2-(trifluoromethyl)imidazo[1,2-a]pyridin-3-yl]methyl}benzoyl)amino]tetrahydro-2H-pyran-3-carboxamide;

(3R,4R)-4-({4-[(2-tert-butylimidazo[1,2-a]pyridin-3-yl)methyl]benzoyl}amino)-N-hydroxytetrahydro-2H-pyran-3-carboxamide;

N-{(1R,2S)-2-[(hydroxyamino)carbonyl]cyclopentyl}-4-[(2-isopropylimidazo[1,2-a]pyridin-3-yl)methyl]benzamide;

(3R,4R)-N-hydroxy-4-({4-[(2-isopropylimidazo[1,2-a]pyridin-3-yl)methyl]benzoyl}amino)tetrahydro-2H-pyran-3-carboxamide;

4-[(2-tert-butylimidazo[1,2-a]pyridin-3-yl)methyl]-N-{(1R,2S)-2-[(hydroxyamino)carbonyl]cyclopentyl}benzamide;

(3R,4R)-4-({4-[(2-cyclobutylimidazo[1,2-a]pyridin-3-yl)methyl]benzoyl}amino)-N-hydroxytetrahydro-2H-pyran-3-carboxamide;

N-{(1R,2S)-2-[(hydroxyamino)carbonyl]cyclopentyl}-4-{[2-(trifluoromethyl)imidazo[1,2-a]pyridin-3-yl]methyl}benzamide;

4-[(2-cyclobutylimidazo[1,2-a]pyridin-3-yl)methyl]-N-{(1R,2S)-2-[(hydroxyamino)carbonyl]cyclopentyl}benzamide;

(3R,4R)-4-({4-[(2-cyclopropylimidazo[1,2-a]pyridin-3-yl)methyl]benzoyl}amino)-N-hydroxytetrahydro-2H-pyran-3-carboxamide;

(3R,4R)-4-({4-[(2-ethylpyrazolo[1,5-a]pyridin-3-yl)methyl]benzoyl}amino)-N-hydroxytetrahydro-2H-pyran-3-carboxamide;

(3R,4R)-N-hydroxy-4-[(4-{[2-(trifluoromethyl)pyrazolo[1,5-a]pyridin-3-yl]methyl}benzoyl)amino]tetrahydro-2H-pyran-3-carboxamide;

(3R,4R)-N-hydroxy-4-[(4-{[2-(methoxymethyl)pyrazolo[1,5-a]pyridin-3-yl]methyl}benzoyl)amino]tetrahydro-2H-pyran-3-carboxamide;

(3R,4R)-N-hydroxy-4-[(4-{[2-(1-hydroxy-1-methylethyl)pyrazolo[1,5-a]pyridin-3-yl]methyl}benzoyl)amino]tetrahydro-2H-pyran-3-carboxamide;

(3R,4R)-N-hydroxy-4-({4-[(2-isopropylpyrazolo[1,5-a]pyridin-3-yl)methyl]benzoyl}amino)tetrahydro-2H-pyran-3-carboxamide;

(3R,4R)-4-({4-[(2-tert-butylpyrazolo[1,5-a]pyridin-3-yl)methyl]benzoyl}amino)-N-hydroxytetrahydro-2H-pyran-3-carboxamide;

(3R,4R)-4-({4-[(2-cyclopropylpyrazolo[1,5-a]pyridin-3-yl)methyl]benzoyl}amino)-N-hydroxytetrahydro-2H-pyran-3-carboxamide;

(3R,4R)-4-({4-[(2-cyclobutylpyrazolo[1,5-a]pyridin-3-yl)methyl]benzoyl}amino)-N-hydroxytetrahydro-2H-pyran-3-carboxamide;

4-[(2-cyclobutylpyrazolo[1,5-a]pyridin-3-yl)methyl]-N-{(1R,2S)-2-[(hydroxyamino)carbonyl]cyclopentyl}benzamide;

(3R,4R)-N-hydroxy-4-({4-[(2-phenylpyrazolo[1,5-a]pyridin-3-yl)methyl]benzoyl}amino)tetrahydro-2H-pyran-3-carboxamide;

(3R,4R)-4-({4-[(2-cyclopentylpyrazolo[1,5-a]pyridin-3-yl)methyl]benzoyl}amino)-N-hydroxytetrahydro-2H-pyran-3-carboxamide;

(3R,4R)-N-hydroxy-4-({4-[(2-tetrahydro-2H-pyran-4-ylpyrazolo[1,5-a]pyridin-3-yl)methyl]benzoylamino)tetrahydro-2H-pyran-3-carboxamide;

N-{(1R,2S)-2-[(hydroxyamino)carbonyl]cyclopentyl}-4-{[2-(trifluoromethyl)pyrazolo[1,5-a]pyridin-3-yl]methyl}benzamide;

tert-butyl (3S,4S)-3-[(hydroxyamino)carbonyl]-4-[(4-{[2-(trifluoromethyl)pyrazolo[1,5-a]pyridin-3-yl]methyl}benzoyl)amino]pyrrolidine-1-carboxylate;

(3S,4S)-N-hydroxy-4-[(4-{[2-(trifluoromethyl)pyrazolo[1,5-a]pyridin-3-yl]methyl}benzoyl)amino]pyrrolidine-3-carboxamide;

(3R,4R)-N-hydroxy-4-[(4-{[7-methyl-2-(trifluoromethyl)pyrazolo[1,5-a]pyridin-3-yl]methyl}benzoyl)amino]tetrahydro-2H-pyran-3-carboxamide;

(3R,4R)-N-hydroxy-4-({4-[(1-methylimidazo[1,5-a]pyridin-3-yl)methyl]benzoyl}amino)tetrahydro-2H-pyran-3-carboxamide;

(3R,4R)-N-hydroxy-4-[(4-{[1-(trifluoromethyl)imidazo[1,5-a]pyridin-3-yl]methyl}benzoyl)amino]tetrahydro-2H-pyran-3-carboxamide;

(3R,4R)-N-hydroxy-4-[(4-{[3-(trifluoromethyl)imidazo[1,5-a]pyridin-1-yl]methyl}benzoyl)amino]tetrahydro-2H-pyran-3-carboxamide; and, (3R,4R)-N-hydroxy-4-({4-[(3-methylimidazo[1,5-a]pyridin-1-yl)methyl]benzoyl}amino)tetrahydro-2H-pyran-3-carboxamide;

or a pharmaceutically acceptable salt form thereof.

[9] In another preferred embodiment, the present invention provides a novel compound of formula I, wherein;
$Z^a$ is

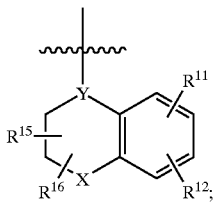

X is S, SO, $SO_2$, O, or $NR^{14}$;
Y is N or $CR^{17}$;
$R^{11}$ and $R^{12}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$;
$R^{14}$, at each occurrence, is independently selected from H, $C_{1-4}$ alkyl, phenyl, and benzyl;
$R^{15}$ and $R^{16}$, at each occurrence, are independently selected from H, $R^{c1}$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$;
alternatively, when $R^{15}$ and $R^{16}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, 0–2 heteroatoms selected from the group consisting of N, O, and $S(O)_p$, and substituted with 0–2 $R^{c1}$;
alternatively, when $R^{15}$ and $R^{16}$ are attached to the same carbon atom, together with the carbon atom to which they are attached, they form a 3–7 membered carbocyclic or heterocyclic ring consisting of: carbon atoms, 0–2 carbonyl groups, 0–3 double bonds, and 0–2 heteroatoms selected from the group consisting of N, O, and $S(O)_p$; this ring is substituted with 0–2 $R^{c1}$; and,
$R^{17}$ is selected from H, Cl, F, and $C_{1-4}$ alkyl.

[10] In a preferred embodiment, the present invention provides a novel compound of formula I, wherein;
$Z^a$ is

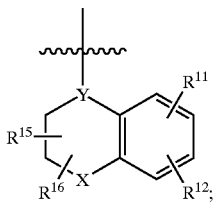

X is S, SO, $SO_2$, O, or $NR^{14}$;
Y is N or $CR^{17}$;
$R^{11}$ and $R^{12}$, at each occurrence, are independently selected from H. $R^c$, $C_{1-4}$ alkyl substituted with 0–3 $R^{c1}$, and phenyl substituted with 0–3 $R^{c1}$;
$R^{14}$, at each occurrence, is independently selected from H, $C_{1-4}$ alkyl, and benzyl;
$R^{15}$ and $R^{16}$, at each occurrence, are independently selected from H, $R^{c1}$, $C_{1-4}$ alkyl substituted with 0–3 $R^{c1}$, and phenyl;

alternatively, when $R^{15}$ and $R^{16}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$;
alternatively, when $R^{15}$ and $R^{16}$ are attached to the same carbon atom, together with the carbon atom to which they are attached they form a 3–6 membered carbocyclic or heterocyclic ring consisting of: carbon atoms, 0–1 carbonyl groups, 0–2 double bonds, and 0–2 heteroatoms selected from the group consisting of N, O, and $S(O)_p$; this ring is substituted with 0–1 $R^{c1}$; and,
$R^{17}$ is selected from H, Cl, F, and $C_{1-4}$ alkyl.

[11] In another preferred embodiment, the present invention provides a novel compound of formula II, wherein;
ring B is selected from the group:

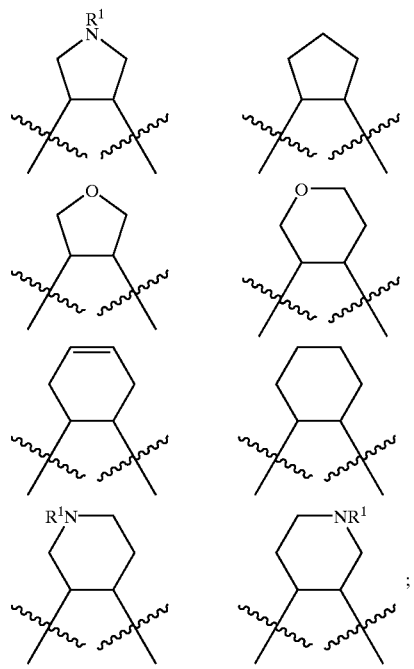

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and,
$Z^a$ is selected from the group:

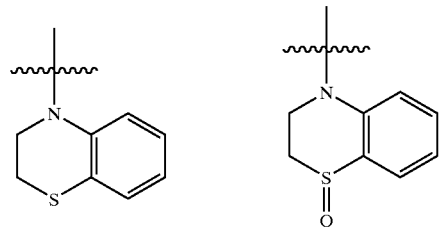

-continued

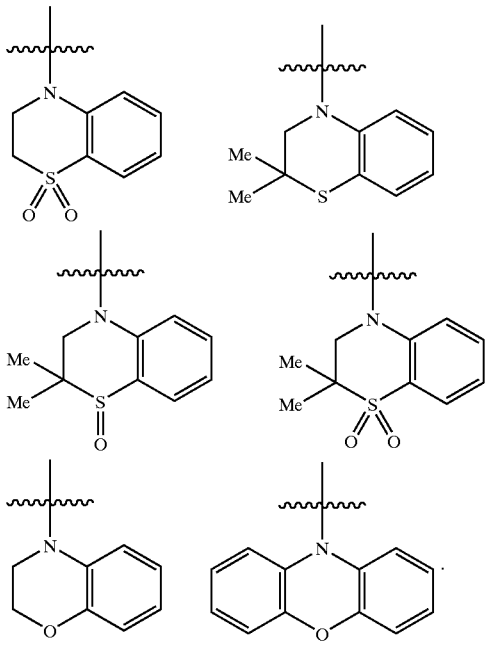

[12] In another preferred embodiment, the present invention provides a compound selected from the group:
tert-butyl (3S,4S)-3-{[4-(2,3-dihydro-4H-1,4-benzothiazin-4-ylmethyl)benzoyl]amino}-4-[(hydroxyamino)carbonyl]-1-pyrrolidinecarboxylate;
tert-butyl (3S,4S)-3-[(hydroxyamino)carbonyl]-4-({4-[(1-oxido-2,3-dihydro-4H-1,4-benzothiazin-4-yl)methyl]benzoyl}amino)-1-pyrrolidinecarboxylate;
(3S,4S)-4-{[4-(2,3-dihydro-4H-1,4-benzothiazin-4-ylmethyl)benzoyl]amino}-N-hydroxy-3-pyrrolidinecarboxamide;
(3S,4S)-N-hydroxy-4-({4-[(1-oxido-2,3-dihydro-4H-1,4-benzothiazin-4-yl)methyl]benzoyl}amino)-3-pyrrolidinecarboxamide;
(3S,4S)-N-hydroxy-4-({4-[(1-oxido-2,3-dihydro-4H-1,4-benzothiazin-4-yl)methyl]benzoyl}amino)-1-(2-propynyl)-3-pyrrolidinecarboxamide;
(3S,4S)-N-hydroxy-1-isopropyl-4-({4-[(1-oxido-2,3-dihydro-4H-1,4-benzothiazin-4-yl)methyl]benzoyl}amino)-3-pyrrolidinecarboxamide;
tert-butyl (3S,4S)-3-({4-[(1,1-dioxido-2,3-dihydro-4H-1,4-benzothiazin-4-yl)methyl]benzoyl}amino)-4-[(hydroxyamino)carbonyl]-1-pyrrolidinecarboxylate;
(3S,4S)-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-(2-propynyl)-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-isopropyl-3-pyrrolidinecarboxamide;
(3S,4S)-1-(2-butynyl)-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-isobutyl-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-methyl-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-(isopropylsulfonyl)-3-pyrrolidinecarboxamide;
(3S,4S)-1-acetyl-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-1-(2,2-dimethylpropanoyl)-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-phenyl-3-pyrrolidinecarboxamide;
(3S,4S)-4-({4-[(1,1-dioxido-2,3-dihydro-4H-1,4-benzothiazin-4-yl)methyl]benzoyl}amino)-1(4-fluorophenyl)-N-hydroxy-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-(4-methoxyphenyl)-3-pyrrolidinecarboxamide;
(3S,4S)-1-(cyclopropylmethyl)-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-1-cyclopentyl-4-({4-[(1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-tetrahydro-2H-pyran-4-yl-3-pyrrolidinecarboxamide;
(3S,4S)-4-({4-[(1,1-dioxido-2,3-dihydro-4H-1,4-benzothiazin-4-yl)methyl]benzoyl}amino)-N-hydroxy-1-neopentyl-3-pyrrolidinecarboxamide;
4-[(1,1-dioxido-2,3-dihydro-4H-1,4-benzothiazin-4-yl)methyl]-N-cis-{2-[(hydroxyamino)carbonyl]cyclopentyl}benzamide;
(3R,4S)-4-({4-[(1,1-dioxido-2,3-dihydro-4H-1,4-benzothiazin-4-yl)methyl]benzoyl}amino)-N-hydroxytetrahydro-3-furancarboxamide;
(3R,4R)-4-({4-[(1,1-dioxido-2,3-dihydro-4H-1,4-benzothiazin-4-yl)methyl]benzoyl}amino)-N-hydroxytetrahydro-2H-pyran-3-carboxamide;
tert-butyl (3S,4S)-3-({4-[(2,2-dimethyl-2,3-dihydro-4H-1,4-benzothiazin-4-yl)methyl]benzoyl}amino)-4-[(hydroxyamino)carbonyl]-1-pyrrolidinecarboxylate;
tert-butyl (3S,4S)-3-({4-[(2,2-dimethyl-1-oxido-2,3-dihydro-4H-1,4-benzothiazin-4-yl)methyl]benzoyl}amino)-4-[(hydroxyamino)carbonyl]-1-pyrrolidinecarboxylate;
tert-butyl (3S,4S)-3-({4-[(2,2-dimethyl-1,1-dioxido-2,3-dihydro-4H-1,4-benzothiazin-4-yl)methyl]benzoyl}amino)-4-[(hydroxyamino)carbonyl]-1-pyrrolidinecarboxylate;
(3S,4S)-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(2,2-dimethyl-1,1-dioxido-2,3-dihydro-4H-1,4-benzothiazin-4-yl)methyl]benzoyl}amino)-N-hydroxy-1-(2-propynyl)-3-pyrrolidinecarboxamide;
(3S,4S)-4-({4-[(2,2-dimethyl-1,1-dioxido-2,3-dihydro-4H-1,4-benzothiazin-4-yl)methyl]benzoyl}amino)-N-hydroxy-1-isopropyl-3-pyrrolidinecarboxamide;
(3S,4S)-4-({4-[(2,2-dimethyl-1,1-dioxido-2,3-dihydro-4H-1,4-benzothiazin-4-yl)methyl]benzoyl}amino)-N-hydroxy-1-isobutyl-3-pyrrolidinecarboxamide;
(3S,4S)-1-butyl-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide;
(3S,4S)-4-({4-[(2,2-dimethyl-1,1-dioxido-2,3-dihydro-4H-1,4-benzothiazin-4-yl)methyl]benzoyl}amino)-N-hydroxy-1-neopentyl-3-pyrrolidinecarboxamide;

(3R,4R)-4-({4-[(2,2-dimethyl-1,1-dioxido-2,3-dihydro-4H-1,4-benzothiazin-4-yl)methyl]benzoyl}amino)-N-hydroxytetrahydro-2H-pyran-3-carboxamide;

(3R,4S)-4-({4-[(2,2-dimethyl-1,1-dioxido-2,3-dihydro-4H-1,4-benzothiazin-4-yl)methyl]benzoyl}amino)-N-hydroxytetrahydro-3-furancarboxamide;

4-[(2,2-dimethyl-1,1-dioxido-2,3-dihydro-4H-1,4-benzothiazin-4-yl)methyl]-N-cis-{2-[(hydroxyamino)carbonyl]cyclopentyl}benzamide;

tert-butyl (3S,4S)-3-{[4-(2,3-dihydro-4H-1,4-benzoxazin-4-ylmethyl)benzoyl]amino}-4-[(hydroxyamino)carbonyl]-1-pyrrolidinecarboxylate; and, tert-butyl (3S,4S)-3-[(hydroxyamino)carbonyl]-4-{[4-(10H-phenoxazin-10-ylmethyl)benzoyl]amino}-1-pyrrolidinecarboxylate;

or a pharmaceutically acceptable salt form thereof.

[13] In another preferred embodiment, the present invention provides a novel compound of formula I, wherein;
$Z^a$ is

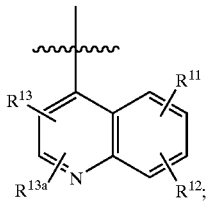

$R^{11}$ and $R^{12}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$; and $R^{13}$ and $R^{13a}$, at each occurrence, is independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$; and, alternatively, when $R^{13}$ and $R^{13a}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, and 0–2 heteroatoms selected from the group consisting of N, O, and $S(O)_p$, and substituted with 0–2 $R^{c1}$.

[14] In a preferred embodiment, the present invention provides a novel compound of formula I, wherein;
$Z^a$ is

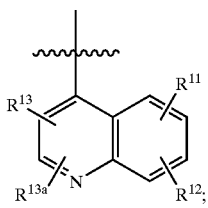

$R^{13}$ and $R^{13a}$, at each occurrence, are independently selected from H, $R^c$, $C_{1-4}$ alkyl substituted with 0–3 $R^{c1}$, $C_{3-6}$ cycloalkyl substituted with 0–2 $R^{c1}$, phenyl substituted with 0–3 $R^{c1}$, and a 5–6 membered heterocycle consisting of: carbon atoms and 1–4 heteroatoms selected from the group consisting of N, O, and $S(O)_p$, and substituted with 0–3 $R^{c1}$; and, alternatively, when $R^{13}$ and $R^{13a}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$.

[15] In another preferred embodiment, the present invention provides a novel compound of formula II, wherein;

ring B is selected from the group:

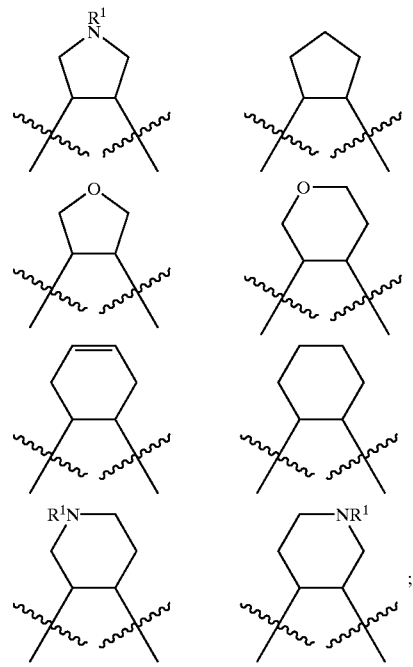

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

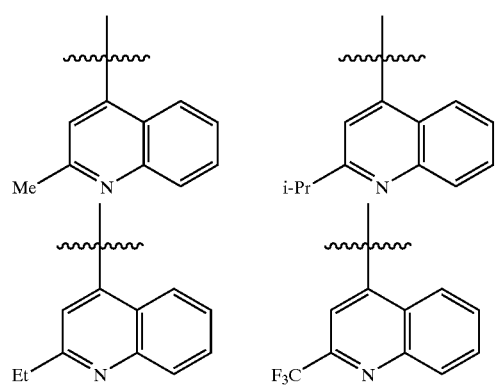

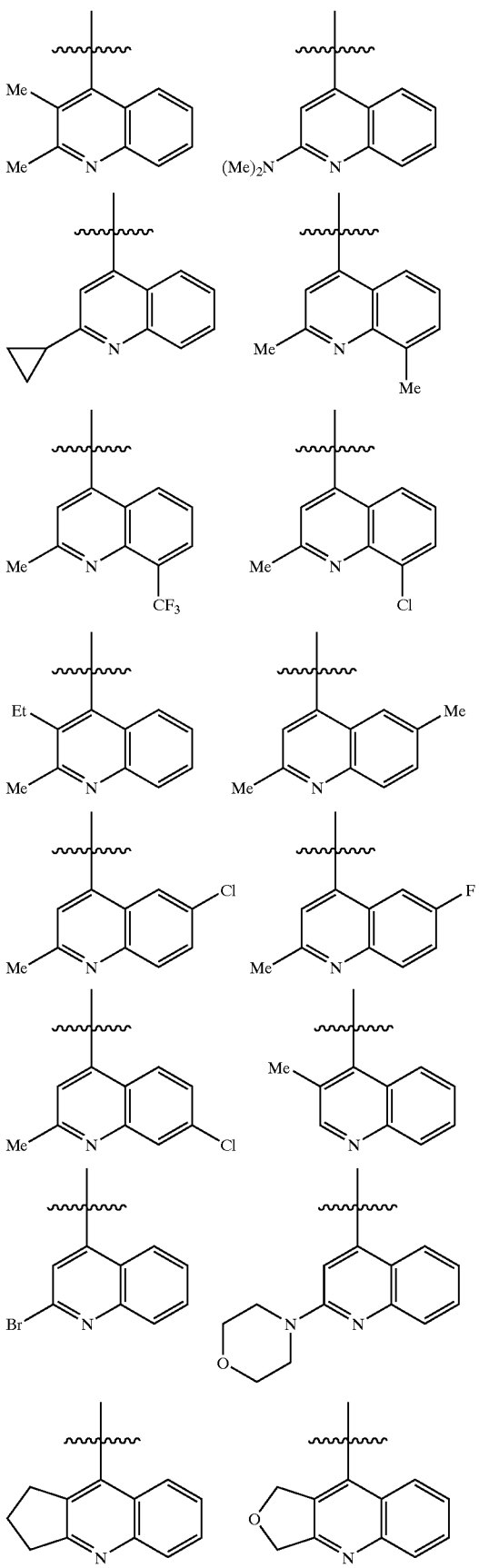
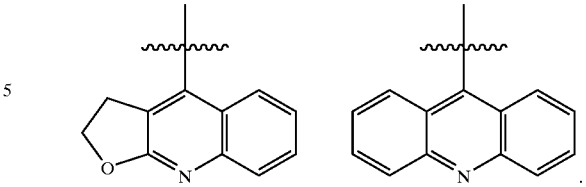

[16] In another preferred embodiment, the present invention provides a compound selected from the group:

tert-butyl (3S,4S)-3-[(hydroxyamino)carbonyl]-4-({4-[(2-methyl-4-quinolinyl)methyl]benzoyl}amino)-1-pyrrolidinecarboxylate;

(3S,4S)-N-hydroxy-4-({4-[(2-methyl-4-quinolinyl)methyl]benzoyl}amino)-3-pyrrolidinecarboxamide;

(3S,4S)-N-hydroxy-4-({4-[(2-methyl-4-quinolinyl)methyl]benzoyl}amino)-1-(2-propynyl)-3-pyrrolidinecarboxamide;

(3S,4S)-N-hydroxy-1-isopropyl-4-({4-[(2-methyl-4-quinolinyl)methyl]benzoyl}amino)-3-pyrrolidinecarboxamide;

(3S,4S)-N-hydroxy-1-isobutyl-4-({4-[(2-methyl-4-quinolinyl)methyl]benzoyl}amino)-3-pyrrolidinecarboxamide;

(3S,4S)-1-butyl-N-hydroxy-4-({4-[(2-methyl-4-quinolinyl)methyl]benzoyl}amino)-3-pyrrolidinecarboxamide;

(3S,4S)-1-(2-butynyl)-N-hydroxy-4-({4-[(2-methyl-4-quinolinyl)methyl]benzoyl}amino)-3-pyrrolidinecarboxamide;

(3S,4S)-N-hydroxy-1-methyl-4-({4-[(2-methyl-4-quinolinyl)methyl]benzoyl}amino)-3-pyrrolidinecarboxamide;

(3S,4S)-1-allyl-N-hydroxy-4-({4-[(2-methyl-4-quinolinyl)methyl]benzoyl}amino)-3-pyrrolidinecarboxamide;

(3S,4S)-1-(cyclopropylmethyl)-N-hydroxy-4-({4-[(2-methyl-4-quinolinyl)methyl]benzoyl}amino)-3-pyrrolidinecarboxamide;

(3S,4S)-1-cyclopentyl-N-hydroxy-4-({4-[(2-methyl-4-quinolinyl)methyl]benzoyl}amino)-3-pyrrolidinecarboxamide;

(3S,4S)-N-hydroxy-4-({4-[(2-methyl-4-quinolinyl)methyl]benzoyl}amino)-1-neopentyl-3-pyrrolidinecarboxamide;

(3S,4S)-N-hydroxy-4-({4-[(2-methyl-4-quinolinyl)methyl]benzoyl}amino)-1-tetrahydro-2H-pyran-4-yl-3-pyrrolidinecarboxamide;

(3S,4S)-N-hydroxy-4-({4-[(2-methyl-4-quinolinyl)methyl]benzoyl}amino)-1-phenyl-3-pyrrolidinecarboxamide;

(3S,4S)-1-(4-fluorophenyl)-N-hydroxy-4-({4-[(2-methyl-4-quinolinyl)methyl]benzoyl}amino)-3-pyrrolidinecarboxamide;

(3S,4S)-N-hydroxy-1-(methoxyphenyl)-4-({4-[(2-methyl-4-quinolinyl)methyl]benzoyl}amino)-3-pyrrolidinecarboxamide;

(3S,4S)-1-acetyl-N-hydroxy-4-({4-[(2-methyl-4-quinolinyl)methyl]benzoyl}amino)-3-pyrrolidinecarboxamide;

(3S,4S)-1-(2,2-dimethylpropanoyl)-N-hydroxy-4-({4-[(2-methyl-4-quinolinyl)methyl]benzoyl}amino)-3-pyrrolidinecarboxamide;

(3S,4S)-N-hydroxy-1-(isopropylsulfonyl)-4-({4-[(2-methyl-4-quinolinyl)methyl]benzoyl}amino)-3-pyrrolidinecarboxamide;

(3S,4S)-1-(butylsulfonyl)-N-hydroxy-4-({4-[(2-methyl-4-quinolinyl)methyl]benzoyl}amino)-3-pyrrolidinecarboxamide; methyl (3S,4S)-3-[(hydroxyamino)carbonyl]-4-({4-[(2-methyl-4-quinolinyl)methyl]benzoyl}amino)-1-pyrrolidinecarboxylate;

(3R,4S)-N-hydroxy-4-({4-[(2-methyl-4-quinolinyl)methyl]
benzoyl}amino)tetrtahydro-3-furancarboxamide;

(3R,4R)-N-hydroxy-4-({4-[(2-methyl-4-quinolinyl)methyl]
benzoyl}amino)tetrahydro-2H-pyran-3-carboxamide;

N-cis-{2-[(hydroxyamino)carbonyl]cyclopentyl}-4-[(2-methyl-4-quinolinyl)methyl]benzamide;

tert-butyl (3S,4S)-3-[(hydroxyamino)carbonyl]-4-({4-[(2-isopropyl-4-quinolinyl)methyl]benzoyl}amino)-1-pyrrolidinecarboxylate;

(3S,4S)-N-hydroxy-4-({4-[(2-isopropyl-4-quinolinyl)
methyl]benzoyl}amino)-3-pyrrolidinecarboxamide;

(3S,4S)-N-hydroxy-4-({4-[(2-isopropyl-4-quinolinyl)
methyl]benzoyl}amino)-1-(2-propynyl)-3-
pyrrolidinecarboxamide;

(3S,4S)-N-hydroxy-1-isopropyl-4-({4-[(2-isopropyl-4-
quinolinyl)methyl]benzoyl}amino)-3-
pyrrolidinecarboxamide;

(3S,4S)-N-hydroxy-4-({4-[(2-isopropyl-4-quinolinyl)
methyl]benzoyl}amino)-1-methyl-3-
pyrrolidinecarboxamide;

(3S,4S)-1-cyclopentyl-N-hydroxy-4-({4-[(2-isopropyl-4-
quinolinyl)methyl]benzoyl}amino)-3-
pyrrolidinecarboxamide;

(3R,4R)-N-hydroxy-4-({4-[(2-isopropyl-4-quinolinyl)
methyl]benzoyl}amino) tetrahydro-2H-pyran-3-
carboxamide;

N-cis-{2-[(hydroxyamino)carbonyl]cyclopentyl}-4-[(2-isopropyl-4-quinolinyl)methyl]benzamide;

(3R,4S)-N-hydroxy-4-({4-[(2-isopropyl-4-quinolinyl)
methyl]benzoyl}amino)tetrtahydro-3-furancarboxamide;

tert-butyl (3S,4S)-3-({4-[(2-ethyl-4-quinolinyl)methyl]
benzoyl}amino)-4-[(hydroxyamino)carbonyl]-1-
pyrrolidinecarboxylate;

(3S,4S)-4-({4-[(2-ethyl-4-quinolinyl)methyl]
benzoyl}amino)-N-hydroxy-3-pyrrolidinecarboxamide;

(3S,4S)-4-({4-[(2-ethyl-4-quinolinyl)methyl]
benzoyl}amino)-N-hydroxy-1-(2-propynyl)-3-
pyrrolidinecarboxamide;

(3S,4S)-1-(2-butynyl)-4-({4-[(2-ethyl-4-quinolinyl)methyl]
benzoyl}amino)-N-hydroxy-3-pyrrolidinecarboxamide;

(3R,4R)-4-({4-[(2-ethyl-4-quinolinyl)methyl]
benzoyl}amino)-N-hydroxytetrahydro-2H-pyran-3-
carboxamide;

4-[(2-ethyl-4-quinolinyl)methyl]-N-{cis-2-
[(hydroxyamino)carbonyl]cyclopentyl}-benzamide;

(3R,4S)-4-({4-[(2-ethyl-4-quinolinyl)methyl]
benzoyl}amino)-N-hydroxytetrtahydro-3-
furancarboxamide;

tert-butyl (3S,4S)-3-[(hydroxyamino)carbonyl]-4-({4-[(2-
(trifluoromethyl)-4-quinolinyl)methyl]benzoyl}amino)-
1-pyrrolidinecarboxylate;

(3R,4R)-N-hydroxy-4-[(4-{[2-(trifluoromethyl)-4-
quinolinyl]methyl}benzoyl)amino]tetrahydro-2H-pyran-
3-carboxamide;

N-{cis-2-[(hydroxyamino)carbonyl]cyclopentyl}-4-{[2-
(trifluoromethyl)-4-quinolinyl]methyl}benzamide;

tert-butyl (3S,4S)-3-[(hydroxyamino)carbonyl]-4-({4-[(2,3-
dimethyl-4-quinolinyl)methyl]benzoyl}amino)-1-
pyrrolidinecarboxylate;

(3R,4R)-4-({4-[(2,3-dimethyl-4-quinolinyl)methyl]
benzoyl}amino)-N-hydroxytetrahydro-2H-pyran-3-
carboxamide;

4-[(2,3-dimethyl-4-quinolinyl)methyl]-N-{cis-2-
[(hydroxyamino)carbonyl]cyclopentyl}benzamide;

(3S,4S)-N-hydroxy-4-[(4-{[2-(trifluoromethyl)-4-
quinolinyl]methyl}benzoyl)amino]-1-(2-propynyl)-3-
pyrrolidinecarboxamide;

(3R,4S)-N-hydroxy-4-[(4-{[2-(trifluoromethyl)-4-
quinolinyl]methyl}benzoyl)amino]-tetrahydro-3-
furancarboxamide;

(3S,4S)-4-({4-[(2,3-dimethyl-4-quinolinyl)methyl]
benzoyl}amino)-N-hydroxy-1-(2-propynyl)-3-
pyrrolidinecarboxamide;

(3R,4S)-N-hydroxy-4-({4-[(2,3-dimethyl-4-quinolinyl)
methyl]benzoyl}amino)-tetrahydro-3-furancarboxamide;

(3R,4R)-4-[(4-{[2-(dimethylamino)-4-quinolinyl]
methyl}benzoyl)amino]-N-hydroxytetrahydro-2H-pyran-
3-carboxamide;

(3R,4S)-4-({4-[(2-cyclopropyl-4-quinolinyl)methyl]
benzoyl}amino)-N-hydroxytetrahydro-3-
furancarboxamide;

(3R,4R)-4-({4-[(2-cyclopropyl-4-quinolinyl)methyl]
benzoyl}amino)-N-hydroxytetrahydro-2H-pyran-3-
carboxamide;

(3R,4S)-4-{[4-(1,3-dihydrofuro[3,4-b]quinolin-9-ylmethyl)
benzoyl]amino}-N-hydroxytetrahydro-3-
furancarboxamide;

(3R,4R)-4-{[4-(1,3-dihydrofuro[3,4-b]quinolin-9-ylmethyl)
benzoyl]amino}-N-hydroxytetrahydro-2H-pyran-3-
carboxamide;

tert-butyl (3S,4S)-4-({4-[(2,8-dimethyl-4-quinolinyl)
methyl]benzoyl}amino)-3-[(hydroxyamino)carbonyl]-1-
pyrrolidinecarboxylate;

4-[(2,8-dimethyl-4-quinolinyl)methyl]-N-{cis-2-
[(hydroxyamino)carbonyl]cyclopentyl}benzamide;

(3R,4R)-4-({4-[(2,8-dimethyl-4-quinolinyl)methyl]
benzoyl}amino)-N-hydroxytetrahydro-2H-pyran-3-
carboxamide;

(3R,4S)-4-({4-[(2,8-dimethyl-4-quinolinyl)methyl]
benzoyl}amino)-N-hydroxytetrahydro-3-
furancarboxamide;

(3R,4R)-N-hydroxy-4-[(4-{[2-methyl-8-(trifluoromethyl)-
4-quinolinyl]methyl}benzoyl)amino]tetrahydro-2H-
pyran-3-carboxamide;

(3R,4R)-4-({4-[(8-chloro-2-methyl-4-quinolinyl)methyl]
benzoyl}amino)-N-hydroxytetrahydro-2H-pyran-3-
carboxamide;

(3R,4S)-4-({4-[(8-chloro-2-methyl-4-quinolinyl)methyl]
benzoyl}amino)-N-hydroxytetrahydro-3-
furancarboxamide;

(3R,4R)-4-({4-[(3-ethyl-2-methyl-4-quinolinyl)methyl]
benzoyl}amino)-N-hydroxytetrahydro-2H-pyran-3-
carboxamide;

(3R,4S)-4-([4-[(3-ethyl-2-methyl-4-quinolinyl)methyl]
benzoyl}amino)-N-hydroxytetrahydro-3-
furancarboxamide;

4-[(3-ethyl-2-methyl-4-quinolinyl)methyl]-N-[cis-2-
[(hydroxyamino)carbonyl]cyclopentyl}benzamide;

(3R,4S)-4-({4-[(2,6-dimethyl-4-quinolinyl)methyl]
benzoyl}amino)-N-hydroxytetrahydro-3-
furancarboxamide;

4-[(2,6-dimethyl-4-quinolinyl)methyl]-N-{cis-2-
[(hydroxyamino)carbonyl]cyclopentyl}benzamide;

(3R,4R)-N-hydroxy-4-({4-[(2,6-dimethyl-4-quinolinyl)
methyl]benzoyl}amino) tetrahydro-2H-pyran-3-
carboxamide;

(3R,4S)-4-({4-[(6-chloro-2-methyl-4-quinolinyl)methyl]
benzoyl}amino)-N-hydroxytetrahydro-3-
furancarboxamide;

(3R,4R)-4-({4-[(6-chloro-2-methyl-4-quinolinyl)methyl]
benzoyl}amino)-N-hydroxytetrahydro-2H-pyran-3-
carboxamide;

(3R,4R)-4-({4-[(6-fluoro-2-methyl-4-quinolinyl)methyl]
benzoyl}amino)-N-hydroxytetrahydro-2H-pyran-3-
carboxamide;

(3R,4R)-4-({4-[(7-chloro-2-methyl-4-quinolinyl)methyl] benzoyl}amino)-N-hydroxytetrahydro-2H-pyran-3-carboxamide;

(3R,4R)-4-{[4-(2,3-dihydro-1H-cyclopenta[b]quinolin-9-ylmethyl)benzoyl]amino}-N-hydroxytetrahydro-2H-pyran-3-carboxamide;

(3R,4R)-4-{[4-(2,3-dihydrofuro[2,3-b]quinolin-4-ylmethyl) benzoyl]amino}-N-hydroxytetrahydro-2H-pyran-3-carboxamide;

(3R,4R)-4-{[4-(acridin-9-ylmethyl)benzoyl]amino}-N-hydroxytetrahydro-2H-pyran-3-carboxamide;

(3R,4R)-4-({4-[(3-methyl-4-quinolinyl)methyl] benzoyl}amino)-N-hydroxytetrahydro-2H-pyran-3-carboxamide;

(3R,4R)-4-({4-[(2-bromoquinolin-4-yl)methyl] benzoyl}amino)-N-hydroxytetrahydro-2H-pyran-3-carboxamide; and, (3R,4R)-N-hydroxy-4-({4-[(2-morpholin-4-ylquinolin-4-yl) methyl]benzoyl}amino)tetrahydro-2H-pyran-3-carboxamide;

or a pharmaceutically acceptable salt form thereof.

In another preferred embodiment, the present invention provides a novel compound, wherein;
ring B is a 5–6 membered non-aromatic carbocyclic or heterocyclic ring consisting of: carbon atoms, 0–1 carbonyl groups, 0–2 double bonds, and 0–2 ring heteroatoms selected from O, N, and $NR^1$, provided that ring B contains other than a O—O bond.

In another preferred embodiment, the present invention provides a novel compound, wherein;
ring B is a 5–6 membered non-aromatic carbocyclic or heterocyclic ring consisting of: carbon atoms, 0–1 carbonyl groups, 0–1 double bonds, and 0–1 ring heteroatoms selected from O, N, and $NR^1$.

In another preferred embodiment, the present invention provides a novel compound, wherein;
ring B is selected from the group:

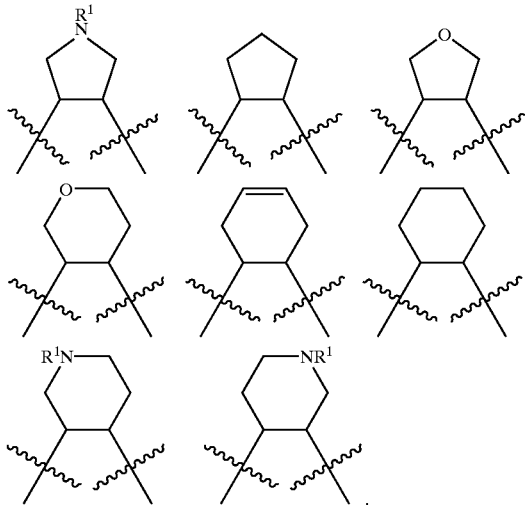

In another preferred embodiment, the present invention provides a novel compound, wherein;
$R^1$ is selected from Q, $C_{1-6}$ alkylene-Q, $C_{2-6}$ alkenylene-Q, $C_{2-6}$ alkynylene-Q, $C(O)(CR^aR^{a1})_s$-Q, $C(O)$—$C_{2-6}$ alkenylene-Q, $C(O)O(CR^aR^{a1})_s$-Q, $C(O)NR^aR^{a1}$, $C(O)NR^a(CR^aR^{a1})_s$-Q, and $S(O)_p(CR^aR^{a1})_s$-Q.

In another preferred embodiment, the present invention provides a novel compound, wherein;
$R^1$ is selected from Q, $C_{1-6}$ alkylene-Q, $C_{2-4}$ alkenylene-Q, $C_{2-4}$ alkynylene-Q, $C(O)(CR^aR^{a1})_s$-Q, $C(O)$—$C_{2-6}$ alkenyl, $C(O)O(CR^aR^{a1})_s$-Q, $C(O)NR^a$-Q, and $S(O)_p(CR^aR^{a1})_s$-Q;

In another preferred embodiment, the present invention provides a novel compound, wherein;
$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl.

In another preferred embodiment, the present invention provides a novel compound, wherein;
$R^2$ is selected from Q, $C_{1-6}$ alkylene-Q, $C_{2-6}$ alkenylene-Q, $C_{2-6}$ alkynylene-Q, $C(O)(CR^aR^{a1})_s$-Q, $C(O)$—$C_{2-6}$ alkenylene-Q, $C(O)O(CR^aR^{a1})_s$-Q, $C(O)NR^a(CR^aR^{a1})_s$-Q, and $S(O)_p(CR^aR^{a1})_s$-Q.

In another preferred embodiment, the present invention provides a novel compound, wherein;
$R^2$ is selected from Q, $C_{1-4}$ alkylene-Q, $C_{2-4}$ alkenylene-Q, $C_{2-4}$ alkynylene-Q, $C(O)$-Q, $C(O)$—$C_{2-6}$ alkenyl, $C(O)O$-Q, $C(O)NR^a$-Q, and $S(O)_p$-Q.

In another preferred embodiment, the present invention provides a novel compound, wherein;
Q is selected from H, cyclopropyl substituted with 0–1 $R^d$, cyclobutyl substituted with 0–1 $R^d$, cyclopentyl substituted with 0–1 $R^d$, cyclohexyl substituted with 0–1 $R^d$, phenyl substituted with 0–3 $R^d$ and a heterocycle substituted with 0–2 $R^d$, wherein the heterocycle is selected from pyridyl, quinolinyl, thiazolyl, furanyl, tetrahydrofuranyl, imidazolyl, isoxazolyl, pyranyl, tetrahydro-2H-pyranyl, morpholinyl, piperidinyl, piperazinyl, and pyrrolidinyl.

In another preferred embodiment, the present invention provides a novel compound, wherein;
Q is selected from H, cyclopropyl, cyclobutyl, cyclopentyl, cyclohexyl, tetrahydro-2H-pyran-4-yl, and phenyl substituted with 0–2 $R^d$.

In another preferred embodiment, the present invention provides a novel compound, wherein;
$R^3$ is selected from $Q^1$, Cl, F, $C_{1-4}$ alkylene-$Q^1$, $C_{2-4}$ alkenylene-$Q^1$, and $C_{2-4}$ alkynylene-$Q^1$; and
$Q^1$ is selected from H and phenyl.

In another preferred embodiment, the present invention provides a novel compound, wherein;
$R^3$ is H, $C_{1-4}$ alkyl, $C_{2-4}$ alkenyl, $C_{2-4}$ alkynyl, phenyl, and benzyl.

In another preferred embodiment, the present invention provides a novel compound, wherein;
$R^3$ is H and $C_{1-4}$ alkyl.

In another preferred embodiment, the present invention provides a novel compound, wherein;
$R^c$, at each occurrence, is independently selected from $C_{1-6}$ alkyl, $OR^a$, Cl, F, Br, $NR^aR^{a1}$, $C(O)R^a$, $C(O)NR^aR^{a1}$, $S(O)_2NR^aR^{a1}$, $S(O)_pR^{a2}$, $CF_3$, $OCF_3$, $CF_2CF_3$, $CH_2F$, and $CHF_2$.

In another preferred embodiment, the present invention provides a novel compound, wherein;
$R^{c1}$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, $OCF_3$, $CF_2CF_3$, $CH_2F$, and $CHF_2$.

In another preferred embodiment, the present invention provides a novel compound, wherein;
$R^d$, at each occurrence, is independently selected from $C_{1-6}$ alkyl, $OR^a$, Cl, F, Br, =O, $NR^aR^{a1}$, $C(O)R^a$, $C(O)NR^aR^{a1}$, $S(O)_2NR^aR^{a1}$, $S(O)_pR^{a2}$, $CF_3$, and phenyl.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating an inflammatory disorder, comprising: administering to a patient in need thereof a therapeutically effective amount of a compound of the present invention or a pharmaceutically acceptable salt form thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a pharmaceutically acceptable salt form thereof.

In another embodiment, the present invention provides a novel method comprising: administering a compound of the present invention or a pharmaceutically acceptable salt form thereof in an amount effective to treat a condition or disease mediated by MMPs, TACE, aggrecanase, or a combination thereof.

In another embodiment, the present invention provides a novel method of treating a disease or condition, wherein the disease or condition is selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used for the treatment of an inflammatory disorder.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat an inflammatory disorder.

In another preferred embodiment, the present invention provides a novel article of manufacture, further comprising:
(d) a second container;
wherein components (a) and (b) are located within the second container and component (c) is located within or outside of the second container.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. C is and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

Preferably, the molecular weight of compounds of the present invention is less than about 500, 550, 600, 650, 700, 750, 800, 850, or 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "independently selected from", "independently, at each occurrence" or similar language, means that the labeled R substitution group may appear more than once and that each appearance may be a different atom or molecule found in the definition of that labeled R substitution group. Thus if the labeled $R^a$ substitution group appear four times in a given permutation of Formula I, then each of those labeled $R^a$ substitution groups may be a different group falling in the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon—carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{1-0}$alkenyl groups. "Alkynyl" or "alkynylene" is intended to include hydrocarbon chains of either a straight or branched configuration and one or more triple carbon—carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{1-0}$alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4H-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, imidazo[1,2-a]pyridinyl, imidazo[1,5-a]pyridinyl, and pyrazolo[1,5-a]pyridinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anti-inflammatory effect, or some other beneficial effect of the combination compared with the individual components.

Other features of the invention will become apparent in the course of the following descriptions of exemplary embodiments that are given for illustration of the invention and are not intended to be limiting thereof.

The compounds of the present invention can be prepared in a number of ways known to one skilled in the art of organic synthesis. A general description of the synthetic methods for preparing the compounds of the present invention can be found in WO01/70673, which is hereby incorporated herein by reference.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "µL" for microliter or microliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer

Example 1 tert-butyl (3S,4S)-3-[(hydroxyamino)carbonyl]-4-[(4-{[2-(methylthio)-1H-benzimidazol-yl]methyl}benzoyl)amino]-1-pyrrolidinecarboxylate (1a) A solution of benzyl methyl maleate (15.0 g, 68.2 mmol) in benzene (1 L) at reflux was treated with a mixture of glycine (8.3 g, 2 eq) and para-formaldehyde (8.3 g, 4 eq) portionwise over 1 h. The mixture was heated at reflux for 2 h further. The mixture was filtered through a plug of silica and concentrated providing the desired amine (19.3 g, 100%). MS found: $(M+H)^+=264$.

(1b) The amine from reaction (1a) (7.3 g, 27.5 mmol) in N,N-dimethylformamide (DMF) was treated with di-t-butyl dicarbonate (9.0 g, 1.5 eq), triethylamine (5.8 mL, 1.5 eq), and hydroxylamine hydrochloride (0.2 g, 0.1 eq) and stirred for 17 h. The mixture was partitioned between water and ether (100 mL each) and the aqueous layer further extracted with ether (100 mL). The combined ether layers were washed with water and brine (100 mL each) dried ($MgSO_4$) and concentrated. Silica gel column chromatography (ethyl acetate-hexane, 3:2) yielded the desired ester (6.39 g, 64%). MS found: $(M-Bu+H)^+=308$.

(1c) The ester from reaction (1b) (8.3 g, 22.9 mmol) in methanol (100 mL) was treated with 10% palladium hydroxide on carbon (2.28 g, 0.1 eq) and stirred under a balloon of hydrogen for 3.5 h. The mixture was purged with nitrogen, filtered through a plug of Celite®, washed with excess methanol, and the filtrate concentrated providing the desired acid (6.0 g, 96%). The acid was converted to the (S)-α-methylbenzylamine salt and recrystallized from ethyl acetate to give the desired acid following neutralization (HCl). MS found: $(M+Na)^+=296$.

(1d) The acid from reaction (1c) (2.73 g, 0.01 mmol) in benzene (100 mL) was treated with triethylamine (2.1 mL, 1.5 eq) and diphenylphosphorylazide (2.58 mL, 1.2 eq) and stirred at rt for 1 h. Benzyl alcohol (1.03 mL, 1.0 eq) was added and the mixture heated to reflux for 1.5 h. The mixture was cooled and partitioned between ethyl acetate and saturated aqueous $NaHCO_3$ (100 mL each). The organic layer was washed further with $NaHCO_3$ and brine (100 mL each), dried ($MgSO_4$), and concentrated. Silica gel column chromatography (ethyl acetate-hexane, 3:2) yielded the desired carbamate (2.86 g, 76%). MS found: $(M+H)^+=379$.

(1e) The carbamate from reaction (1d) (2.86 g, 7.6 mmol) in methanol (38 mL) was treated with 10% palladium hydroxide on carbon (0.53 g, 0.1 eq) and stirred under a balloon of hydrogen for 1.5 h. The mixture was purged with nitrogen, filtered through a plug of Celite®, washing with excess methanol, and the filtrate concentrated providing the desired amine (1.85 g, 100%). MS found: $(M-Bu)=189$.

(1f) A solution of methyl-(4-bromomethyl)benzoate (1.0 g, 4.4 mmol) in dimethylsulfoxide (DMSO) (43 mL) was treated with 2-(methylthio)-benzimidazole (0.7 g, 1 eq) and $Cs_2CO_3$ (2.1 g, 1.5 eq) and stirred for 2 h at rt. The mixture was then partitioned between water and ethyl acetate (40 mL each) and the aqueous layer was further extracted with ethyl acetate (40 mL) and the combined organic layers washed with brine (40 mL), dried ($Na_2SO_4$), filtered and concentrated. Flash Chromatography ($SiO_2$, MeOH/dichloromethane, 1:40 v/v) provided the desired ester (0.8 g, 62%) as a white sold. MS found: $(M+H)^+=313$.

(1g) The ester (0.8 g, 2.7 mmol) from reaction (1f) in MeOH (6 mL) was treated with 1N NaOH (3 mL) and stirred at reflux for 3 h. The reaction was cooled to 0° C. and acidified with HCl (conc). The white solid was filtered and washed with water and ether and dried on vacuum (0.7 g, 72%). MS found: $(M+H)^+=299$.

(1h) The amine from reaction (1e) (37 mg, 0.15 mmol) and the acid from reaction (1 g) (62 mg, 1.1 eq) in DMF (1.5 mL) was treated with BOP reagent (81 mg, 1.2 eq) and diisopropylethylamine (DIEA) (90 mg, 2.5 eq) and stirred overnight. The reaction was quenched with ice and saturated aqueous ammonium chloride ($NH_4Cl$) and extracted with ethyl acetate (2×10 mL), washed with brine, dried ($Na_2SO_4$), filtered and concentrated. Flash chromatography (ethyl acetate/hexane 3:1, v/v) furnished the desired ester (79 mg, 99%). MS found: $(M+H)^+=525$.

(1i) Preparation of hydroxylamine/sodium methoxide solution: hydroxylamine hydrochloride (2.4 g, 34.5 mmol) and MeOH (9 mL) were heated to 55° C. Sodium methoxide (25% wt in MeOH, 11.85 mL, 1.5 eq) was added, the mixture stirred at 55° C. for 5 min and cooled to rt then 0° C. Filtration afforded a clear solution assumed to be ca. 1.64 M. The solution is prepared and used fresh.

A solution of 1.64 M hydroxylamine solution (1.8 mL, 20 eq) was added to the ester from reaction (1 h) (78 mg, 0.15 mmol) then stirred for 0.5 h. The mixture was adjusted to pH 7 with 1 N hydrochloric acid (1.8 mL). Reverse phase HPLC purification (gradient elution, water/acetonitrile 85-15 to 60–40, 0.1% TFA) provided the hydroxamic acid (37 mg, 33%). MS found: $(M+H)^+=526$.

Example 2

(3S,4S)-N-hydroxy-4-[(4-{[2-(methylthio)-1H-benzimidazol-1-yl]methyl}benzoyl)amino]-3-pyrrolidinecarboxamide (2a) A solution of dichloromethane/trifluoroacetic acid (TFA) (1 mL, 1:1, v/v) was added to the hydroxamic acid from reaction (1i) (22 mg, 0.03 mmol) and stirred for 0.5 h. The solution was concentrated and freeze dried from water to give the desired amine salt (29 mg, 100%). MS found: $(M+H)^+=426$.

Example 3

(3S,4S)-N-hydroxy-1-(methylsulfonyl)-4-[(4-{[2-(methylthio)-1H-benzimidazol-1-yl]methyl}benzoyl)amino]-3-pyrrolidinecarboxamide (3a) The ester (2.5 g, 4.7 mmol) from reaction (1 h) was treated with a solution of TFA/dichloromethane (1:1, v/v, 20 mL) and stirred at rt for 10 min. The solvent was evaporated under reduced pressure and the mixture partitioned between ethyl acetate and 1N NaOH. The aqueous layer was extracted further with ethyl acetate (6×50 mL) and then dried and concentrated to give the desired amine (1.5 g, 50%). MS found: $(M+H)^+=425$.

(3b) The amine from reaction (3a) (100 mg, 0.15 mmol) in dichloromethane (1.5 mL) was treated with triethylamine (93 mg, 6 eq) and methanesulfonyl chloride (53 mg, 3 eq) and stirred at rt for 2 h. The reaction was quenched with ice and water and extracted with dichloromethane (2×10 mL), washed with brine (5 mL), dried ($Na_2SO_4$), filtered and concentrated. Flash chromatography (ethyl acetate) furnished the desired sulfonamide (79 mg, 99%). MS found: $(M+H)^+=525$.

(3c) Using analogous procedures to reaction (1i) the product from reaction (3b) (62 mg, 0.12 mmol) was converted to the desired hydroxamate (61 mg, 80%). MS found: $(M+H)^+=504$.

Example 4

(3S,4S)-N-hydroxy-4-[(4-{[2-(methylthio)-1H-benzimidazol-1-yl]methyl}benzoyl)amino]-1-(2-propynyl)-3-pyrrolidinecarboxamide (4a) The amine from reaction (3a) (100 mg, 0.15 mmol), in chloroform at 0° C. was treated with triethylamine (47 mg, 3 eq) and propargyl bromide (80% wt. in toluene, 68 mg, 3 eq) and stirred at rt for 1 h. The mixture was quenched with ice/water and extracted with ethyl acetate (2×10 mL), washed with brine (5 mL), dried (Na$_2$SO$_4$), filtered and concentrated. Flash chromatography (ethyl acetate) furnished the desired amine (40 mg, 56%). MS found: (M+H)$^+$=463.

(4b) Using analogous procedures to reaction (3c), the product from reaction (4a) (79 mg, 0.17 mmol) was converted to the desired hydroxamic acid (36 mg, 31%). MS found: (M+H)$^+$=464.

Example 5

(3S,4S)-N-hydroxy-1-methyl-4-[(4-{[2-(methylthio)-1H-benzimidazol-1-yl]methyl}benzoyl)amino]-3-pyrrolidinecarboxamide (5a) The amine from reaction (3a) (149 mg, 0.23 mmol) in dichloromethane (2.3 mL) was treated with formaldehyde (37% aqueous solution, 37 mg, 2 eq), NaBH(OAc)$_3$ (96 mg, 2 eq) and diisopropylethylamine (91 mg, 4 eq) and stirred at rt for 2 h. The reaction was quenched with ice/H$_2$O and basified with saturated aqueous NaHCO$_3$. The mixture was extracted with dichloromethane (2×10 mL) and washed with brine (5 mL), dried (Na$_2$SO$_4$), filtered and concentrated. Flash chromatography (dichloromethane/MeOH, 9:1, v/v) furnished the desired tertiary amine (80 mg, 80%). MS found: (M+H)$^+$=439.

(5b) Using analogous procedures to reaction (3c), the product from reaction (5a) (79 mg, 0.17 mmol) was converted to the desired hydroxamic acid (35 mg, 29%). MS found: (M+H)$^+$=440.

Example 6

(3S,4S)-N-hydroxy-1-isopropyl-4-[(4-{[2-(methylthio)-1H-benzimidazol-1-yl]methyl}benzoyl)amino]-3-pyrrolidinecarboxamide (6a) Using procedures analogous to (5a) and (3c), the amine from reaction (3a) (140 mg, 0.21 mmol) and acetone (17 mg, 1.5 eq) were converted to the desired hydroxamic acid (38 mg, 18% yield, 2 steps). MS found: (M+H)$^+$=468.

Example 7

(3S,4S)-1-acetyl-N-hydroxy-4-[(4-{[2-(methylthio)-1H-benzimidazol-1-yl]methyl}benzoyl)amino]-3-pyrrolidinecarboxamide (7a) Using procedures analogous to (3b) and (3c), the amine from reaction (3a) (100 mg, 0.15 mmol) and acetyl chloride (24 mg, 1.5 eq) were converted to the desired amide then hydroxamic acid (62 mg, 70% yield, 2 steps). MS found: (M+H)$^+$=468.

Example 8

(3S,4S)-N-hydroxy-4-[(4-{[2-(methylthio)-1H-benzimidazol-1-yl]methyl}benzoyl)amino]-1-(propylsulfonyl)-3-pyrrolidinecarboxamide (8a) Using procedures analogous to (3b) and (3c), the amine from reaction (3a) (110 mg, 0.15 mmol) and n-propylsulfonyl chloride (26 mg, 1.2 eq) were converted to the desired sulfonamide then hydroxamic acid (44 mg, 59% yield, 2 steps). MS found: (M+H)$^+$=532.

Example 9

(3S,4S)-N-hydroxy-1-(isopropylsulfonyl)-4-[(4-{[2-(methylthio)-1H-benzimidazol-1-yl]methyl}benzoyl)amino]-3-pyrrolidinecarboxamide (9a) Using procedures analogous to (3b) and (3c), the amine from reaction (3a) (90 mg, 0.15 mmol) and isopropylsulfonyl chloride (26 mg, 1.2 eq) were converted to the desired sulfonamide then hydroxamic acid (45 mg, 47% yield, 2 steps). MS found: (M+H)$^+$=532.

Example 10 tert-butyl (3S,4S)-3-[(hydroxyamino)carbonyl]-4-({4-[(2-methyl-1H-benzimidazol-1-yl)methyl]benzoyl}amino)-1-pyrrolidinecarboxylate (10a) Using procedures analogous to (1f)-(1 h), 2-methylbenzimidazole was converted to the desired carbamate (199 mg, 19% yield, 3 steps). MS Found: (M–H)$^-$=492.

(10b) Using analogous procedures to (1i), the carbamate from reaction (10a) (175 mg, 0.35 mmol) was converted to the desired hydroxamic acid (82 mg, 47%). MS found: (M+H)$^+$=494.

Example 11

(3S,4S)-N-hydroxy-4-({4-[(2-methyl-1H-benzimidazol-1-yl)methyl]benzoyl}amino)-3-pyrrolidinecarboxamide (11a) Using procedures analogous to (2a) the product from (10b), (25 mg, 0.04 mmol) was converted to the desired amine (27 mg, 100%). MS found: (M+H)$^+$=394.

Example 12

(3S,4S)-N-hydroxy-4-({4-[(2-methyl-1H-benzimidazol-1-yl)methyl]benzoyl}amino)-1-(2-propynyl)-3-pyrrolidinecarboxamide (12a) Using procedures analogous to (3a), the carbamate from reaction (10a) (1.23 g, 2.5 mmol) was converted to the desired amine bis-TFA salt (1.48 g, 95%). MS found: (M+H)$^+$=393.

(12b) Using procedures analogous to (4a)-(4b) the amine from reaction (12a) was converted to the desired hydroxamic acid (14 mg, 34%). MS found: (M+H)$^+$=432.

Example 13

(3S,4S)-1-(2-butynyl)-N-hydroxy-4-({4-[(2-methyl-1H-benzimidazol-1-yl)methyl]benzoyl}amino)-3-pyrrolidinecarboxamide (13a) Using procedures analogous to (4a)-(4b), the amine from reaction (12a) (100 mg, 0.16 mmol) and 1-bromo-2-butyne (2.4 eq) were converted to the desired hydroxamic acid (11 mg, 5% yield, 2 steps). MS found: (M+H)$^+$=446.

Example 14

(3S,4S)-1-(3-butenyl)-N-hydroxy-4-({4-[(2-methyl-1H-benzimidazol-1-yl)methyl]benzoyl}amino)-3-pyrrolidinecarboxamide (14a) Using procedures analogous to (13a), the amine from reaction (12a) (100 mg, 0.16 mmol) and 4-bromo-1- butene (2.4 eq) was converted to the desired hyroxamate (25 mg, 23% yield, 2 steps). MS found: (M+H)$^+$=449.

Example 15

N-{(1R,2S)-2-[(hydroxyamino)carbonyl]cyclopentyl}-4-[(2-methyl-1H-benzimidazol-1-yl)methyl]benzamide (15a) Using procedures analogous to (10a) and (1 h)-(1i), methyl (1S,2R)-2-aminocyclopentane-1-carboxylate hydrochloride (for a procedure of the synthesis see: Davies, S. G. et al. *Synlett*, 1993, 461) (56 mg, 0.3 mmol) was converted the desired hydroxamic acid (55 mg, 35% yield, 2 steps). MS found: (M+H)$^+$=393.

Example 16

(3S,4S)-N-hydroxy-1-isopropyl-4-({4-[(2-methyl-1H-benzimidazol-1-yl)methyl]benzoyl}amino)-3-pyrrolidinecarboxamide (16a) Using analogous procedures to (6a), the amine from reaction (12a) (89 mg, 0.14 mmol) was converted to the desired hydroxamic acid (42 mg, 44% yield, 2 Steps). MS found: (M+H)$^+$=436.

Example 17

(3S,4S)-N-hydroxy-4-({4-[(2-methyl-1H-benzimidazol-1-yl)methyl]benzoyl}amino)-1-neopentyl-3-pyrrolidinecarboxamide (17a) Using analogous procedures to (6a), the amine from reaction (12a) (100 mg, 0.16 mmol) and trimethylacetaldehyde (1.5 eq) were converted to the desired hydroxamic acid (42 mg, 38% yield, 2 Steps). MS found: (M+H)$^+$=464.

Example 18 tert-butyl (3S,4S)-3-[(hydroxyamino)carbonyl]-4-({4-[(2-isopropyl-1H-benzimidazol-1-yl)methyl]benzoyl}amino)-1-pyrrolidinecarboxylate (18a) Using procedures analogous to (1f)-(1 h), 2-isopropylbenzimidazole was converted to the desired carbamate (146 mg, 25% yield, 3 steps). MS found: (M+H)$^+$=521.

(18b) Using analogous procedures to (1i), the carbamate from reaction (18a) (135 mg, 0.26 mmol) was converted to the desired hydroxamic acid (81 mg, 60%). MS found: (M+H)$^+$=522.

Example 19

(3S,4S)-N-hydroxy-4-({4-[(2-isopropyl-1H-benzimidazol-1-yl)methyl]benzoyl}amino)-3-pyrrolidinecarboxamide (19a) Using procedures analogous to (2a), the product from (18b) (26 mg, 0.04 mmol) was converted to the desired amine (8 mg, 30%). MS found: (M+H)$^+$=422.

Example 20

(3S,4S)-N-hydroxy-4-({4-[(2-isopropyl-1H-benzimidazol-1-yl)methyl]benzoyl}amino)-1-methyl-3-pyrrolidinecarboxamide (20a) Using procedures analogous to (3a), the carbamate from reaction (18a) (1.57 g, 3.02 mmol) was converted to the desired amine (1.27 g, 100%). MS found: (M+H)$^+$=421.

(20b) Using procedures analogous to (5a)-(5b), the amine from reaction (20a) (100 mg, 0.24 mmol) was converted to the desired hydroxamic acid (43 mg, 26% yield, 2 steps). MS found: (M+H)$^+$=436.

Example 21

(3S,4S)-N-hydroxy-4-({4-[(2-isopropyl-1H-benzimidazol-1-yl)methyl]benzoyl}amino)-1-propyl-3-pyrrolidinecarboxamide (21a) Using procedures analogous to (5a)-(5b), the amine from reaction (20a) (100 mg, 0.24 mmol) and propionaldehyde (1.5 eq) were converted to the desired hydroxamic acid (14 mg, 8% yield, 2 steps). MS found: (M+H)$^+$=464.

Example 22

(3S,4S)-N-hydroxy-1-isopropyl-4-({4-[(2-isopropyl-1H-benzimidazol-1-yl)methyl]benzoyl}amino)-3-pyrrolidinecarboxamide (22a) Using procedures analogous to (6a), the amine from reaction (20a) (100 mg, 0.24 mmol) was converted to the desired hydroxamic acid (51 mg, 31% yield, 2 steps). MS found: (M+H)$^+$=464.

Example 23

(3S,4S)-N-hydroxy-4-({4-[(2-isopropyl-1H-benzimidazol-1-yl)methyl]benzoyl}amino)-1-(2-propynyl)-3-pyrrolidinecarboxamide (23a) Using procedures analogous to (4a)-(4b), the amine from reaction (20a) (73 mg, 0.17 mmol) was converted to the desired hydroxamic acid (30 mg, 23% yield, 2 steps). MS found: (M+H)$^+$=460.

Example 24

(3S,4S)-1-(3-butenyl)-N-hydroxy-4-({4-[(2-isopropyl-1H-benzimidazol-1-yl)methyl]benzoyl}amino)-3-pyrrolidinecarboxamide (24a) Using procedures analogous to (14a), the amine from reaction (20a) (62 mg, 0.15 mmol) was converted to the desired hydroxamic acid (28 mg, 26% yield, 2 steps). MS found: (M+H)$^+$=476.

Example 25

(3S,4S)-1-(2-butynyl)-N-hydroxy-4-({4-[(2-isopropyl-1H-benzimidazol-1-yl)methyl]benzoyl}amino)-3-pyrrolidinecarboxamide (25a) Using procedures analogous to (13a), the amine from reaction (20a) (93 mg, 0.22 mmol) was converted to the desired hydroxamic acid (39 mg, 29% yield, 2 steps). MS found: (M+H)$^+$=475.

Example 26

(3S,4S)-N-hydroxy-4-({4-[(2-isopropyl-1H-benzimidazol-1-yl)methyl]benzoyl}amino)-1-(propylsulfonyl)-3-pyrrolidinecarboxamide (26a) Using procedures analogous to (8a), the amine from reaction (20a) (100 mg, 0.24 mmol) was converted to the desired hydroxamic acid (55 mg, 37% yield, 2 steps). MS found: (M+H)$^+$=527.

Example 27

(3S,4S)-1-(butylsulfonyl)-N-hydroxy-4-({4-[(2-isopropyl-1H-benzimidazol-1-yl)methyl]benzoyl}amino)-3-pyrrolidinecarboxamide (27a) Using procedures analogous to (8a), the amine from reaction (20a) (100 mg, 0.24 mmol) and butylsulfonyl chloride (1 eq) converted to the desired hydroxamic acid (40 mg, 26% yield, 2 steps). MS found: $(M+H)^+=542$.

Example 28

(3S,4S)-N-hydroxy-4-({4-[(2-isopropyl-1H-benzimidazol-1-yl)methyl]benzoyl}amino)-1-(isopropylsulfonyl)-3-pyrrolidinecarboxamide (28a) Using procedures analogous to (9a), the amine from reaction (20a) (100 mg, 0.24 mmol) was converted to the desired hydroxamic acid (39 mg, 26% yield, 2 steps). MS found: $(M+H)^+=527$.

Example 29

N-{(1R,2S)-2-[(hydroxyamino)carbonyl]cyclopentyl}-4-[(2-isopropyl-1H-benzimidazol-1-yl)methyl]benzamide (29a) Using procedures analogous to (1 h)-(1i), methyl (1S,2R)-2-aminocyclopentane-1-carboxylate hydrochloride (43 mg, 0.24 mmol) and 4-[(2-isopropyl-1H-benzimidazol-1-yl)methyl]benzoic acid (1 eq) were converted to the desired hydroxamic acid (77 mg, 77% yield, 2 steps). MS found: $(M+H)^+=421$.

Example 30

(3S,4S)-N-hydroxy-1-isobutyl-4-({4-[(2-isopropyl-1H-benzimidazol-1-yl)methyl]benzoyl}amino)-3-pyrrolidinecarboxamide (30a) Using procedures analogous to (17a), the amine from reaction (20a) (73 mg, 0.17 mmol) and isobutyraldehyde (1.5 eq) were converted to the desired hydroxamic acid (17 mg, 15% yield, 2 steps). MS found: $(M+H)^+=478$.

Example 31

(3S,4S)-N-hydroxy-4-({4-[(2-isopropyl-1H-benzimidazol-1-yl)methyl]benzoyl}amino)-1-neopentyl-3-pyrrolidinecarboxamide (31a) Using procedures analogous to (17a), the amine from reaction (20a) (73 mg, 0.17 mmol) was converted to the desired hydroxamic acid (16 mg, 15% yield, 2 steps). MS found: $(M+H)^+=492$.

Example 32 tert-butyl (3S,4S)-3-[(hydroxyamino)carbonyl]-4-[(4-{[2-(trifluoromethyl)-1H-benzimidazol-1-yl]methyl}benzoyl)amino]-1-pyrrolidinecarboxylate (32a) Using procedures analogous to (1f)-(1 h), 2-trifluoromethylbenzimidazole was converted to the desired carbamate (104 mg, 93% yield, 3 steps). MS found: $(M+H)^+=547$.

(32b) Using analogous procedures to (1i), the carbamate from reaction (32a) (103 mg, 0.19 mmol) was converted to the desired hydroxamic acid (83 mg, 66%). MS found: $(M+H)^+=548$.

Example 33

(3S,4S)-N-hydroxy-4-[(4-{[2-(trifluoromethyl)-1H-benzimidazol-1-yl]methyl}benzoyl)amino]-3-pyrrolidinecarboxamide (33a) Using procedures analogous to (2a), the product from (32b) (52 mg, 0.09 mmol) was converted to the desired amine (56 mg, 93%). MS found: $(M+H)^+=448$.

Example 34

(3S,4S)-N-hydroxy-1-isopropyl-4-[(4-{[2-(trifluoromethyl)-1H-benzimidazol-1-yl]methyl}benzoyl)amino]-3-pyrrolidinecarboxamide (34a) Using procedures analogous to (5a), the carbamate from reaction (32a) (2.4 g, 4.4 mmol) was converted to the desired amine salt (3.0 g, 100%). MS found: $(M+H)^+=446$.

(34b) Using procedures analogous to (6a), the amine from reaction (34a) (150 mg, 0.22 mmol) was converted to the desired hydroxamate (15 mg, 15% yield, 2 steps). MS found: $(M+H)^+=489$.

Example 35

(3S,4S)-N-hydroxy-1-(2-propynyl)-4-[(4-{[2-(trifluoromethyl)-1H-benzimidazol-1-yl]methyl}benzoyl)amino]-3-pyrrolidinecarboxamide (35a) Using procedures analogous to (4a)-(4b), the amine from reaction (34a) (150 mg, 0.22 mmol) was converted to the desired hydroxamate (18 mg, 12% yield, 2 steps). MS found: $(M+H)^+=486$.

Example 36

(3S,4S)-1-(2-butynyl)-N-hydroxy-4-[(4-{[2-(trifluoromethyl)-1H-benzimidazol-1-yl]methyl}benzoyl)amino]-3-pyrrolidinecarboxamide (36a) Using procedures analogous to (13a), the amine from reaction (34a) (150 mg, 0.22 mmol) was converted to the desired hydroxamate (13 mg, 10% yield, 2 steps). MS found: $(M+H)^+=500$.

Example 37

(3S,4S)-1-(3-butenyl)-N-hydroxy-4-[(4-{[2-(trifluoromethyl)-1H-benzimidazol-1-yl]methyl}benzoyl)amino]-3-pyrrolidinecarboxamide (37a) Using procedures analogous to (14a), the amine from reaction (34a) (150 mg, 0.22 mmol) was converted to the desired hydroxamate (9 mg, 6% yield, 2 steps). MS Found $(M+H)^+=502$.

Example 39

(3R,4R)-N-hydroxy-4-({4-[(2-isopropyl-1H-benzimidazol-1-yl)methyl]benzoyl}amino)tetrahydro-2H-pyran-3-carboxamide (39a) LiHMDS (1.0 M in THF, 52.5 mL, 1.05 eq) was added dropwise to a solution of tetrahydro-4H-pyran-4-one (5.0 g, 50 mmol) in THF (200 mL) at −78° C. The resulting solution was stirred at −20° C. for 1 h, then cooled back to −78° C. To this mixture was added methyl cyanoformate (4.75 mL, 1.2 eq) dropwise. Ten min after completion of the addition, the reaction was quenched with aqueous NH₄Cl and extracted with ether (200 mL). The organic layer was washed with brine (100 mL), dried (MgSO₄), and concentrated. Silica gel column chromatography (ether-hexane, 1:4, 2:3, then 3:2) yielded an oil containing both ketone and enol forms of the product (5.4 g, ca. 30% purity). MS found: $(M+H)^+=159.1$.

(39b) The ester from (39a) was dissolved in benzene (200 mL) and treated with (R)-α-methylbenzylamine (3 mL) and ytterbium(III) trifluoromethanesulfonate (200 mg). The mixture was heated to reflux under Dean-Stark conditions for 2 h, concentrated, and purified by silica gel column chromatography (ethyl acatete-hexane, 1:4) to yield the desired enamine as a white solid (3.6 g, 27.5% yield, 2 steps).

(39c) The enamine from (39b) (3.5 g, 13.4 mmol) in acetonitrile-acetic acid (1:1, 80 mL) was treated with NaBH(OAc)$_3$ and stirred for 2 h at 0° C. Following concentration in vacuo, the residue was dissolved in ether (200 mL), washed with saturated NaHCO$_3$ until the aqueous phase was basic, dried (MgSO$_4$), and concentrated to yield an oil (3.39 g, 96%). MS found: (M+H)$^+$=264.3.

(39d) The intermediate from (39c) (1.86 g, 7.06 mmol) in methanol (100 mL) was treated with 10% palladium hydroxide on carbon (0.6 g, 3.5% mol) and aqueous 1N hydrochloric acid (10 mL, 1.4 eq) and stirred under a H$_2$-balloon for 72 h. The catalyst was removed by filtration. Removal of solvent provided the desired amine as hydrochloric acid salt (1.42 g, 100%, 80%ee). MS found: (M+H)$^+$=160.3.

(39e) Using procedures analogous to (1 h)-(1i), the amine from reaction (39d) (15 mg, 0.07 mmol) and 4-[(2-isopropyl-1H-benzimidazol-1-yl)methyl]benzoic acid (26 mg, 1.2 eq) were converted to the desired hydroxamic acid (16 mg, 52% yield, 2 steps). MS found: (M+H)$^+$=437.

Alternatively, the product of (39e) can be prepared by the following steps (39f)-(39(h).

(39f) Using procedures analogous to (39a–39d), ethyl cyanoformate was converted to the desired ethyl (3R,4R)-4-aminotetrahydro-2H-pyran-3-carboxylate (40%, 4 steps, 60%ee). MS Found (M+H)$^+$=174.

(39g) Using analogous procedures to (1 h) the amine from (39f) (247 mg, 0.86 mmol) and 4-[(2-isopropyl-1H-benzimidazol-1-yl)methyl]benzoic acid (278 mg, 1.1 eq) were converted to the desired ester (207 mg, 54%). The enantiomers were separated using a Chiracel OJ 2 inch column using 20% EtOH/hexane with a flowrate of 45 mL/min and wavelength=254 nm. The (3R,4R) enantiomer was isolated (82 mg, 41%). MS found: (M+H)$^+$=450.

(39 h) Using procedures analogous to (1i) the ester from (39 g) (82 mg, 0.18 mmol) was converted to the desired hydroxamic acid (65 mg, 66%). MS found: (M+H)$^+$=437.

Example 40

(3R,4R)-N-hydroxy-4-[(4-{[2-(trifluoromethyl)-1H-benzimidazol-1-yl]methyl}benzoyl)amino]tetrahydro-2H-pyran-3-carboxamide (40a) Using procedures analogous to (1 h)-(1i), the amine from reaction (39d) (13 mg, 0.07 mmol) and 4-{[2-(trifluoromethyl)-1H-benzimidazol-1-yl]methyl}benzoic acid (26 mg, 1.2 eq) were converted to the desired hydroxamic acid (8 mg, 25% yield, 2 steps). MS found: (M+H)$^+$=463.

Alternatively, the product of (40a) can be prepared by the following steps (40b)-(40c).

(40b) Using analogous procedures to (1 h) the amine from (39f) (180 mg, 0.63 mmol) and the acid from (32b) (221 mg, 1.1 eq) were converted to the desired ester (200 mg, 69%). The enantiomers were separated using a Chiracel OJ 2 inch column using 20% EtOH/hexane with a flowrate of 45 mL/min and wavelength=254 nm. The (3R,4R) enantiomer was isolated (87 mg, 69%). MS found: (M+H)$^+$=476.

(40c) Using procedures analogous to (1i) the ester from (40b) (87 mg, 0.18 mmol) was converted to the desired hydroxamic acid (60 mg, 82%). MS found: (M+H)$^+$=463.

Alternatively, the product of (40a) can be prepared by the following steps (40d)-(40f).

(40d) the enamine from (39b) (20.0 g, 76.5 mmol) in methanol-tetrahydrofuran (3:2, 80 mL) was hydrogenated in the presence of PtO$_2$ (210 mg) under pressure (17.5 bar) for 16 h at 40° C. After cooling to ambient temperature and purging with nitrogen gas, the catalyst was removed by filtration. The filtrate was co-evaporated with ethyl acetate (3×150 mL) and concentrated in vacuo. The residue was dissolved in isopropyl acetate (120 mL) and 30% HBr in acetic acid (12.5 mL) was added between 10 and 15° C., followed by n-heptane (72 mL). Solids were filtered and washed with isopropyl acetate (100 mL). Drying in vacuo provided a white, crystalline solid (17.9 g, 68%, 94.8% ee). MS found: (M+H)$^+$=264.

(40e) The intermediate from (40d) (15.3 g, 44.4 mmol) in methanol (100 mL) was hydrogenated in the presence of 10% palladium on carbon (50% wet, 2.8 g, 3.0% mol) under pressure (7.0 bar) for 16 h at 40° C. The catalyst was removed by filtration and the filtrate was concentrated to an oil. The oily residue was co-evaporated with isopropyl acetate (2×50 mL) to give a solid (10.7 g, 99%). MS found: (M+H)$^+$=160.

(40f) Using procedures analogous to (1 h)-(1i), the amine salt from reaction (40e) (7.14 g, 29.7 mmol) and 4-{[2-(trifluoromethyl)-1H-benzimidazol-1-yl]methyl}benzoic acid (10.0 g, 1.05 eq) were converted to the desired hydroxamic acid (4.8 g, 84% yield, 2 steps). MS found: (M+H)$^+$=463.

Example 42

(3S,4S)-N-hydroxy-1-(propylsulfonyl)-4-[(4-{[2-(trifluoromethyl)-1H-benzimidazol-1-yl]methyl}benzoyl)amino]-3-pyrrolidinecarboxamide (42a) Using procedures analogous to (8a), the amine from reaction (34a) (100 mg, 0.18 mmol) was converted to the desired hydroxamic acid (19 mg, 19% yield, 2 steps). MS found: (M+H)$^+$=554.

Example 43

(3S,4S)-N-hydroxy-1-(isopropylsulfonyl)-4-[(4-{[2-(trifluoromethyl)-1H-benzimidazol-1-yl]methyl}benzoyl)amino]-3-pyrrolidinecarboxamide (43a) Using procedures analogous to (9a), the amine from reaction (34a) (100 mg, 0.18 mmol) was converted to the desired hydroxamic acid (37 mg, 37% yield, 2 steps). MS found: (M+H)$^+$=554.

Example 44

(3S,4S)-1-(butylsulfonyl)-N-hydroxy-4-[(4-{[2-(trifluoromethyl)-1H-benzimidazol-1-yl]methyl}benzoyl)amino]-3-pyrrolidinecarboxamide (44a) Using procedures analogous to (9a), the amine from reaction (34a) (100 mg, 0.18 mmol) and n-butylsulfonyl chloride (1.5 eq) were converted to the desired sulfonamide then hydroxamic acid (28 mg, 28% yield, 2 steps). MS found: (M+H)$^+$=567.

Example 45

(3S,4S)-1-acetyl-N-hydroxy-4-[(4-{[2-(trifluoromethyl)-1H-benzimidazol-1-yl]methyl}benzoyl)amino]-3-pyrrolidinecarboxamide (45a) Using procedures analogous to (7a), the amine from reaction (34a) (100 mg, 0.18 mmol) was converted to the desired hydroxamic acid (19 mg, 41% yield, 2 steps). MS found: (M+H)⁺=490.

Example 46

(3S,4S)-N-hydroxy-1-(4-pentenoyl)-4-[(4-{[2-(trifluoromethyl)-1H-benzimidazol-1-yl]methyl}benzoyl)amino]-3-pyrrolidinecarboxamide (46a) Using procedures analogous to (7a), the amine from reaction (34a) (100 mg, 0.18 mmol) and 4-pentenoyl chloride (1.5 eq) were converted to the desired amide then hydroxamic acid (35 mg, 37% yield, 2 steps). MS found: (M)⁺=529.

Example 47

(3S,4S)-N-hydroxy-1-isobutyl-4-[(4-{[2-(trifluoromethyl)-1H-benzimidazol-1-yl]methyl}benzoyl)amino]-3-pyrrolidinecarboxamide (47a) Using procedures analogous to (30a), the amine from reaction (34a) (100 mg, 0.18 mmol) was converted to the desired hydroxamic acid (31 mg, 40% yield, 2 steps). MS found: (M+H)⁺=504.

Example 48

(3S,4S)-N-hydroxy-1-neopentyl-4-[(4-{[2-(trifluoromethyl)-1H-benzimidazol-1-yl]methyl}benzoyl)amino]-3-pyrrolidinecarboxamide (48a) Using procedures analogous to (17a), the amine from reaction (34a) (100 mg, 0.18 mmol) was converted to the desired hydroxamic acid (22 mg, 19% yield, 2 steps). MS found: (M+H)⁺=518.

Example 49 cis-N-{-2-[(hydroxyamino)carbonyl]cyclopentyl}-4-{[2-(trifluoromethyl)-1H-benzimidazol-1-yl]methyl}benzamide (49a) Using analogous procedures to (1 h)-(1i), cis-ethyl-2-amino-1-cyclopentanecarboxylate hydrochloride (48 mg, 24 mmol) and 4-{[2-(trifluoromethyl)-1H-benzimidazol-1-yl]methyl}benzoic acid (72 mg, 22 mmol) were converted to the desired hydroxamic acid (72 mg, 71% yield, 2 steps). MS found: (M)⁺=446.

Example 50

(3R,4S)-N-hydroxy-4-[(4-{[2-(trifluoromethyl)-1H-benzimidazol-1-yl]methyl}benzoyl)amino] tetrahydro-3-furancarboxamide (50a) Sodium hydride (60% dispersion in mineral oil) (5.28 g, 1.1 eq) in ether (120 mL) was treated with methyl glycolate (10.8 g, 120 mmol) dropwise, slowly. The mixture was stirred for 30 min and cooled to 0° C. Methyl acrylate (12.39 g, 1.2 eq) was added dropwise to the 0° C. solution. The mixture was stirred for 15 min, warmed to rt and stirred for 1 h. The reaction was cooled to 0° C. and quenched by addition of 5% aqueous H₂SO₄ (200 mL). The layers were separated and the aqueous layer extracted with ether (2×250 mL). The combined ether layers were washed with brine (150 mL), dried with MgSO₄, filtered and concentrated. Flash chromatography (ethyl acetate/hexanes, 75:25) provided the desired keto-ester (9.9 g, 57%).

(50b) The keto-ester (3.3 g, 23.0 mmol) from reaction (46a) in benzene (100 mL) was treated with (R)-α-methylbenzyl amine (3.0 mL, 1.02 eq) and ytterbium(III) triflate (0.29 g, 0.02 eq) and heated to reflux using Dean-Stark conditions for 3 h, then treated with more (R)-alpha-methylbenzyl amine (0.5 mL) and heated 1 h further. The solution was cooled to rt and washed with water (50 mL), dried with MgSO₄, filtered and concentrated. Flash chromatography (ethyl acetate/hexanes, 40:60) provided the desired enamine (2.7 g, 48%). MS found: (M+H)⁺=248.

(50c) The enamine (3.43 g, 13.9 mmol) from reaction (46b) in acetic acid/dichloromethane/acetonitrile (1:1:1, 42 mL) was treated with NaBH(OAc)₃ and stirred for 5 h. The reaction was cooled to 0° C. and neutralized with saturated aqueous NaHCO₃ and extracted with dichloromethane (3×100 mL), dried (MgSO₄), filtered and concentrated. Flash chromatography (ethyl acetate/hexanes, 30:70) provided the desired amine (1.01 g, 29%) as a 3:1 mixture of diastereomers. MS found: (M+H)⁺=250.

(50d) A mixture of the amine (838 mg, 3.38 mmol) from reaction (46c), 20% palladium hydroxide on carbon (240 mg, 0.1 eq) in methanol was shaken on a Parr apparatus under 50 psi of hydrogen for 2 h. The mixture was filtered and concentrated to provide the desired amine (495 mg, 100%, 40%ee). MS found: (M+H)⁺=146.

(50e) Using analogous procedures to (1 h)-(1i), the amine from (50d) (59 mg, 0.4 mmol) and 4-{[2-(trifluoromethyl)-1H-benzimidazol-1-yl]methyl}benzoic acid (1.1 eq) were converted to the desired hydroxamic acid (62 mg, 34% yield, 2 steps). MS found: (M)⁺=449.

Alternatively, the product of (50e) can be prepared by the following steps (50f)-(50 g).

(50f) using analogous procedures to (1 h) the amine from (50d) (242 mg, 1.33 mmol) and the acid from (32b) (427 mg, 1 eq) were converted to the desired ester (416 mg, 70%). The enantiomers were separated using a Chiracel OJ 2 inch column using 35% EtOH/hexane with a flowrate of 45 mL/min and wavelength=254 nm. The (3R,4S) enantiomer was isolated (274 mg, 69%). MS found: (M+H)⁺=448.

(50g) Using procedures analogous to (1i) the ester from (50f) (260 mg, 0.58 mmol) was converted to the desired hydroxamic acid (212 mg, 82%). MS found: (M+H)⁺=449.

Example 51 tert-butyl (3S,4S)-3-[(hydroxyamino)carbonyl]-4-({4-[(2-phenyl-1H-benzimidazol-1-yl)methyl]benzoyl}amino)-1-pyrrolidinecarboxylate (51a) Using analogous procedures to (1f)-(1i), 2-phenylbenzimidazole (0.6 g, 2.9 mmol) was converted to the desired hydroxamic acid (101 mg, 74% yield, 4 steps). MS found: (M+H)⁺=556.

Example 52

(3S,4S)-N-hydroxy-4-({4-[(2-phenyl-1H-benzimidazol-1-yl)methyl]benzoyl}amino)-3-pyrrolidinecarboxamide (52a) Using procedures analogous to (2a), the product from reaction (51a) (68 mg, 0.1 mmol) was converted to the desired hydroxamic acid (68 mg, 100%). MS found: (M+H)⁺=456.

Example 53 tert-butyl (3S,4S)-3-({4-[(2-tert-butyl-1H-benzimidazol-1-yl)methyl]benzoyl}amino)-4-[(hydroxyamino)carbonyl]-1-pyrrolidinecarboxylate (53a) Using analogous procedures to (1f)-(1 h), 2-t-butylbenzimidazole (1.2 g, 8 mmol) was converted to the desired carbamate (923 mg, 72% yield, 3 steps). MS found: (M+H)⁺=536.

(53b) Using procedures analogous to (1i), the product from reaction (53a) was converted to the desired hydroxamic acid (86 mg, 48%). MS found: (M+H)$^+$=537.

Example 54

(3S,4S)-4-({4-[(2-tert-butyl-1H-benzimidazol-1-yl)methyl]benzoyl}amino)-N-hydroxy-3-pyrrolidinecarboxamide (54a) Using procedures analogous to (2a), the product from reaction (53b) (34 mg, 0.05 mmol) was converted to the desired hydroxamic acid (32 mg, 95%). MS found: (M+H)$^+$=436.

Example 55

(3S,4S)-4-({4-[(2-tert-butyl-1H-benzimidazol-1-yl)methyl]benzoyl}amino)-N-hydroxy-1-(2-propynyl)-3-pyrrolidinecarboxamide (55a) Using procedures analogous to (3a), the carbamate from reaction (53a) (0.62 g, 1.2 mmol) was converted to the desired amine (345 mg, 69%). MS found: (M+H)$^+$=435.

(55b) Using procedures analogous to (4a) and (1i), the amine from reaction (55a) (52 mg, 0.12 mmol) was converted to the desired hydroxamic acid (75 mg, 89% yield, 2 steps). MS found: (M+H)$^+$=475.

Example 56

(3S,4S)-4-({4-[(2-tert-butyl-1H-benzimidazol-1-yl)methyl]benzoyl}amino)-1-(2-butynyl)-N-hydroxy-3-pyrrolidinecarboxamide (56a) Using procedures analogous to (13a), the amine from reaction (55a) (52 mg, 0.12 mmol) was converted to the desired hydroxamic acid (30 mg, 35% yield, 2 steps). MS found: (M+H)$^+$=489.

Example 57

(3S,4S)-4-({4-[(2-tert-butyl-1H-benzimidazol-1-yl)methyl]benzoyl}amino)-N-hydroxy-1-isopropyl-3-pyrrolidinecarboxamide (57a) Using procedures analogous to (6a), the amine from reaction (55a) (48 mg, 0.11 mmol) was converted to the desired hydroxamic acid (38 mg, 50% yield, 2 steps). MS found: (M+H)$^+$=479.

Example 58 cis-4-[(2-tert-butyl-1H-benzimidazol-1-yl)methyl]-N-{2-[(hydroxyamino)carbonyl]cyclopentyl}benzamide (58a) Using analogous procedures to (1 h)-(1i), cis-ethyl-2-amino-1-cyclopentanecarboxylate hydrochloride (48 mg, 24 mmol) and 4-[(2-tert-butyl-1H-benzimidazol-1-yl)methyl]benzoic acid (69 mg, 22 mmol) were converted to the desired hydroxamic acid (72 mg, 52% yield, 2 steps). MS found: (M)$^+$=435.

Example 59

(3R,4R)-4-({4-[(2-tert-butyl-1H-benzimidazol-1-yl)methyl]benzoyl}amino)-N-hydroxytetrahydro-2H-pyran-3-carboxamide (59a) Using procedures analogous to (58a), the amine from reaction (39f) as the TFA salt (61 mg, 0.24 mmol) was converted to the desired hydroxamic acid-(62 mg, 49%). MS found: (M)$^+$=452.

Example 60

(3R,4S)-4-({4-[(2-tert-butyl-1H-benzimidazol-1-yl)methyl]benzoyl}amino)-N-hydroxytetrahydro-3-furancarboxamide (60a) Using procedures analogous to (58a), the amine from (50d) (58 mg, 0.4 mmol) was converted to the desired hydroxamic acid (60 mg, 27%). MS found: (M)$^+$=437.

Example 61 tert-butyl (3S,4S)-3-[(4-{[2-(difluoromethyl)-1H-benzimidazol-1-yl]methyl}benzoyl)amino]-4-(hydroxyamino)carbonyl]-1-pyrrolidinecarboxylate (61a) Using analogous procedures to (1f)-(15), 2-(difluoromethyl)-benzimidazole (1.68 g, 11 mmol) was converted to the desired carbamate (521 mg, 21% yield, 3 steps). MS found: (M+H)$^+$=529.

(61b) Using procedures analogous to (1i), the product from reaction (53a) (106 mg, 0.2 mmol) was converted to the desired hydroxamic acid (92 mg, 87%). MS found: (M+H)$^+$=530.

Example 62

(3S,4S)-4-[(4-{[2-(difluoromethyl)-1H-benzimidazol-1-yl]methyl}benzoyl)amino]-N-hydroxy-3-pyrrolidinecarboxamide (62a) Using procedures analogous to (2a), the product from reaction (61b) (20 mg, 0.04 mmol) was converted to the desired hydroxamic acid (17 mg, 83%). MS found: (M+H)$^+$=430.

Example 63

(3S,4S)-4-[(4-{[2-(difluoromethyl)-1H-benzimidazol-1-yl]methyl}benzoyl)amino]-N-hydroxy-1-isopropyl-3-pyrrolidinecarboxamide (63a) Using procedures analogous to (3a), the carbamate from reaction (53a) (0.42 g, 0.8 mmol) was converted to the desired amine (298 mg, 88%). MS found: (M+H)$^+$=429.

(63b) Using procedures analogous to (6a), the amine from reaction (63a) (59 mg, 0.14 mmol) was converted to the desired hydroxamic acid (46 mg, 44% yield, 2 steps). MS found: (M+H)$^+$=472.

Example 64

(3S,4S)-4-[(4-{[2-(difluoromethyl)-1H-benzimidazol-1-yl]methyl}benzoyl)amino]-N-hydroxy-1-(2-propynyl)-3-pyrrolidinecarboxamide (64a) Using procedures analogous to (12a), the amine from reaction (63a) (59 mg, 0.14 mmol) was converted to the desired hydroxamic acid (32 mg, 54% yield, 2 steps). MS found: (M+H)$^+$=468.

Example 65

(3S,4S)-4-[(4-{[2-(difluoromethyl)-1H-benzimidazol-1-yl]methyl}benzoyl)amino]-N-hydroxy-1-isobutyl-3-pyrrolidinecarboxamide (65a) Using procedures analogous to (47a), the amine from reaction (63a) (95 mg, 0.22 mmol) was converted to the desired hydroxamic acid (40 mg, 30% yield, 2 steps). MS found: (M+H)$^+$=486.

Example 66

(3S,4S)-4-[(4-{[2-(difluoromethyl)-1H-benzimidazol-1-yl]methyl}benzoyl)amino]-N-hydroxy-1-neopentyl-3-pyrrolidinecarboxamide (66a) Using procedures analogous to (17a), the amine from reaction (63a) (95 mg, 0.22 mmol) was converted to the desired hydroxamic acid (56 mg, 42% yield, 2 steps). MS found: (M+H)$^+$=500.

Example 67

4-{[2-(difluoromethyl)-1H-benzimidazol-1-yl]methyl}-N-cis-2-[(hydroxyamino)carbonyl]cyclopentyl}benzamide (67a) Using analogous procedures to (1 h)-(1i), cis-ethyl-2-amino-1-cyclopentanecarboxylate hydrochloride (44 mg, 23 mmol) and 4-[(2-difluoromethyl-1-benzimidazole)methyl]benzoic acid (68 mg, 23 mmol) were converted to the desired hydroxamic acid (65 mg, 65% yield, 2 steps). MS found: (M)$^+$=443.

Example 68

(3R,4R)-4-[(4-{[2-(difluoromethyl)-1H-benzimidazol-1-yl]methyl}benzoyl)amino]-N-hydroxytetrahydro-2H-pyran-3-carboxamide (68a) Using procedures analogous to (67a), the amine from reaction (39f) as the TFA salt (62 mg, 0.24 mmol) was converted to the desired hydroxamic acid (56 mg, 56%). MS found: (M)$^+$=452.

Example 69

(3R,4S)-4-[(4-{[2-(difluoromethyl)-1H-benzimidazol-1-yl]methyl}benzoyl)amino]-N-hydroxytetrahydro-3-furancarboxamide (69a) Using procedures analogous to (67a), the amine from (50d) (34 mg, 0.23 mmol) was converted to the desired hydroxamic acid (45 mg, 45%). MS found: (M)$^+$=431.

Example 70

4-[(2-cyclopropyl-1H-benzimidazol-1-yl)methyl]-N-{(1R,2S)-2-[(hydroxyamino)carbonyl]cyclopentyl}benzamide (70a) Cyclopropanecarboxylic acid (4 g, 52 mmol) was treated with phenylenediamine bis-hydrochloride (1 eq) and polyphosphoric acid (52 mL) and heated to 160° C. for 6 h. The reaction was cooled to 0° C. and diluted with water, then basified with NaOH (50% aqueous) until pH>10. The solution was extracted with ethyl acetate, dried (MgSO$_4$), filtered and concentrated, purified by flash chromatography (100% ethyl acetate) giving 2-cyclopropylbenzimidazole (1.1 g, 13%). MS found: (M+H)$^+$=159.

(70b) Using procedures analogous (1f)-(1 g), the product from reaction (70a) (0.7 g, 3.0 mmol) was converted to the desired carboxylic acid (375 mg, 43%). MS found: (M+H)$^+$=293.

(70c) Using procedures analogous to (1 h)-(1i), the product from reaction (70b) (56 mg, 0.3 mmol) and methyl (1S,2R)-2-aminocyclopentanecarboxylate hydrochloride (103 mg, 0.34 mmol) were converted to the desired hydroxamic acid (68 mg, 41% yield, 2 steps). MS found: (M+H)$^+$=419.

Example 71

(3R,4R)-4-({4-[(2-cyclopropyl-1H-benzimidazol-1-yl)methyl]benzoyl}amino)-N-hydroxytetrahydro-2H-pyran-3-carboxamide (71a) Using procedures analogous to (1 h)-(1i), the acid from reaction (70b) (165 mg, 0.57 mmol) and the amine from reaction (39f) as the TFA salt (1.4 eq) were converted to the desired hydroxamic acid (35 mg, 32% yield, 2 steps). MS found: (M)$^+$=435.

Example 72

(3R,4S)-4-({4-[(2-cyclopropyl-1H-benzimidazol-1-yl)methyl]benzoyl}amino)-N-hydroxytetrahydro-3-furancarboxamide (72a) Using procedures analogous to (1 h)-(1i), the acid from reaction (70b) (40 mg, 0.147 mmol) and the amine from (50d) (1 eq) were converted to the desired hydroxamic acid (6 mg, 8% yield, 2 steps). MS found: (M)$^+$=421.

Example 73

4-[(2-cyclobutyl-1H-benzimidazol-1-yl)methyl]-N-{(1R,2S)-2-[(hydroxyamino)carbonyl]cyclopentyl}benzamide (73a) Using procedures analogous to (70a)-(70b), cyclobutanecarboxylic acid (5.2 g, 52 mmol) was converted to the desired acid (646 mg, 8%). MS found: (M)$^+$=307.

(73b) Using procedures analogous to (70c), the product from reaction (73a) (184 mg, 0.6 mmol) was converted to the desired hydroxamic acid (120 mg, 50% yield, 2 steps). MS found: (M)$^+$=434.

Example 74

(3R,4R)-4-({4-[(2-cyclobutyl-1H-benzimidazol-1-yl)methyl]benzoyl}amino)-N-hydroxytetrahydro-2H-pyran-3-carboxamide (74a) Using procedures analogous to (1 h)-(1i), the acid from reaction (73a) (73 mg, 0.24 mmol) and the amine from reaction (39f) as the TFA salt (0.9 eq) were converted to the desired hydroxamic acid (57 mg, 46% yield, 2 steps). MS found: (M+H)$^+$=449.

Example 75

(3R,4R)-N-hydroxy-4-[(4-{[2-(1-methylcyclopropyl)-1H-benzimidazol-1-yl]methyl}benzoyl)amino]tetrahydro-2H-pyran-3-carboxamide (75a) Using procedures similar to (1 h), phenylenediamine bis-hydrochloride (6.9 g, 38 mmol) and 1-methylcyclopropanecarboxylic acid (3.8 g, 1 eq) were converted to the desired amide (4.0 g, 55%). MS found: (M+H)$^+$=191.

(75b) The amide from reaction (75a), (1.9 g, 10 mmol) in acetic acid (30 mL) was heated at 60° C. for 3 h. The mixture was concentrated, dissolved in ethyl acetate (20 mL), washed with saturated aqueous Na$_2$CO$_3$, saturated aqueous NaHCO$_3$, water, brine (10 ml each), dried (MgSO$_4$), filtered and concentrated to give the desired benzimidazole (1.7 g, 98%). MS found: (M+H)⁺=173.

(75c) Using procedures analogous to (1f)-(1 g), the product from reaction (75b) (1 g, 5.8 mmol) was converted to the desired acid (1.25 g, 76%). MS found: (M+H)⁺=307.

(75d) Using procedures analogous to (74a), the acid from reaction (75c) (56 mg, 0.18 mmol) was converted to the desired hydroxamic acid (33 mg, 36% yield, 2 steps). MS found: (M+H)⁺=449.

Example 76

N-{(1R,2S)-2-[(hydroxyamino)carbonyl]cyclopentyl}-4-{[2-(1-methylcyclopropyl)-1H-benzimidazol-1-yl]methyl}benzamide (76a) Using procedures analogous to (67a), the acid from reaction (75c) (107 mg, 0.34 mmol) was converted to the desired hydroxamic acid (42 mg, 25% yield, 2 steps). MS found: (M+H)⁺=433.

Example 79

(3R,4R)-4-[(4-{[2-(fluoromethyl)-1H-benzimidazol-1-yl]methyl}benzoyl)amino]-N-hydroxytetrahydro-2H-pyran-3-carboxamide (79a) Using procedures analogous to (75a)-(75c), fluoroacetic acid (2 g, 26 mmol) was converted to the desired acid (1.4 g, 12% yield, 3 steps). MS found: (M+H)⁺=285.

(79b) Using procedures analogous to (75d), the acid from reaction (79a) (52 mg, 0.18 mmol) was converted to the desired hydroxamic acid (25 mg, 27% yield, 2 steps). MS found: (M+H)⁺=427.

Example 80

4-{[2-(fluoromethyl)-1H-benzimidazol-1-yl]methyl}-N-{(1R,2S)-2-[(hydroxyamino)carbonyl]cyclopentyl}benzamide (80a) Using procedures analogous to (29a), the acid from reaction (79a) (100 mg, 0.34 mmol) was converted to the desired hydroxamic acid (40 mg, 25% yield, 2 steps). MS found: (M+H)⁺=411.

Example 81

(3R,4R)-4-[(4-{[2-(1-fluoro-1-methylethyl)-1H-benzimidazol-1-yl]methyl}benzoyl)amino]-N-hydroxytetrahydro-2H-pyran-3-carboxamide (81a) Ethyl-2-hydroxyisobutyrate (6 g, 45 mmol) in dichloromethane (60 mL) was treated with (diethylamino)sulfur trifluoride (DAST) (1.5 eq) at −78° C., then warmed to rt and stirred for 2 h. The mixture was quenched with saturated NaHCO₃ (aq) and extracted with ethyl acetate, washed with water, brine, dried (MgSO₄) filtered and concentrated to give the desired ester (2.5 g, 41%). MS found: (M+H)⁺=176.

(81b) Using procedures analogous to (1 g) and (75a)-(75c), the ester from reaction (81a) (2 g, 15 mmol) was converted to the desired acid (374 mg, 8%, 5 Steps). MS found: (M+H)⁺=313.

(81c) Using procedures analogous to (75d) the acid from (81b) (44 mg, 0.14 mmol) and the amine from (39f) (1 eq) gave the desired hydroxamic acid (13 mg, 16% yield, 2 steps). MS found: (M+H)⁺=455.

Alternatively, the product of (81c) can be prepared by the following step (81d).

(81d) using analogous procedures to (81c), the acid from reaction (81b) (77 mg, 0.25 mmol) and the amine from reaction (40e) (1 eq) was converted to the desired hydroxamic acid (55 mg, 50% yield, 2 steps). MS found: (M+H)⁺=455.

Example 82

4-{[2-(1-fluoro-1-methylethyl)-1H-benzimidazol-1-yl]methyl}-N-{(1R,2S)-2-[(hydroxyamino)carbonyl]cyclopentyl}benzamide (82a) Using procedures analogous to (75a)-(75c) and (29a), the ester from reaction (81a) (2 g, 15 mmol) was converted to the desired hydroxamic acid (10 mg, 25% yield, 7 steps). MS found: (M+H)⁺=439.

Example 83

(3S,4R)-N-hydroxy-4-({4-[(2-isopropyl-1H-benzimidazol-1-yl)methyl]benzoyl}amino)tetrahydro-2H-pyran-3-carboxamide (83a) Using procedures analogous to (1 h), the amine from reaction (39f) as the TFA salt (310 mg, 0.46 mmol, 60% ee) and 4-hydroxymethylbenzoic acid (1.2 eq) were converted to the desired amide (300 mg, 100%). The enantiomers were separated by Chiralcel OJ column (2 inch column, 20% EtOH/hexane, 25 mL/min, 254 nm) giving 160 mg of the (3R,4R)-isomer and the (3S,4S) enantiomer (25 mg).

(83b) The (3R,4R)-enantiomer from reaction (83a) (158 mg, 0.52 mmol) in dichloromethane (5 mL) was treated with carbon tetrabromide (1.25 eq) and triphenylphosphine (1.5 eq) for 3.6 h. The mixture was diluted with dichloromethane, washed with brine, fried (MgSO₄), filtered and concentrated. Flash Chromatography (ethyl acetate) gave the desired bromide (130 mg, 63%). MS found: (M+H)⁺=370.

(83c) Using analogous procedures to (1f) and (1i), the bromide from reaction (83b) (62 mg, 0.17 mmol) was converted to the desired hydroxamic acid (34 mg, 38%). MS found: (M+H)⁺=437.

Example 84

(3R,4S)-N-hydroxy-4-({4-[(2-isopropyl-1H-benzimidazol-1-yl)methyl]benzoyl}amino)tetrahydro-2H-pyran-3-carboxamide (84a) Using analogous procedures to (83b)-(83c), the (3S,4S) enantiomer from reaction (83a) (25 mg, 0.07 mmol, 84%ee) was converted to the desired hydroxamic acid (9 mg, 18%). MS found: (M+H)⁺=437.

Example 85 tert-butyl (3S,4S)-3-({4-[(2-chloro-1H-benzimidazol-1-yl)methyl]benzoyl}amino)-4-[(hydroxyamino)carbonyl]-1-pyrrolidinecarboxylate (85a) Using methods analogous to reaction conditions in (1f), methyl 4-(bromomethyl)-benzoate (1.35 g, 5.90 mmol) was reacted with chlorobenzimidazole (1.0 g, 5.90 mmol) to yield the desired ester (1.79 g, 91%). MS found: (M+H)⁺=301.

(85b) Using reaction conditions analogous to (1 g), the ester from reaction (85a) (251.7 mg, 0.84 mmol) provided the desired acid (168 mg, 70%).

(85c) Using conditions analogous to (1 h), the acid from reaction (85b) (80 mg, 0.28 mmol) afforded the desired amide (58 mg, 41%). MS found: $(M+H)^+$=513.

(85d) Using conditions analogous to (1i), the amide from reaction (85c) (58 mg, 0.113 mmol) yielded the desired hydroxamic acid (33.2 mg, 6.5%). MS found: $(M+H)^+$=514.3.

Example 86 tert-butyl (3S,4S)-3-[(hydroxyamino)carbonyl]-4-({4-[(2-methoxy-1H-benzimidazol-1-yl)methyl]benzoyl}amino)-1-pyrrolidinecarboxylate (86a) To the solid (85a) (200 mg, 0.67 mmol) was added (7 mL, 1.34 mmol, 25% v/v) NaOMe, MeOH solution at rt. The reaction was then heated to 40° C. for 3 h. The solution was then cooled to 0° C. using water. The water layer was concentrated in vacuo to yield the desired ester (66 mg, 33%). MS found: $(M+H)^+$=297.

(86b) Using conditions analogous to (1 g), the ester from reaction (86a) (66 mg, 0.22 mmol) provided the desired acid (62 mg, 99%). MS found: $(M+H)^+$=283.

(86c) Using conditions analogous to (1 h), the acid from (86b) was coupled with the amine from (1e) to provide the desired amide (11.2 mg, 11%). MS found: $(M+H)^+$=510.

(86d) Using conditions analogous to (1i), the amide from (86c) was reacted with the hydroxylamine solution to provide the desired hydroxamic acid (5.2 mg, 50%). MS found: $(M)^+$=510.

Example 87 tert-butyl (3S,4S)-3-[(hydroxyamino)carbonyl]-4-({4-[(2-methyl-1H-imidazo[4,5-b]pyridin-1-yl)methyl]benzoyl}amino)-1-pyrrolidinecarboxylate (87a) To the solid 2,3-diamino pyridine (5 g, 45.8 mmol) was added polyphosphoric acid (150 g) and then glacial acetic acid (2.8 g, 45.8 mmol). The gel was heated to 230° C. for 5 h. The reaction was cooled to rt and then quenched using (50% w/v) NaOH. The material was extracted from the aqueous phase using dichloromethane (3×300 mL). The organic layers were collected and dried (MgSO$_4$) and concentrated in vacuo to provide the desired pyridyl benzimidazole (3.0 g, 50%). MS found: $(M+H)^+$=134.

(87b) Using conditions analogous to (1f), the product from (87a) (1.0 g, 7.51 mmol) was reacted with the methyl 4-(bromomethyl)benzoate to provide the desired ester (652 mg, 31%). MS found: $(M+H)^+$=282.

(87c) Using conditions analogous to (1 g), the product from (87b) (300 mg, 1.07 mmol) was reacted to provide the desired acid (263 mg, 92%). MS found: $(M+H)^+$=261.

(87d) Using conditions analogous to (1 h), the product from (87c) (260 mg, 0.97 mmol) was reacted with the amine from (1e) to provide the desired amide (124 mg, 100%). MS found: $(M+H)^+$=494.

(87e) Using conditions analogous to (1i), the product from (87d) (124 mg, 0.251 mmol) was reacted with the hydroxylamine solution to afford the desired hydroxamic acid (57 mg, 46%). MS found: $(M+H)^+$=495.

Example 88 tert-butyl (3S,4S)-3-[(hydroxyamino)carbonyl]-4-{[4-(1H-imidazo[4,5-b]pyridin-1-ylmethyl)benzoyl]amino}-1-pyrrolidinecarboxylate (88a) Using conditions analogous to (1f), 4-azabenzimidazole (1.0 g, 8.39 mmol) was reacted with methyl 4-(bromomethyl)-benzoate to furnish the desired ester (933 mg, 42%). MS found: $(M+H)^+$=268.

(88b) Using conditions analogous to (1 g), the product from (88a) (150 mg, 0.52 mmol) was derived to the desired acid (130 mg, 100%). MS found: $(M+H)^+$=254.

(88c) Using conditions analogous to (1 h), the product from reaction (88b) (107 mg, 0.42 mmol) was reacted with the amine from (1e) (103 mg, 0.42) to provide the desired amide (202.3 mg, 100%). MS found: $(M+H)^+$=480.

(88d) Using conditions analogous to (1i), the product from reaction (88c) (202.3 mg, 0.4 mmol) was reacted with hydroxylamine solution to furnish the desired hydroxymate (31 mg, 16%). MS found: $(M+H)^+$=482.

Example 92

(3R,4R)-4-({4-[(2-chloro-1H-benzimidazol-1-yl)methyl]benzoyl}amino)-N-hydroxy-3-pyrrolidinecarboxamide (92a) Using conditions analogous to the procedure from (2a), the product from (85d) (30 mg, 0.06 mmol) provided the desired free amine (24 mg, 100%). MS found: $(M+H)^+$=414.

Example 93

(3S,4S)-N-hydroxy-4-{[4-(1H-imidazo[4,5-b]pyridin-1-ylmethyl)benzoyl]amino}-3-pyrrolidinecarboxamide (93a) Using conditions analogous to the procedure from (2a), the product from (87e) (10 mg, 0.02 mmol) was converted to the free amine (8 mg, 100%). MS found: $(M+H)^+$=482.

Example 94

(3S,4S)-N-hydroxy-4-({4-[(2-methyl-1H-imidazo[4,5-b]pyridin-1-yl)methyl]benzoyl}amino)-3-pyrrolidinecarboxamide (94a) Using conditions analogous to the procedure from (2a), the product from (88d) (34 mg, 0.07 mmol) provided the desired free amine (21 mg, 79%). MS found: $(M+H)^+$=320.

Example 95 tert-butyl (3S,4S)-3-[(hydroxyamino)carbonyl]-4-({4-[(2-methyl-5-nitro-1H-benzimidazol-1-yl)methyl]benzoyl}amino)-1-pyrrolidinecarboxylate (95a) Using conditions analogous to (1f), 2-methyl-5-nitro-benzimidazole (101 mg, 0.568 mmol) was reacted with methyl 4-(bromomethyl)-benzoate to provide the desired ester (71 mg, 40%). MS found: $(M+H)^+$=326.

(95b) Using conditions analogous to (1 g), the product from (95a) (71 mg, 0.218 mmol) was converted to the desired acid (68 mg, 100%). MS found: $(M+H)^+$=312.

(95c) Using conditions analogous to (1 h), the product from (95b) (65 mg, 0.209 mmol) was converted to the desired amide (48 mg, 43%). MS found: $(M+H)^+$=539.

(95d) Using conditions analogous to (1i), the product from (95c) (48 mg, 0.089 mmol) was converted to the desired hydroxamic acid (15.6 mg, 33%). MS found: $(M+H)^+$=540.

Example 96 tert-butyl (3S,4S)-3-[(hydroxyamino)carbonyl]-4-({4-[(2-methyl-6-nitro-1H-benzimidazol-1-yl)methyl]benzoyl}amino)-1-pyrrolidinecarboxylate (96a) Using conditions analogous to (95a), 2-methyl-5-nitro-benzimidazole (101 mg, 0.568 mmol) was converted to the regioisomeric ester (57 mg, 32%). MS found: $(M+H)^+$=326.

(96b) Using conditions analogous to (1 g), the product from (96a) (57 mg, 0.175 mmol) was converted to the desired acid (55 mg, 100%). MS found: (M+H)$^+$=312.

(96c) Using conditions analogous to (1 h), the product (96b) (55 mg, 0.175 mmol) was coupled with the amine from (1e) to provide the desired amide (44 mg, 46%). MS found: (M+H)$^+$=539.

(96d) Using conditions analogous to (1i), the product from (96c) (44 mg, 0.082 mmol) was converted to the desired hydroxamic acid (16 mg, 35%). MS found: (M+H)$^+$=540.

Example 97 tert-butyl (3S,4S)-3-({4-[(5-chloro-2-methyl-1H-benzimidazol-1-yl)methyl]benzoyl}amino)-4-[(hydroxyamino)carbonyl]-1-pyrrolidinecarboxylate (97a) Using conditions analogous to (95a), 2-methyl-5-chloro benzimidazole (95 mg, 0.568 mmol) was converted to the desired ester (73 mg, 43%). MS found: (M+H)$^+$=315.

(97b) Using conditions analogous to (1 g), the product from (97a) (73 mg, 0.232 mmol) was converted to the desired acid (70 mg, 100%). MS found: (M+H)$^+$=301.

(97c) Using conditions analogous to (1 h), the product from (97b) (970 mg, 0.232 mmol) was converted to the desired amide (56 mg, 46%). MS found: (M+H)$^+$=529.

(97d) Using conditions analogous to (1i), the product from (97c) (56 mg, 0.106 mmol) was converted to the desired hydroxamic acid (19.1 mg, 35%). MS found: (M+H)$^+$=530.

Example 98 tert-butyl (3S,4S)-3-({4-[(6-chloro-2-methyl-1H-benzimidazol-1-yl)methyl]benzoyl}amino)-4-[(hydroxyamino)carbonyl]-1-pyrrolidinecarboxylate (98a) Using conditions analogous to (97a), 2-methyl-5-chloro-bezimidazole (95 mg, 0.568 mmol) was converted to the desired regioisomer (78 mg, 46%). MS found: (M+H)$^+$=315.

(98b) Using conditions analogous to (1 g), the product from (98a) (78 mg, 0.248 mmol) was converted to the desired acid (75 mg, 100%). MS found: (M+H)$^+$=301.

(98c) Using conditions analogous to (1 h), the product from (98b) (75 mg, 0.248 mmol) was coupled with the amine from (1e) to provide the desired amide (99 mg, 74%). MS found: (M+H)$^+$=529.

(98d) Using conditions analogous to (1i), the product from (98c) (99 mg, 0.189 mmol) was converted to the desired hydroxamic acid (100 mg, 100%). MS found: (M+H)$^+$=530.

Example 99

4-[(2-cyclopropyl-1H-benzimidazol-1-yl)methyl]-N-{(1R,6S)-6-[(hydroxyamino)carbonyl]-3-cyclohexen-1-yl}benzamide (99a) To a solution of commercially available (1S,2R)-1-methyl cis-1,2,3,6-tetrahydrophthalate (500 mg, 2.72 mmol) at −20° C. in 24 mL acetone was added ethyl chloroformate (0.39 mL, 4.08 mmol). The reaction was stirred for 30 min at 0° C. and then NaN$_3$ (442 mg, 6.8 mmol) in 1.5 mL water was added. The reaction was then quenched with 50 mL water. The reaction mixture was extracted using benzene (3×100 mL). The organic layers were collected, washed with brine and dried (Na$_2$SO$_3$). The reaction was then heated to provide the desired isocyanate (254 mg, 52%). MS found: (M+H)$^+$=182.

(99b) To the product from reaction (99a) (254 mg, 1.4 mmol) in 5 mL THF was added HCl (7 ml, 7 mmol). The reaction was heated to 60° C. for 4 h. The solvent was then removed in vacuo to give the desired amine salt (266 mg, 100%). MS found: (M+H)$^+$=190.

(99c) Using conditions analogous to the procedure in (1 h), the product from (99b) (30 mg, 0.16 mmol) was coupled with 4-[(2-cyclopropyl-1H-benzimidazol-1-yl)methyl] benzoic acid (47 mg, 0.16 mmol) to provide the desired amide (71 mg, 100%). MS found: (M+H)$^+$=430.

(99d) Using conditions analogous to the procedure in (1i), the product from (99c) (71 mg, 0.16 mmol) was reacted with the hydroxylamine solution to provide the desired hydroxamic acid (5 mg, 2%). MS found: (M+H)$^+$=431.

Example 100

4-[(2-cyclobutyl-1H-benzimidazol-1-yl)methyl]-N-{(1R,6S)-6-[(hydroxyamino)carbonyl]-3-cyclohexen-1-yl}benzamide (100a) Using conditions analogous to the procedure in (1 h), the product from (99b) (30 mg, 0.16 mmol) was coupled with 4-[(2-cyclobutyl-1H-benzimidazol-1-yl)methyl] benzoic acid (49 mg, 0.16 mmol) to provide the desired amide (71 mg, 100%). MS found: (M+H)$^+$=444.

(100b) Using conditions analogous to the procedure in (1i), the product from (100a) (71 mg, 0.16 mmol) was reacted with the hydroxylamine solution to provide the desired hydroxamic acid (17 mg, 6%). MS found: (M+H)$^+$=445.

Example 101

N-{(1R,6S)-6-[(hydroxyamino)carbonyl]-3-cyclohexen-1-yl}-4-[(2-isopropyl-1H-benzimidazol-1-yl)methyl]benzamide (101a) Using analogous conditions to the procedure in (1 h), the product from (99b) (30 mg, 0,16 mmol) was coupled with 4-[(2-isopropyl-1H-benzimidazol-1-yl)methyl]benzoic acid to provide the desired amide (69 mg, 100%). MS found: (M+H)$^+$=432.

(101b) Using analogous conditions to the procedure in (1i), the product from (101a) (69 mg, 0.16 mmol) was reacted with the hydroxylamine solution to provide the desired hydroxamic acid (2 mg, 5%). MS found: (M+H)$^+$=434.

Example 102

N-{(1R,2S)-2-[(hydroxyamino)carbonyl] cyclohexyl}-4-[(2-isopropyl-1H-benzimidazol-1-yl) methyl]benzamide (102a) To a solution of the product from (99b) (134 mg, 0.7 mmol) was added Pd(OH)$_2$/C (9.8 mg, 0.07 mg) in a glass vessel. The vessel was charged with hydrogen at 60 psi for 3 h with vigorous shaking. The reaction mixture was then filtered and the solvent removed in vacuo to furnish the desired saturated phthalate (109 mg, 100%). MS found: (M+H)$^+$=156.

(102b) Using analogous conditions to the procedure in (1 h), the product from (102a) (30 mg, 0.19 mmol) was coupled with 4-[(2-isopropyl-1H-benzimidazol-1-yl)methyl]benzoic acid to provide the desired amide (82 mg, 100%). MS found: (M+H)$^+$=434.

(102c) Using analogous conditions to the procedure in (1i), the product from (102b) (82 mg, 0.19 mmol) was reacted with the hydroxylamine solution to provide the desired hydroxamic acid (4 mg, 5%). MS found: (M+H)$^+$=435.

Example 103

4-[(2-cyclopropyl-1H-benzimidazol-1-yl)methyl]-N-{(1R,2S)-2-[(hydroxyamino)carbonyl]cyclohexyl}benzamide (103a) Using conditions analogous to the procedure in (1 h), the product from (102a) (30 mg, 0.19 mmol) was coupled with 4-[(2-cyclobutyl-1H-benzimidazol-1-yl)methyl]benzoic acid (61.4 mg, 0.21 mmol) to provide the desired amide (82 mg, 100%). MS found: (M+Na)$^+$=454.

(103b) Using conditions analogous to the procedure in (1i), the product from (103a) (82 mg, 0.19 mmol) was reacted with the hydroxylamine solution to provide the desired hydroxamic acid (2 mg, 2.4%). MS found: (M+Na)$^+$=432.

Example 104

4-[(2-cyclobutyl-1H-benzimidazol-1-yl)methyl]-N-{(1R,2S)-2-[(hydroxyamino)carbonyl]cyclohexyl}benzamide (104a) Using conditions analogous to the procedure in (1 h), the product from (102a) (30 mg, 0.19 mmol) was coupled with 4-[(2-cyclobutyl-1H-benzimidazol-1-yl)methyl]benzoic acid (64 mg, 0.21 mmol) to provide the desired amide (90 mg, 100%). MS found: (M+H)$^+$=444.

(104b) Using conditions analogous to the procedure in (1i), the product from (104a) (90 mg, 0.16 mmol) was reacted with the hydroxylamine solution to provide the desired hydroxamic acid (5 mg, 6%). MS found: (M+H)$^+$=446.

Example 105

N-{(1R,2S)-2-[(hydroxyamino)carbonyl]cyclohexyl}-4-{[2-(trifluoromethyl)-1H-benzimidazol-1-yl]methyl}benzamide (105a) Using conditions analogous to the procedure in (1 h), the product from (102a) (100 mg, 0.64 mmol) was coupled with 4-{[2-(trifluoromethyl)-1H-benzimidazol-1-yl]methyl}benzoic acid (205 mg, 0.64 mmol) to provide the desired amide (156 mg, 5%). MS found: (M+H)$^+$=461.

(105b) Using conditions analogous to the procedure in (1i), the product from (105a) (156 mg, 0.339 mmol) was reacted with the hydroxylamine solution to provide the desired hydroxamic acid (20 mg, 13%). MS found: (M+H)$^+$=462.

Example 106

4-[(2-tert-butyl-1H-benzimidazol-1-yl)methyl]-N-{(1R,2S)-2-[(hydroxyamino)carbonyl]cyclohexyl}benzamide (106a) Using conditions analogous to the procedure in (1 h), the product from (102a) (100 mg, 0.64 mmol) was coupled with 4-[(2-tert-butyl-1H-benzimidazol-1-yl)methyl]benzoic acid (49 mg, 0.16 mmol) to provide the desired amide (218 mg, 75%). MS found (M+H)$^+$=448.

(106b) Using conditions analogous to the procedure in (1i), the product from (106a) (216 mg, 0.16 mmol) was reacted with the hydroxylamine solution to provide the desired hydroxamic acid (60 mg, 27%). MS found: (M+H)$^+$=449.

Example 112 tert-butyl (3S,4R)-3-[(hydroxyamino)carbonyl]-4-[(4-{[2-(1-methylcyclopropyl)-1H-benzimidazol-1-yl]methyl}benzoyl)amino]-1-piperidinecarboxylate (112a) Diisopropylethylamine (82 mL, 2.5 eq) and (BOC)$_2$O (36.0 g, 1.3 eq) were added to a solution of methyl 4-oxo-3-piperidinecarboxylate (24.6 g, 137 mmol) in CH$_2$Cl$_2$ (600 mL) at 0° C. After overnight at rt, sat. NaHCO$_3$ (50 mL) was added to the reaction mixture. The mixture was washed with water (2×30 mL), brine (30 mL), dried (MgSO$_4$) and concentrated in vacuo. Silica gel chromatography (ethyl acetate-hexane, 50:50) provided the desired product (29.8 g, 93%).

(112b) Yb(OTf)$_3$ (1.41 g, 0.02 eq) was added to a mixture of the intermediate from (112a) (29.2 g, 113 mmol) and (R)-α-methylbenzylamine (16.1 mL, 1.1 eq) in benzene. The mixture was heated to reflux for 3 h with azotropic removal of water using a Dean-Stark trap. The mixture was concentrated in vacuo. The residue was filtered through a silica gel pad and the filter cake washed with ethyl acetate-hexane (10:90) until free of product. The filtrated was concentrated to give the desired enamine product (40.8 g, 100%). MS found: (M+H)$^+$=361.

(112c) NaHB(OAc)$_3$ (58.8 g, 2.5 eq) was added to a solution of the enamine from (112b) (40.0 g, 111 mmol) in acetic acid (180 mL) and acetonitrile (180 mL) at 0° C. After 2 h at 0° C., the mixture was concentrated in vacuo. The residue was diluted with CH$_2$Cl$_2$ (1 L), washed with Na$_2$CO$_3$ (3×50 mL), brine (50 mL), dried (MgSO$_4$) and concentrated in vacuo. Silica gel chromatography (ethyl acetate-hexane, 10:90 then 20:80) provided the desired amine product as a 5:1 mixture of two diastereomers as judged by $^1$H NMR (37.0 g, 92%). MS found: (M+H)$^+$=363.

(112d) Pd(OH)$_2$/C (6.0 g) was added to the amine from (112c) (36.8 g, 101 mmol) in methanol (600 mL), water (60 mL) and acetic acid (15 mL). The mixture was purged with hydrogen and stirred under balloon pressure hydrogen overnight. Following removal of catalyst by filtration, the filtrate was concentrated to give the desired amine (22.8 g, 87%). MS found: (M+H)$^+$=259.

(112e) Using procedures analogous to (1 h)-(1i), the acid from reaction (75c) (95 mg, 0.31 mmol) and the amine from reaction (112d) (1 eq) were converted to the desired hydroxamic acid (50 mg, 29% yield, 2 steps). MS found: (M+H)$^+$=548.

Example 113

(3S,4R)-N-hydroxy-4-[(4-{[2-(1-methylcyclopropyl)-1H-benzimidazol-1-yl]methyl}benzoyl)amino]-3-piperidinecarboxamide (113a) Using procedures analogous to (2a), the product from (112e) (25 mg, 0.04 mmol) was converted to the desired amine (27 mg, 100%). MS found: (M+H)$^+$=448.

Example 134 tert-butyl (3S,4S)-4-[(hydroxyamino)carbonyl]-3-[(4-{[2-(trifluoromethyl)-1H-benzimidazol-1-yl]methyl}benzoyl)amino]-1-piperidinecarboxylate (134a) A mixture of ethyl 1-benzyl-3-oxo-4-piperidinecarboxylate hydrochloride (50 g, 168 mmol), (BOC)₂O (50 g, 1.36 eq), Et₃N (35.2 mL, 1.5 eq), Pd(OH)₂/C (10 g) and ethanol (400 mL) was hydrogenated at 50 psi overnight. Following removal of catalyst by filtration, the filtrate was concentrated, diluted with ethyl acetate (1 L), washed with 0.5 N HCl (300 mL), sat. NaHCO₃ (150 mL), brine (100 mL), dried (MgSO₄) and concentrated in vacuo. Silica gel chromatography (ethyl acetate-hexane, 5:95 then 10:90) provided the desired product (39.0 g, 86%). MS found: $(M+H)^+=272$.

(134b–d) Following the procedures similar to steps (112b–d) and (1 h), the intermediate from (134a) and 4-(2-methyl-4-quinolinylmethoxy)benzoic acid were converted to the desired amide. The material obtained through this route was 40% ee as determined by analytical chiral HPLC. The enantiomeric purity of the major enantiomer was improved to >99% ee using preparative chiral HPLC. The minor enantiomer was also collected. MS found: $(M+H)^+=548$.

(134e) Using procedures analogous to (1e), the major enantiomer from reaction (134d) (15 g, 29 mmol) was converted to the desired phenol (11.5 g, 100%). MS found: $M+H)^+=393$.

(134f) The phenol from reaction (134e) (4.39 g, 11.2 mmol) in dichloromethane (110 mL) was cooled to 0° C. and treated with Hunig's base (1.25 eq), N-phenyltriflamide (1.25 eq) and stirred overnight at rt. The reaction was washed with water, dried (MgSO₄), filtered and concentrated and purified by flash chromatography giving the desired triflate (5.7 g, 97%). MS found: $(M+H)^+=525$.

(134g) The triflate from reaction (134f) (5.7 g, 10.8 mmol) in DMF (100 mL) was treated with Pd(OAc)₂(0.1 eq), KOAc (5 eq) and 1,1'-bis(diphenylphosphino)ferrocene (dppf) (0.2 eq) and CO was bubbled through the mixture while heating to 60° C. until the starting material had been consumed (by TLC analysis). The reaction was diluted with water, extracted with ethyl acetate, washed with water then brine, dried with MgSO₄, filtered and concentrated to give 4.5 g of the crude acid which was taken on without further purification. The crude acid (429 mg, 1.02 mmol) in THF (10 mL) was treated with borane-THF complex (1.0 M in THF, 5 mL, 5 mmol). The reaction was quenched with saturated aqueous NH₄Cl, extracted with ethyl acetate, washed with water, brine, dried (MgSO₄), filtered and concentrated. Flash chromatography purification gave the desired alcohol (89 mg, 22%). MS found: $(M+H)^+=407$.

(134h) Using procedures analogous to (83b), (1f) and (1i), the alcohol from reaction (134 g) (89 mg, 0.22 mmol) and 2-trifluoromethylbenzimidazole were converted to the desired hydroxamic acid (47 mg, 34%). MS found: $(M+Na)^+=584$.

Example 135

(3S,4S)-N-hydroxy-3-[(4-{[2-(trifluoromethyl)-1H-benzimidazol-1-yl]methyl}benzoyl)amino]-4-piperidinecarboxamide (135a) Using procedures analogous to (2a), the product from reaction (135 g) (15 mg, 0.03 mmol) was converted to the desired hydroxamic acid (15 mg, 100%). MS found: $(M+H)^+=462$.

Example 139

(3R,4R)-4-({4-[(2-(1,1-difluoro-ethyl)-1H-benzimidazol-1-yl)methyl]benzoyl}amino)-N-hydroxytetrahydro-2H-pyran-3-carboxamide (139a) Using procedures analogous to (81a)-(81b), ethyl pyruvate (2.50 g, 21.5 mmol) was converted to the desired acid (272 mg, 4% 6 steps). MS found: $(M+H)^+=317$.

(139b) Using procedures analogous to (137a) the acid from reaction (139a) (77 mg, 0.25 mmol) and the amine from (40e) (1 eq) was converted to the desired hydroxamic acid (55 mg, 50% yield, 2 steps). MS found: $(M+H)^+=459$.

Example 140

(3R,4R)-N-hydroxy-4-[(4-{[2-(trifluoromethyl)-1H-imidazo[4,5-b]pyridin-1-yl]methyl}benzoyl)amino] tetrahydro-2H-pyran-3-carboxamide (140a) Using procedures analogous to (70a)-(70b), 2,3-diaminopyridine (2.00 g, 18.3 mmol) and trifluoroacetic acid (1 eq) was converted to the desired carboxylic acid (430 mg, 7% yield, 3 steps). MS found: $(M+H)^+=322$.

(140b) Using procedures analogous to (1 h-li), the product from reaction (140a) (94 mg, 0.29 mmol) and the amine from (40e) (1 eq) were converted to the desired hydroxamic acid (60 mg, 37% yield, 2 steps). MS found: $(M+H)^+=464$.

Example 141

(3R,4R)-N-hydroxy-4-[(4-{[2-(methoxymethyl)-1H-benzimidazol-1-yl]methyl}benzoyl)amino] tetrahydro-2H-pyran-3-carboxamide (141a) Using procedures analogous to (70a)-(70b), 1,2-phenylenediamine (2.16 g, 20.0 mmol) and methoxyacetic acid were converted to the desired carboxylic acid (160 mg, 2.7% yield, 3 steps). MS found: $(M+H)^+=296$.

(141b) Using procedures analogous to (1 h) to (1i), the product from reaction (141a) (74 mg, 0.25 mmol) and the amine from (40e) (1 eq) were converted to the desired hydroxamic acid (40 mg, 29% yield, 2 steps). MS found: $(M+H)^+=439$.

Example 201 tert-butyl (3S,4S)-3-[(hydroxyamino)carbonyl]-4-({4-[(2-methyl-1H-indol-3-yl)methyl] benzoyl}amino)-1-pyrrolidinecarboxylate (201a) To a solution of trifluoroacetic acid (TFA) (1.16 mL, 15 mmol) in CH₂Cl₂ and triethylsilane (4.79 mL, 30 mmol) was added a solution of methyl 4-formylbenzoate (1.81 g, 11 mmol) and 2-methylindole (1.31 g, 10 mmol). The reaction was stirred 10 min at 0° C. and then quenched by adding the reaction solution to NaOH. Additional NaOH was added to get the pH to 8. The aqueous layer was extracted with EtOAc (1×100 mL) to obtain the crude compound. The crude was flashed (hexanes to 25% EtOAc/hexanes) to yield the desired ester (2.18 g, 78%). MS found: $(M+Na)^+=302$.

(201b) To a suspension of (201a) (1.79 mmol, 500 mg) in MeOH (5 mL) was added LiOH (0.9 mL, 1.79 mmol, 2M) solution. The reaction was stirred for 16 h and then quenched to pH 7 with HCl (1N). The reaction mixture was filtered to afford the desired acid (475 mg, 100%). MS found: $(M+H)^+=266$.

(201c) To a solution of (201b) was added the amine from reaction (1e) (183 mg, 0.75 mmol), Hunig's base (0.3 mL, 1.50 mmol), and benzotriazol-1-yloxyltris(dimethylamino)-phosphonium hexafluorophosphate (BOP) (365 mg, 0.83 mmol). The reaction was stirred overnight at ambient temperature and then quenched with NH₄Cl. The reaction mixture was extracted with EtOAc (2×200 mL) and the organic layers separated and concentrated in vacuo. The crude material was flashed (hexanes to 20% EtOAc/ hexanes) to afford the desired amide (142 mg, 38%). MS found: $(M+Na)^+=514$.

(201d) Using analogous procedures to (1i) the product from reaction (201c) (334 mg, 0.679 mmol) was converted to the desired hydroxamic acid (40 mg, 12% yield). MS found: $(M+H)^+=493$.

Example 202 tert-butyl (3S,4S)-3-({4-[(1,2-dimethyl-1H-indol-3-yl)methyl]benzoyl}amino)-4-[(hydroxyamino)carbonyl]-1-pyrrolidinecarboxylate (202a) To a suspension of the ester from reaction (201a) (500 mg, 1.79 mmol) in 5 mL ether was added 18-crown-6 (47 mg, 0.179 mmol) followed by potassium t-butoxide (221 mg, 1.97 mmol). The reaction was stirred for 10 min and then cooled to 0° C. Methyl iodide (MeI) was subsequently added and the reaction was warmed to ambient temperature overnight. The reaction solution was quenched with water and extracted with $Et_2O$ (2×50 ml). Concentrate layers were flashed (10% hexanes/EtOAc) to afford (202a) (472 mg, 90%).

(202b) Using analogous procedures from (201b), the ester product from (202a) (472 mg, 1.61 mmol) provided the desired acid (393 mg, 88%). MS found: $(M+H)^+=288$.

(202c) Using procedures analogous to reaction (201c), the product from (202b) (0.716 mmol, 200 mg) was converted to the desired ester (300 mg, 83%). MS found: $(M+H)^+=506$.

(202d) Using procedures analogous to (1i), the product from (202c) (300 mg, 0.595 mmol) afforded the desired hydroxamic acid (108 mg, 35%). MS found: $(M+H)^+=507$.

Example 203

(3S,4S)-N-hydroxy-4-({4-[(2-methyl-1H-indol-3-yl)methyl]benzoyl}amino)-3-pyrrolidinecarboxamide (203a) To the product from reaction (201d) (40 mg, 0.08 mmol) was added a solution of dichloromethane/TFA (5 ml, 1:1, v/v) solution. The reaction was allowed to sit for 10 min and then the solvents were removed in vacuo. The compound was freeze dried from water to afford the desired amine (33.8 mg, 82%). MS found: $(M+H)^+=393$.

Example 204

(3S,4S)-4-({4-[(1,2-dimethyl-1H-indol-3-yl)methyl]benzoyl}amino)-N-hydroxy-3-pyrrolidinecarboxamide (204a) Using a procedure analogous to (203a), the ester product from (202d) (40 mg, 0.08 mmol) was reacted to afford the desired amine (33.8 mg, 82%). MS found: $(M+H)^+=407$.

Example 205

(3S,4S)-N-hydroxy-1-isopropyl-4-({4-[(2-methyl-1H-indol-3-yl)methyl]benzoyl}amino)-3-pyrrolidinecarboxamide (205a) Using analogous procedures to (3a) the carbamate from reaction (201a) (1.7 g, 3.51 mmol) was converted to the desired amine (1.01 g, 74%). MS Found: $(M+H)^+=392$.

(205b) Using procedures analogous to reaction (6a) the amine from reaction (205a) (100 mg, 0.255 mmol) was converted to the desired ester. (74.6 mg, 68%). MS found: $(M+H)^+=434$.

(205c) Using procedures analogous to (1i), the product from (205b) (74.6 mg, 0.172 mmol) afforded the desired hydroxamic acid (17.2 mg, 23%). MS found: $(M+H)^+=435$.

Example 206

(3S,4S)-N-hydroxy-4-({4-[(2-methyl-1H-indol-3-yl)methyl]benzoyl}amino)-1-(2-propynyl)-3-pyrrolidinecarboxamide (206a) Using procedures analogous to (4a)-(4b) the amine from reaction (205a) (100 mg, 0.255 mmol) was converted to the desired hydroxamic acid (30 mg, 44%). MS found: $(M+H)^+=431$.

Example 207

(3R,4R)-N-hydroxy-4-({4-[(2-methyl-1H-indol-3-yl)methyl]benzoyl}amino)tetrahydro-2H-pyran-3-carboxamide (207a) Using procedures analogous to (1 h)-(1i) the amine from reaction (39f) as a TFA salt (329 mg, 1.9 mmol) and the acid from reaction (201b) (1 eq) were converted to the desired hydroxamic acid (140 mg, 18% yield) MS Found: $(M+H)^+=408$.

Alternatively, the product of (207a) can be prepared by the following steps (207b)-(207c).

(207b) using a procedure analogous to (201c) the acid product from (201b) (0.79 mmol, 209 mg) was reacted with the amine (40e) (0.79 mmol, 189 mg) to afford the desired amide (320 mg, 99%). MS found: $(M+H)^+=407$.

(207c) Using a procedure analogous to (1i) the product from (207b) (320 mg, 0.79) was reacted to afford the desired hydroxamic acid (51 mg, 16%). MS found: $(M+H)^+=408$.

Example 208

(3R,4R)-N-hydroxy-4-({4-[(2-methyl-1H-indol-1-yl)methyl]benzoyl}amino)tetrahydro-2H-pyran-3-carboxamide (208a) To a solution of 2-methyl indole (7.60 mmol, 1.00 g) was added 18-crown-6 (60 mg, 0.06 mmol) and subsequently powdered KOH (416 mg, 7.60 mmol) and methyl 4(bromomethyl)benzoate (1 eq). The reaction was heated to 100° C. for 2 h, and was added additional KOH (416 mg, 7.60 mmol). The reaction was stirred for another 1 h. The reaction was cooled and then quenched with HCl and extracted with EtOAc (2×100 mL). The organic layers were collected, dried and concentrated in vacuo. The crude was flashed to yield the desired acid (798 mg, 40%). MS found: $(M+H)^+=274$.

(208b) Using procedures analogous to (201c)-(201d) the product from reaction (208a) (19.4 mg, 0.073 mmol) and the amine from reaction (39f) as a TFA salt (20 mg, 0.073 mmol) were converted to the desired hydroxamic acid (3 mg, 11%). MS found: $(M+H)^+=422$.

Example 209

N-{(1R,2S)-2-[(hydroxyamino)carbonyl]cyclopentyl}-4-[(2-methyl-1H-indol-1-yl)methyl]benzamide (209a) Using procedures analogous to (208b), methyl (1S,2R)-2-aminocyclopentane carboxylate (40 mg, 0.224 mmol) and the product from reaction (208a) (60 mg, 0.224 mmol) were converted to the desired hydroxamic acid. (15 mg, 17%). MS found: $(M+H)^+=392$.

Example 210 tert-butyl (3S,4S)-3-({4-[(2,3-dimethyl-1H-indol-1-yl)methyl]benzoyl}amino)-4-[(hydroxyamino)carbonyl]-1-pyrrolidinecarboxylate (210a) To a solution of 2,3-dimethyl indole (1.0 g, 6.89 mmol) in DMF (30 mL) was added 18-crown-6 (56 mg, 0.21 mmol), KOH (386 mg, 6.89 mmol) and methyl 4-(bromomethyl)benzoate (1.58 g, 6.89 mmol). The reaction after flash chromatography afforded the desired ester (720 mg, 36%). MS found: $(M-Me+H)^+=279$.

(210b) Using a procedure analogous to (201b), the product from (210a) (2.45 mmol, 720 mg) was reacted to afford the acid (347 mg, 48%). MS found: $(M+H)^+=279$.

(210c) Using a procedure analogous to (201c), the amine product from (1e), (0.358 mmol, 100 mg) was reacted with the product from reaction (210b) (0.358 mmol, 88 mg) to afford the desired amide (180 mg, 99%). MS found: $(M+H)^+=506$.

(210d) Using a procedure analogous to (201d), the product from (210c) (0.358 mmol, 180 mg) was reacted to afford the desired hydroxamic acid (60 mg, 34%). MS found: $(M+H)^+=507$.

Example 211 tert-butyl (3S,4S)-3-[(hydroxyamino)carbonyl]-4-({4-[(2-isopropyl-1H-indol-1-yl)methyl]benzoyl}amino)-1-pyrrolidinecarboxylate (211a) To a solution of 2-isopropylindole (for a synthesis see: Smith, A. B. et al. *Tetrahedron*, 1986, 2957) (50 mg, 0.314 mmol) in DMSO (5 mL) was added 18-crown-6 (2.5 mg, 9.42 µmol), powdered KOH (18 mg, 0.314 mmol) and methyl 4-(bromomethyl)benzoate (72 mg, 0.314 mmol). The reaction was stirred at ambient temperature for 10 min. The reaction afforded the desired ester (67 mg, 70%). MS found: $(M-Me)^-=292$.

(211b) Using a procedure analogous to (201b), the product from (211a) (67 mg, 0.218 mmol) was reacted to afford the desired acid (52 mg, 81%). MS found: $(M+H)^+=293$.

(211c) Using an analogous procedure as in (201c), the amine product from (1e) (43 mg, 0.177 mmol) was coupled to the product from reaction (211b) (52 mg, 0.177 mmol) to afford the desired amide (92 mg, 98%). MS found: $(M+H)^+=542$.

(211d) Using a procedure analogous to (201d), the product from (211c) (90.9 mg, 0.179 mmol) was reacted with the hydroxylamine solution to yield the desired hydroxamic acid (24 mg, 27%). MS found: $(M+H)^+=543$.

Example 212

(3S,4S)-N-hydroxy-4-({4-[(2-isopropyl-1H-indol-1-yl)methyl]benzoyl}amino)-3-pyrrolidinecarboxamide (212a) Using a procedure analogous to (202a), the product from (211d) (6 mg, 0.0115 mmol) was reacted to afford the desired amine (6 mg, 100%). MS found: $(M+H)^+=421$.

Example 213

(3S,4S)-4-({4-[(2,3-dimethyl-1H-indol-1-yl)methyl]benzoyl}amino)-N-hydroxy-3-pyrrolidinecarboxamide (213a) Using a procedure analogous to (202a), the product from (210b) (11 mg, 0.0217 mmol) was reacted to afford the desired amine (11 mg, 100%). MS found: $(M+H)^+=407$.

Example 214

(3R,4R)-4-({4-[(2,3-dimethyl-1H-indol-1-yl)methyl]benzoyl}amino)-N-hydroxytetrahydro-2H-pyran-3-carboxamide (214a) Using a procedure analogous to (201c), the amine product from (40e) (0.358 mmol, 86 mg) was reacted with the product from (210b) (0.358 mmol, 100 mg) to afford the desired amide (149 mg, 99%). MS found: $(M+H)^+=421$.

(214b) Using a procedure analogous to (1i), the product from (214a) was reacted to afford the desired hydroxamic acid (35 mg, 23%). MS found: $(M+H)^+=422$.

Example 215

(3R,4R)-N-hydroxy-4-[(4-{[2-(trifluoromethyl)-1H-indol-1-yl]methyl}benzoyl)amino]tetrahydro-2H-pyran-3-carboxamide (215a) Using procedures previously described in the chemical literature (Smith et al. *Tetrahedron Letters*, 1985, 3757–3760) N-trimethylsilyl toluidine was prepared by reacting toluidine (100 mmol, 10.7 g), triethylamine (300 mmol, 42 mL) and trimethylsiyl chloride (300 mmol, 38 mL) to afford the desired amine (14.9 g, 83%). MS found: $(M+H)^+=218$.

(215b) Using procedures previously described in the chemical literature (Smith et al. *Tetrahedron Letters*, 1985, 3757–3760), the amine product from (215a), (39.1 mmol) was reacted with (86 mmol, 43 mL) n-BuLi, (39.1 mmol, 5.9 mL) TMEDA all in (400 mL) hexanes, and (47 mmol, 6 mL) ethyl trifluoroacetate in (200 mL) THF for 6 h to afford the desired indole (1.88 g, 26%).

(215c) To a solution of the product from (215b) (0.53 mmol, 98 mg) in DMSO (5 mL), methyl 4-(bromomethyl)benzoate (0.53 mmol, 121 mg, KOH (1.06 mmol, 59.4 mg) and 18-crown-6 (0.02 mmol, 5 mg) were added, after flash chromatography, to afford the desired acid (103 mg, 61%). MS found: $(M-H)^-=318$.

(215d) Using a procedure analogous to (201c), the product from (215c) (0.174 mmol, 56 mg) was reacted with the amine from (40e) (0.174 mmol, 42 mg) to afford the desired amide. (80 mg, 99%). MS found: $(M+H)^+=461$.

(215e) Using a procedure analogous to (1i), the product from (215d) (0.174 mmol, 80 mg) was reacted to afford the desired hydroxamic acid. (46 mg, 60%). MS found: $(M+H)^+=462$.

Example 216

(3R,4R)-4-({4-[(2-ethyl-1H-indol-1-yl)methyl]benzoyl}amino)-N-hydroxytetrahydro-2H-pyran-3-carboxamide (216a) Using a procedure analogous to (215b), the product from (215a) (39 mmol, 7 g) was reacted with ethyl propionate (47 mmol, 5.4 mL) to afford the desired indole. (5 g, 88%).

(216b) Using a procedure analogous to (215c), the product from (216a) (0.69 mmol, 100 mg) was reacted with the methyl-4(bromomethyl)benzoate (0.69 mmol, 158 mg) to afford the desired acid. (130 mg, 63%). MS found: $(M+H)^+=279$.

(216c) Using a procedure analogous to (201c), the product from (216b) (0.21 mmol, 59 mg) was reacted with the amine from (40e) (50 mg, 0.21 mmol) to afford the desired amide. (64 mg, 73%). MS found: $(M+H)^+=421$.

(216d) Using a procedure analogous to (1i), the product from (216c) (0.15 mmol, 64 mg) was reacted to afford the desired hydroxamic acid (11 mg, 17%). MS found: $(M+H)^+$=422.

Example 217

(3R,4S)-4-({4-[(2-ethyl-1H-indol-1-yl)methyl]benzoyl}amino)-N-hydroxytetrahydrofuran-3-carboxamide (217a) Using a procedure analogous to (201c), the product from (216b) (0.16 mmol, 45 mg) was reacted with the amine HCl salt from (50d) (0.16 mmol, 24 mg) to afford the desired amide. (46 mg, 71%). MS found: $(M+H)^+$=407.

(217b) Using a procedure analogous to (1i), the product from (217a) was reacted to afford the desired hydroxamic acid (2 mg, 4%). MS found: $(M+H)^+$=408.

Example 218

(3R,4S)-4-({4-[(2,3-dimethyl-1H-indol-1-yl)methyl]benzoyl}amino)-N-hydroxytetrahydrofuran-3-carboxamide (218a) Using a procedure analogous to (201c), the amine product from (50d) as an HCl salt (0.16 mmol, 24 mg) was reacted with the product from (210b) (0.16 mmol, 46 mg) to afford the desired amide (45 mg, 71%). MS found: $(M+H)^+$=407.

(218b) Using a procedure analogous to (1i), the product from (218a) (0.113 mmol, 45 mg) was reacted to afford the desired hydroxamic acid (10 mg, 9%). MS found: $(M+H)^+$=430.

Example 219

(3R,4R)-4-({4-[(2-ethyl-1H-indol-3-yl)methyl]benzoyl}amino)-N-hydroxytetrahydro-2H-pyran-3-carboxamide (219a) Using an analogous procedure to (201a), the product from (216a) (6.89 mmol, 1 g) was reacted to afford the desired ester (160 mg, 8%). MS found: $(M+H)^+$=294.

(219b) Using an analogous procedure as (201b), the product from (219a) was reacted to afford the desired acid (28 mg, 60%). MS found: $(M+H)^+$=280.

(219c) Using a procedure analogous to (201c), the product from (219b) (0.16 mmol, 45 mg) was reacted with the amine from (40e) (0.1 mmol, 28 mg) to afford the desired amide. (35 mg, 86%). MS found: $(M+H)^+$=421.

(219d) Using a procedure analogous to (1i), the product from (219c) (0.08 mmol, 34.6 mg) was reacted to afford the desired hydroxamic acid (2 mg, 6%). MS found: $(M+H)^+$=422.

Example 220

(3R,4S)-4-({4-[(2-ethyl-1H-indol-3-yl)methyl]benzoyl}amino)-N-hydroxytetrahydrofuran-3-carboxamide (220a) Using a procedure analogous to (201c), the amine from (50d) as an HCl salt (0.11 mmol, 16 mg) was reacted with the product from (219b) (0.11 mmol, 30 mg) to afford the desired amide (44 mg, 99%). MS found: $(M+H)^+$=407.

(220b) Using a procedure analogous to (1i), the product from (220a) (0.08 mmol, 44 mg) was reacted to afford the desired hydroxamic acid (16 mg, 36%). MS found: $(M+H)^+$=408.

Example 222

(3R,4S)-N-hydroxy-4-[(4-{[2-(trifluoromethyl)-1H-indol-1-yl]methyl}benzoyl)amino]tetrahydrofuran-3-carboxamide (222a) Using a procedure analogous to (201c), the product from (215c) (29 mg, 0.086 mmol) was reacted with the amine salt (50d) (0.086 mmol, 13 mg) to afford the desired amide (29 mg, 38%). MS found: $(M+H)^+$=447.

(222b) Using a procedure analogous to (1i), the product from (222a) (0.065 mmol, 29 mg) was reacted to afford the desired hydroxamic acid (16 mg, 55%). MS found: $(M+H)^+$=448.

Example 223

(3R,4R)-N-hydroxy-4-({4-[(3-methyl-1H-indol-1-yl)methyl]benzoyl}amino)tetrahydro-2H-pyran-3-carboxamide (223a) Using a procedure analogous to (215c) (15.25 mmol, 2 g) of 2-methyl indole was reacted with (15.25 mmol, 3.5 g) methyl-4-(bromomethyl)benzoate to afford the desired acid (2.9 g, 73%). MS found: $(M+H)^+$=266.

(223b) Using a procedure analogous to (201c), the product from (223a) (0.4 mmol, 106 mg) was reacted with the amine (40e) to afford the desired amide (161 mg, 99%). MS found: $(M+H)^+$=407.

(223c) Using a procedure analogous to (1i), the product from (223c) (0.37 mmol, 150 mg) was reacted to afford the desired hydroxamic acid (55 mg, 37%). MS found: $(M+H)^+$=408.

Example 224

(3R,4S)-N-hydroxy-4-({4-[(3-methyl-1H-indol-1-yl)methyl]benzoyl}amino)tetrahydrofuran-3-carboxamide (224a) Using a procedure analogous (223a)-(223c), the product from (223a) (0.312 mmol, 83 mg) was reacted with the amine HCl salt (50d) (0.312 mmol, 45 mg) to afford the desired hydroxamic acid (50 mg, 38%). MS found: $(M-H)^-$=392.

Example 225

(3R,4R)-4-({4-[(1,2-dimethyl-1H-indol-3-yl)methyl]benzoyl}amino)-N-hydroxytetrahydro-2H-pyran-3-carboxamide (225a) Using a procedure analogous to (202b)-(202d), the product from (202b) (0.217 mmol, 61 mg) was reacted with the amine (40e) (0.167 mmol, 40 mg) to afford the desired hydroxamic acid (30 mg, 43%). MS found: $(M+H)^+$=422.

Example 226

N-cis-2-[(hydroxyamino)carbonyl]cyclopentyl}-4-[(3-methyl-1H-indol-1-yl)methyl]benzamide (226a) Using a procedure analogous to (202b)-(202d), the product from (202b) (0.207 mmol, 55 mg) was reacted with the cis-ethyl-2-aminocyclopentane carboxylate (0.207 mmol, 55 mg) to afford the desired hydroxamic acid (35 mg, 44%). MS found: $(M+H)^+$=392.

Example 227

(3R,4S)-4-({4-[(1,2-dimethyl-1H-indol-3-yl)methyl]benzoyl}amino)-N-hydroxytetrahydrofuran-3-carboxamide (227a) Using a procedure analogous to (202b)-(202d), the product from (202b) (0.173 mmol, 25 mg) was reacted with the amine HCl salt (50d) (0.225 mmol, 63 mg) to afford the desired hydroxamic acid (10 mg, 10%). MS found: (M+H)+=408.

Example 228

(3R,4S)-4-({4-[(2-ethyl-1-methyl-1H-indol-3-yl)methyl]benzoyl}amino)-N-hydroxytetrahydrofuran-3-carboxamide (228a) Using a procedure analogous to (202b) the product from (216b) was reacted to afford the desired acid (60 mg, 39%). MS found: (M−H)−=292.

(228b) Using a procedure analogous to (202c)-(202d), the product from (228a) (0.4 mmol, 117 mg) was reacted with the amine HCl salt (50d) (0.4 mmol, 57 mg) to afford the desired hydroxamic acid (5 mg, 14%). MS found: (M+H)+= 422.

Example 229

(3R,4R)-4-({4-[(2-ethyl-1-methyl-1H-indol-3-yl)methyl]benzoyl}amino)-N-hydroxytetrahydro-2H-pyran-3-carboxamide (229b) Using an analogous procedure to (228a)-(228b), the product from (228a) (0.21 mmol, 62 mg) was reacted with the amine from (40e) (0.21 mmol, 50 mg) to afford the desired hydroxamic acid (7 mg, 26%). MS found: (M+H)+= 437.

Example 301 tert-butyl (3S,4S)-3-{[4-(2,3-dihydro-4H-1,4-benzothiazin-4-ylmethyl)benzoyl]amino}-4-[(hydroxyamino)carbonyl]-1-pyrrolidinecarboxylate (301a) $K_2CO_3$ (4.4 g, 31.9 mmol) and 1,2-dibromoethane (690 μL, 8.0 mmol) were added to a solution of 2-aminothiophenol (1.0 g, 8.0 mmol) in 20 mL of acetone at rt. The reaction mixture was stirred overnight. The insoluble material was filtered off and the solvent was removed in vacuum. The residue was purified on silica gel column to provide 3,4-dihydro-2H-1,4-benzothiazine (0.8 g, 66%). MS (ES+): 152 (M+1).

(301b) $K_2CO_3$ (5.2 g, 37.7 mmol) and methyl 4-bromomethylbenzoate (2.8 g, 12.6 mmol) were added to a solution of (301a) (1.9 g, 12.6 mmol) in 20 mL of anhydrous DMF. The reaction mixture was heated to 80° C. overnight. After cooling down, the solid was filtered off and rinsed with DMF. The solvent was removed in vacuum and the residue was purified on silica gel column to provide methyl 4-(2,3-dihydro-4H-1,4-benzothiazin-4-ylmethyl)benzoate (3.02 g, 80%). MS (ES+): 300 (M+1).

(301c) A solution of NaOH (1N, 1.2 mL) was added to a solution of (301b) (170 mg, 0.57 mmol) in 4 mL of MeOH. The reaction mixture was heated to 50° C. overnight. Upon completion, the aliquot was neutralized with HCl (1N, 1.2 mL). The solvent was removed and the residue was dissolved in MeOH. After filtration and concentration, 4-(2,3-dihydro-4H-1,4-benzothiazin-4-ylmethyl)benzoic acid was obtained in quantitative yield. MS (AP+): 286 (M+1).

(301d) 1-tert-butyl 3-methyl (3S,4S)-4-amino-1,3-pyrrolidinedicarboxylate (1e) (58 mg, 0.21 mmol), diisopropylethylamine (122 mg, 165 μL, 0.95 mmol), and DMF (2.0 mL) were added to a flask charged with (301c) (54 mg, 0.19 mmol). The whole mixture was cooled to 0° C. and then added BOP (100 mg, 0.23 mmol) in one portion. The resulting solution was stirred overnight and TLC showed completion of the reaction. The solution was diluted with ethyl acetate and washed with $H_2O$ and brine, and dried over $MgSO_4$. After filtration and concentration, the residue was purified in silica gel to provide the desired product (64 mg, 66%). MS (ES+): 512 (M+1).

(301e) 1 mL of $NH_2OH/NaOMe/MeOH$ (1.64M) was added to a flask charged with the product from (301d) (64 mg, 0.13 mmol) at 0° C. The mixture was stirred for 20 min before it was quenched with 1 mL of aqueous HCl (1N). The resulting solution was purified by reverse phase HPLC to provide the desired title compound (25 mg, 31%). MS (ES+): 513 (M+1).

Example 302 tert-butyl (3S,4S)-3-[(hydroxyamino)carbonyl]-4-({4-[(1-oxido-2,3-dihydro-4H-1,4-benzothiazin-4-yl)methyl]benzoyl}amino)-1-pyrrolidinecarboxylate (302a) Example 302 (30 mg, 36% yield) was isolated from the product from reaction (301e). MS (ES+): 529 (M+1).

Example 303

(3S,4S)-4-{[4-(2,3-dihydro-4H-1,4-benzothiazin-4-ylmethyl)benzoyl]amino}-N-hydroxy-3-pyrrolidinecarboxamide (303a) TFA (2 mL) was added to a solution of (301e) (10 mg, 0.016 mmol) in 2 mL of dichloromethane. The resulting solution was stirred for 30 min and the solvent was removed in vacuum. The desired product was obtained in quantitative yield. MS (ES+): 413 (M+1).

Example 304

(3S,4S)-N-hydroxy-4-({4-[(1-oxido-2,3-dihydro-4H-1,4-benzothiazin-4-yl)methyl]benzoyl}amino)-3-pyrrolidinecarboxamide (304a) TFA (2 mL) was to a solution of (302a) (10 mg, 0.016 mmol) in 2 mL of dichloromethane. The resulting solution was stirred for 30 min and the solvent was removed under vacuum. The desired product was obtained in quantitative yield. MS (ES+): 429 (M+1).

Example 305

(3S,4S)-N-hydroxy-4-({4-[(1-oxido-2,3-dihydro-4H-1,4-benzothiazin-4-yl)methyl]benzoyl}amino)-1-(2-propynyl)-3-pyrrolidinecarboxamide (305a) A solution of Oxone® (2.2 g, 3.54 mmol) in 20 mL of $H_2O$ was added slowly to a solution of (301b) (2.12 g, 7.1 mmol) in 20 mL of MeOH. Upon completion of the reaction, the solution was diluted with ethyl acetate, washed with saturated $NaHCO_3$ and dried over $MgSO_4$. After filtration and concentration, the residue was purified on silica gel column to provide methyl 4-[(1-oxido-2,3-dihydro-4H-1,4-benzothiazin-4-yl)methyl]benzoate (1.39 g, 65%). MS (AP+): 316 (M+1).

(305b) Following a procedure similar to (301c), the product from (305a) was converted to the corresponding acid in quantitative yield. MS (AP+): 302 (M+1).

(305c) Following a procedure similar to (301d), the product from (305b) (80 mg, 0.26 mmol) was coupled with (1e) to provide the desired product (147 mg, 94% yield). MS (AP+): 528 (M+1).

(305d) TFA (1 mL) was added to a solution of (305c) (140 mg, 0.26 mmol) in 1 mL of dichloromethane. The mixture was stirred for 30 min and the solvent was removed to provide (305d) in quantitative yield. MS (ES$^+$): 428 (M+1).

(305e) Triethylamine (36 mg, 0.35 mmol) and propargyl bromide (42 mg, 0.36 mmol) were added to a solution of the TFA salt (305d) (76 mg, 0.11 mmol) in 1.5 mL of chloroform at 0° C. The reaction mixture was stirred at 0° C. for 10 min and then at rt for 1 h. The reaction was quenched with iced water and then diluted with ethyl acetate. The organic layer was washed with H$_2$O, brine and dried over MgSO$_4$. After filtration and concentration, the residue was purified on silica gel to provide (305e) (26 mg, 48%). MS (ES$^+$): 466(M+1).

(305f) Following a procedure similar to (301e), the product from (305e) (24 mg, 0.052 mmol) was converted to the corresponding hydroxamate (305f) as a TFA salt (20 mg, 67%). MS (ES$^+$): 467(M+1).

Example 306

(3S,4S)-N-hydroxy-1-isopropyl-4-({4-[(1-oxido-2,3-dihydro-4H-1,4-benzothiazin-4-yl)methyl] benzoyl}amino)-3-pyrrolidinecarboxamide (306a) Diisopropylethylamine (45 mg, 0.35 mmol), acetone (12 mg, 0.2 mmol), and NaBH(OAc)$_3$ (45 mg, 0.21 mmol) were added to a solution of the TFA salt from (305d) (92 mg, 0.15 mmol) in 2 mL of dichloromethane at rt. The reaction was stirred for 4 h for completion and the solution was directly loaded on silica gel column to provide (306a) (40 mg, 60%). MS (AP$^-$): 468(M−1).

(306b) Following a procedure similar to (301e), the product from (306a) (40 mg, 0.085 mmol) was converted to the corresponding hydroxamate (306b) as a TFA salt (30 mg, 60%). MS (ES$^+$): 471(M+1).

Example 307 tert-butyl (3S,4S)-3-({4-[(1,1-dioxido-2,3-dihydro-4H-1,4-benzothiazin-4-yl)methyl]benzoyl}amino)-4-[(hydroxyamino)carbonyl]-1-pyrrolidinecarboxylate (307a) A solution of Oxone® (15.5 g, 25.3 mmol) in 30 mL of H$_2$O was added slowly to a solution of (301b) (3.02 g, 10.1 mmol) in 80 mL of MeOH. Upon completion of the reaction, the solution was diluted with ethyl acetate, washed with saturated NaHCO$_3$ and dried over MgSO$_4$. After filtration and concentration, the residue was purified on silica gel column to provide methyl 4-[(1,1-dioxido-2,3-dihydro-4H-1,4-benzothiazin-4-yl)methyl]benzoate (1.25 g, 37%). MS (AP$^+$): 332 (M+1).

(307b) Following a procedure similar to (301c), the product form (307a) was converted to the corresponding acid (307b) in quantitative yield. MS (ES$^+$): 318 (M+1).

(307c) Following a procedure similar to (301d), the product from (307b) (590 mg, 1.9 mmol) was coupled with (1e) to provide (307c) (907 mg, 88%). MS (AP$^-$): 542 (M−1).

(307d) Following a procedure similar to (301e), the product from (307c) (30 mg, 0.055 mmol) was converted to the corresponding hydroxamate (307d) as a TFA salt (20 mg, 55%). MS (ES$^-$): 657 (M+TFA−1).

Example 308

(3S,4S)-4-({4-[(1,1-dioxido-2,3-dihydro-4H-1,4-benzothiazin-4-yl)methyl]benzoyl}amino)-N-hydroxy-3-pyrrolidinecarboxamide (308a) Following a procedure similar to (302a), the product from (307d) was converted to the desired product (308a) in quantitative yield. MS (ES$^+$): 445 (M+1).

Example 309

(3S,4S)-4-({4-[(1,1-dioxido-2,3-dihydro-4H-1,4-benzothiazin-4-yl)methyl]benzoyl}amino)-N-hydroxy-1-(2-propynyl)-3-pyrrolidinecarboxamide (309a) Following a procedure similar to (305d), the product from (307c) was converted to (309a) in quantitative yield. MS (AP$^+$): 485 (M+CH$_3$CN+1).

(309b) Following a procedure similar to (305e), the product from (309a) as a TFA salt (65 mg, 0.1 mmol) was converted to the corresponding product (309b) (33 mg, 71%). MS (AP$^+$): 482 (M+1).

(309c) Following a procedure similar to (301e), the product from (309b) (45 mg, 0.09 mmol) was converted to the corresponding hydroxamate (309c) as a TFA salt (40 mg, 74%). MS (ES$^+$): 483 (M+1)

Example 310

(3S,4S)-4-({4-[(1,1-dioxido-2,3-dihydro-4H-1,4-benzothiazin-4-yl)methyl]benzoyl}amino)-N-hydroxy-1-isopropyl-3-pyrrolidinecarboxamide (310a) Following a procedure similar to (306a), the TFA salt from (309a) (150 mg, 0.22 mmol) was converted to (310a) (73 mg, 68%). MS (ES$^+$): 486(M+1).

(310b) Following a procedure similar to (301e), the product from (310a) (60 mg, 0.12 mmol) was converted to the corresponding hydroxamate (310b) as a TFA salt (60 mg, 83%). MS (ES$^+$): 487(M+1).

Example 311

(3S,4S)-1-(2-butynyl)-4-({4-[(1,1-dioxido-2,3-dihydro-4H-1,4-benzothiazin-4-yl)methyl] benzoyl}amino)-N-hydroxy-3-pyrrolidinecarboxamide (311a) Following a procedure similar to (305e), the product from (309a) (50 mg, 0.07 mmol) was alkylated with 1-bromo-2-butyne to provide (311a) (35 mg, >95%). MS (ES$^+$): 496 (M+1).

(311b) Following a procedure similar to (301e), the product from (311a) (35 mg, 0.07 mmol) was converted to the corresponding hydroxamate (311b) as a TFA salt (30 mg, 70%). MS (ES$^+$): 497 (M+1).

Example 312

(3S,4S)-4-({4-[(1,1-dioxido-2,3-dihydro-4H-1,4-benzothiazin-4-yl)methyl]benzoyl}amino)-N-hydroxy-1-isobutyl-3-pyrrolidinecarboxamide (312a) Following a procedure similar to (306a), the TFA salt from (309a) (35 mg, 0.06 mmol) was converted to (312a) (30 mg, >95%). MS (ES$^+$): 500(M+1).

(312b) Following a procedure similar to (301e), the product from (312a) (30 mg, 0.06 mmol) was converted to the corresponding hydroxamate (312b) as a TFA salt (21 mg, 57%). MS (ES$^+$): 501 (M+1)

Example 313

(3S,4S)-4-({4-[(1,1-dioxido-2,3-dihydro-4H-1,4-benzothiazin-4-yl)methyl]benzoyl}amino)-N-hydroxy-1-methyl-3-pyrrolidinecarboxamide (313a) Following a procedure similar to (306a), the TFA salt from (309a) (45 mg, 0.08 mmol) was converted to (313a) (35 mg, >95%). MS (ES$^+$): 458(M+1).

(313b) Following a procedure similar to (301e), the product from (313a) (35 mg, 0.08 mmol) was converted to the corresponding hydroxamate (313b) as a TFA salt (21 mg, 46%). MS (ES$^+$): 459 (M+1).

Example 314

(3S,4S)-4-({4-[(1,1-dioxido-2,3-dihydro-4H-1,4-benzothiazin-4-yl)methyl]benzoyl}amino)-N-hydroxy-1-(isopropylsulfonyl)-3-pyrrolidinecarboxamide (314a) Diisopropylethylamine (200 μL, 1.1 mmol) and isopropylsulfonyl chloride (17 μL, 0.15 mmol) were added to a solution of the TFA salt from (309a) (50 mg, 0.09 mmol) in 3 mL of dichloromethane at rt. The reaction was quenched by addition of 2 drops of MeOH and the solution was directly transferred on silica gel column to provide (314a) (30 mg, 61%). MS (ES$^+$): 550 (M+1).

(314b) Following a procedure similar to (301e), the product from (314a) (30 mg, 0.05 mmol) was converted to the corresponding hydroxamate (314b) as a TFA salt (29 mg, >95%). MS (ES$^+$): 551 (M+1).

Example 315

(3S,4S)-1-acetyl-4-({4-[(1,1-dioxido-2,3-dihydro-4H-1,4-benzothiazin-4-yl)methyl]benzoyl}amino)-N-hydroxy-3-pyrrolidinecarboxamide (315a) Following a procedure similar to (314a), the TFA salt from (309a) (50 mg, 0.09 mmol) was converted to the corresponding product (315a) (40 mg, >95%). MS (ES$^+$): 486 (M+1).

(315b) Following a procedure similar to (301e), the product from (315a) (40 mg, 0.08 mmol) was converted to the corresponding hydroxamate (315b) as a TFA salt (30 mg, 75%). MS (ES$^+$): 487 (M+1).

Example 316

(3S,4S)-1-(2,2-dimethylpropanoyl)-4-({4-[(1,1-dioxido-2,3-dihydro-4H-1,4-benzothiazin-4-yl)methyl]benzoyl}amino)-N-hydroxy-3-pyrrolidinecarboxamide (316a) Following a procedure similar to (314a), the TFA salt from (309a) (32 mg, 0.06 mmol) was converted to the corresponding product (316a) (27 mg, 85%). MS (ES$^+$): 528 (M+1).

(316b) Following a procedure similar to (301e), the product from (316a) (27 mg, 0.05 mmol) was converted to the corresponding hydroxamate (316b) as a TFA salt (20 mg, 75%). MS (ES$^+$): 529 (M+1).

Example 317

(3S,4S)-4-({4-[(1,1-dioxido-2,3-dihydro-4H-1,4-benzothiazin-4-yl)methyl]benzoyl}amino)-N-hydroxy-1-phenyl-3-pyrrolidinecarboxamide (317a) Triethylamine (46 μL, 0.33 mmol), phenyl boronic acid (13 mg, 0.1 mmol) and 4A molecule sieves (100 mg) were added to a solution of the TFA salt from (309a) (37 mg, 0.067 mmol) in 2 mL of dichloromethane. To this mixture was added copper acetate (15 mg, 0.08 mmol) and the mixture was stirred under air until the reaction went to completion. The solution was filtered and washed with ethyl acetate. The filtrate was concentrated and the residue was loaded on silica gel column to provide (317a) (29 mg, 83%). MS (ES$^+$): 520 (M+1).

(317b) Following a procedure similar to (301e), the product from (317a) (29 mg, 0.056 mmol) was converted to the corresponding hydroxamate (317b) as a TFA salt (18 mg, 51%). MS (ES$^+$): 521 (M+1).

Example 318

(3S,4S)-4-({4-[(1,1-dioxido-2,3-dihydro-4H-1,4-benzothiazin-4-yl)methyl]benzoyl}amino)-1-(4-fluorophenyl)-N-hydroxy-3-pyrrolidinecarboxamide (318a) Following a procedure similar to (317a), the TFA salt from (309a) (41 mg, 0.074 mmol) was converted to (318a) (25 mg, 63%). MS (ES$^+$): 538 (M+1).

(318b) Following a procedure similar to (301e), the product from (318a) (25 mg, 0.046 mmol) was converted to the corresponding hydroxamate (318b) as a TFA salt (20 mg, 66%). MS (ES$^+$): 539 (M+1).

Example 319

(3S,4S)-4-({4-[(1,1-dioxido-2,3-dihydro-4H-1,4-benzothiazin-4-yl)methyl]benzoyl}amino)-N-hydroxy-1-(4-methoxyphenyl)-3-pyrrolidinecarboxamide (319a) Following a procedure similar to (317a), the TFA salt from (309a) (41 mg, 0.074 mmol) was converted to (319a) (21 mg, 52%). MS (ES$^+$): 550 (M+1).

(319b) Following a procedure similar to (301e), the product from (319a) (21 mg, 0.038 mmol) was converted to the corresponding hydroxamate (319b) as a TFA salt (13 mg, 52%). MS (ES$^+$): 551 (M+1).

Example 320

(3S,4S)-1-(cyclopropylmethyl)-4-({4-[(1,1-dioxido-2,3-dihydro-4H-1,4-benzothiazin-4-yl)methyl]benzoyl}amino)-N-hydroxy-3-pyrrolidinecarboxamide (320a) Following a procedure similar to (306a), the TFA salt from (309a) (48 mg, 0.09 mmol) was converted to (320a) (40 mg, 89%). MS (ES$^+$): 498(M+1).

(320b) Following a procedure similar to (301e), the product from (320a) (40 mg, 0.08 mmol) was converted to the corresponding hydroxamate (320b) as a TFA salt (33 mg, 67%). MS (ES$^+$): 499(M+1).

Example 321

(3S,4S)-1-cyclopentyl-4-({4-[(1,1-dioxido-2,3-dihydro-4H-1,4-benzothiazin-4-yl)methyl]benzoyl}amino)-N-hydroxy-3-pyrrolidinecarboxamide (321a) Following a procedure similar to (306a), the TFA salt from (309a) (45 mg, 0.08 mmol) was converted to (321a) (40 mg, 97%). MS (ES$^+$): 512(M+1).

(321b) Following a procedure similar to (301e), the product from (321a) (40 mg, 0.08 mmol) was converted to the corresponding hydroxamate (321b) as a TFA salt (40 mg, 80%). MS (ES$^+$): 513 (M+1)

Example 322

(3S,4S)-4-({4-[(1,1-dioxido-2,3-dihydro-4H-1,4-benzothiazin-4-yl)methyl]benzoyl}amino)-N-hydroxy-1-tetrahydro-2H-pyran-4-yl-3-pyrrolidinecarboxamide (322a) Following a procedure similar to (306a), the TFA salt from (309a) (45 mg, 0.08 mmol) was converted to (322a) (40 mg, 95%). MS (ES$^+$): 528(M+1).

(322b) Following a procedure similar to (301e), the product from (322a) (40 mg, 0.076 mmol) was converted to the corresponding hydroxamate (322b) as a TFA salt (37 mg, 76%). MS (ES$^+$): 529 (M+1).

Example 323

(3S,4S)-4-({4-[(1,1-dioxido-2,3-dihydro-4H-1,4-benzothiazin-4-yl)methyl]benzoyl}amino)-N-hydroxy-1-neopentyl-3-pyrrolidinecarboxamide (323a) Following a procedure similar to (306a), the TFA salt from (309a) (45 mg, 0.08 mmol) was converted to (323a) (40 mg, 95%). MS (ES$^+$): 514(M+1).

(323b) Following a procedure similar to (301e), the product from (323a) (40 mg, 0.076 mmol) was converted to the corresponding hydroxamate (323b) as a TFA salt (35 mg, 73%). MS (ES$^+$): 515 (M+1).

Example 324

4-[(1,1-dioxido-2,3-dihydro-4H-1,4-benzothiazin-4-yl)methyl]-N-{cis-2-[(hydroxyamino)carbonyl]cyclopentyl}benzamide (324a) Following a procedure similar to (301d), the product from (307b) (128 mg, 0.4 mmol) was coupled with methyl cis-2-aminocyclopentanecarboxylate.HCl (87 mg, 0.45 mmol) to provide (324a) (94 mg, 51%). MS (AP$^+$): 443 (M+1).

(324b) Following a procedure similar to (301e), the product from (324a) (94 mg, 0.21 mmol) was converted to the corresponding hydroxamate (324b) as a TFA salt (61 mg, 52%). MS (ES$^+$): 444 (M+1)

Example 325

(3R,4S)-4-({4-[(1,1-dioxido-2,3-dihydro-4H-1,4-benzothiazin-4-yl)methyl]benzoyl}amino)-N-hydroxytetrahydro-3-furancarboxamide (325a) Following a procedure similar to (301d), the product from (307b) (101 mg, 0.31 mmol) was coupled with methyl (3R,4S)-4-aminotetrahydro-3-furancarboxylate (50d) (65 mg, 40% ee, 0.36 mmol) to provide (325a) (25 mg, 18%). MS (AP$^+$): 445 (M+1).

(325b) Following a procedure similar to (301e), the product from (325a) (25 mg, 0.056 mmol) was converted to the corresponding hydroxamate (325b) as a TFA salt (18 mg, 58%). MS (ES$^+$): 446(M+1).

Example 326

(3R,4R)-4-({4-[(1,1-dioxido-2,3-dihydro-4H-1,4-benzothiazin-4-yl)methyl]benzoyl}amino)-N-hydroxytetrahydro-2H-pyran-3-carboxamide (326a) Following a procedure similar to (301d), the product from (307b) (101 mg, 0.31 mmol) was coupled with ethyl (3R, 4R)-4-aminotetrahydro-2H-pyran-3-carboxylate (39f) (100 mg, 60% ee, 0.35 mmol) to provide (326a) (64 mg, 43%). MS (ES$^+$): 473 (M+1).

(326b) Following a procedure similar to (301e), the product from (326a) (65 mg, 0.14 mmol) was converted to the corresponding hydroxamate (326b) as a TFA salt (60 mg, 75%). MS (ES$^+$): 460(M+1).

Example 327 tert-butyl (3S,4S)-3-({4-[(2,2-dimethyl-2,3-dihydro-4H-1,4-benzothiazin-4-yl)methyl]benzoyl}amino)-4-[(hydroxyamino)carbonyl]-1-pyrrolidinecarboxylate (327a) K$_2$CO$_3$ (5.6 g, 40.9 mmol) and ethyl 2-bromoisobutyrate (6.0 mL, 40.9 mmol) were added to a solution of 2-aminothiophenol (5.12 g, 40.9 mmol) in 50 mL of anhydrous DMF at 0° C. The mixture was stirred at that temperature for 2 h and then heated to 100° C. for 10 h. After cooling down, the solid was filtered off and the solvent was stripped off. The resulting solid was washed with a mixture of dichloromethane and hexane (1:1) to provide the pure product (327a) (4.9 g, 62%). MS (AP$^+$): 194(M+1).

(327b) To a solution of (327a) (2.0 g, 10.4 mmol) in 40 mL of anhydrous THF at –78° C. was added a solution of LAH in THF (1.0M, 10.4 mL). The reaction mixture was stirred overnight before it was quenched with ethyl acetate, MeOH and H$_2$O. The solution was extracted with ethyl acetate and the organic layer was dried over MgSO$_4$. After filtration and concentration, the residue was purified on silica gel column to provide (327b) (1.5 g, 80%). MS (AP$^+$): 180(M+1).

(327c) To a solution of (327b) (4.0 g, 22.3 mmol) in 50 mL of anhydrous THF at 0° C. was added NaH (1.1 g, 60% ee, 26.8 mmol). The mixture was stirred for 30 min before a solution of methyl bromomethylbenzoate in 20 mL of anhydrous THF was added. The reaction was stirred overnight and was quenched with H$_2$O. The solution was extracted with ethyl acetate and washed with H$_2$O and brine, and dried over MgSO$_4$. After filtration and concentration, the residue was purified on silica gel to provide (327c) (5.2 g, 71%). MS (ES$^+$): 328(M+1).

(327d) Following a procedure similar to (301c), the product from (327c) (900 mg, 2.7 mmol) was converted to the corresponding acid (327d) (400 mg, 45%). MS (AP$^+$): 314(M+1).

(327e) Following a procedure similar to (301d), the product from (327d) (%0 mg, 0.25 mmol) was coupled with (1e) (62 mg, 0.25 mmol) to provide (327e) (120 mg, 89%). MS (AP$^+$): 540 (M+1).

(327f) Following a procedure similar to (301e), the product from (327e) (60 mg, 0.11 mmol) was converted to the corresponding hydroxamate (327f) as a TFA salt (20 mg, 28%). MS (ES$^-$): 653 (M+TFA−1).

Example 328 tert-butyl (3S,4S)-3-({4-[(2,2-dimethyl-1-oxido-2,3-dihydro-4H-1,4-benzothiazin-4-yl)methyl]benzoyl}amino)-4-[(hydroxyamino)carbonyl]-1-pyrrolidinecarboxylate (328a) In the same procedure of (327f), the product from (328a) (20 mg, 27%) was isolated by reverse HPLC. MS (ES$^-$): 669 (M+TFA−1).

Example 329 tert-butyl (3S,4S)-3-({4-[(2,2-dimethyl-1,1-dioxido-2,3-dihydro-4H-1,4-benzothiazin-4-yl)methyl]benzoyl}amino)-4-[(hydroxyamino)carbonyl]-1-pyrrolidinecarboxylate (329a) Following a procedure similar to (307a), the product from (327c) (2.3 g, 7.0 mmol) was converted to the corresponding sulfone (329a) (1.4 g, 56%). MS (ES$^+$): 719 (2M+1).

(329b) Following a procedure similar to (301c), the product from (329a) (1.4 g, 3.9 mmol) was converted to the corresponding acid (329b) in quantitative yield. MS (ES$^+$): 346(M+1).

(329c) Following a procedure similar to (301d), the product from (329b) (26 mg, 0.07 mmol) was coupled with (1e) (19 mg, 0.07 mmol) to provide (329c) (29 mg, 67%). MS (ES⁻): 606 (M+Cl−1).

(329d) Following a procedure similar to (301e), the product from (329c) (25 mg, 0.05 mmol) was converted to the corresponding hydroxamate (329d) as a TFA salt (20 mg, 58%). MS (ES⁻): 685 (M+TFA−1).

Example 330

(3S,4S)-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide (330a) Following a procedure similar to (302a), the product from (329d) was converted to the desired product (330a) in quantitative yield. MS (ES⁺): 473 (M+1).

Example 331

(3S,4S)-4-({4-[(2,2-dimethyl-1,1-dioxido-2,3-dihydro-4H-1,4-benzothiazin-4-yl)methyl]benzoyl}amino)-N-hydroxy-1-(2-propynyl)-3-pyrrolidinecarboxamide (331a) Following a procedure similar to (305d), the product from (329c) was converted to (331a) in quantitative yield. MS (ES⁺): 472 (M+1).

(331b) Following a procedure similar to (305e), the TFA salt of (331a) (100 mg, 0.17 mmol) was converted to (331b) (55 mg, 63%). MS (ES⁺): 510 (M+1).

(331c) Following a procedure similar to (301e), the product from (331b) (55 mg, 0.1 mmol) was converted to the corresponding hydroxamate (331c) as a TFA salt (35 mg, 56%). MS (ES⁺): 511 (M+1).

Example 332

(3S,4S)-4-({4-[(2,2-dimethyl-1,1-dioxido-2,3-dihydro-4H-1,4-benzothiazin-4-yl)methyl]benzoyl}amino)-N-hydroxy-1-isopropyl-3-pyrrolidinecarboxamide (332a) Following a procedure similar to (306a), the TFA salt of (331a) (100 mg, 0.17 mmol) was converted to (332a) (80 mg, 91%). MS (ES⁺): 514 (M+1).

(332b) Following a procedure similar to (301e), the product from (332a) (80 mg, 0.16 mmol) was converted to the corresponding hydroxamate (332b) as a TFA salt (63 mg, 64%). MS (ES⁺): 515 (M+1).

Example 333

(3S,4S)-4-({4-[(2,2-dimethyl-1,1-dioxido-2,3-dihydro-4H-1,4-benzothiazin-4-yl)methyl]benzoyl}amino)-N-hydroxy-1-isobutyl-3-pyrrolidinecarboxamide (333a) Following a procedure similar to (306a), the TFA salt of (331a) (55 mg, 0.09 mmol) was converted to (333a) (35 mg, 74%). MS (ES⁺): 528 (M+1).

(333b) Following a procedure similar to (301e), the product from (333a) (35 mg, 0.066 mmol) was converted to the corresponding hydroxamate (333b) as a TFA salt (28 mg, 66%). MS (ES⁺): 529 (M+1).

Example 334

(3S,4S)-1-butyl-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide (334a) Following a procedure similar to (306a), the TFA salt of (331a) (35 mg, 0.06 mmol) was converted to (334a) (21 mg, 66%). MS (ES⁺): 528 (M+1).

(334b) Following a procedure similar to (301e), the product from (334a) (20 mg, 0.037 mmol) was converted to the corresponding hydroxamate (334b) as a TFA salt (17 mg, 87%). MS (ES⁺): 529 (M+1).

Example 335

(3S,4S)-4-({4-[(2,2-dimethyl-1,1-dioxido-2,3-dihydro-4H-1,4-benzothiazin-4-yl)methyl]benzoyl}amino)-N-hydroxy-1-neopentyl-3-pyrrolidinecarboxamide (335a) Following a procedure similar to (306a), the TFA salt of (331a) (35 mg, 0.06 mmol) was converted to (335a) (20 mg, 61%). MS (ES⁺): 542 (M+1).

(335b) Following a procedure similar to (301e), the product from (335a) (20 mg, 0.033 mmol) was converted to the corresponding hydroxamate (335b) as a TFA salt (18 mg, 83%). MS (ES⁺): 543 (M+1).

Example 336

(3R,4R)-4-({4-[(2,2-dimethyl-1,1-dioxido-2,3-dihydro-4H-1,4-benzothiazin-4-yl)methyl]benzoyl}amino)-N-hydroxytetrahydro-2H-pyran-3-carboxamide (336a) Following a procedure similar to (301d), the product from (329b) (50 mg, 0.14 mmol) was coupled with ethyl (3R, 4R)-4-aminotetrahydro-2H-pyran-3-carboxylate (39f) (46 mg, 60% ee, 0.16 mmol) to provide (336a) (31 mg, 54%). MS (ES⁺): 501 (M+1).

(336b) Following a procedure similar to (301e), the product from (336a) (28 mg, 0.056 mmol) was converted to the corresponding hydroxamate (336b) as a TFA salt (20 mg, 59%). MS (ES⁺): 488 (M+1).

Example 337

(3R,4S)-4-({4-[(2,2-dimethyl-1,1-dioxido-2,3-dihydro-4H-1,4-benzothiazin-4-yl)methyl]benzoyl}amino)-N-hydroxytetrahydro-3-furancarboxamide (337a) Following a procedure similar to (301d), the product from (329b) (108 mg, 0.49 mmol) was coupled with (50d) (100 mg, 40% ee, 0.55 mmol) to provide (337a) (66 mg, 29%). MS (ES⁺): 473 (M+1).

(337b) Following a procedure similar to (301e), the product from (337a) (55 mg, 0.11 mmol) was converted to the corresponding hydroxamate (337b) as a TFA salt (40 mg, 62%). MS (ES⁺): 474 (M+1).

Example 338

4-[(2,2-dimethyl-1,1-dioxido-2,3-dihydro-4H-1,4-benzothiazin-4-yl)methyl]-N-{cis-2-[(hydroxyamino)carbonyl]cyclopentyl}benzamide (338a) Following a procedure similar to (301d), the product from (329b) (40 mg, 0.1 mmol) was coupled with ethyl cis-2-aminocyclopentanecarboxylate.HCl (23 mg, 0.11 mmol) to provide (338a) (48 mg, 95%). MS (ES⁺): 485 (M+1).

(338b) Following a procedure similar to (301e), the product from (338a) (45 mg, 0.09 mmol) was converted to the corresponding hydroxamate (338b) as a TFA salt (45 mg, 85%). MS (ES⁺): 494 (M+Na).

Example 339 tert-butyl (3S,4S)-3-{[4-(2,3-dihydro-4H-1,4-benzoxazin-4-ylmethyl)benzoyl]amino}-4-[(hydroxyamino)carbonyl]-1-pyrrolidinecarboxylate (339a) Following a procedure similar to (327b), 2H-1,4-benzoxazole (3.0 g, 20 mmol) was converted to (339a) (2.5 g, 91%). MS (AP⁺): 136 (M+1).

(339b) Following a procedure similar to (301b), the product from (339a) (2.4 g, 18 mmol) was converted to (339b) (4.0 g, 78%). MS (AP+): 284(M+1).

(339c) Following a procedure similar to (301c), the product from (339b) (3.9 g, 14 mmol) was converted to the corresponding acid (339c) in quantitative yield. MS (ES+): 270 (M+1).

(339d) Following a procedure similar to (301d), the product from (339c) (100 mg, 0.37 mmol) was coupled (1e) (101 mg, 0.40 mmol) to provide (339d) (180 mg, >95%). MS (ES+): 496 (M+1).

(339e) Following a procedure similar to (301e), the product from (339d) (50 mg, 0.1 mmol) was converted to the corresponding hydroxamate (339e) as a TFA salt (50 mg, 82%). MS (ES+): 497 (M+1).

Example 340 tert-butyl (3S,4S)-3-[(hydroxyamino)carbonyl]-4-{[4-(10H-phenoxazin-10-ylmethyl)benzoyl]amino}-1-pyrrolidinecarboxylate (340a) Following a procedure similar to (301b), phenoxazine (2.0 g, 11 mmol) was converted to (340a) (0.7 g, 19%). MS (ES+): 332 (M+1).

(340b) Following a procedure similar to (301c), the product from (340a) (2.5 g, 7.6 mmol) was converted to the corresponding acid (340b) (1.83 g, 84%). MS (AP+): 318 (M+1).

(340c) Following a procedure similar to (301d), the product from (340b) (35 mg, 0.11 mmol) was coupled with (1e) (30 mg, 0.12 mmol) to provide (340c) (36 mg, 61%). MS (AP+): 544 (M+1).

(340d) Following a procedure similar to (301e), the product from (340c) (25 mg, 0.046 mmol) was converted to the corresponding hydroxamate (340d) as a TFA salt (20 mg, 66%). MS (ES−): 657 (M+TFA−1).

Example 401 tert-butyl (3S,4S)-3-[(hydroxyamino)carbonyl]-4-({4-[(2-methyl-4-quinolinyl)methyl]benzoyl}amino)-1-pyrrolidinecarboxylate (401a) 2-hydroxy-4-methylquinoline (17.4 g, 109 mmol) and phosphorus oxytribromide (47.1 g, 164 mmol) were added to a round-bottom flask. The mixture was heated to 130° C. for several hours. After cooling down to rt, the residue was partitioned between saturated Na$_2$CO$_3$ and ethyl acetate. The organic layer was separated and the aqueous layer was extracted with ethyl acetate (5×300 mL). The combined organic layer was washed with H$_2$O (2×400 mL) and brine (1×400 mL) and dried over MgSO$_4$. After filtration and concentration, the residue was purified on silica gel to provide 4-bromo-2-methylquinoloine (8.8 g, 36%). MS (AP+): 221.8, 223.8 (M+1).

(401b) 4-Bromo-2-methylquinoline (401a) (1.0 g, 4.5 mmol) was dissolved in 10 mL of anhydrous THF and the resulting solution was cooled down to −78° C. A solution of n-BuLi (3.0 mL, 1.6M, 4.8 mmol) was added slowly and the resulting solution was maintained at −78° C. for 5 min. Meanwhile, in another flask methyl 4-formylbenzoate (0.9 g, 5.4 mmol) was dissolved in 20 mL of anhydrous THF and the resulting solution was cooled to −78° C. before the lithium reagent made above was cannulated. The whole mixture was stirred for 30 min before quenched with MeOH. The solution was then diluted with ethyl acetate and washed with H$_2$O and brine. After dried over MgSO$_4$, the organic solution was filtered and concentrated. The residue was purified on silica gel to provide methyl 4-[hydroxy(2-methyl-4-quinolinyl)methyl]benzoate (0.9 g, 65%). MS (AP+): 308 (M+1).

(401c) The product from (401b) (105 mg, 0.34 mmol) was dissolved in 1 mL of dichloromethane. The solution was cooled to 0° C. and triethylamine (95 μL, 0.68 mmol) and MsCl (32 μL, 0.41 mmol) were added. The ice bath was removed and the reaction was monitored by TLC until the disappearance of starting material. The solution was diluted with ethyl acetate and washed with H$_2$O and brine. The organic layer was dried over MgSO$_4$, filtered, and concentrated. The residue was purified to provide methyl 4-{(2-methyl-4-quinolinyl)[(methylsulfonyl)oxy]methyl}benzoate (130 mg, quantitative yield). MS (AP+): 386 (M+1).

(401d) A solution of (401c) (120 mg, 0.31 mmol) in 3 mL of MeOH was added to a suspension of the Pd/C catalyst (60 mg, 10%) in 2 mL of MeOH. The reaction took place after the flask was purged with H$_2$. The reaction was monitored using TLC until disappearance of the starting material. After filtered, the solution was concentrated and the residue was purified on silica gel to provide methyl 4-[(2-methyl-4-quinolinyl)methyl]benzoate (90 mg, quantitative yield). MS (AP+): 292 (M+1).

(401e) A solution of aqueous NaOH (1N, 35 mL) was added to a solution of (401d) (5.0 g, 17.2 mmol) in 100 mL of MeOH. The reaction mixture was heated up to 60° C. until completion of the reaction, monitored by TLC. Upon the completion, one equivalent of aqueous HCl (1N, 35 mL) was added to neutralize the base. The solution was concentrated to dryness and the residue was redissolved in MeOH. After filtration, the methanolic solution was concentrated again to provide 4-[(2-methyl-4-quinolinyl)methyl]benzoic acid (4.8 g, quantitative yield). MS (ES+): 278 (M+1).

(401f) (1e) (58 mg, 0.24 mmol), diisopropylethylamine (78 mg, 105 μL, 0.6 mmol), dichloromethane (2.0 mL) and DMF (2.0 mL) were added to a flask charged with (401e) (55 mg, 0.2 mmol). The whole mixture was cooled to 0° C. and then BOP (124 mg, 0.28 mmol) was added in one portion. The resulting solution was stirred overnight and TLC showed completion of the reaction. The solution was diluted with ethyl acetate and washed with H$_2$O and brine, and dried over MgSO$_4$. After filtration and concentration, the residue was purified in silica gel to provide 1-tert-butyl 3-methyl (3S,4S)-4-({4-[(2-methyl-4-quinolinyl)methyl]benzoyl}amino)-1,3-pyrrolidinedicarboxylate (90 mg, 90%). MS (ES+): 504 (M+1).

(401g) 1.4 mL of NH$_2$OH/NaOMe/MeOH at 0° C. was added to a flask charged with compound 101f (80 mg, 0.16 mmol). The mixture was stirred for 20 min before it was quenched with 1.4 mL of aqueous HCl (1N). The resulting solution was purified by reverse phase HPLC to provide the desired title compound (401 g) (60 mg, 61%). MS (ES+): 505 (M+1).

Example 402

(3S,4S)-N-hydroxy-4-({4-[(2-methyl-4-quinolinyl)methyl]benzoyl}amino)-3-pyrrolidinecarboxamide (402a) 2 mL of TFA was added to a solution of the product from (401 g) (5 mg, 0.01 mmol) in 2 mL of dichloromethane. The resulting solution was stirred for 30 min and the solvent was removed under vacuum. The desired product (402a) was obtained in quantitative yield. MS (ES+): 405 (M+1).

Example 403

(3S,4S)-N-hydroxy-4-({4-[(2-methyl-4-quinolinyl)methyl]benzoyl}amino)-1-(2-propynyl)-3-pyrrolidinecarboxamide (403a) 2 mL of TFA was added to a solution of (401f) (110 mg, 0.22 mmol) in 2 mL of dichloromethane. The resulting mixture was stirred for 30 min and the solvent was removed in vacuum. Methyl (3S,4S)-4-({4-[(2-methyl-4-quinolinyl)methyl]benzoyl}amino)-3-pyrrolidinecarboxylate (403a) was obtained as a TFA salt in quantitative yield. MS (ES$^+$): 404(M+1).

(403b) The TFA salt (403a) (92 mg, 0.15 mmol) was dissolved in 2 mL of chloroform and the solution was cooled to 0° C. Triethylamine (88 mg, 122 μL, 0.87 mmol) and propargyl bromide (65 mg, 50 μL, 0.44 mmol) were added subsequently. The mixture was stirred until disappearance of compound (403a). The solution was diluted with ethyl acetate and washed with H$_2$O and brine, and dried over MgSO$_4$. After filtration and concentration, the residue was purified on silica gel to provide methyl (3S,4S)-4-({4-[(2-methyl-4-quinolinyl)methyl]benzoyl}amino)-1-(2-propynyl)-3-pyrrolidinecarboxylate (36 mg, 56%). MS (AP$^+$): 442 (M+1).

(403c) 0.4 mL of NH$_2$OH/NaOMe/MeOH (1.64M) was added to a flask charged with (403b) (30 mg, 0.07 mmol) at 0° C. The solution was stirred for 15 min and was quenched with equal amount of aqueous HCl solution (1N). The resulting solution was purified on reverse phase HPLC to provide (3S, 4S)-N-hydroxy-4-({4-[(2-methyl-4-quinolinyl)methyl]benzoyl}amino)-1-(2-propynyl)-3-pyrrolidinecarboxamide as a TFA salt (25 mg, 55%). MS (ES$^+$): 443 (M+1).

Example 404

(3S,4S)-N-hydroxy-1-isopropyl-4-({4-[(2-methyl-4-quinolinyl)methyl]benzoyl}amino)-3-pyrrolidinecarboxamide (404a) Diisopropylethylamine (28 mg, 38 μL, 0.22 mmol), acetone (6 mg, 8 μL) and NaBH(OAc)$_3$ (23 mg, 0.11 mmol) were added to a solution of the TFA salt (403a) (46 mg, 0.073 mmol) in 1 mL of dichloromethane. The whole mixture was stirred until the reaction went to completion. The solution was diluted with ethyl acetate and washed with saturated NaHCO$_3$, H$_2$O and brine. The organic layer was dried over MgSO$_4$. After filtration and concentration, the residue was purified on silica gel to provide methyl (3S,4S)-1-isopropyl-4-({4-[(2-methyl-4-quinolinyl)methyl]benzoyl}amino)-3-pyrrolidinecarboxylate (20 mg, 63%). MS (ES$^+$): 446(M+1).

(404b) Following a procedure similar to (403c), the product from (404a) (20 mg, 0.045 mmol) was converted to the corresponding hydroxamate (404b) as a TFA salt (15 mg; 50%). MS (ES$^+$): 447 (M+1).

Example 405

(3S,4S)-N-hydroxy-1-isobutyl-4-({4-[(2-methyl-4-quinolinyl)methyl]benzoyl}amino)-3-pyrrolidinecarboxamide (405a) The TFA salt (403a) (70 mg, 0.11 mmol) was dissolved in 1 mL of dichloromethane. Diisopropylethylamine (43 mg, 60 μL, 0.33 mmol), isobutyraldehyde (12 mg, 5 μL) and NaBH(OAc)$_3$ (35 mg, 0.17 mmol) were added. The whole mixture was stirred until the reaction went to completion. The solution was diluted with ethyl acetate and washed with saturated NaHCO$_3$, H$_2$O and brine. The organic layer was dried over MgSO$_4$. After filtration and concentration, the residue was purified on silica gel to provide methyl (3S,4S)-1-isobutyl-4-({4-[(2-methyl-4-quinolinyl)methyl]benzoyl}amino)-3-pyrrolidinecarboxylate (40 mg, 78%). MS (ES$^+$): 460 (M+1).

(405b) Following a procedure similar to (403c), the product from (405a) (40 mg, 0.087 mmol) was converted to the corresponding hydroxamate (405b) as a TFA salt (20 mg, 34%). MS (ES$^+$): 461 (M+1).

Example 406

(3S,4S)-1-butyl-N-hydroxy-4-({4-[(2-methyl-4-quinolinyl)methyl]benzoyl}amino)-3-pyrrolidinecarboxamide (406a) The TFA salt (403a) (43 mg, 0.07 mmol) was dissolved in 4 mL of dichloromethane. Diisopropylethylamine (26 mg, 36 μL, 0.2 mmol), butyraldehyde (8 mg, 10 μL) and NaBH(OAc)$_3$ (22 mg, 0.1 mmol) were added. The whole mixture was stirred until the reaction went to completion. The solution was diluted with ethyl acetate and washed with saturated NaHCO$_3$, H$_2$O and brine. The organic layer was dried over MgSO$_4$. After filtration and concentration, the residue was purified on silica gel to provide methyl (3S,4S)-1-butyl-N-hydroxy-4-({4-[(2-methyl-4-quinolinyl)methyl]benzoyl}amino)-3-pyrrolidinecarboxylate (20 mg, 64%). MS (ES$^+$): 460 (M+1).

(406b) Following a procedure similar to (403c), the product from (406a) (15 mg, 0.03 mmol) was converted to the corresponding hydroxamate (406b) as a TFA salt (7 mg, 34%). MS (ES$^+$): 461 (M+1).

Example 407

(3S,4S)-1-(2-butynyl)-N-hydroxy-4-({4-[(2-methyl-4-quinolinyl)methyl]benzoyl}amino)-3-pyrrolidinecarboxamide (407a) The TFA salt (403a) (70 mg, 0.11 mmol) was dissolved in 4 mL of chloroform and the solution was cooled to 0° C. Triethylamine (67 mg, 95 μL, 0.67 mmol) and 1-bromo-2-butynye (44 mg, 30 μL, 0.33 mmol) were added subsequently. The mixture was stirred until disappearance of compound (403a). The solution was diluted with ethyl acetate and washed with H$_2$O and brine, and dried over MgSO$_4$. After filtration and concentration, the residue was purified on silica gel to provide methyl (3S,4S)-1-(2-butynyl)-4-({4-[(2-methyl-4-quinolinyl)methyl]benzoyl}amino-3-pyrrolidinecarboxylate (17 mg, 34%). MS (ES$^+$): 456 (M+1).

(407b) Following a procedure similar to (403c), the product from (407a) (14 mg, 0.03 mmol) was converted to the corresponding hydroxamate (407b) as a TFA salt (10 mg, 50%). MS (ES$^+$): 457 (M+1).

Example 408

(3S,4S)-N-hydroxy-1-methyl-4-({4-[(2-methyl-4-quinolinyl)methyl]benzoyl}amino)-3-pyrrolidinecarboxamide (408a) Diisopropylethylamine (49 mg, 66 μL, 0.38 mmol), 37% aqueous formaldehyde (20 μL) and NaBH(OAc)$_3$ (40 mg, 0.19 mmol) were added to a solution of the TFA salt (403a) (80 mg, 0.13 mmol) in 4 mL of DMF. The whole mixture was stirred until the reaction went to completion. The solution was diluted with ethyl acetate and washed with saturated NaHCO$_3$, H$_2$O and brines The organic layer was dried over MgSO$_4$. After filtration and concentration, the residue was purified on silica gel to provide (408a) (50 mg, 93%). MS (ES$^+$): 418 (M+1).

(408b) Following a procedure similar to (403c), the product from (408a) (50 mg, 0.12 mmol) was converted to the corresponding hydroxamate (408b) as a TFA salt (40 mg, 52%). MS (ES$^+$): 419 (M+1).

Example 409

(3S,4S)-1-allyl-N-hydroxy-4-({4-[(2-methyl-4-quinolinyl)methyl]benzoyl}amino)-3-pyrrolidinecarboxamide (409a) Triethylamine (96 mg, 132 µL, 0.95 mmol) and allyl bromide (35 mg, 25 µL) were added to a solution of the TFA salt (403a) (60 mg, 0.1 mmol) in 4 mL of dichloromethane. The whole mixture was stirred until the reaction went to completion. The solution was diluted with ethyl acetate and washed with H$_2$O and brine. The organic layer was dried over MgSO$_4$. After filtration and concentration, the residue was purified on silica gel to provide (409a) (25 mg, 62%). MS (ES$^+$): 444 (M+1).

(409b) Following a procedure similar to (403c), the product from (409a) (20 mg, 0.045 mmol) was converted to the corresponding hydroxamate (409b) as a TFA salt (15 mg, 50%). MS (ES$^+$): 445 (M+1).

Example 410

(3S,4S)-1-(cyclopropylmethyl)-N-hydroxy-4-({4-[(2-methyl-4-quinolinyl)methyl]benzoyl}amino)-3-pyrrolidinecarboxamide (410a) Diisopropylethylamine (33 mg, 44 µL, 0.25 mmol), cyclopropanecarboxaldehyde (9 mg, 10 µL) and NaBH(OAc)$_3$ (27 mg, 0.13 mmol) were added to a solution of the TFA salt (403a) (40 mg, 0.063 mmol) in 4 mL of dichloromethane. The whole mixture was stirred until the reaction went to completion. The solution was directly loaded on silica gel column to provide (410a) (16 mg, 55%). MS (ES$^+$): 458 (M+1).

(410b) Following a procedure similar to (403c), the product from (410a) (12 mg, 0.026 mmol) was converted to the corresponding hydroxamate (410b) as a TFA salt (15 mg, 56%). MS (ES$^+$): 459 (M+1).

Example 411

(3S,4S)-1-cyclopentyl-N-hydroxy-4-({4-[(2-methyl-4-quinolinyl)methyl]benzoyl}amino)-3-pyrrolidinecarboxamide (411a) Diisopropylethylamine (33 mg, 44 µL, 0.25 mmol), cyclopentanone (11 mg, 11 µL) and NaBH(OAc)$_3$ (27 mg, 0.13 mmol) were added to a solution of the TFA salt (403a) (40 mg, 0.063 mmol) in 4 mL of dichloromethane. The whole mixture was stirred until the reaction went to completion. The solution was directly loaded on silica gel column to provide (411a) (20 mg, 66%). MS (AP$^+$): 472 (M+1).

(411b) Following a procedure similar to (403c), compound (411a) (15 mg, 0.032 mmol) was converted to the corresponding hydroxamate (411b) as a TFA salt (15 mg, 67%). MS (ES$^+$): 473 (M+1).

Example 412

(3S,4S)-N-hydroxy-4-({4-[(2-methyl-4-quinolinyl)methyl]benzoyl}amino)-1-neopentyl-3-pyrrolidinecarboxamide (412a) Diisopropylethylamine (33 mg, 44 µL, 0.25 mmol), trimethylacetylaldehyde (11 mg, 14 µL) and NaBH (OAc)$_3$ (27 mg, 0.13 mmol) were added to a solution of the TFA salt (403a) (40 mg, 0.063 mmol) in 4 mL of dichloromethane. The whole mixture was stirred until the reaction went to completion. The solution was directly loaded on silica gel column to provide (412a) (23 mg, 77%). MS (ES$^+$): 474 (M+1).

(412b) Following a procedure similar to (403c), the product from (412a) (20 mg, 0.042 mmol) was converted to the corresponding hydroxamate (412b) as a TFA salt (15 mg, 51%). MS (ES$^+$): 475 (M+1).

Example 413

(3S,4S)-N-hydroxy-4-({4-[(2-methyl-4-quinolinyl)methyl]benzoyl}amino)-1-tetrahydro-2H-pyran-4-yl-3-pyrrolidinecarboxamide (413a) The TFA salt (403a) (40 mg, 0.063 mmol) was dissolved in 4 mL of dichloromethane. Diisopropylethylamine (33 mg, 44 µL, 0.25 mmol), tetrahydro-4H-pyran-4-one (11 mg, 14 µL) and NaBH(OAc)$_3$ (27 mg, 0.13 mmol) were added. The whole mixture was stirred until the reaction went to completion. The solution was directly loaded on silica gel column to provide (413a) (25 mg, 80%). MS (ES$^+$): 488 (M+1).

(413b) Following a procedure similar to (403c), the product from (413a) (20 mg, 0.041 mmol) was converted to the corresponding hydroxamate (413b) as a TFA salt (15 mg, 50% yield). MS (ES$^+$): 489 (M+1).

Example 414

(3S,4S)-N-hydroxy-4-({4-[(2-methyl-4-quinolinyl)methyl]benzoyl}amino)-1-phenyl-3-pyrrolidinecarboxamide (414a) The TFA salt (403a) (80 mg, 0.13 mmol) was dissolved in 2 mL of dichloromethane. Triethylamine (78 mg, 120 µL, 0.75 mmol), phenyl boronic acid (31 mg, 0.25 mmol) and 4A molecule sieves (100 mg) were added. To this mixture was added copper acetate (35 mg, 0.19 mmol) and it was stirred under air until the reaction went to completion. The solution was filtered and washed with ethyl acetate. The filtrate was concentrated and the residue was loaded on silica gel column to provide (414a) (50 mg, 81%). MS (ES$^+$): 480 (M+1).

(414b) Following the procedure similar to (403c), the product from (414a) (45 mg, 0.094 mmol) was converted to the corresponding hydroxamate (414b) as a TFA salt (20 mg, 30%). MS (ES$^+$): 481 (M+1).

Example 415

(3S,4S)-1-(4-fluorophenyl)-N-hydroxy-4-({4-[(2-methyl-4-quinolinyl)methyl]benzoyl}amino)-3-pyrrolidinecarboxamide (415a) Triethylamine (67 mg, 92 µL, 0.66 mmol), 4-flourophenyl boronic acid (31 mg, 0.22 mmol) and 4A molecule sieves (100 mg) were added to a solution of the TFA salt 103a (70 mg, 0.11 mmol) in 5 mL of dichloromethane. To this mixture was added copper(II) acetate (30 mg, 0.17 mmol) and it was stirred under air until the reaction went to completion. The solution was filtered and washed with ethyl acetate. The filtrate was concentrated and the residue was loaded on silica gel column to provide (415a) (36 mg, 68%). MS (ES+): 498 (M+1).

(415b) Following the procedure similar to (403c), compound (415a) (30 mg, 0.06 mmol) was converted to the corresponding hydroxamate (415b) as a TFA salt (10 mg, 23%). MS (ES+): 499 (M+1)

Example 416

(3S,4S)-N-hydroxy-1-(4-methoxyphenyl)-4-({4-[(2-methyl-4-quinolinyl)methyl]benzoyl}amino)-3-pyrrolidinecarboxamide (416a) Triethylamine (68 mg, 94 μL, 0.67 mmol), 4-methoxyphenyl boronic acid (34 mg, 0.22 mmol) and 4A molecule sieves (100 mg) were added to a solution of the TFA salt (403a) (71 mg, 0.11 mmol) in 5 mL of dichloromethane. To this mixture was added copper(II) acetate (31 mg, 0.17 mmol) and it was stirred under air until the reaction went to completion. The solution was filtered and washed with ethyl acetate. The filtrate was concentrated and the residue was loaded on silica gel column to provide (416a) (31 mg, 54%). MS (ES−): 544 (M+Cl−).

(416b) Following the procedure similar to (403c), the product from (416a) (30 mg, 0.06 mmol) was converted to the corresponding hydroxamate (416b) as a TFA salt (10 mg, 23%). MS (ES+): 511 (M+1).

Example 417

(3S,4S)-1-acetyl-N-hydroxy-4-({4-[(2-methyl-4-quinolinyl)methyl]benzoyl}amino)-3-pyrrolidinecarboxamide (417a) The TFA salt (403a) (75 mg, 0.121 mmol) was dissolved in 4 mL of chloroform. Triethylamine (72 mg, 100 μL, 0.71 mmol), acetic anhydride (36 mg, 34 μL, 0.36 mmol) were added to the solution at 0° C. The mixture was stirred for 4 h and was directly loaded on silica gel column to provide (417a) (40 mg, 75%). MS (ES+): 891 (2M+1).

(417b) Following the procedure similar to (403c), the product from (417a) (35 mg, 0.079 mmol) was converted to the corresponding hydroxamate (417b) as a TFA salt (20 mg, 45%). MS (ES+): 447 (M+1).

Example 418

(3S,4S)-1-(2,2-dimethylpropanoyl)-N-hydroxy-4-({4-[(2-methyl-4-quinolinyl)methyl]benzoyl}amino)-3-pyrrolidinecarboxamide (418a) The TFA salt (403a) (70 mg, 0.111 mmol) was dissolved in 5 mL of dichloromethane. Triethylamine (68 mg, 100 μL, 0.67 mmol) and trimethylacetyl chloride (40 mg, 40 μL, 0.33 mmol) were added to the solution at 0° C. The mixture was stirred for 2 h and was directly loaded on silica gel column to provide (418a) (48 mg, 89%). MS (ES+): 488 (M+1).

(418b) Following the procedure similar to (403c), the product from (418a) (45 mg, 0.092 mmol) was converted to the corresponding hydroxamate (418b) as a TFA salt (20 mg, 36%). MS (ES+): 489 (M+1).

Example 419

(3S,4S)-N-hydroxy-1-(isopropylsulfonyl)-4-({4-[(2-methyl-4-quinolinyl)methyl]benzoyl}amino)-3-pyrrolidinecarboxamide (419a) The TFA salt (403a) (60 mg, 0.095 mmol) was dissolved in 4 mL of dichloromethane. Triethylamine (38 mg, 53 μL, 0.38 mmol) and isopropylsulfonyl chloride (20 mg, 16 μL, 0.14 mmol) were added to the solution at 0° C. The mixture was stirred for 2 h and was directly loaded on silica gel column to provide (419a) (28 mg, 58%). MS (ES+): 510 (M+1).

(419b) Following the procedure similar to (403c), the product from (419a) (22 mg, 0.043 mmol) was converted to the corresponding hydroxamate (419b) as a TFA salt (10 mg, 37%). MS (ES+): 511 (M+1).

Example 420

(3S,4S)-1-(butylsulfonyl)-N-hydroxy-4-({4-[(2-methyl-4-quinolinyl)methyl]benzoyl}amino)-3-pyrrolidinecarboxamide (420a) The TFA salt (403a) (74 mg, 0.12 mmol) was dissolved in 5 mL of dichloromethane. Triethylamine (71 mg, 98 μL, 0.70 mmol) and n-butylsulfonyl chloride (55 mg, 46 μL, 0.35 mmol) were added to the solution at 0° C. The mixture was stirred for 4 h and was directly loaded on silica gel column to provide (420a) (40 mg, 65%). MS (ES−): 558 (M+Cl−).

(420b) Following the procedure similar to (403c), the product from (420a) (35 mg, 0.067 mmol) was converted to the corresponding hydroxamate (420b) as a TFA salt (7 mg, 16%). MS (ES+): 525 (M+1).

Example 421 methyl (3S,4S)-3-[(hydroxyamino)carbonyl]-4-({4-[(2-methyl-4-quinolinyl)methyl]benzoyl}amino)-1-pyrrolidinecarboxylate (421a) The TFA salt (403a) (66 mg, 0.10 mmol) was dissolved in 5 mL of dichloromethane. Triethylamine (106 mg, 150 μL, 1.05 mmol) and methyl chloroformate (30 mg, 24 μL, 0.31 mmol) were added to the solution at 0° C. The mixture was stirred for 5 h and was directly loaded on silica gel column to provide (421a) (45 mg, >95%). MS (ES+): 496 (M+Cl−).

(421b) Following the procedure similar to (403c), the product from (421a) (40 mg, 0.086 mmol) was converted to the corresponding hydroxamate (421b) as a TFA salt (20 mg, 40%). MS (ES+): 463 (M+1).

Example 422

(3R,4S)-N-hydroxy-4-({4-[(2-methyl-4-quinolinyl)methyl]benzoyl}amino)tetrtahydro-3-furancarboxamide (422a) (50d) (65 mg, 40% ee, 0.36 mmol), diisopropylethylamine (186 mg, 125 μL, 1.44 mmol), and dichloromethane (5.0 mL) were added to a flask charged with the acid (401e) (100 mg, 0.36 mmol). The whole mixture was cooled to 0° C. and then BOP (192 mg, 0.43 mmol) was added in one portion. The resulting solution was stirred overnight and TLC showed completion of the reaction. The mixture was directly loaded on silica gel column to provide the desired product (422a) (67 mg, 46%). MS (ES+): 405 (M+1).

(422b) Following the procedure similar to (403c), the product from (422a) (67 mg, 0.17 mmol) was converted to the corresponding hydroxamate (422b) as a TFA salt (40 mg, 46%). MS (ES+): 406 (M+1).

Example 423

(3R,4R)-N-hydroxy-4-({4-[(2-methyl-4-quinolinyl)methyl]benzoyl}amino)tetrahydro-2H-pyran-3-carboxamide (423a) (39f) (285 mg, 1.0 mmol, 60%ee), triethylamine (2.0 mL), and dichloromethane (15.0 mL) were added to a flask charged with the acid (401e) (310 mg, 1.1 mmol). The whole mixture was cooled to 0° C. and then BOP (520 mg, 1.17 mmol) was added in one portion. The resulting solution was stirred overnight and TLC showed completion of the reaction. The mixture was directly loaded on silica gel column to provide (423a) (350 mg, 84%). MS (ES$^+$): 433 (M+1).

(423b) Following the procedure similar to (403c), the product from (423a) (75 mg, 0.17 mmol) was converted to the corresponding hydroxamate (423b) as a TFA salt (77 mg, 85%). MS (ES$^+$): 420 (M+1).

Example 424

N-{cis-2-[(hydroxyamino)carbonyl]cyclopentyl}-4-[(2-methyl-4-quinolinyl)methyl]benzamide (424a) Ethyl cis-2-aminocyclopentanecarboxylate.HCl (23 mg, 0.144 mmol), diisopropylethylamine (74 mg, 0.58 mmol), and dichloromethane (25.0 mL) were added to a flask charged with the acid from (401e) (40 mg, 0.144 mmol). The whole mixture was cooled to 0° C. and then BOP (770 mg, 0.17 mmol) was added in one portion. The resulting solution was stirred overnight and TLC showed completion of the reaction. The mixture was directly loaded on silica gel column to provide the desired product (424a) (44 mg, 73%). MS (ES$^+$): 833 (2M+1).

(424b) Following the procedure similar to (403c), the product from (424a) (40 mg, 0.1 mmol) was converted to the corresponding hydroxamate (424b) as a TFA salt (20 mg, 40%). MS (ES$^+$): 404 (M+1).

Example 425 tert-butyl (3S,4S)-3-[(hydroxyamino)carbonyl]-4-({4-[(2-isopropyl-4-quinolinyl)methyl]benzoyl}amino)-1-pyrrolidinecarboxylate (425a) Malonic acid-(4.1 g, 40 mmol) was mixed with phosphorus oxytribromide (35 g) in an open vessel at 60° C. Aniline (4.65 g) was carefully added in portion and the mixture was then heated at 130° C. for 3 h. The resulting tar-like crust was cooled and carefully poured into iced water. The solution was neutralized with 1N NaOH and the solid formed was collected. The solid was dissolved in dichloromethane and purified by chromatography to provide 2,4-dibromoquinoline (5.2 g, 44%). MS (ES$^+$): 288 (M+1).

(425b) Tetrakis(triphenylphosphine)palladium (1.1 g, 1 mmol) and 2-propenylmagnium bromide solution (0.5M, 10 mmol, 20 mL) were added to a solution of (425a) (2.9 g, 10.1 mmol) in 20 mL of THF at 0° C. The reaction mixture was stirred at rt for 2 days and was quenched with MeOH. The solution was diluted with ethyl acetate and washed with H$_2$O and brine, and dried over MgSO$_4$. After filtration and concentration, the residue was purified to provide 4-bromo-2-isopropenylquinoline (1.54 g, 61%). MS (ES$^+$): 248, 250 (M+1).

(425c) A solution of n-BuLi (2.5M, 7.5 mmol, 3 mL) was added to a solution of (425b) (1.55 g, 6.25 mmol) in 20 mL of anhydrous THF at −78° C. The resulting solution was cannulated to another flask charged with methyl 4-formylbenzoate (1.34 g, 8.1 mmol) in 20 mL of anhydrous THF at −78° C. The reaction mixture was stirred for 3 h at −78° C. before quenched with MeOH. The solution was then diluted with ethyl acetate and washed with H$_2$O and brine, and dried over MgSO$_4$. After filtration and concentration, the residue was purified on silica gel column to provide methyl 4-[hydroxy(2-isopropenyl-4-quinolinyl)methyl]benzoate (0.95 g, 46%). MS (AP$^+$): 333 (M+1).

(425d) The product from (425c) (950 mg, 2.85 mmol) was dissolved in 100 mL of dichloromethane. The solution was cooled to 0° C. and triethylamine (2.0 mL, 14.3 mmol) and MsCl (0.44 mL, 5.7 mmol) were added. The ice bath was removed and the reaction been monitored by TLC until the disappearance of starting material. The solution was diluted with ethyl acetate and washed with H$_2$O and brine. The organic layer was dried over MgSO$_4$, filtered, and concentrated. The residue was purified to provide (425d) (1.0 g, >95%). MS (ES$^+$): 412 (M+1).

(425e) A solution of the mesylate from (425d) (1.0 g, 0.2.43 mmol) in 10 mL of MeOH and 10 mL of EtOAc was added to a suspension of the Pd/C catalyst (250 mg, 10%) in 20 mL of MeOH. The reaction took place after the flask was purged with H$_2$. The reaction monitored by TLC until disappearance of the starting material. After filtered, the solution was concentrated and the residue was purified on silica gel to provide the desired product (425e) as a methanesulfuric acid salt (1.0 g, quantitative yield). MS (ES$^+$): 320 (M+1).

(425f) A solution of aqueous NaOH (1N, 5 mL) was added to a solution of (425e) (1.0 g, 2.4 mmol) in 10 mL of MeOH. The reaction mixture was heated up to 60° C. until completion of the reaction, monitored by TLC. Upon the completion, one equivalent of aqueous HCl (1N, 5 mL) was added to neutralize the base. The solution was concentrated to dryness and the residue was redissolved in MeOH. After filtration, the methanolic solution was concentrated again to provide the desired product (425f) (700 mg, >95%). MS (ES$^+$): 306 (M+1).

(425 g) (1e) (160 mg, 0.65 mmol), diisopropylethylamine (339 mg, 0.45 mL, 2.62 mmol), dichloromethane (10.0 mL) to a flask charged with the acid 125f (200 mg, 0.65 mmol). The whole mixture was cooled to 0° C. and then BOP (348 mg, 0.78 mmol) was added in one portion. The resulting solution was stirred overnight and TLC showed completion of the reaction. The solution was directly loaded on silica gel column to provide the desired product (425 g) (300 mg, 85%). MS (ES$^+$): 532 (M+1).

(425 h) Following the procedure similar to (403c), the product from (425 g) (30 mg, 0.056 mmol) was converted to the corresponding hydroxamate (425 h) as a TFA salt (25 mg, 69% yield). MS (ES$^+$): 533(M+1).

Example 426

(3S,4S)-N-hydroxy-4-({4-[(2-isopropyl-4-quinolinyl)methyl]benzoyl}amino)-3-pyrrolidinecarboxamide (426a) 2 mL of TFA was added to a solution of (425 h) (17 mg, 0.026 mmol) in 2 mL of dichloromethane. The resulting solution was stirred for 30 min and the solvent was removed under vacuum. The desired product (426a) was obtained in quantitative yield. MS (ES$^+$): 433 (M+1).

Example 427

(3S,4S)-N-hydroxy-4-({4-[(2-isopropyl-4-quinolinyl)methyl]benzoyl}amino)-1-(2-propynyl)-3-pyrrolidinecarboxamide (427a) The product from (425 g) (265 mg, 0.50 mmol) was dissolved in 2 mL of dichloromethane and then 2 mL of TFA was added to the solution. The resulting mixture was stirred for 30 min and the solvent was removed in vacuum. The desired product (427a) was obtained as a TFA salt in quantitative yield. MS (ES$^+$): 432(M+1).

(427b) The TFA salt from (427a) (50 mg, 0.076 mmol) was dissolved in 0.1 mL of chloroform and the solution was cooled to 0° C. Triethylamine (77 mg, 106 μL, 0.76 mmol) and propargyl bromide (56 mg, 42 μL, 0.38 mmol) were added subsequently. The mixture was stirred until disappearance of the product from (127a). The solution was directly loaded on silica gel column to provide the desired product (427b) (24 mg, 67%). MS (ES$^+$): 470 (M+1).

(427c) 1 mL of NH$_2$OH/NaOMe/MeOH (1.64M) was added to a flask charged with the product from (427b) (24 mg, 0.05 mmol) at 0° C. The solution was stirred for 15 min and was quenched with an equal amount of aqueous HCl solution (1N). The resulting solution was purified on reverse phase HPLC to provide (427c) as a TFA salt (20 mg, 57%). MS (ES$^+$): 471 (M+1).

Example 428

(3S,4S)-N-hydroxy-1-isopropyl-4-({4-[(2-isopropyl-4-quinolinyl)methyl]benzoyl}amino)-3-pyrrolidinecarboxamide (428a) Diisopropylethylamine (98 mg, 132 μL, 0.76 mmol), acetone (22 mg, 28 μL) and NaBH(OAc)$_3$ (80 mg, 0.38 mmol) were added to a solution of the TFA salt from (427a) (50 mg, 0.076 mmol) in 1 mL of dichloromethane. The whole mixture was stirred until the reaction went to completion. The solution was directly loaded on silica gel column to provide (428a) (18 mg, 50%). MS (ES$^+$): 474 (M+1).

(428b) Following the procedure similar to (403c), the product from (428a) (18 mg, 0.038 mmol) was converted to the corresponding hydroxamate (428b) as a TFA salt (20 mg, 75%). MS (ES$^+$): 475 (M+1).

Example 429

(3S,4S)-N-hydroxy-4-({4-[(2-isopropyl-4-quinolinyl)methyl]benzoyl}amino)-1-methyl-3-pyrrolidinecarboxamide (429a) Diisopropylethylamine (98 mg, 132 μL, 0.76 mmol), 37% formaldehyde (30 mg, 30 μL) and NaBH(OAc)$_3$ (80 mg, 0.38 mmol) were added to a solution of the TFA salt from (427a) (50 mg, 0.076 mmol) in 5 mL of dichloromethane. The whole mixture was stirred until the reaction went to completion. The solution was directly loaded on silica gel column to provide (429a) (24 mg, 70%). MS (ES$^+$): 446 (M+1).

(429b) Following the procedure similar to (403c), the product from (429a) (24 mg, 0.054 mmol) was converted to the corresponding hydroxamate (429b) as a TFA salt (15 mg, 41% yield). MS (ES$^+$): 447 (M+1).

Example 430

(3S,4S)-1-cyclopentyl-N-hydroxy-4-({4-[(2-isopropyl-4-quinolinyl)methyl]benzoyl}amino)-3-pyrrolidinecarboxamide (430a) Diisopropylethylamine (102 mg, 138 μL, 0.79 mmol), cyclopentanone (40 mg, 42 μL) and NaBH(OAc)$_3$ (101 mg, 0.48 mmol) were added to a solution of the TFA salt from (427a) (100 mg, 0.158 mmol) in 5 mL of dichloromethane. The whole mixture was stirred until the reaction went to completion. The solution was directly loaded on silica gel column to provide (430a) (65 mg, 86%). MS (ES$^+$): 472 (M+1).

(430b) Following the procedure similar to (403c), the product from (430a) (65 mg, 0.137 mmol) was converted to the corresponding hydroxamate (430b) as a TFA salt (50 mg, 52%). MS (ES$^+$): 473 (M+1).

Example 431

(3R,4R)-N-hydroxy-4-({4-[(2-isopropyl-4-quinolinyl)methyl]benzoyl}amino)tetrahydro-2H-pyran-3-carboxamide (431a) (39f) (47 mg, 60% ee, 0.16 mmol), diisopropylethylamine (85 mg, 114 μL) and dichloromethane (5.0 mL) were added to a flask charged with the acid from (425f) (50 mg, 0.16 mmol). The whole mixture was cooled to 0° C. and then BOP (87 mg, 0.20 mmol) was added in one portion. The resulting solution was stirred overnight and TLC showed completion of the reaction. The mixture was directly loaded on silica gel column to provide the desired product (431a) (39 mg, 52%). MS (ES$^+$): 461 (M+1).

(431b) Following the procedure similar to (403c), the product from (431a) (30 mg, 0.067 mmol) was converted to the corresponding hydroxamate (431b) as a TFA salt (20 mg, 53%). MS (ES$^+$): 448 (M+1)

Example 432

N-{cis-2-[(hydroxyamino)carbonyl]cyclopentyl}-4-[(2-isopropyl-4-quinolinyl)methyl]benzamide (432a) Ethyl cis-2-aminocyclopentanecarboxylate.HCl (32 mg, 0.16 mmol), diisopropylethylamine (85 mg, 114 μL), and dichloromethane (5.0 mL) were added to a flask charged with the acid from (425f) (50 mg, 0.16 mmol). The whole mixture was cooled to 0° C. and then BOP (87 mg, 0.20 mmol) was added in one portion. The resulting solution was stirred overnight and TLC showed completion of the reaction. The mixture was directly loaded on silica gel column to provide the desired product (432a) (35 mg, 48%). MS (ES$^+$): 445 (M+1).

(432b) Following the procedure similar to (403c), the product from (432a) (30 mg, 0.067 mmol) was converted to the corresponding hydroxamate (432b) as a TFA salt (20 mg, 53%). MS (ES$^-$): 544 (M+TFA-1).

Example 433

(3R,4S)-N-hydroxy-4-({4-[(2-isopropyl-4-quinolinyl)methyl]benzoyl}amino)tetrtahydro-3-furancarboxamide (433a) (50d) (35 mg, 40% ee, 0.24 mmol), diisopropylethylamine (125 mg, 168 μL, 0.96 mmol) and dichloromethane (5.0 mL) were added to a flask charged with the acid from (425f) (75 mg, 0.24 mmol). The whole mixture was cooled to 0° C. and then BOP (128 mg, 0.29 mmol) was added in one portion. The resulting solution was stirred overnight and TLC showed completion of the reaction. The mixture was directly loaded on silica gel column to provide the desired product (433a) (65 mg, 62%). MS (ES$^+$): 433 (M+1).

(433b) Following the procedure similar to (403c), the product from (433a) (65 mg, 0.15 mmol) was converted to the corresponding hydroxamate (433b) as a TFA salt (40 mg, 50%). MS (ES$^+$): 434 (M+1).

Example 434 tert-butyl (3S,4S)-3-({4-[(2-ethyl-4-quinolinyl)methyl]benzoyl}amino)-4-[(hydroxyamino)carbonyl]-1-pyrrolidinecarboxylate (434a) 2-Ethyl-4-hydroxyquinoline was prepared according to a known procedure (*J. Med. Chem.* 1992, 35, 4036).

2-Ethyl-4-hydroxyquinoline (5.0 g, 28.9 mmol) and phosphorus oxytribromide (12.4 g, 43.3 mmol) were added to a round-bottom flask. The mixture was heated to 120° C. for 4 h. After cooling down to rt, ice was added and the aqueous solution was extracted with ethyl acetate. The organic layer was washed with saturated $Na_2CO_3$, $H_2O$, brine, and dried over $MgSO_4$. After filtration and concentration, the residue was purified on silica gel to provide 4-bromo-2-ethylquinoline (434a) (3.6 g, 53%). MS ($AP^+$): 235.9, 237.9 (M+1).

(434b) Following a similar procedure of (401b), 4-bromo-2-ethylquinoline (3.0 g, 12.7 mmol) was converted to methyl 4-[hydroxy(2-ethyl-4-quinolinyl)methyl]benzoate (434b) (2.82 g, 69%). MS ($AP^+$): 322 (M+1).

(434c) Following a similar procedure of (401c), the product from (434b) was converted to methyl 4-{(2-ethyl-4-quinolinyl)[(methylsulfonyl)oxy]methyl}benzoate in quantitative yield. MS ($AP^+$): 400 (M+1).

(434d) Following a similar procedure of (401d), the product from (434c) was converted to methyl 4-[(2-ethyl-4-quinolinyl)methyl]benzoate in 94% yield. MS ($AP^+$): 306 (M+1).

(434e) Following a similar procedure of (401e), the product from (434d) was converted to 4-[(2-ethyl-4-quinolinyl)methyl]benzoic acid in quantitative yield. MS ($ES^+$): 292 (M+1).

(434f) Following a similar procedure of (401f), the acid from (434e) (200 mg, 1.03 mmol) was coupled with (1e) (252 mg, 1.03 mmol) to provide 1-tert-butyl 3-methyl (3S, 4S)-4-({4-[(2-ethyl-4-quinolinyl)methyl]benzoyl}amino)-1,3-pyrrolidinedicarboxylate (450 mg, 84%). MS ($ES^-$): 552 (M+$Cl^-$−1).

(434g) Following the procedure similar to (403c), the product from (434f) (20 mg, 0.04 mmol) was converted to the corresponding hydroxamate (434 g) as a TFA salt (15 mg, 60%). MS ($ES^+$): 519 (M+1).

Example 435

(3S,4S)-4-({4-[(2-ethyl-4-quinolinyl)methyl]
benzoyl}amino)-N-hydroxy-3-
pyrrolidinecarboxamide (435a) Following a procedure similar to (402a), the product from (434 g) (9 mg, 0.014 mmol) was converted to the corresponding product (435a) as a TFA salt (10 mg, quantitative yield). MS ($ES^+$): 419 (M+1).

Example 436

(3S,4S)-4-({4-[(2-ethyl-4-quinolinyl)methyl]
benzoyl}amino)-N-hydroxy-1-(2-propynyl)-3-
pyrrolidinecarboxamide (436a) Following a procedure similar to (403a), the product from (434f) (410 mg, 0.79 mmol) was converted to methyl (3S,4S)-4-({4-[(2-ethyl-4-quinolinyl)methyl]benzoyl}amino-3-pyrrolidinecarboxylate in quantitative yield. MS ($ES^+$): 418 (M+1).

(436b) Following a procedure similar to (403b), the product from (436a) (100 mg, 0.15 mmol) was converted to the corresponding product, methyl (3S,4S)-4-({4-[(2-ethyl-4-quinolinyl)methyl]benzoyl}amino-1-(2-propynyl)-3-pyrrolidinecarboxylate (31 mg, 44%).

(436c) Following a procedure similar to (403c), the product from (436b) (30 mg, 0.065 mmol) was converted to the corresponding hydroxamate (436c) (25 mg, 68%). MS ($ES^+$): 457 (M+1).

Example 437

(3S,4S)-1-(2-butynyl)-4-({4-[(2-ethyl-4-quinolinyl)
methyl]benzoyl}amino)-N-hydroxy-3-
pyrrolidinecarboxamide (437a) Following a procedure similar to (407a), the product from (436a) (100 mg, 0.15 mmol) was converted to methyl (3S,4S)-1-(2-butynyl)-4-({4-[(2-ethyl-4-quinolinyl)methyl]benzoyl}amino)-3-pyrrolidinecarboxylate (33 mg, 45%). MS ($ES^+$): 470 (M+1).

(437b) Following a procedure similar to (403c), the product from (437a) (30 mg, 0.064 mmol) was converted to the corresponding hydroxamate (437b) (25 mg, 68%). MS ($ES^+$): 471 (M+1).

Example 438

(3R,4R)-4-({4-[(2-ethyl-4-quinolinyl)methyl]
benzoyl}amino)-N-hydroxytetrahydro-2H-pyran-3-
carboxamide (438a) Following a procedure similar to (423a), the product from (434e) (50 mg, 0.17 mmol) was coupled with (39f) (60% ee) to provide (438a) (70 mg, 92%). MS ($ES^+$): 447 (M+1). (438b) Following a procedure similar to (403c), the product from (438a) (70 mg, 0.157 mmol) was converted to the corresponding hydroxamate (438b) as a TFA salt (40 mg, 47% yield). MS ($ES^+$): 434 (M+1).

Example 439

4-[(2-ethyl-4-quinolinyl)methyl]-N-{cis-2-
[(hydroxyamino)carbonyl]cyclopentyl}-benzamide (439a) Following a procedure similar to (424a), the product from (434e) (50 mg, 0.17 mmol) was coupled with ethyl cis-2-aminocyclopentanecarboxylate.HCl to provide the desired product (439a) (64 mg, 90%). MS ($ES^+$): 861(2M+1).

(439b) Following the procedure similar to (403c), the product from (439a) (60 mg, 0.13 mmol) was converted to the corresponding hydroxamate (439b) as a TFA salt (40 mg, 58%). MS ($ES^+$): 418 (M+1).

Example 440

(3R,4S)-4-({4-[(2-ethyl-4-quinolinyl)methyl]
benzoyl}amino)-N-hydroxytetrtahydro-3-
furancarboxamide (440a) Following a procedure similar to (422a), the product from (434e) (70 mg, 0.24 mmol) was coupled with (50d) (40% ee) to provide (440a) (65 mg, 65%). MS ($ES^-$): 453 (M+Cl−1).

(440b) Following the procedure similar to (403c), the product from (440a) (65 mg, 0.15 mmol) was converted to the corresponding hydroxamate (440b) as a TFA salt (40 mg, 50%). MS ($ES^+$): 420 (M+1).

Example 441 tert-butyl (3S,4S)-3-[(hydroxyamino)carbonyl]-4-
({4-[(2-(trifluoromethyl)-4-quinolinyl)methyl]
benzoyl}amino)-1-pyrrolidinecarboxylate (441a) Following a procedure similar to (434a), 4-hydroxy-2-trifluoromethylquinoline (9.89 g, 46.4 mmol) was converted to 4-bromo-2-trifluoromethylquinoline (12.5 g, 97%). MS ($AP^+$): 276 (M+1).

(441b) Following a similar procedure of (401b), 4-bromo-2-trifluoromethylquinoline (1.0 g, 3.6 mmol) was converted to methyl 4-[hydroxy(2-thifluoromethyl-4-quinolinyl)methyl]benzoate (0.38 g, 29%). MS (AP$^+$): 362 (M+1).

(441c) Following a similar procedure of (401c), the product from (441b) (0.36 g, 1 mmol) was converted to methyl 4-{(2-trifluoromethyl-4-quinolinyl)[(methylsulfonyl) oxy]methyl}benzoate in quantitative yield. MS (AP$^+$): 440 (M+1).

(441d) Following a similar procedure of (401d), the product from (441c) was converted to methyl 4-[(2-trifluoromethyl-4-quinolinyl)methyl]benzoate in quantitative yield. MS (ES$^+$): 346 (M+1).

(441e) Following a similar procedure of (401e), the product from (441d) was converted to 4-[(2-trifluoromethyl-4-quinolinyl)methyl]benzoic acid in quantitative yield. MS (AP$^+$): 332 (M+1).

(441f) Following a similar procedure of (401f), the acid from (441e) (184 mg, 0.44 mmol) was coupled with (1e) (130 mg, 0.50 mmol) to provide 1-tert-butyl 3-methyl (3S,4S)-4-({4-[(2-trifluoromethyl-4-quinolinyl)methyl]benzoyl}amino)-1,3-pyrrolidinedicarboxylate (154 mg, 62%). MS (AP$^+$): 558 (M+1).

(441g) Following the procedure similar to (403c), the product from (441f) (36 mg, 0.06 mmol) was converted to the corresponding hydroxamate (441 g) as a TFA salt (33 mg, 80%). MS (ES$^+$): 559 (M+1).

Example 442

(3R,4R)-N-hydroxy-4-[(4-{[2-(trifluoromethyl)-4-quinolinyl]methyl}benzoyl)amino]tetrahydro-2H-pyran-3-carboxamide (442a) Following a procedure similar to (423a), the product from (441e) (53 mg, 0.15 mmol) was coupled with (39f) (60% ee) to provide the corresponding product (442a) (39 mg, 54%). MS (AP$^+$): 487 (M+1).

(442b) Following a procedure similar to (403c), the product from (442a) (38 mg, 0.078 mmol) was converted to the corresponding hydroxamate (442b) as a TFA salt (35 mg, 75%). MS (ES$^+$): 474 (M+1).

Example 443

N-{cis-2-[(hydroxyamino)carbonyl]cyclopentyl}-4-{[2-(trifluoromethyl)-4-quinolinyl]methyl}benzamide (443a) Following a procedure similar to (424a), the product from (441e) (71 mg, 0.17 mmol) was coupled with ethyl cis-2-aminocyclopentanecarboxylate.HCl to provide the desired product (443a) (40 mg, 51%). MS (AP$^+$): 471 (M+1).

(443b) Following the procedure similar to (403c), the product from (443a) (40 mg, 0.085 mmol) was converted to the corresponding hydroxamate (443b) as a TFA salt (29 mg, 60%). MS (ES$^+$): 458 (M+1).

Example 444 tert-butyl (3S,4S)-3-[(hydroxyamino)carbonyl]-4-({4-[(2,3-dimethyl-4-quinolinyl)methyl]benzoyl}amino)-1-pyrrolidinecarboxylate (444a) Ethyl 2-methylacetoacetate (28.8 g, 200 mmol) and catalytic p-toluenesulfuric acid were added to a solution of aniline (18.6 g, 200 mmol) in 200 mL of benzene. The mixture was heated to reflux and water generated in the reaction was collected. Upon the collection of theoretical amount of water, the solution was cooled and insoluble material was filtered off. After concentration of the organic solution, the crude material (444a) (39.0 g, 89%) was purified for the next reaction. MS (ES$^+$): 220 (M+1).

(444b) In a flask with distillation head and thermometer to monitor internal temperature was added 120 mL of phenylether. In an additional funnel was charged a solution of (444a) (10.0 g, 45.6 mmol) in 20 mL of phenylether. The flask was preheated to 240° C. and the (444a) solution was added at a rate to control temperature between 240–245° C. After addition complete, the internal temperature of the flask was maintained at 245° C. for 25 min while distilling off ethanol. After cooling down the flask, the solid was filtered off and washed with hexane. The solid thus obtained is 2,3-dimethyl-4-hydroxyquinoline (7.5 g, 95%). MS (ES$^+$): 174 (M+1).

(444c) Following a procedure similar to (434a), the product from (444b) (7.5 g, 43 mmol) was converted to 4-bromo-2,3-dimethylquinoline (6.87 g, 67%). MS (ES$^+$): 236 (M+1).

(444d) Following a similar procedure of (401b), 2-bromo-2,3-dimethylquinoline (3.4 g, 14.6 mmol) was converted to methyl 4-[hydroxy(2,3-dimethyl-4-quinolinyl)methyl]benzoate (0.61 g, 13%). MS (ES$^+$): 322 (M+1).

(444e) Following a similar procedure of (401c), the product from (444d) (0.61 g, 1.9 mmol) was converted to methyl 4-{(2,3-dimethyl-4-quinolinyl)[(methylsulfonyl)oxy]methyl}benzoate (0.66 g, 87%). MS (ES$^+$): 400 (M+1).

(444f) Following a similar procedure of (401d), the product from (444e) was converted to methyl 4-[(2,3-dimethyl-4-quinolinyl)methyl]benzoate in quantitative yield. MS (AP$^+$): 306 (M+1).

(444g) Following a similar procedure of (401e), the product from (444f) was converted to 4-[(2,3-dimethyl-4-quinolinyl)methyl]benzoic acid in quantitative yield. MS (AP$^+$): 292 (M+1).

(444h) Following a similar procedure of (401f), the acid from (444 g) (145 mg, 0.44 mmol) was coupled with (1e) (130 mg, 0.53 mmol) to provide 1-tert-butyl 3-methyl (3S,4S)-4-({4-[(2,3-dimethyl-4-quinolinyl)methyl]benzoyl}amino)-1,3-pyrrolidinedicarboxylate (159 mg, 69%). MS (AP$^+$): 518 (M+1).

(444i) Following the procedure similar to (403c), the product from (444 h) (40 mg, 0.077 mmol) was converted to the corresponding hydroxamate (444I) as a TFA salt (34 mg, 70%). MS (ES$^+$): 519 (M+1).

Example 445

(3R,4R)-4-({4-[(2,3-dimethyl-4-quinolinyl)methyl]benzoyl}amino)-N-hydroxytetrahydro-2H-pyran-3-carboxamide (445a) Following a procedure similar to (423a), the acid from (444 g) (47 mg, 0.15 mmol) was coupled with (39f) (60% ee) to provide the corresponding product (445a) (45 mg, 69%). MS (ES$^+$): 448 (M+1).

(445b) Following a procedure similar to (403c), the product from (445a) (45 mg, 0.1 mmol) was converted to the corresponding hydroxamate (445b) as a TFA salt (44 mg, 80%). MS (ES$^+$): 434 (M+1).

Example 446

4-[(2,3-dimethyl-4-quinolinyl)methyl]-N-{cis-2-[(hydroxyamino)carbonyl]cyclopentyl}benzamide (446a) Following a procedure similar to (424a), the acid from (444 g) (56 mg, 0.17 mmol) was coupled with ethyl cis-2-aminocyclopentanecarboxylate.HCl to provide the desired product (446a) (59 mg, 80%). MS (ES+): 431 (M+1).

(446b) Following the procedure similar to (403c), the product from (446a) (50 mg, 0.13 mmol) was converted to the corresponding hydroxamate (446b) as a TFA salt (46 mg, 66%). MS (ES+): 418 (M+1).

Example 447

(3S,4S)-N-hydroxy-4-[(4-{[2-(trifluoromethyl)-4-quinolinyl]methyl}benzoyl)amino]-1-(2-propynyl)-3-pyrrolidinecarboxamide (447a) To a solution of (441f) in 3 mL of $CH_2Cl_2$ was added 1.0 mL of TFA. The reaction was followed by TLC. Upon the completion of the reaction, the solution was concentrated under reduced pressure to dryness to provide the desired product (447a) in quantitative yield. MS (AP+): 458 (M+1).

(447b) To a flask charged with the product from (442a) (61 mg, 0.09 mmol) were added 2.0 mL of $CH_2Cl_2$, DIEA (78 µL, 0.45 mmol) and propargyl bromide (24 µL, 0.27 mmol). The mixture was stirred under $N_2$ for 2 days. Upon completion of the reaction, the solvent was removed and the residue was directly loaded on column and purified by flash column chromatography to provide the desired product (447b) (29 mg, 64%). MS (AP+): 496 (M+1).

(447c) Following the procedure similar to (403c), the product from (447b) (28 mg, 0.056 mmol) was converted to the corresponding hydroxamate (447c) as a TFA salt (30 mg, 88%). MS (ES+): 497 (M+1).

Example 448

(3R,4S)-N-hydroxy-4-[(4-{[2-(trifluoromethyl)-4-quinolinyl]methyl}benzoyl)amino]-tetrahydro-3-furancarboxamide (448a) Following a procedure similar to (424a), the product from (441e) (71 mg, 0.17 mmol) was coupled with (50d) (40% ee) to provide the desired product (448a) (23 mg, 25%). MS (AP+): 459 (M+1).

(448b) Following the procedure similar to (403c), the product from (448a) (22 mg, 0.047 mmol) was converted to the corresponding hydroxamate (448b) as a TFA salt (18 mg, 75%). MS (ES+): 460 (M+1).

Example 449

(3S,4S)-4-({4-[(2,3-dimethyl-4-quinolinyl)methyl]benzoyl}amino)-N-hydroxy-1-(2-propynyl)-3-pyrrolidinecarboxamide (449a) Following the procedure similar to (447a), the product from (444 h) (132 mg, 0.25 mmol) was converted to the desired product (449a) in quantitative yield. MS (AP+): 418 (M+1).

(449b) Following the procedure similar to (447b), the product from (449a) (80 mg, 0.13 mmol) was converted to the desired product (449b) (26 mg, 45%). MS (AP+): 456 (M+1).

(449c) Following the procedure similar to (403c), the product from (449b) (26 mg, 0.056 mmol) was converted to the corresponding hydroxamate (449c) as a TFA salt (23 mg, 60%). MS (ES+): 457 (M+1).

Example 450

(3R,4S)-N-hydroxy-4-({4-[(2,3-dimethyl-4-quinolinyl)methyl]benzoyl}amino)-tetrahydro-3-furancarboxamide (450a) Following a procedure similar to (424a), the product from (446 g) (68 mg, 0.20 mmol) was coupled with (50d) (40% ee) to provide the desired product (450a) (57 mg, 68%). MS (AP+): 419 (M+1).

(450b) Following the procedure similar to (403c), the product from (450a) (50 mg, 0.12 mmol) was converted to the corresponding hydroxamate (450b) as a TFA salt (39 mg, 61%). MS (ES+): 420 (M+1).

Example 451

(3R,4R)-4-[(4-{[2-(dimethylamino)-4-quinolinyl]methyl}benzoyl)amino]-N-hydroxytetrahydro-2H-pyran-3-carboxamide (451a) Malonic acid (4.1 g, 40 mmol) was mixed with phosphorus oxytribromide (35 g) in an open vessel at 60° C. Aniline (4.65 g) was carefully added in portion and the mixture was then heated at 130° C. for 3 h. The resulting tar-like material was cooled and carefully transferred into iced water. The solution was neutralized with 1N NaOH and the solid formed was collected. The solid was dissolved into dichloromethane and purified by chromatography to provide 2,4-dibromoquinoline (451a) (5.2 g, 44%). MS (ES+): 288 (M+1).

(451b) The product from (451a) (2.0 g, 7.0 mmol) was dissolved in 10 mL of 40% dimethylamine solution in $H_2O$. The reaction mixture was allowed to stir overnight. The solution was diluted to 40 mL with $H_2O$ and it was extracted with EtOAc for three times. The combined organic layer was dried over $MgSO_4$. After concentration, the residue was purified on silica gel column to provide 4-bromo-2-dimethylaminoquinoline (451b) (0.69 g, 40%). MS (AP+): 251 (M+1).

(451c) Following a procedure similar to (401b), the product from (451b) (0.67 g, 2.7 mmol) was converted to the corresponding product (451c) (0.15 g, 17%). MS (AP+): 337 (M+1).

(451d) Following a procedure similar to (401c), the product from (451c) (0.15 g, 0.46 mmol) was converted to the corresponding product (451d) in quantitative yield. MS (AP+): 415(M+1).

(451e) Following a procedure similar to (401d), the product from (451d) (0.19 g, 0.46 mmol) was hydrogenated to the corresponding product (451e) (106 mg, 57%). MS (AP+): 321 (M+1).

(451f) Following a procedure similar to (401e), the product from (451e) (0.1 g, 0.26 mmol) was converted to the corresponding acid (451f) in quantitative yield. MS (ES+): 307 (M+1).

(451 g) Following a procedure similar to (401f), the product from (451f) (39 mg, 0.13 mmol) was coupled with (39f) (60% ee) to provide the desired product (451 g) (20 mg, 33%). MS (ES+): 462 (M+1).

(451 h) Following a procedure similar to (403c), the product from (451 g) (20 mg, 0.04 mmol) was converted to the corresponding hydroxamate (451 h) (20 mg, 88%) as a TFA salt. MS (ES+): 449 (M+1).

Example 452

(3R,4S)-4-({4-[(2-cyclopropyl-4-quinolinyl)methyl]benzoyl}amino)-N-hydroxytetrahydro-3-furancarboxamide (452a) To a flask were charged aniline (6.55 g, 70 mmol), methyl 3-cyclopropyl-3-oxo-propionate(10.0 g, 70 mmol), p-TSOH (0.3 g) and 100 mL of benzene. The mixture was heated to reflux and water was thus removed via Dean-Stark apparatus. After cooled down, insoluble material was filtered and the filtrate was concentrated. The resulting residue was purified on silica gel column to provide the desired enamine product (452a) (4.5 g, 30%). MS (AP$^+$): 218 (M+1).

(452b) The product from (452a) (4.5 g, 0.021 mol) was dissolved in 50 mL of Ph$_2$O and the solution was heated to 240° C. for 1 h. After cooled down, the solution was diluted with hexane and the precipitate (452b) (3.5 g, 90%) was collected. MS (AP$^+$): 186 (M+1).

(452c) To a solution of the product from (452b) (1.0 g, 5.4 mmol) in 50 mL of anhydrous THF at −78° C. was added LiHMDS (1.0 M, 5.4 mL, 5.4 mmol). The solution was stirred for 1 h, followed by addition of a solution of 2-[N,N-bis(trifluoromethylsulfonyl)amino]-5-chloropyridine (2.33 g, 5.9 mmol) in 10 mL of THF. The mixture was allowed to warm to rt overnight. The reaction was quenched with 100 mL of H$_2$O and THF was removed under reduced pressure. The aqueous layer was extracted with EtOAc (4×75 mL) and the combined organic layer was dried over MgSO$_4$. After filtration and concentration, the residue was purified on silica gel column to provide the corresponding product (452c) (1.21 g, 79%). MS (ES$^+$): 318 (M+1).

(452d) To a solution of the product from (452c) (0.90 g, 3.1 mmol) in 15 mL of DMF were added LiCl (0.27 g, 6.3 mmol), Pd(PPh$_3$)$_4$ (0.36 g, 10 mol %, 0.31 mmol) and 4-(methoxycarbonyl)benzyl zinc bromide (0.5 M, 12.5 mL) (Shiota, T. et al. *J. Org. Chem.* 1999, 64, 453). The solution was stirred at rt overnight. DMF solvent was removed under reduced pressure and the residue was taken into 100 mL of H$_2$O. The aqueous phase was extracted by EtOAc (5×50 mL). The combined organic layer was washed with H$_2$O and saturated NaCl and dried over MgSO$_4$. After filtration and concentration, the residue was purified on silica gel column to provide the desired product (452d) (0.45 g, 45%). MS (ES$^+$): 318 (M+1).

(452e) Following a procedure similar to (401e), the product from (452d) (0.57 g, 1.6 mmol) was converted to the corresponding product (452e) (0.49 g, 84%). MS (ES$^+$): 304 (M+1).

(452f) Following a procedure similar to (401f), the product from (452e) (50 mg, 0.16 mmol) was coupled with (50d) (40% ee) to provide the desired product (452f) (49 mg, 69%). MS (ES$^+$): 431 (M+1).

(452g) Following a procedure similar to (403c), the product from (452f) (40 mg, 0.09 mmol) was converted to the corresponding hydroxamate (452 g) (39 mg, 80%) as a TFA salt. MS (ES$^+$): 432 (M+1).

Example 453

(3R,4R)-4-({4-[(2-cyclopropyl-4-quinolinyl)methyl]benzoyl}amino)-N-hydroxytetrahydro-2H-pyran-3-carboxamide (453a) Following a procedure similar to (423a), the product from (452e) (50 mg, 0.17 mmol) was coupled with methyl (3R,4R)-4-aminotetrahydro-2H-pyran-3-carboxylate to provide the desired product (453a) (72 mg, 92%) MS (ES$^+$): 445 (M+1).

(453b) Following a procedure similar to (403c), the product from (453a) (65 mg, 0.15 mmol) was converted to the corresponding hydroxamate (453b) (41 mg, 50%) as a TFA salt. MS (ES$^+$): 446 (M+1).

Example 454

(3R,4S)-4-{[4-(1,3-dihydrofuro[3,4-b]quinolin-9-ylmethyl)benzoyl]amino}-N-hydroxytetrahydro-3-furancarboxamide (454a) To a flask were charged aniline (3.92 g, 42 mmol), methyl 4-oxotetrahydro-3-furancarboxylate (6.1 g, 42 mmol) (Dowd, P. and Choi, S. *Tetrahedron,* 1991, 47, 4847), p-TsOH (0.3 g) and 100 mL of benzene. The mixture was heated to reflux and water was thus removed via Dean-Stark apparatus. After cooled down, insoluble material was filtered and the filtrate was concentrated to provide crude material in quantitative yield. The crude material was used directly for next step. The crude material thus obtained was dissolved in 150 mL of Ph$_2$o and the solution was heated to 240° C. for 1 h. After cooled down, the solution was diluted with hexane and the precipitate (454a) (2.7 g, 34%) was collected. MS (ES$^+$): 188 (M+1).

(454b) Following a procedure similar to (452c), the product from (454a) (2.7 g, 14.4 mmol) was converted to the corresponding product (454b) (3.2 g, 69%). MS (AP$^+$): 320 (M+1).

(454c) Following a procedure similar to (452d), the product from (452b) (3.2 g, 10.0 mmol) was coupled with 4-(methoxycarbonyl)benzyl zinc bromide to provide the desired product (454c) (1.2 mg, 38%). MS (ES$^+$): 320 (M+1).

(454d) Following a procedure similar to (401e), the product from (454c) (1.2 g, 3.7 mmol) was converted to the corresponding product (454d) (1.1 g, 95%). MS (ES$^-$): 304 (M−1).

(454e) Following a procedure similar to (401f), the product from (454e) (40 mg, 0.13 mmol) was coupled with (50d) (40% ee) to provide the desired product (454e) (60 mg, >95%). MS (ES$^+$):(433 (M+1).

(454f) Following a procedure similar to (403c), the product from (454e) (60 mg, 0.13 mmol) was converted to the corresponding hydroxamate (454f) (58 mg, 81%) as a TFA salt. MS (ES$^+$): 434 (M+1).

Example 455

(3R,4R)-4-{[4-(1,3-dihydrofuro[3,4-b]quinolin-9-ylmethyl)benzoyl]amino}-N-hydroxytetrahydro-2H-pyran-3-carboxamide (455a) Following a procedure similar to (423a), the product from (454d) (40 mg, 0.13 mmol) was coupled with methyl (3R,4R)-4-aminotetrahydro-2H-pyran-3-carboxylate to provide the desired product (453a) (55 mg, 94%). MS (ES$^+$): 447 (M+1).

(455b) Following a procedure similar to (403c), the product from (455a) (55 mg, 0.12 mmol) was converted to the corresponding hydroxamate (455b) (48 mg, 71%) as a TFA salt. MS (ES$^+$): 448 (M+1).

Example 456 tert-butyl (3S,4S)-4-({4-[(2,8-dimethyl-4-quinolinyl)methyl]benzoyl}amino)-3-[(hydroxyamino)carbonyl]-1-pyrrolidinecarboxylate (456a) Following a procedure similar to (454a), 2-methylaniline (21.4 g, 0.2 mol) was condensed with methyl acetoacetate (23.2 g, 0.2 mol) to provide the desired 2,8-dimethyl-4-hydroxyquinoline (456a) (13.0 g, 38%). MS (AP$^+$): 173 (M+1).

(456b) Following a procedure similar to (434a), the product from (456a) (10.0 g, 58.4 mmol) was converted to the corresponding bromide (456b) (11.0 g, 80%). MS (AP$^+$): 236 (M+1).

(456c) Following a similar procedure of (401b), the product from (456b) (9.6 g, 41 mmol) was converted to the corresponding product (456c) (9.0 g, 69%). MS (ES$^+$): 322 (M+1).

(456d) Following a similar procedure of (401c), the product from (456c) (9.0 g, 28 mmol) was converted to the corresponding product (456d) in quantitative yield. MS (ES$^+$): 400 (M+1).

(456e) Following a similar procedure of (401d), the product from (456d) was converted to the corresponding product (456e) in quantitative yield. MS (ES$^+$): 306 (M+1).

(456f) Following a similar procedure of (401e), the product from (456e) was converted to the corresponding product (456f) in 86% yield. MS (ES$^+$): 292 (M+1).

(456g) Following a similar procedure of (401f), the product from (456f) (114 mg, 0.39 mmol) was coupled with (1e) (80 mg, 0.33 mmol) to provide the desired product (456 g) (150 mg, 88%). MS (ES$^+$): 518 (M+1).

(456h) Following the procedure similar to (403c), the product from (456 g) (100 mg, 0.19 mmol) was converted to the corresponding hydroxamate (456 h) (95 mg, 77%) as a TFA salt. MS (ES$^+$): 519 (M+1).

Example 457

4-[(2,8-dimethyl-4-quinolinyl)methyl]-N-{cis-2-[(hydroxyamino)carbonyl]cyclopentyl}benzamide (457a) Following a procedure similar to (424a), the product from (456f) (63 mg, 0.22 mmol) was coupled with ethyl cis-2-aminocyclopentanecarboxylate.HCl (35 mg, 0.18 mmol) to provide the desired product (457a) (80 mg, >95%). MS (ES$^+$): 431 (M+1).

(457b) Following the procedure similar to (403c), the product from (457a) (69 mg, 0.16 mmol) was converted to the corresponding hydroxamate (457b) (60 mg, 89%) as a TFA salt. MS (ES$^+$): 418 (M+1).

Example 458

(3R,4R)-4-({4-[(2,8-dimethyl-4-quinolinyl)methyl]benzoyl}amino)-N-hydroxytetrahydro-2H-pyran-3-carboxamide (458a) Following a procedure similar to (423a), the product from (456f) (69 mg, 0.23 mmol) was coupled with methyl (3R,4R)-4-aminotetrahydro-2H-pyran-3-carboxylate (50 mg, 0.20 mmol) to provide the desired product (458a) (75 mg, 87%). MS (ES$^+$): 433 (M+1).

(458b) Following a procedure similar to (403c), the product from (458a) (75 mg, 0.17 mmol) was converted to the corresponding hydroxamate (458b) (58 mg, 62%) as a TFA salt. MS (ES$^+$): 434 (M+1).

Example 459

(3R,4S)-4-({4-[(2,8-dimethyl-4-quinolinyl)methyl]benzoyl}amino)-N-hydroxytetrahydro-3-furancarboxamide (459a) Following a procedure similar to (401f), the product from (456f) (84 mg, 0.29 mmol) was coupled with (50d) (40% ee) (35 mg, 0.24 mmol) to provide the desired product (459a) (75 mg, 74%). MS (ES$^+$): 419 (M+1).

(459b) Following a procedure similar to (403c), the product from (459a) (71 mg, 0.17 mmol) was converted to the corresponding hydroxamate (459b) (50 mg, 55%) as a TFA salt. MS (ES$^+$): 420 (M+1).

Example 460

(3R,4R)-N-hydroxy-4-[(4-{[2-methyl-8-(trifluoromethyl)-4-quinolinyl]methyl}benzoyl)amino]tetrahydro-2H-pyran-3-carboxamide (460a) Following a procedure similar to (454a), 2-trifluoromethylaniline (16.1 g, 0.1 mol) was condensed with methyl acetoacetate to provide the desired product (460a) (12.0 g, 53%). MS (ES$^+$): 228 (M+1).

(460b) Following a procedure similar to (452c), the product from (460a) (1.0 g, 4.5 mmol) was converted to the corresponding product (460b) (1.49 g, 92%). MS (ES$^+$): 360 (M+1).

(460c) Following a procedure similar to (452d), the product from (460b) (1.49 g, 4.15 mmol) was coupled with 4-(methoxycarbonyl)benzyl zinc bromide to provide the desired product (460c) (1.25 g, 83%). MS (ES$^+$): 360 (M+1).

(460d) Following a procedure similar to (401e), the product from (460c) (0.95 g, 2.65 mmol) was converted to the corresponding product (460d) (0.90 g, >95%). MS (ES$^+$): 346 (M+1).

(460e) Following a procedure similar to (423a), the product from (460d) (40 mg, 0.11 mmol) was coupled with methyl (3R,4R)-4-aminotetrahydro-2H-pyran-3-carboxylate (29 mg, 0.11 mmol) to provide the desired product (460e) (52 mg, 95%). MS (ES$^+$): 487 (M+1).

(460f) Following a procedure similar to (403c), the product from (460e) (52 mg, 0.11 mmol) was converted to the corresponding hydroxamate (460f) (36 mg, 55%) as a TFA salt. MS (ES$^+$): 488 (M+1).

Example 461

(3R,4R)-4-({4-[(8-chloro-2-methyl-4-quinolinyl)methyl]benzoyl}amino)-N-hydroxytetrahydro-2H-pyran-3-carboxamide (461a) Following a procedure similar to (454a), 2-chloroaniline (12.7 g, 0.1 mol) was condensed with methyl acetoacetate to provide the desired product (461a) (16.6 g, 85%). MS (ES$^+$): 194 (M+1).

(461b) Following a procedure similar to (452c), the product from (461a) (1.0 g, 5.1 mmol) was converted to the corresponding product (461b) (1.27 g, 76%). MS (ES$^+$): 387 (M+Na+CH$_3$CN).

(461c) Following a procedure similar to (452d), the product from (461b) (1.25 g, 3.8 mmol) was coupled with 4-(methoxycarbonyl)benzyl zinc bromide to provide the desired product (461c) (0.70 g, 56%). MS (AP$^+$): 326 (M+1).

(461d) Following a procedure similar to (401e), the product from (461c) (0.7 g, 2.15 mmol) was converted to the corresponding product (461d) (0.67 g, >95%). MS (AP$^+$): 312 (M+1).

(461e) Following a procedure similar to (423a), the product from (461d) (50 mg, 0.16 mmol) was coupled with methyl (3R,4R)-4-aminotetrahydro-2H-pyran-3-carboxylate (40 mg, 0.16 mmol) to provide the desired product (461e) (25 mg, 35%). MS (ES$^+$): 453 (M+1).

(461f) Following a procedure similar to (403c), the product from (461e) (20 mg, 0.044 mmol) was converted to the corresponding hydroxamate (461f) (15 mg, 60%) as a TFA salt. MS (ES$^+$): 454 (M+1).

Example 462

(3R,4S)-4-({4-[(8-chloro-2-methyl-4-quinolinyl)methyl]benzoyl}amino)-N-hydroxytetrahydro-3-furancarboxamide (462a) Following a procedure similar to (424a), the product from (461d) (50 mg, 0.16 mmol) was coupled with (50d) (40% ee) to provide the desired product (462a) (40 mg, 57%). MS (ES$^+$): 439 (M+1).

(462b) Following the procedure similar to (403c), the product from (462a) (35 mg, 0.08 mmol) was converted to the corresponding hydroxamate (462b) (25 mg, 57%) as a TFA salt. MS (ES+): 440 (M+1).

Example 463

(3R,4R)-4-({4-[(3-ethyl-2-methyl-4-quinolinyl)methyl]benzoyl}amino)-N-hydroxytetrahydro-2H-pyran-3-carboxamide

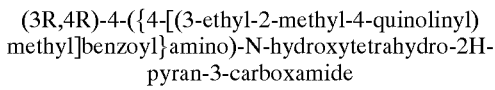

(463a) Following a procedure similar to (444a), ethyl 2-ethylacetoacetate (31.6 g, 200 mmol) was condensed with aniline to provide the desired enamine (463a) in quantitative yield. MS (AP+): 235 (M+1).

(463b) Following a procedure similar to (444b), the product from (463a) (10.0 g, 43 mmol) was converted to the corresponding product (446b) (7.6 g, 95%). MS (AP+): 188 (M+1).

(463c) Following a procedure similar to (401a), the product from (463b) (7.5 g, 40 mmol) was converted to the corresponding product (6.4 g, 63%). MS (AP+): 252 (M+1).

(463d) Following a procedure similar to (401b), the product from (463c) (6.3 g, 25.2 mmol) was converted to the corresponding product (5.4 g, 64%). MS (AP+): 377 (M+CH$_3$CN+1).

(463e) Following a procedure similar to (401c), the product from (463d) (5.4 g, 16.1 mmol) was converted to the corresponding product (6.60 g, >95%). MS (AP+): 414 (M+1).

(463f) Following a procedure similar to (401d), the product from (463e) (6.6 g, 16.0 mmol) was reduced to the corresponding product (5.1 g, >95%). MS (AP+): 350 (M+CH$_3$CN+1).

(463 g) Following a procedure similar to (401e), the product from (463f) (5.0 g, 15.7 mmol) was converted to the corresponding product (3.4 g, 72%). MS (AP+): 306 (M+1).

(463 h) Following a procedure similar to (423a), the product from (463 g) (50 mg, 0.16 mmol) was coupled with methyl (3R,4R)-4-aminotetrahydro-2H-pyran-3-carboxylate to provide the desired product (463 h) (70 mg, 92%). MS (ES+): 447 (M+1).

(463i) Following a procedure similar to (403c), the product from (463 h) (65 mg, 0.15 mmol) was converted to the corresponding hydroxamate (463i) (40 mg, 48%) as a TFA salt. MS (ES+): 448 (M+1).

Example 464

(3R,4S)-4-({4-[(3-ethyl-2-methyl-4-quinolinyl)methyl]benzoyl}amino)-N-hydroxytetrahydro-3-furancarboxamide

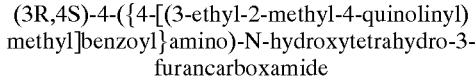

(464a) Following a procedure similar to (424a), the product from (463 g) (50 mg, 0.16 mmol) was coupled with (50d) (40% ee) to provide the desired product (464a) (60 mg, 85%). MS (ES+): 433 (M+1).

(464b) Following the procedure similar to (403c), the product from (464a) (55 mg, 0.12 mmol) was converted to the corresponding hydroxamate (464b) (40 mg, 75%) as a TFA salt. MS (ES+): 434 (M+1).

Example 465

4-[(3-ethyl-2-methyl-4-quinolinyl)methyl]-N-{cis-2-[(hydroxyamino)carbonyl]cyclopentyl}benzamide

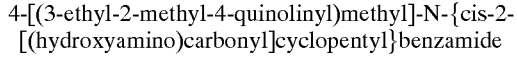

(465a) Following a procedure similar to (424a), the product from (463 g) (50 mg, 0.16 mmol) was coupled with ethyl cis-2-aminocyclopentanecarboxylate.HCl to provide the desired product (465a) (70 mg, 95%). MS (ES+): 889 (2M+1).

(465b) Following the procedure similar to (403c), the product from (465a) (65 mg, 0.15 mmol) was converted to the corresponding hydroxamate (465b) (50 mg, 61%) as a TFA salt. MS (ES+): 432 (M+1).

Example 466

(3R,4S)-4-({4-[(2,6-dimethyl-4-quinolinyl)methyl]benzoyl}amino)-N-hydroxytetrahydro-3-furancarboxamide

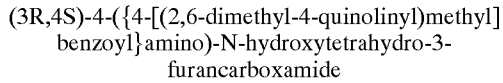

(466a) Following a procedure similar to (454a), 4-methylaniline (21.4 g, 0.2 mol) was condensed with methyl acetoacetate to provide the desired product (466a) (22.0 g, 62%). MS (AP+): 174 (M+1).

(466b) Following a procedure similar to (434a), the product from (466a) (22 g, 127 mmol) was converted to the corresponding product (466b) (15.1 g, 50%). MS (AP+): 236 (M+1).

(466c) Following a procedure similar to (401b), the product from (466b) (10.0 g, 42.3 mmol) was converted to the corresponding product (466c) (8.4 g, 62%). MS (AP+): 363 (M+CH$_3$CN+1).

(466d) Following a procedure similar to (401c), the product from (466c) (8.4 g, 26.4 mmol) was converted to the corresponding product (466d) in quantitative yield. MS (AP+): 400 (M+1).

(466e) Following a procedure similar to (401d), the product from (466d) (10.4 g, 26.0 mmol) was hydrogenated to the corresponding product (466e) in quantitative yield. MS (AP+): 306 (M+1).

(466f) Following a procedure similar to (401e), the product from (466e) (8.0 g, 26.0 mmol) was converted to the corresponding product (466f) (7.0 g, >95%). MS (ES+): 292 (M+1).

(466 g) Following a procedure similar to (424a), the product from (466f) (50 mg, 0.17 mmol) was coupled with (50d) (40% ee) to provide the desired product (466 g) (70 mg, 95%). MS (ES+): 419 (M+1).

(466 h) Following a procedure similar to (403c), the product from (466 g) (70 mg, 0.17 mmol) was converted to the corresponding hydroxamate (466 h) (50 mg, 55%) as a TFA salt. MS (ES+): 420(M+1).

Example 467

4-[(2,6-dimethyl-4-quinolinyl)methyl]-N-{cis-2-[(hydroxyamino)carbonyl]cyclopentyl}benzamide

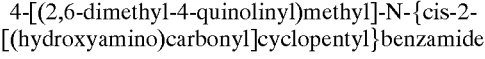

(467a) Following a procedure similar to (424a), the product from (466f) (50 mg, 0.17 mmol) was coupled with ethyl cis-2-aminocyclopentanecarboxylate.HCl to provide the desired product (467a) (70 mg, >95%). MS (ES+): 431(M+1).

(467b) Following the procedure similar to (403c), the product from (467a) (70 mg, 0.17 mmol) was converted to the corresponding hydroxamate (467b) (50 mg, 68%) as a TFA salt. MS (ES+): 418 (M+1).

Example 468

(3R,4R)-N-hydroxy-4-({4-[(2,6-dimethyl-4-quinolinyl)methyl]benzoyl}amino)tetrahydro-2H-pyran-3-carboxamide

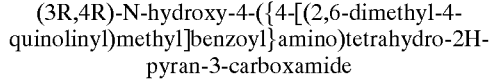

(468a) Following a procedure similar to (423a), the product from (466f) (50 mg, 0.17 mmol) was coupled with methyl (3R,4R)-4-aminotetrahydro-2H-pyran-3-carboxylate to provide the desired product (468a) (72 mg, >95%). MS (ES+): 433 (M+1).

(468b) Following a procedure similar to (403c), the product from (468a) (70 mg, 0.17 mmol) was converted to the corresponding hydroxamate (468b) (45 mg, 47%) as a TFA salt. MS (ES+): 434 (M+1).

Example 469

(3R,4S)-4-({4-[(6-chloro-2-methyl-4-quinolinyl) methyl]benzoyl}amino)-N-hydroxytetrahydro-3-furancarboxamide (469a) Following a procedure similar to (454a), 4-chloroaniline (25.5 g, 0.2 mol) was condensed with methyl acetoacetate to provide the desired product (469a) (17.6 g, 45%). MS (AP+): 194 (M+1).

(469b) Following a procedure similar to (452c), the product from (469a) (1.0 g, 5.16 mmol) was converted to the corresponding product (469b) (0.72 g, 43%). MS (AP+): 326 (M+1).

(469c) Following a procedure similar to (452d), the product from (469b) (0.7 g, 2.15 mmol) was coupled with 4-(methoxycarbonyl)benzyl zinc bromide to provide the desired product (469c) (0.49 g, 70%). MS (AP+): 326 (M+1).

(469d) Following a procedure similar to (401e), the product from (469c) (0.49 g, 1.5 mmol) was converted to the corresponding product (469d) in quantitative yield. MS (AP+): 312 (M+1).

(469e) Following a procedure similar to (401f), the product from (469d) (50 mg, 0.16 mmol) was coupled with (50d) (40% ee) to provide the desired product (469e) (69 mg, >95%). MS (ES+): 439 (M+1).

(469f) Following a procedure similar to (403c), the product from (469e) (60 mg, 0.14 mmol) was converted to the corresponding hydroxamate (469f) (40 mg, 52%) as a TFA salt. MS (ES+): 440 (M+1).

Example 470

(3R,4R)-4-({4-[(6-chloro-2-methyl-4-quinolinyl) methyl]benzoyl}amino)-N-hydroxytetrahydro-2H-pyran-3-carboxamide (470a) Following a procedure similar to (423a), the product from (469d) (50 mg, 0.17 mmol) was coupled with methyl (3R,4R)-4-aminotetrahydro-2H-pyran-3-carboxylate to provide the desired product (470a) (70 mg, >95%). MS (ES+): 453 (M+1).

(470b) Following a procedure similar to (403c), the product from (470a) (65 mg, 0.14 mmol) was converted to the corresponding hydroxamate (470b) (40 mg, 50%) as a TFA salt. MS (ES+): 454 (M+1).

Example 471

(3R,4R)-4-({4-[(6-fluoro-2-methyl-4-quinolinyl) methyl]benzoyl}amino)-N-hydroxytetrahydro-2H-pyran-3-carboxamide (471a) Following a procedure similar to (454a), 4-fluoroaniline (11.1 g, 0.1 mol) was condensed with methyl acetoacetate to provide the desired product (471a) (10.5 g, 59%). MS (ES+): 178 (M+1).

(471b) Following a procedure similar to (452c), the product from (471a) (2.0 g, 11.3 mmol) was converted to the corresponding product (471b) (1.93 g, 55%). MS (ES+): 310 (M+1).

(471c) Following a procedure similar to (452d), the product from (471b) (0.38 g, 1.2 mmol) was coupled with 4-(methoxycarbonyl)benzyl zinc bromide to provide the desired product (471c) (0.13 g, 34%). MS (AP+): 310 (M+1).

(471d) Following a procedure similar to (452e), the product from (471c) (0.13 g, 0.4 mmol) was converted to the corresponding product (471d) (82 mg, 66%). MS (AP+): 296 (M+1).

(471e) Following a procedure similar to (423a), the product from (471d) (40 mg, 0.13 mmol) was coupled with methyl (3R,4R)-4-aminotetrahydro-2H-pyran-3-carboxylate to provide the desired product (471e) (48 mg, 84%). MS (ES+): 437 (M+1).

(471f) Following a procedure similar to (403c), the product from (471e) (44 mg, 0.10 mmol) was converted to the corresponding hydroxamate (471f) (50 mg, 90%) as a TFA salt. MS (ES+): 438 (M+1).

Example 472

(3R,4R)-4-({4-[(7-chloro-2-methyl-4-quinolinyl) methyl]benzoyl}amino)-N-hydroxytetrahydro-2H-pyran-3-carboxamide (472a) Following a procedure similar to (454a), 3-chloroaniline (12.7 g, 0.1 mol) was condensed with methyl acetoacetate to provide the desired product (472a) (7.7 g, 79%). MS (AP+): 194 (M+1).

(472b) Following a procedure similar to (452c), the product from (472a) (2.0 g, 10.3 mmol) was converted to the corresponding product (472b) (1.56 g, 46%). MS (AP+): 326 (M+1).

(472c) Following a procedure similar to (452d), the product from (472b) (1.5 g, 4.6 mmol) was coupled with 4-(methoxycarbonyl)benzyl zinc bromide to provide the desired product (472c) (0.47 g, 31%). MS (ES+): 326 (M+1).

(472d) Following a procedure similar to (452e), the product from (472c) (0.47 g, 1.4 mmol) was converted to the corresponding product (472d) (375 mg, 84%). MS (ES+): 353 (M+CH$_3$CN+1).

(472e) Following a procedure similar to (423a), the product from (472d) (27 mg, 0.09 mmol) was coupled with methyl (3R,4R)-4-aminotetrahydro-2H-pyran-3-carboxylate to provide the desired product (472e) (21 mg, 53%). MS (ES+): 453 (M+1).

(472f) Following a procedure similar to (403c), the product from (472e) (21 mg, 0.05 mmol) was converted to the corresponding hydroxamate (472f) (25 mg, 89%) as a TFA salt. MS (ES+): 454 (M+1).

Example 473

(3R,4R)-4-{[4-(2,3-dihydro-1H-cyclopenta[b] quinolin-9-ylmethyl)benzoyl]amino}-N-hydroxytetrahydro-2H-pyran-3-carboxamide (473a) Following a procedure similar to (454a), methyl 2-oxocyclopentanecarboxylate (5.0 g, 35.1 mmol) was condensed with aniline to provide the desired product (473a) (6.0 g, 92%). MS (AP+): 185 (M+1).

(473b) Following a procedure similar to (452c), the product from (473a) (0.37 g, 2.0 mmol) was converted to the corresponding product (473b) (0.35 g, 55%). MS (ES+): 318 (M+1).

(473c) Following a procedure similar to (452d), the product from (473b) (0.35 g, 1.1 mmol) was coupled with 4-(methoxycarbonyl)benzyl zinc bromide to provide the desired product (473c) (0.09 g, 26%). MS (ES+): 635 (2M+1).

(473d) Following a procedure similar to (452e), the product from (473c) (90 mg, 0.3 mmol) was converted to the corresponding product (473d) (70 mg, 73%).

(473e) Following a procedure similar to (423a), the product from (473d) (70 mg, 0.2 mmol) was coupled with methyl (3R,4R)-4-aminotetrahydro-2H-pyran-3-carboxylate to provide the desired product (473e) (89 mg, 88%). MS (AP+): 445 (M+1).

(473f) Following a procedure similar to (403c), the product from (473e) (80 mg, 0.18 mmol) was converted to the corresponding hydroxamate (473f) (100 mg, >95%) as a TFA salt. MS (ES+): 446 (M+1).

Example 474

(3R,4R)-4-{[4-(2,3-dihydrofuro[2,3-b]quinolin-4-ylmethyl)benzoyl]amino}-N-hydroxytetrahydro-2H-pyran-3-carboxamide (474a) Following a procedure similar to (434a), 9(10H)-acridone (5.0 g, 25.6 mmol) was converted to the corresponding product (474a) (4.5 g, 68%). MS (AP+): 259 (M+1).

(474b) Following a procedure similar to (452d), the product from (474a) (0.5 g, 1.9 mmol) was coupled with 4-(methoxycarbonyl)benzyl zinc bromide to provide the desired product (474b) (0.4 g, 63%). MS (ES+): 328 (M+1).

(474c) Following a procedure similar to (401e), the product from (474b) (390 mg, 1.2 mmol) was converted to the corresponding product (474c) (370 mg, >95%). MS (AP+): 314 (M+1).

(474d) Following a procedure similar to (423a), the product from (474c) (40 mg, 0.13 mmol) was coupled with methyl (3R,4R)-4-aminotetrahydro-2H-pyran-3-carboxylate to provide the desired product (474d) (60 mg, >95%). MS (ES+): 455 (M+1).

(474e) Following a procedure similar to (403c), the product from (474d) (50 mg, 0.11 mmol) was converted to the corresponding hydroxamate (474e) (40 mg, 64%) as a TFA salt. MS (ES+): 456 (M+1).

Example 475

(3R,4R)-4-{[4-(acridin-9-ylmethyl)benzoyl]amino}-N-hydroxytetrahydro-2H-pyran-3-carboxamide (475a) The dihydrofuran-fused bromide (475a) was prepared from diethyl(2-methoxyethyl)malonate in a manner similar to the literature method (Leach, C. A. et al. *J. Med. Chem.* 1992, 35, 1845; and Sato, T. et al. *Bull. Chem. Soc. Jpn.* 1957, 30, 710).

(475b) Following a similar procedure of (401b), the product from (475a) (300 mg, 1.2 mmol) was converted to the corresponding product (475b) (40 mg, 10%). MS (AP+): 336 (M+1).

(475c) Following a similar procedure of (401c), the product from (475b) (50 mg, 0.15 mmol) was converted to the corresponding product (475c) in quantitative yield. MS (AP+): 413 (M+1).

(475d) Following a similar procedure of (401d), the product from (475c) was converted to the corresponding product (475d) in quantitative yield. MS (ES+): 319 (M+1).

(475e) Following a similar procedure of (401e), the product from (475d) was converted to the corresponding product (475e) in quantitative yield. MS (AP+): 305 (M+1).

(475f) Following a procedure similar to (423a), the product from (475e) (35 mg, 0.09 mmol) was coupled with methyl (3R,4R)-4-aminotetrahydro-2H-pyran-3-carboxylate to provide the desired product (475f) (40 mg, 91%). MS (ES+): 447 (M+1).

(475 g) Following a procedure similar to (403c), the product from (475f) (40 mg, 0.09 mmol) was converted to the corresponding hydroxamate (475 g) (45 mg, 89%) as a TFA salt. MS (ES+): 448 (M+1).

Example 476

(3R,4R)-4-({4-[(3-methyl-4-quinolinyl)methyl] benzoyl}amino)-N-hydroxytetrahydro-2H-pyran-3-carboxamide (476a) To a solution of 3-methylquinoline (2.0 g, 14 mmol) in 10 mL of HOAc was added 2.0 mL of 30% $H_2O_2$. The mixture was heated at 70° C. overnight. After cooled down, the reaction solution was neutralized by aqueous 50% NaOH and the resulting solution was extracted by $CHCl_3$. The organic layer was dried over $MgSO_4$. After filtration and concentration, the desired product (476a) was obtained in quantitative yield. MS (ES+): 160 (M+1).

(476b) To a flask charged with the product from (476a) (0.5 g, 3.14 mmol) was added a mixture of conc.$HNO_3$ (1.5 mL) and conc. $H_2SO_4$ (2.5 mL). The solution was gradually heated up to 95° C. for 2 h. Upon completion, the solution was cooled to 0° C. with ice bath and gradually 5 mL of ice-water was added. The solution was neutralized with saturated $K_2CO_3$ solution and the resulting solution was extracted with $CHCl_3$. The organic layer was dried over $MgSO_4$. After filtration and concentration, the desired product (476b) (0.55 g, 85%) was obtained. MS (ES+): 205 (M+1).

(476c) A solution of (476b) (0.55 g, 2.7 mmol) in 20 mL of $CH_2Cl_2$ was treated with $PBr_3$ (2.2 g, 8.1 mmol) at 0° C. The reaction was warmed up to rt and then refluxed. Upon completion, it was neutralized with saturated $NaHCO_3$ and extracted with EtOAc. The organic layer was dried over $MgSO_4$. After filtration and concentration, the residue was purified by flash column chromatography to provide the desired product (476c) (0.34 g, 57%). MS (ES+): 224 (M+1).

(476d) Following a similar procedure of (401b), the product from (476c) (340 mg, 1.5 mmol) was converted to the corresponding product (476d) (62 mg, 13%). MS (AP+): 308 (M+1).

(476e) Following a similar procedure of (401c), the product from (476d) (60 mg, 0.2 mmol) was converted to the corresponding product (476e) in quantitative yield. MS (AP+): 386 (M+1).

(476f) Following a similar procedure of (401d), the product from (476e) was converted to the corresponding product (476f) in 50% yield. MS (ES+): 292 (M+1).

(476 g) Following a similar procedure of (401e), the product from (475d) was converted to the corresponding product (476 g) in quantitative yield. MS (AP+): 278 (M+1).

(476 h) Following a procedure similar to (423a), the product from (476 g) (50 mg, 0.18 mmol) was coupled with methyl (3R,4R)-4-aminotetrahydro-2H-pyran-3-carboxylate to provide the desired product (476 h) (18 mg, 24%). MS (ES+): 419 (M+1).

(476i) Following a procedure similar to (403c), the product from (476 h) (18 mg, 0.04 mmol) was converted to the corresponding hydroxamate (476i) (7 mg, 30%) as a TFA salt. MS (ES+): 420 (M+1).

Example 477

(3R,4R)-4-({4-[(2-bromoquinolin-4-yl)methyl]benzoyl}amino)-N-hydroxytetrahydro-2H-pyran-3-carboxamide (477a) Following a procedure similar to (452d), the product from (451a) (1.0 g, 3.5 mmol) was coupled with 4-(methoxycarbonyl)benzyl zinc bromide without Pd(PPh$_3$)$_4$ to provide the desired product (477a) (0.75 g, 61%). MS (AP$^+$): 357 (M+1).

(477b) Following a procedure similar to (401e), the product from (477a) (0.1 g, 0.28 mmol) was converted to the corresponding product (477b) (90 mg, >95%). MS (ES$^+$): 342 (M+1).

(477c) Following a procedure similar to (423a), the product from (477b) (47 mg, 0.14 mmol) was coupled with methyl (3R,4R)-4-aminotetrahydro-2H-pyran-3-carboxylate to provide the desired product (477c) (65 mg, >95%). MS (AP$^+$): 483 (M+1).

(477d) Following a procedure similar to (403c), the product from (477c) (60 mg, 0.12 mmol) was converted to the corresponding hydroxamate (477d) (45 mg, 63%) as a TFA salt. MS (ES$^+$): 484 (M+1).

Example 478

(3R,4R)-N-hydroxy-4-({4-[(2-morpholin-4-ylquinolin-4-yl)methyl]benzoyl}amino)tetrahydro-2H-pyran-3-carboxamide (478a) To a solution of the product from (477a) (100 mg, 0.28 mmol) in 5 mL of THF was added morpholine (24 mg, 0.28 mmol). The mixture was heated at 50° C. overnight. After completion of the reaction, the solvent was removed under reduced pressure and the residue was purified on silica gel column to provide the desired product (478a) (28 mg, 27%). MS (ES$^+$): 363 (M+1).

(478b) Following a procedure similar to (401e), the product from (478a) (27 mg, 0.08 mmol) was converted to the corresponding product (478b) (18 mg, 67%). MS (ES$^+$): 342 (M+1).

(478c) Following a procedure similar to (423a), the product from (478b) (15 mg, 0.04 mmol) was coupled with methyl (3R,4R)-4-aminotetrahydro-2H-pyran-3-carboxylate to provide the desired product (478c) (14 mg, 65%). MS (AP$^+$): 490 (M+1).

(478d) Following a procedure similar to (403c), the product from (478c) (14 mg, 0.03 mmol) was converted to the corresponding hydroxamate (478d) (12 mg, 67%) as a TFA salt. MS (ES$^+$): 491 (M+1).

Example 501

(3R,4R)-N-hydroxy-4-({4-[(2-methyl-1-benzofuran-3-yl)methyl]benzoyl}amino)tetrahydro-2H-pyran-3-carboxamide (501a) A solution of 2-methoxyacetophenone (2.50 g, 15.2 mmol) in THF (50 ml) was treated with sodium hydride (730 mg, 1.2 eq) at rt and stirred for 30 min. To this mixture was added methyl 4-(bromomethyl)benzoate (3.83 g, 1.1 eq) and kept at rt for 12 h. The mixture was quenched with saturated sodium bicarbonate (15 ml) and extracted with ethyl acetate (300 ml) then further washed with water (20 ml), brine (20 ml), dried (MgSO$_4$) and concentrated. Flash chromatography (ethyl acetate-hexane, 1:9) furnished the desired ester (3.60 g, 76%). MS found: (M+H)$^+$=313.

(501b) A 1.0 M solution of boron tribromide in dichloromethane (45 ml, 4 eq) was added dropwise to the solution of the product from reaction (501a) (3.50 g, 11.2 mmol) in dichloromethane (120 ml) at −78° C. over 20 min. The resultant mixture was slowly warmed up to 0° C. for 1 h. It was poured into diethyl ether (200 ml) at rt and stirred for 10 min. To the mixture was carefully added saturated sodium bicarbonate (50 ml). The organic layer was separated and the aqueous layer was extracted with diethyl ether (2×100 mL). The combined organic layers was washed with brine (50 ml), dried (MgSO$_4$) and concentrated. Flash chromatography (ethyl acetate-hexane, 1:9) furnished the desired benzofuran (2.20 g, 70%). MS found: (M+CH$_3$CN+H)$^+$= 322.

(501c) Following a procedure similar to (1 g), the product from (501b) (1.30 g, 4.64 mmol) was converted to the desired acid (1.20 g, 97%). MS found: (M−H)$^-$=265.

(501d) Using procedures analogous to (1 h) to (1i), the product from reaction (501c) (91 mg, 0.29 mmol) and the amine from reaction (40e) was converted to the desired hydroxamic acid (38 mg, 49% yield, 2 steps). MS found: (M−H)$^-$=407.

Example 502 tert-butyl (3S,4S)-3-[(hydroxyamino)carbonyl]-4-({4-[(2-methyl-1-benzofuran-3-yl)methyl]benzoyl}amino)pyrrolidine-1-carboxylate (502a) Using procedures analogous to (1 h) to (1i), the product from reaction (501c) (91 mg, 0.29 mmol) was converted to the desired hydroxamic acid (20 mg, 14% yield, 2 steps). MS found: (M−H)$^-$=492.

Example 503

(3S,4S)-N-hydroxy-4-({4-[(2-methyl-1-benzofuran-3-yl)methyl]benzoyl}amino)pyrrolidine-3-carboxamide (503a) Using a procedure similar to (2a), the product from reaction (502a) (10 mg, 0.020 mmol) was converted to the desired amine salt (10 mg, 97%). MS found: (M+H)$^+$=394.

Example 504

(3R,4R)-N-hydroxy-4-({4-[(2-isopropyl-1-benzofuran-3-yl)methyl]benzoyl}amino)tetrahydro-2H-pyran-3-carboxamide (504a) Potassium t-butoxide (3.37 g, 3.0 eq) and 3-methyl-2-butanone (2.58 g, 3.0 eq) were added to liquid ammonia (30 ml) at −78° C. and warmed up to −10° C. for 10 min. To the mixture was added with 2-iodoanisole (2.34 g, 10.0 mmol) and benzoyl peroxide (50 mg). The bath was removed and the mixture irradiated with light for 15 min. The reaction mixture was quenched with saturated ammonia chloride (10 ml) and added ethyl acetate (200 ml) then further washed with water (20 ml), brine (20 ml), dried (MgSO$_4$) and concentrated. Flash chromatography (ethyl acetate-hexane, 1:9) furnished the desired ester (730 mg, 38%). MS found: (M+H)$^+$=193.

(504b) Using procedures analogous to (501a) to (501c), the product from reaction (504b) (700 mg, 3.64 mmol) was converted to the desired carboxylic acid (306 mg, 29% yield, 3 steps). MS found: (M−H)$^-$=293.

(504c) Using procedures analogous to (1 h) to (1i), the product from reaction (504b) (49 mg, 0.17 mmol) and the amine from reaction (40e) was converted to the desired hydroxamic acid (30 mg, 42% yield, 2 steps). MS found: $(M+H)^+=437$.

Example 505 tert-butyl (3S,4S)-3-[(hydroxyamino)carbonyl]-4-({4-[(2-isopropyl-1-benzofuran-3-yl)methyl]benzoyl}amino)pyrrolidine-1-carboxylate (505a) Using procedures analogous to (1 h) to (1i), the product from reaction (504b) (72 mg, 0.25 mmol) was converted to the desired hydroxamic acid (60 mg, 49% yield, 2 steps). MS found: $(M+Na)^+=544$.

Example 506

(3S,4S)-N-hydroxy-4-({4-[(2-isopropyl-1-benzofuran-3-yl)methyl]benzoyl}amino)pyrrolidine-3-carboxamide (506a) Using a procedure similar to (2a), the product from reaction (505a) (50 mg, 0.058 mmol) was converted to the desired amine salt (31 mg, 100%). MS found: $(M+H)^+=422$.

Example 601

(3R,4R)-N-hydroxy-4-({4-[(2-methylimidazo[1,2-a]pyridin-3-yl)methyl]benzoyl}amino)tetrahydro-2H-pyran-3-carboxamide (601a) To a solution of methyl 4-iodobenzoate (29 mmol, 7.6 g) in acetonitrile (290 mL) was added 3-buten-2-ol (3.6 mL, 41 mmol), triethylamine (41 mmol, 5.7 mL) and palladium(II)acetate (2.9 mmol, 651 mg). The reaction was heated to 60° C. for 6 h to afford the desired ketone after flash chromatography (2.3 g, 38%). MS found: $(M+H)^+=408$.

(601b) To a solution of (601a) (238 mg, 1.15 mmol) in THF (5 mL) was added phenyl trimethyltribromide (1.15 mmol, 480 mg) to afford the desired bromide after flash chromatography (145 mg, 44%). MS found: $(M-Br+OH)=222$.

(601c) To a solution of the product from (601b)(0.53 mmol, 150 mg) in 2,2'-dimethoxyethane was added 2-aminopyridine (1.59 mmol, 150 mg) and the reaction heated at 100° C. for 2 h to afford the desired ester after flash chromatography (41 mg, 28%). MS found: $(M-H)^-=279$.

(601c) To a suspension of the product from (601c) (0.15 mmol, 41 mg) in (7 mL) MeOH was added NaOH (5 mmol, 5 mL, 1M) and the reaction was heated to 90° C. for 1 h and then quenched to pH 7 with HCl (1N). The reaction mixture was filtered to afford the desired acid (40 mg, 99%). MS found: $(M+H)^+=267$.

(601d) To a solution of (601c) was added the amine from reaction (40e) (125 mg, 0.45 mmol), Hunig's base (0.17 mL, 0.9 mmol), and benzotriazol-1-yloxyltris(dimethylamino)-phosphonium hexafluorophosphate (BOP) (218 mg, 0.5 mmol). The reaction was stirred for 2 h at ambient temperature and then quenched with NH$_4$Cl. The reaction mixture was filtered to afford the desired amide (177 mg, 97%). MS found: $(M+H)^+=407$.

(601e) Using analogous procedures to (1i), the product from reaction (601d) (170 mg, 0.37 mmol) was converted to the desired hydroxamic acid (55 mg, 32% yield). MS found: $(M+H)^+=408$.

Example 602

(3R,4R)-N-hydroxy-4-[(4-{[2-(trifluoromethyl)imidazo[1,2-a]pyridin-3-yl]methyl}benzoyl)amino]tetrahydro-2H-pyran-3-carboxamide (602a) To a solution of 2-aminopyridine (53 mmol, 4.99 g) in ethanol (67 mL) was added 1,1,1-trifluoro-3-bromoacetone (53 mmol, 10 g). The reaction was heated to 70° C. for 1 h. The reaction was cooled to ambient temperature, filtered and the filtrate concentrated in vacuo. The crude material was redissolved in CH$_2$Cl$_2$ and (10 mL) Hunig's Base was added. The reaction was stirred overnight and subsequently quenched using H$_2$O and the aqueous layer extracted with CH$_2$Cl$_2$ (1×100 mL). The organic layers were washed using brine (1×30 mL) and dried over MgSO$_4$. The organic layers were then concentrated in vacuo and then purified via flash chromatography to afford the desired imidazopyridine (2 g, 21%). MS found: $(M+H_2O)^+=205$.

(602b) The product from (602a) (1.1 mmol, 200 mg) in ethanol (2 mL) was reacted with bromine (1.1 mmol, 0.056 mL). The reaction was stirred for 10 min and then concentrated in vacuo. The crude residue was then dissolved in a NaHCO$_3$ (5 mL) and diethyl ether mixture (20 mL). The aqueous layer was extracted further with diethyl ether (4×15 mL). The organic layer was washed with brine (1×20 mL) and then dried over MgSO$_4$, then concentrated in vacuo to afford the desired imidazopyridine (281 mg, 96%). MS found: $(M+2)^+=267$.

(602c) Using the product from (602b) (1.5 mmol, 281 mg) was added 4-(methoxycarbonyl)benzyl zinc bromide (1.8 mmol, 3.6 mL, 0.5M) and palladium(0)tetrakis(triphenylphosphine) (0.15 mmol, 174 mg). The reaction was stirred for 12 h and then quenched using NH$_4$Cl. The aqueous layer was extracted using (1×50 mL) EtOAc. The organic layers were washed using an NaCl (sat) solution (1×20 mL) and then dried over MgSO$_4$ and then concentrated in vacuo to afford the desired ester (158 mg, 30%). MS found: $(M+H-Me)^+=321$.

(602d) To a suspension of the product from (602c) (1.2 mmol, 400 mg) in (10 mL) MeOH was added NaOH (10 mmol, 10 mL, 1M) and the reaction was heated to 90° C. for 1 h and then quenched to pH 7 with HCl (1N). The reaction mixture was filtered to afford the desired acid (365 mg, 95%). MS found: $(M+H)^+=321$.

(602e) To a solution of the product from (602d) (0.375 mmol, 120 mg) was added the amine from reaction (39d) (0.375 mmol, 105 mg), Hunig's base (0.75 mmol, 0.14 mL), and benzotriazol-1-yloxyltris(dimethylamino)-phosphonium hexafluorophosphate (BOP) (0.4 mmol, 183 mg,). The reaction was stirred for 2 h at ambient temperature and then quenched with NH$_4$Cl. The reaction mixture was extracted with EtOAc (3×20 mL) and the organic layers separated and concentrated in vacuo. The organic layers were dried using a NaCl (sat) solution (1×20 mL) and then dried over MgSO$_4$. The organic layers were then concentrated in vacuo to afford the desired amide. (172 mg, 99%). MS found: $(M+H)^+=462$.

(602f) Using analogous procedures to (1i), the product from reaction (602e) (0.375 mmol, 172 mg) was converted to the desired hydroxamic acid (129 mg, 74% yield). MS found: $(M+H)^+=463$.

Example 603

(3R,4R)-4-({4-[(2-tert-butylimidazo[1,2-a]pyridin-3-yl)methyl]benzoyl}amino)-N-hydroxytetrahydro-2H-pyran-3-carboxamide (603a) Using a procedure analogous to (602a–f) 2-aminopyridine (37.2 mmol, 3.5 g) was reacted with bromopinacolone (1 eq, 6.7 g) to afford the desired hydroxamic acid (100 mg, 9.6, 6 steps). MS found: $(M+H)^+=451$.

Example 604

N-{(1R,2S)-2-[(hydroxyamino)carbonyl]cyclopentyl}-4-[(2-isopropylimidazo[1,2-a]pyridin-3-yl)methyl]benzamide (604a) To a solution of n-BuLi (122 mmol, 80 mL) at −78° C. in THF (100 mL) was added diisopropylamine (122 mmol, 17 mL). The reaction was stirred for 30 min and subsequently 3-methyl-butan-2-one (93.46 mmol, 10 mL) was added over 8 min via addition funnel. The reaction was warmed to 0° C. for 15 min while stirring and then quenched by adding chlorotrimethylsilane (93.46 mmol, 12 mL) over 10 min while maintaining the temperature at 0° C. The reaction was then stirred for another 45 min and then quenched using aqueous NaHCO$_3$ (sat). The aqueous layer was extracted using hexane (2×60 mL). The organic layer was dried over MgSO$_4$ and then concentrated in vacuo to afford the desired trimethylsilyl enol ether (7.37 g, 49%).

(604b) The product from (604a) (3.35 mmol, 530 mg) in CCl$_4$ (3 mL) was reacted with bromine (3.35 mmol, 0.17 mL) at 0° C. for 30 min. The reaction was then quenched with aqueous NaHCO$_3$ (sat). The aqueous layer was then extracted using (2×10 mL) CH$_2$Cl$_2$. The organic layer was then washed using a NaCl (sat) solution (1×20 mL) and dried with MgSO$_4$. The organic layer was then concentrated in vacuo to afford the desired bromide (545 mg, 99%).

(604c) To a solution of 2-aminopyridine (43 mmol, 4.33 g) in ethanol (40 mL) was added the product from (604b) 1-bromo-3-methyl-butan-2-one (43 mmol, 7.1 g). The reaction was heated to 70° C. for 1 h. The reaction was cooled to ambient temperature, filtered and the filtrate concentrated in vacuo. The crude material was redissolved in CH$_2$Cl$_2$ and (10 mL) Hunig's Base was added. The reaction was stirred overnight and subsequently quenched using H$_2$O and the aqueous layer extracted with CH$_2$Cl$_2$ (1×100 mL). The organic layers were washed with brine (1×30 mL) and dried over MgSO$_4$. The organic layers were then concentrated in vacuo and then purified via flash chromatography to afford the desired imidazopridine (1.8 g, 25%).

(604d) The product from (604c) (11 mmol, 1.7 g) in ethanol (25 mL) was reacted with bromine (11 0.6 mL). The reaction was stirred for 10 min and then concentrated in vacuo. The crude residue was then dissolved in a NaHCO$_3$ (5 mL) and diethyl ether (20 mL). The aqueous layer were extracted with diethyl ether (4×15 mL). The organic layer was washed with brine (1×20 mL) and then dried over MgSO$_4$. The organic layers were then concentrated in vacuo to afford the desired bromide after flash chromatography (1.23 g, 47%). MS found: (M+2)$^+$=239.

(604e) Using the product from (604d) (5.14 mmol, 1.23 g) was added 4-(methoxycarbonyl)benzyl zinc bromide (10.5 mmol, 21 mL, 0.5M) and palladium(0) tetrakistriphenylphosphine (0.514 mmol, 594 mg). The reaction was stirred for 12 h and then quenched using NH$_4$Cl. The aqueous layer was extracted using (1×50 mL) EtOAC. The organic layers were washed using an NaCl (sat) solution (1×20 mL) and then dried over MgSO$_4$. The organic layers were then concentrated in vacuo to afford the desired ester (474 mg, 30%). MS found: (M−H)$^-$=307.

(604f) To a suspension of the product from (602c) (1.2 mmol, 400 mg) in (10 mL) MeOH was added NaOH (10 mmol, 10 mL, 1M) and the reaction was heated to 90° C. for 1 h and then quenched to pH 7 with HCl (1N). The reaction mixture was concentrated in vacuo and then purified via reverse phase high pressure liquid chromatography to afford the desired acid (322 mg, 71%). MS found: (M+H)$^+$=295

(604g) To a solution of the product from (604f) (0.18 mmol, 53 mg) was added the amine as an HCl salt from reaction (50d) (0.18 mmol, 32 mg), Hunig's base (0.36 mmol, 0.1 mL), and benzotriazol-1-yloxytris (dimethylamino)-phosphonium hexafluorophosphate (BOP) (0.196 mmol, 87 mg,). The reaction was stirred for 2 h at ambient temperature and then quenched with NH$_4$Cl. The reaction mixture was extracted with EtOAc (3×20 mL) and the organic layers separated and concentrated in vacuo. The organic layers were washed using an NaCl (sat) solution (1×20 mL) and then dried over MgSO$_4$. The organic layers were then concentrated in vacuo to afford the desired amide (74 mg, 99%). MS found: (M+H)$^+$=420.

(604h) Using analogous procedures to (1i), the product from reaction (604 g) (0.18 mmol, 74 mg) was converted to the desired hydroxamic acid (24 mg, 32% yield). MS found: (M+H)$^+$=421.

Example 605

(3R,4R)-N-hydroxy-4-({4-[(2-isopropylimidazo[1,2-a]pyridin-3-yl)methyl]benzoyl}amino)tetrahydro-2H-pyran-3-carboxamide (605a) Using procedures analogous to (604a)-(604 g), the product from (604f) (0.38 mmol, 112 mg) was reacted with the (40e) to afford the desired amide (165 mg, 99%). MS found: (M+H)$^+$=436.

(605b) Using procedures analogous to (1i), the product from reaction (605a) was reacted to afford the desired hydroxamic acid (87 mg, 52%) MS found: (M+H)$^+$=437.

Example 606

4-[(2-tert-butylimidazo[1,2-a]pyridin-3-yl)methyl]-N-{(1R,2S)-2-[(hydroxyamino)carbonyl]cyclopentyl}benzamide (606a) Using procedures analogous to (603a) the acid (0.19 mmol, 59 mg) was reacted with the amine HCl salt from (50d) to afford the desired amide (82 mg, 99%). MS found: (M+H)$^+$=434.

(606b) Using procedures analogous to (1i), the product from (606a) (0.19 mmol, 82 mg) was reacted to afford the desired hydroxamic acid (24 mg, 29%). MS found: (M+H)$^+$=435.

Example 607

(3R,4R)-4-({4-[(2-cyclobutylimidazo[1,2-a]pyridin-3-yl)methyl]benzoyl}amino)-N-hydroxytetrahydro-2H-pyran-3-carboxamide (607a) Using procedures analogous to (602a)-(602e) 1-(cyclobutyl)ethanone was converted to the desired acid and subsequently reacted with the amine HBr salt from (40e) (0.36 mmol, 101 mg) to afford the desired amide (45 mg, 67%). MS found: (M+H)$^+$=448.

(608b) Using procedures analogous to (1i), the product from (607a) (0.1 mmol, 45 mg) was reacted to afford the desired hydroxamic acid (11 mg, 24%). MS found: (M+H)$^+$=449.

Example 608

N-{(1R,2S)-2-[(hydroxyamino)carbonyl]cyclopentyl}-4-{[2-(trifluoromethyl)imidazo[1,2-a]pyridin-3-yl]methyl}benzamide (608a) Using procedures analogous to (1 h-li), the product from (602d) (0.16 mmol, 50 mg) and methyl (1R,2S)-2-aminocyclopentanecarboxylate.HCl (1 eq) was reacted to afford the desired hydroxamic acid (20 mg, 28%). MS found: (M+H)$^+$=447.

Example 609

4-[(2-cyclobutylimidazo[1,2-a]pyridin-3-yl)methyl]-N-{(1R,2S)-2-[(hydroxyamino)carbonyl]cyclopentyl}benzamide (609a) Using procedures analogous to (607a)-(607b) the 1-Cyclobutyl-ethanone was converted and subsequently reacted with methyl (1R,2S)-2-aminocyclopentanecarboxylate.HCl (1 eq) (0.19 mmol, 34 mg) to afford the desired amide (68 mg, 99%). MS found: (M+H)$^+$=432.

(609b) Using procedures analogous to (1i), the product from (609a) was converted to the desired hydroxamic acid (67 mg, 97%). MS found: (M+H)$^+$=434.

Example 610

(3R,4R)-4-({4-[(2-cyclopropylimidazo[1,2-a]pyridin-3-yl)methyl]benzoyl}amino)-N-hydroxytetrahydro-2H-pyran-3-carboxamide (610a) Using procedures analogous to (607a)-(607 g) 1-Cyclopropyl-ethanone (41.3 mmol, 3.48 g) was converted and subsequently reacted with the amine HBr salt from (40e) (0.27 mmol, 75 mg) to afford the desired amide (117 mg, 99%). MS found: (M+H)$^+$=434.

(610b) Using procedures analogous to (1i), the product from (610a) (0.27 mmol, 117 mg) was reacted to afford the desired hydroxamic acid (4 mg, 3.4%). MS found: (M+H)$^+$=435.

Example 701

(3R,4R)-4-({4-[(2-ethylpyrazolo[1,5-a]pyridin-3-yl)methyl]benzoyl}amino)-N-hydroxytetrahydro-2H-pyran-3-carboxamide (701a) 2-picoline (3.73 g, 2.0 eq) was added to a solution of phenyllithium (40.0 mmol, 2.0 eq) in ethyl ether (45 ml) at rt dropwise over 5 min. The resultant mixture was heated to reflux for 30 min. To the rapidly stirred solution, another solution of methyl propionate (1.76 g, 20.0 mmol) in ethyl ether (5 ml) was added dropwise over 5 min so that the ethyl ether was kept at reflux. After refluxing for additional 30 min, the mixture was cooled down to rt and carefully quenched with saturated sodium bicarbonate (5 ml). To the mixture was added ethyl acetate (200 ml) and washed with water (2×20 ml), brine (20 ml), dried (MgSO$_4$) and concentrated. Flash chromatography (ethyl acetate-hexane, 3:7) furnished the desired ketone (2.0 g, 67%). MS found: (2M+H)$^+$=299.

(701b) The product from reaction (701a) (2.00 g, 13.4 mmol) in THF (50 ml) was treated with 60% sodium hydride (644 mg, 1.2 eq) at rt and stirred for 30 min. Methyl 4-(bromomethyl)benzoate (4.03 g, 1.1 eq) was added to the mixture and stirred at rt for 2 h. The reaction was quenched with saturated sodium bicarbonate (20 ml) and diluted with ethyl acetate (300 ml), further washed with water (2×20 ml), brine (20 ml), dried (MgSO$_4$) and concentrated. Flash chromatography (ethyl acetate-hexane, 2:8) furnished the desired ester (1.60 g, 40%). MS found: (M+H)$^+$=298.

(701c) A solution of the product from reaction (701b) (200 mg, 0.673 mmol) in dichloromethane (5 ml) was added a suspension of o-(mesitylsulfonyl)hydroxylamine (Tamura, Y. et al. Synthesis, 1977, 1) (217 mg, 1.5 eq) in dichloromethane (5 ml) at 0° C. and warmed up to rt for 12 h. The mixture was concentrated and purified by flash chromatography (ethyl acetate-hexane, 1:9) to provide the desired pyrazolopyridine (119 mg, 60%). MS found: (M+H)$^+$=295.

(701d) Following a procedure analogous to (1 g), the product from reaction (701c) (50.0 mg, 0.17 mmol) was converted to the desired carboxylic acid (45 mg, 95%). MS found: (M–H)$^-$=279.

(701e) Using procedures analogous to (1 h) to (1i), the product from reaction (701d) (15 mg, 0.054 mmol) and the amine from (40e) (1 eq) were converted to the desired hydroxamic acid (10 mg, 38% yield, 2 steps). MS found: (M+H)$^+$=423.

Example 702

(3R,4R)-N-hydroxy-4-[(4-{[2-(trifluoromethyl)pyrazolo[1,5-a]pyridin-3-yl]methyl}benzoyl)amino]tetrahydro-2H-pyran-3-carboxamide (702a) The solution of 2-picoline (2.79 g, 30.0 mmol) and pyridine (12.0 ml, 5.0 eq) in anhydrous benzene (80 ml) was treated with trifluoroacetic anhydride (13.0 ml, 3.0 eq) at 0° C. and warmed up to rt for 12 h. The mixture was quenched with saturated sodium bicarbonate (50 ml) and added ethyl acetate (500 ml). It was further washed with water (2×50 ml), brine (50 ml), dried (MgSO$_4$) and concentrated. Flash chromatography (ethyl acetate-hexane, 3:7) furnished the desired ketone (2.80 g, 50%). MS found: (M+H)$^+$=190.

(702b) Using procedures analogous to (701b) to (701d), the product from reaction (702a) (600 mg, 3.17 mmol) was converted to the desired carboxylic acid (90 mg, 9% yield, 3 steps). MS found: (M–H)$^-$=319.

Alternatively, the product of (702b) can be prepared via:

(702c) Ethyl 4,4,4-trifluoro-2-butynoate (7.5 g, 45 mmol) and 1-aminopyridinium iodide (12.1 g, 1.2 eq) were combined in DMF (45 mL) and treated with potassium carbonate (9.4 g, 1.5 eq) and stirred under air for 4 h. The mixture was partitioned between ether and water and extracted further with ether (2×). The organic layers were washed with water and brine, dried (MgSO$_4$), filtered and concentrated to afford a solid (11.6 g, 99%) taken on without further purification.

(702d) The product from (702c) (516 mg, 2.0 mmol) in MeOH (5 mL) was treated with LiOH (2M, 5 mL, 10 eq) and heated to 55° C. for 2.5 h. The reaction was concentrated to remove methanol and neutralized to pH 5 with HCl (conc.), extracted with ethyl acetate, washed with brine, dried (MgSO$_4$), filtered and concentrated to give the desired acid (436 mg, 95%). MS Found: (M–H)$^-$=229.

(702e) The product from (702d) (230 mg, 1.0 mmol) was treated with HBr (48%, 10 mL) and heated to 100° C. for 1.1 h. The mixture was cooled to 0° C. and made basic with NaOH (50%, ca. 10 mL), extracted with ethyl acetate, washed with brine, dried (MgSO$_4$), filtered and concentrated to give the desired product as an oil (145 mg, 78%). MS Found: (M+H)$^+$=187.

(702f) The product from (702e) (80 mg, 0.21 mmol) in ethanol (3 mL) was treated with bromine (0.026 mL, 1.25 eq) and stirred at rt. A further 0.5 eq of bromine were added and the reaction stirred for 15 min. Concentration and flash chromatography (1:1 EtOAc/hexane) gave the desired bromide (95 mg, 84%).

(702g) The bromide from (702f) (530 mg, 2.0 mmol) in THF (10 mL) was cooled to –78° C. and treated with nBuLi (2.5 M, 0.88 mL, 2.2 mmol) and stirred for 5 min. Methyl 4-formylbenzoate (328 mg, 1 eq) in THF was cooled to –78° C. The solution of lithium reagent was transferred to the aldehyde via cannula, the reaction stirred 15 min and quenched with saturated NH$_4$Cl solution. Following extraction (EtOAc), washing (brine), drying (MgSO$_4$), and chromatography the desired alcohol was obtained (340 mg, 49%). MS Found: (M+H)$^+$=351.

(702h) The alcohol from (702 g) (311 mg, 0.89 mmol) in dichloromethane (10 mL) was treated with Et$_3$SiH (0.38 mL, 5 eq) and trifluoroacetic acid (0.79 mL, 5 eq) and stirred for 1 h. Another 2.5 eq each of TFA/Et$_3$SiH was added. After 15 min, the solvents were removed in vacuo and purification by flash chromatography (1:1 EtOAc/hexane) gave the desired ester (265 mg, 89%). MS Found: $(M+H)^+$=335.

(702i) Using analogous procedure to (1 g) the ester from reaction (702 h) was converted to the desired acid equivalent to (702b).

(702j) Using procedures analogous to (1 h) to (1i), the product from reaction (702b) (90 mg, 0.28 mmol) and the amine from (40e) (1 eq) were converted to the desired hydroxamic acid (85 mg, 65% yield, 2 steps). MS found: $(M+H)^+$=463.

Example 703

(3R,4R)-N-hydroxy-4-[(4-{[2-(methoxymethyl) pyrazolo[1,5-a]pyridin-3-yl]methyl}benzoyl)amino] tetrahydro-2H-pyran-3-carboxamide (703a) Using procedures analogous to (701a) to (701d), methyl methoxyacetate (2.08 g, 20.0 mmol) was converted to the desired carboxylic acid (315 mg, 5% yield, 4 steps). MS found: $(M+H)^+$=297.

(703b) Using procedures analogous to (1 h) to (1i), the product from reaction (703a) (80 mg, 0.27 mmol) and the amine from (40e) (1 eq) were converted to the desired hydroxamic acid (55 mg, 46% yield, 2 steps). MS found: $(M+H)^+$=439.

Example 704

(3R,4R)-N-hydroxy-4-[(4-{[2-(1-hydroxy-1-methylethyl)pyrazolo[1,5-a]pyridin-3-yl] methyl}benzoyl)amino]tetrahydro-2H-pyran-3-carboxamide (704a) The mixture of methyl 2-hydroxyisobutyrate (2.36 g, 20.0 mmol), tert-butyldimethylsilyl chloride (3.01 g, 1.0 eq), imidazole (1.36 g, 1.0 eq) in DMF (3 ml) was stirred at rt for 12 h and added saturated sodium bicarbonate (10 ml) then diluted with ethyl acetate (100 ml) and washed with water (2×10 ml), brine (10 ml), dried ($MgSO_4$) and concentrated. The desired ester (3.00 g) was converted to the next step without purification.

(704b) Using procedures analogous to (701a) to (701b), the product from (704a) (3.00 g, 20.0 mmol) was converted to the desired ester (870 mg, 10% yield, 3 steps). MS found: $(M+H)^+$=442.

(704c) The product from reaction (704b) (800 mg, 1.81 mmol was treated with tetrabutylammonium floride (3.62 mmol, 2.0 eq) in THF (10 ml) at rt and stirred for 12 h. The mixture was quenched with saturated sodium bicarbonate (5 ml) and added ethyl acetate (100 ml). It was further washed with water (2×10 ml), brine (10 ml), dried ($MgSO_4$) and concentrated. Flash chromatography (ethyl acetate-hexane, 5:5) furnished the desired alcohol (540 mg, 91%). MS found: $(M+H)^+$=328.

(704d) Using procedures analogous to (701c) to (701d), the product from reaction (704c) (400 mg, 1.22 mmol) was converted to the desired carboxylic acid (180 mg, 34% yield, 2 steps). MS found: $(M+H)^+$=311.

(704e) Using procedures analogous to (1 h) to (1i), the product from reaction (704d) (70 mg, 0.23 mmol) and the amine from (40e) (1 eq) were converted to the desired hydroxamic acid (55 mg, 54% yield, 2 steps). MS found: $(M+H)^+$=453.

Example 705

(3R,4R)-N-hydroxy-4-({4-[(2-isopropylpyrazolo[1, 5-a]pyridin-3-yl)methyl]benzoyl}amino)tetrahydro-2H-pyran-3-carboxamide (705a) Using procedures analogous to (701a) to (701d), methyl isobutyrate (1.02 g, 10.0 mmol) was converted to the desired carboxylic acid (315 mg, 11% yield, 4 steps). MS found: $(M+H)^+$=295.

(705b) Using procedures analogous to (1 h) to (1i), the product from reaction (705a) (80 mg, 0.27 mmol) and the amine from (40e) (1 eq) were converted to the desired hydroxamic acid (60 mg, 51% yield, 2 steps). MS found: $(M+H)^+$=437.

Example 706

(3R,4R)-4-({4-[(2-tert-butylpyrazolo[1,5-a]pyridin-3-yl)methyl]benzoyl}amino)-N-hydroxytetrahydro-2H-pyran-3-carboxamide (706a) Using procedures analogous to (701a) to (701d), methyl trimethylacetate (1.16 g, 10.0 mmol) was converted to the desired carboxylic acid (1.42 g, 34% yield, 4 steps). MS found: $(M+H)^+$=323.

(706b) Using procedures analogous to (1 h) to (1i), the product from reaction (706a) (90 mg, 0.29 mmol) and the amine from (40e) (1 eq) were converted to the desired hydroxamic acid (55 mg, 42% yield; 2 steps). MS found: $(M+H)^+$=451.

Example 707

(3R,4R)-4-({4-[(2-cyclopropylpyrazolo[1,5-a] pyridin-3-yl)methyl]benzoyl}amino)-N-hydroxytetrahydro-2H-pyran-3-carboxamide (707a) Using procedures analogous to (701a) to (701d), methyl cyclopropanecarboxylate (1.00 g, 10.0 mmol) was converted to the desired carboxylic acid (180 mg, 6% yield, 4 steps). MS found: $(M+H)^+$=293.

(707b) Using procedures analogous to (1 h) to (1i), the product from reaction (707a) (70 mg, 0.24 mmol) and the amine from (40e) (1 eq) were converted to the desired hydroxamic acid (45 mg, 43% yield, 2 steps). MS found: $(M+H)^+$=435.

Example 708

(3R,4R)-4-({4-[(2-cyclobutylpyrazolo[1,5-a]pyridin-3-yl)methyl]benzoyl}amino)-N-hydroxytetrahydro-2H-pyran-3-carboxamide (708a) Using procedures analogous to (701a) to (701d), ethyl cyclobutanecarboxylate (1.28 g, 10.0 mmol) was converted to the desired carboxylic acid (252 mg, 8% yield, 4 steps). MS found: $(M-H)^-$=305.

(708b) Using procedures analogous to (1 h) to (1i), the product from reaction (708a) (70 mg, 0.23 mmol) and the amine from (40e) (1 eq) were converted to the desired hydroxamic acid (55 mg, 53% yield, 2 steps). MS found: $(M+H)^+$=449.

Example 709

4-[(2-cyclobutylpyrazolo[1,5-a]pyridin-3-yl) methyl]-N-{(1R,2S)-2-[(hydroxyamino)carbonyl] cyclopentyl}benzamide (709a) Using procedures analogous to (1 h) to (1i), the product from reaction (708a) (31 mg, 0.10 mmol) and methyl-(1S,2R)-2-aminocyclopentane carboxylate (1 eq) were converted to the desired hydroxamic acid (12 mg, 27% yield, 2 steps). MS found: $(M+H)^+$=433.

Example 710

(3R,4R)-N-hydroxy-4-({4-[(2-phenylpyrazolo[1,5-a] pyridin-3-yl)methyl]benzoyl}amino)tetrahydro-2H-pyran-3-carboxamide (710a) Using procedures analogous to (701a) to (701d), methyl benzoate (1.36 g, 10.0 mmol) was converted to the desired carboxylic acid (94 mg, 3% yield, 4 steps). MS found: (M−H)⁻=327.

(710b) Using procedures analogous to (1 h) to (1i), the product from reaction (710a) (18 mg, 0.055 mmol) and the amine from (40e) (1 eq) were converted to the desired hydroxamic acid (16 mg, 62% yield, 2 steps). MS found: (M+H)⁺=471.

Example 711

(3R,4R)-4-({4-[(2-cyclopentylpyrazolo[1,5-a] pyridin-3-yl)methyl]benzoyl}amino)-N-hydroxytetrahydro-2H-pyran-3-carboxamide (711a) Using procedures analogous to (701a) to (701d), methyl cyclopentanecarboxylate (1.28 g, 10.0 mmol) was converted to the desired carboxylic acid (450 mg, 14% yield, 4 steps). MS found: (M+H)⁺=321.

(711b) Using procedures analogous to (1 h) to (1i), the product from reaction (711a) (80 mg, 0.25 mmol) and the amine from (40e) (1 eq) were converted to the desired hydroxamic acid (20 mg, 17% yield, 2 steps). MS found: (M−H)⁻=461.

Example 712

(3R,4R)-N-hydroxy-4-({4-[(2-tetrahydro-2H-pyran-4-ylpyrazolo[1,5-a]pyridin-3-yl)methyl] benzoyl}amino)tetrahydro-2H-pyran-3-carboxamide (712a) Using procedures analogous to (701a) to (701d), methyl 4-tetrahydropyran-carboxylate (722 mg, 5.00 mmol) was converted to the desired carboxylic acid (155 mg, 9% yield, 4 steps). MS found: (M−H)⁻=335.

(712b) Using procedures analogous to (1 h) to (1i), the product from reaction (712a) (70 mg, 0.21 mmol) and the amine from (40e) (1 eq) were converted to the desired hydroxamic acid (20 mg, 19% yield, 2 steps). MS found: (M+H)⁺=479.

Example 713

N-{(1R,2S)-2-[(hydroxyamino)carbonyl] cyclopentyl}-4-{[2-(trifluoromethyl)pyrazolo[1,5-a] pyridin-3-yl]methyl}benzamide (713a) Using procedures analogous to (1 h) to (1i), the product from reaction (702b) (89 mg, 0.28 mmol) and methyl (1S,2R)-2-aminocyclopentane-1-carboxylate hydrochloride (1 eq) were converted to the desired hydroxamic acid (30 mg, 24% yield, 2 steps). MS found: (M+Na)⁺=469.

Example 714 tert-butyl (3S,4S)-3-[(hydroxyamino)carbonyl]-4-[(4-{[2-(trifluoromethyl)pyrazolo[1,5-a]pyridin-3-yl] methyl}benzoyl)amino]pyrrolidine-1-carboxylate (714a) Using procedures analogous to (1 h) to (1i), the product from reaction (702b) (196 mg, 0.614 mmol) was converted to the desired hydroxamic acid (85 mg, 51% yield, 2 steps). MS found: (M+Na)⁺=570.

Example 715

(3S,4S)-N-hydroxy-4-[(4-{[2-(trifluoromethyl) pyrazolo[1,5-a]pyridin-3-yl]methyl}benzoyl)amino] pyrrolidine-3-carboxamide (715a) Using a procedure similar to (2a), the product from reaction (714a) (45 mg, 0.082 mmol) was converted to the desired amine salt (48 mg, 100%). MS found: (M+H)⁺=448.

Example 716

(3R,4R)-N-hydroxy-4-[(4-{[7-methyl-2-(trifluoromethyl)pyrazolo[1,5-a]pyridin-3-yl] methyl}benzoyl)amino]tetrahydro-2H-pyran-3-carboxamide (716a) 2-picoline (14.0 g, 3.0 eq) was added to a freshly prepared solution of hydroxylamine-o-sulfonic acid (5.65 g, 50.0 mmol) in water (32 ml) and heated to 90° C. for 20 min. The mixture was cooled down to rt and added Potassium carbonate (6.90 g, 1.0 eq). It was concentrated by rotatory evaporator at high temperature bath (40° C.). The residue was treated with ethanol (60 ml). The insoluble precipitate of potassium sulfate was removed by filtration. The filtrate was added 57% hydriodic acid (7 ml) and stored at −20° C. for 1 h. The product crashed out of the solution. The solid was filtered and recrystallized from ethanol to provide the desired salt (6.00 g, 51%).

(716b) The mixture of the product from reaction (716a) (1.71 g, 1.2 eq), ethyl 4,4,4-trifluoro-2-butynate (1.00 g, 6.02 mmol) and potassium carbonate (1.25 g, 1.5 eq) was stirred at rt under air for 12 h. Then it was added water (10 ml) and ethyl acetate (200 ml). It was further washed with water (10 ml, 2 times), brine (10 ml), dried (MgSO₄) and concentrated. Flash chromatography (ethyl acetate-hexane, 4:6) furnished the desired pyrozolopyridine (600 mg, 37%). MS found: (M+H)⁺=273.

(716c) Using a procedure similar to (1 g), the product from reaction (716b) (550 mg, 2.02 mmol) was converted to the desired carboxylic acid (480 mg, 97%). MS found: (2M−H)⁻=487.

(716d) The product from reaction (716c) (450 mg, 1.84 mmol) was treated with 48% hydrobromic acid (10 ml) and heated to 100° C. for 2 h. The mixture was cooled down to rt and carefully quenched with 50% sodium hydroxide to basic. Then the aqueous layer was extracted with ethyl ether (3×100 ml). The combined organic layer was washed with brine (20 ml), dried (MgSO₄) and concentrated to provide the desired compound (250 mg, 68%). MS found: (M+H)⁺=201.

(716e) A solution of the product from reaction (716d) (150 mg, 1.25 mmol) in ethanol (5 ml) was treated with bromine (400 mg, 2.0 eq) at rt and stirred for 15 min. Then the mixture was concentrated and purified by flash chromatography (ethyl acetate-hexane, 1:9) to provide the desired bromide (200 mg, 96%).

(716f) A solution of the product from reaction (716e) (190 mg, 0.680 mmol) in THF (5 ml) was treated with n-butyllithium (0.75 mmol, 1.1 eq) at −78° C. and stirred at that temperature for 10 min. This cold solution was canulated into another solution of 4-formyl-benzoic acid methyl ester (123 mg, 1.1 eq) in THF (5 ml) at −78° C. The resultant mixture was stirred at −78° C. for 15 min and quenched with saturated sodium bicarbonate (5 mL). Then it was diluted with ethyl acetate (100 ml) and washed with brine (10 ml), dried (MgSO₄) and concentrated. Flash chromatography (ethyl acetate-hexane, 2:8) furnished the desired alcohol (190 mg, 77%). MS found: (M+H)⁺=365.

(716g) The product from reaction (716f) (180 mg, 0.50 mmol) was treated with triethylsilane (580 mg, 10 eq) and trifluoroacetic acid (570 mg, 10 eq) in dichloromethane (5 ml) at rt and stirred for 1 h. Then the mixture was concentrated and purified by flash chromatography (ethyl acetate-hexane, 1:9) to provide the desired ester (150 mg, 87%). MS found: (M+H)⁺=349.

(716h) Using a procedure similar to (1 g), the product from reaction (716 g) (145 mg, 0.417 mmol) was converted to the desired carboxylic acid (135 mg, 97%). MS found: (M+H)⁺=335.

(716i) Using procedures analogous to (1 h) to (1i), the product from reaction (717 h) (70 mg, 0.209 mmol) and the amine from (40e) (1 eq) were converted to the desired hydroxamic acid (30 mg, 30% yield, 2 steps). MS found: (M−H)$^-$=475.

Example 801

(3R,4R)-N-hydroxy-4-({4-[(1-methylimidazo[1,5-a] pyridin-3-yl)methyl]benzoyl}amino)tetrahydro-2H-pyran-3-carboxamide (801a) 2-(1-Azidoethyl)-pyridine (prepared according to the procedures contained in *Tetrahedron Asymmetry*, 1994, 5, 1973–1978 and Venish et al. *J.Org. Chem.* 1998, 63, 2481–2487) (1.42 g, 9.6 mmol) in methanol (50 mL) was treated with 10% palladium on carbon (0.025 eq) and stirred under a balloon of hydrogen for 7 h. The reaction was purged with nitrogen and filtered to give the desired amine (1.05 g, 90% yield) which was taken on without further purification.

(801b) The amine from reaction (801a) (169 mg, 1.39 mmol) and methyl 4-carbomethoxybenzoate (224 mg, 1.15 mmol) (prepared according to *Tetrahedron Lett.* 2000, 41, 7601) in DMF (10 mL) were treated with BOP reagent (762 mg, 1.5 eq) and Hunig's base (0.636 mL, 3.0 eq) and stirred for 12 h. The reaction was quenched with saturated aqueous NH$_4$Cl and extracted with ethyl acetate (2×), washed with saturated aqueous NaHCO$_3$ and brine, dried (MgSO$_4$) and concentrated. Silica gel column chromatography (MeOH/ ethyl acetate, 1:9) yielded the desired amide (386 mg, 100%). MS (ES$^+$): 299 (M+H).

(801c) The amide from reaction (801b) (340 mg, 1.14 mmol) in acetic anhydride (10 mL) was treated with p-toluenesulfonic acid (20 mg, 0.1 eq) and heated to 100° C. for 90 min. The acetic anhydride was blown off with nitrogen over 12 h. The reaction was concentrated and partitioned between saturated aqueous NaHCO$_3$ and ethyl acetate and the organic layer was washed with brine, dried (MgSO$_4$) and concentrated giving the desired heterocycle (232 mg, 85% yield). MS (ES$^+$): 281 (M+H).

(801d) The amide from (reaction (801c) (222 mg, 0.8 mmol) in methanol (3 mL) was treated with LiOH (2M, 3 mL, 7.5 eq) and stirred at 40° C. The reaction was quenched with 1N HCl until pH 7 and extracted with ethyl acetate, dried (MgSO$_4$) and concentrated to give the desired acid (54 mg, 24% yield) which was taken on without further purification.

(801e) Using procedures analogous to (1 h)-(1i) the amine from reaction (40e) (54 mg, 0.22 mmol) and the acid from reaction (801d) (54 mg, 0.2 mmol) were converted to the desired hydroxamic acid (29 mg, 27%, 2 steps). MS Found: 409 (M+H).

Example 802

(3R,4R)-N-hydroxy-4-[(4-{[1-(trifluoromethyl) imidazo[1,5-a]pyridin-3-yl]methyl}benzoyl)amino] tetrahydro-2H-pyran-3-carboxamide (802a) To 2-carboxyaldehyde pyridine (10.1 mmol, 1.08 g) was added tetrabutylammonium triphenyldifluorosilicate (30.3 mmol, 16.4 g) followed by trimethylsilyltrifluoromethane (30.3, mmol, 4.31 g). The reaction was stirred for 3 h and then concentrated in vacuo and purified via flash chromatography to afford the desired alcohol (798 mg, 45%). MS found: (M−H)$^-$=176.

(802b) To the product from (802a) (4.46 mmol, 790 mg) in CH$_2$Cl$_2$ (10 mL) was added triethylamine (4.46 mmol, 0.8 mL). The reaction was stirred and then cooled to −78° C. To the cooled reaction was added trifluoromethanesulfonic anhydride (4.46 mmol, 0.75 mL) dropwise. The reaction was stirred for 10 min and then quenched with aqueous NaHCO$_3$. The reaction was then extracted using CH$_2$Cl$_2$ (2×20 mL) and the organic layer was washed with brine and dried (MgSO$_4$). The organic layer was concentrated in vacuo to afford the desired triflate (1.38 g, 99%). MS found: (M+H)$^+$=310.

(802c) to the product from (802b) (4.46 mmol, 1.38 g) in DMF (10 mL) was added sodium azide (4.46 mmol, 290 mg). The reaction was stirred at ambient temperature for 20 min and then diluted using an H$_2$O (10 mL) and diethyl ether (50 mL) mixture. The aqueous layer was extracted using diethyl ether (2×10 mL) and the organic layers were washed using an NaCl solution (sat) and dried (MgSO$_4$). The reaction was then concentrated in vacuo to afford the desired azide (900 mg, 99%). MS found: (M−N3+OH)$^+$=176.

(802d) To the product from (802c) (400 mg, 0.44 mmol) was added Pd(OH)$_2$/C (160 mg) and H$_2$. The reaction was shaken under pressure within a glass bottle within the Parr Shaker for 2 h. The reaction was then filtered, concentrated in vacuo and purified via flash chromatography. (226 mg, 30%). MS found: (M+H)$^+$=177.

(802e) Using procedures analogous to (801b)-(801d), the product from (802d) (1.28 mmol, 226 mg) was converted to the desired amide (52 mg, 80%). MS found: (M+H)$^+$=462.

(802f) Using the procedure analogous to (1i), the product from (802e) was converted to the desired hydroxamic acid (33 mg, 63%). MS found: (M+H)$^+$=463.

Example 803

(3R,4R)-N-hydroxy-4-[(4-{[3-(trifluoromethyl) imidazo[1,5-a]pyridin-1-yl]methyl}benzoyl)amino] tetrahydro-2H-pyran-3-carboxamide (803a) To 2-carboxyaldehyde pyridine (28 mmol, 2.95 g) was added 4-(methoxycarbonyl)benzyl zinc bromide (28 mmol, 55 mL, 0.5 M) (prepared according procedures in: Shiota, T. and Yamamori, T. *J. Org. Chem*, 1999, 64, 453) and lithium chloride (112 mmol, 4.75 g). The reaction was stirred 10 min and then quenched using NH$_4$Cl. The aqueous layer was extracted using EtOAc (2×50 mL) and the organic layers washed using an NaCl (sat) (1×20 mL) solution and dried using MgSO$_4$. The organic layer was then concentrated in vacuo and then purified via flash chromatography to afford the desired alcohol (1.99 g, 28%). %). MS found: (M+K)$^+$=181.

(803b) To the product from (803a) (7.73 mmol, 1.99 g) as a solution in CH$_2$Cl$_2$ (5 mL) was added triethylamine (7.73 mmol, 1.43 mL) methanesulfonyl chloride (15.5 mmol, 1.2 mL). The reaction was stirred for 30 min and then quenched using H$_2$O. The organic layer was washed using NaCl (sat) solution (1×10 mL) and dried (MgSO$_4$). The organic layer was then concentrated in vacuo to afford the desired sulfonyl ether (2.5, 99%). MS found: (M+H)$^+$=336.

(803c) To the product from (803b) (7.73 mmol, 2.5 g) was in DMF (16 mL) was added NaN3 (31 mmol, 2.02 mg). The reaction was heated to 60° C. for 1 h and then cooled to ambient temperature and diluted with water (20 mL) and diethyl ether (100 mL). The aqueous layer was separated and then re-extracted (2×100 mL) and washed using NaCl (1×20 mL) and dried (MgSO$_4$). The organic layer was concentrated in vacuo to afford the desired azide (1.14 g, 40%). MS found: (M+H)$^+$=283.

(803d) To the product from (803c) (4.03 mmol, 1.14 g) in THF (100 mL) was added triphenylphosphine (4.03 mmol, 106 g) and H₂O (0.1 mL). The reaction was heated to 70° C. for 1 h and then cooled to ambient temperature. The reaction was concentrated in vacuo and then redissolved in CH₂Cl₂ and then washed using NaCl (sat) (1×20 mL) and dried (MgSO₄). The crude was purified via flash chromatography to afford the desired amine (614 mg, 59%). MS found: (M+H)⁺=257.

(803e) To the product from (803d) (0.98 mmol, 258 mg) in benzene (10 mL) was added acetyl bromide (1.5 mmol, 0.1 mL) and Hunig's Base. The reaction was stirred for 1 h and then quenched using aqueous NaHCO₃ (sat) (10 mL). The reaction was extracted using EtOAc (2×50 mL). The organic layer was washed using an NaCl (sat) solution (1×20 mL) and dried (MgSO₄). The organic layer was concentrated in vacuo and then purified via flash chromatography to afford the desired ester (20 mg, 15%). MS found: (M+H)⁺= 281.

(803f) To the product from (803e) (0.14 mmol, 40 mg) in MeOH (2 mL) was added NaOH (2 mL). The reaction was heated to 70° C. for 20 min and then quenched using HCl (1M) to pH 6. The solution was then extracted with EtOAc (3×30 mL) and the organic layer washed using an NaCl (sat) solution and dried (MgSO₄). The organic layer was concentrated in vacuo to afford the desired acid (35 mg, 95%). MS found: (M+H)⁺=267.

(803g) To a solution of the product from (803f) (0.13 mmol, 37 mg) was reacted with the amine from reaction (40e) (0.13 mmol, 37 mg), Hunig's base (0.26 mmol, 0.048 mL), and benzotriazol-1-yloxyltris(dimethylamino)-phosphonium hexafluorophosphate (BOP) (0.14 mmol, 63 mg,). The reaction was stirred for 2 h at ambient temperature and then quenched with NH₄Cl. The reaction mixture was extracted with EtOAc (3×20 mL) and the organic layers separated and concentrated in vacuo. The organic layers were washed using an NaCl (sat) solution (1×20 mL) and then dried over MgSO₄. The organic layers were then concentrated in vacuo to afford the desired amide (53 mg, 99%). MS found: (M+H)⁺=408.

(803h) Using procedures analogous to (1i), the product from (803 g) was reacted to afford the desired hydroxamic acid (6.3 mg, 12%). MS found: (M+H)⁺=409.

Example 804

(3R,4R)-N-hydroxy-4-({4-[(3-methylimidazo[1,5-a]pyridin-1-yl)methyl]benzoyl}amino)tetrahydro-2H-pyran-3-carboxamide (804a) Using procedures analogous to (803a)-(803 g), the product from (801d) (0.812 mmol, 208 mmol) in THF (10 mL) was reacted with trifluoroacetic anhydride (1.22 mmol, 256 mg) to afford the desired amide (60 mg, 99%). MS found: (M+H)⁺=462.

(804b) Using procedures analogous to (1i), the product from reaction (802a) (0.3 mmol, 60 mg) was reacted to afford the desired hydroxamic acid (36 mg, 26%). MS found: (M+H)⁺=463.

Tables 1–5 below provide representative Examples, the synthesis of which is described above, of the compounds of Formula (I) the present invention.

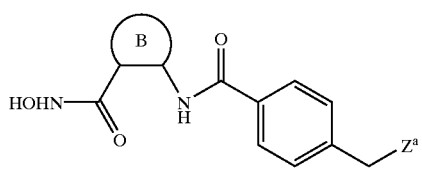

The following structures are intended for ring B in formula (I) in the following tables.

B:

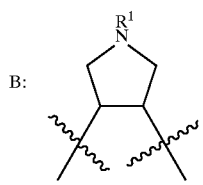 B1

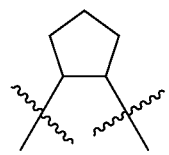 B2

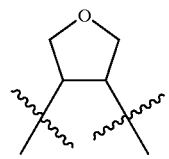 B3

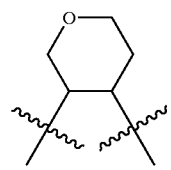 B4

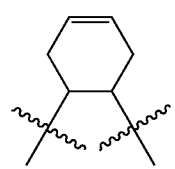 B5

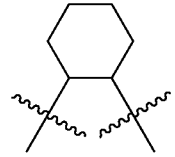 B6

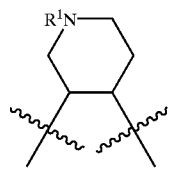 B7

-continued

B8
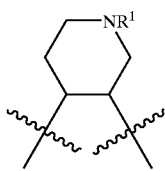

TABLE 1

Z$^a$:

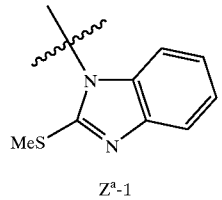 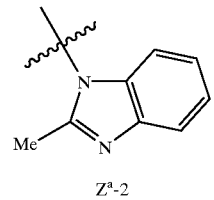

Z$^a$-1     Z$^a$-2

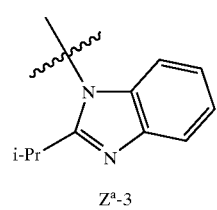 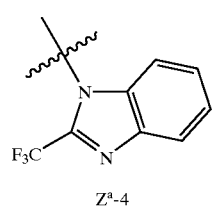

Z$^a$-3     Z$^a$-4

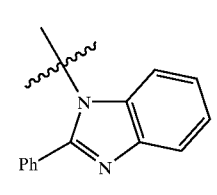 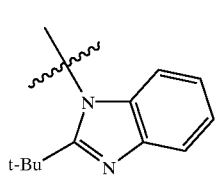

Z$^a$-5     Z$^a$-6

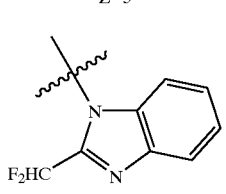 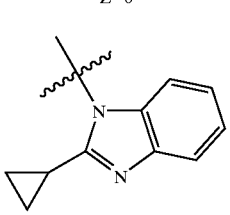

Z$^a$-7     Z$^a$-8

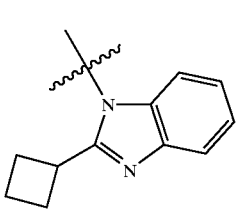 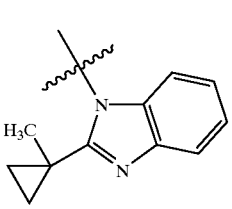

Z$^a$-9     Z$^a$-10

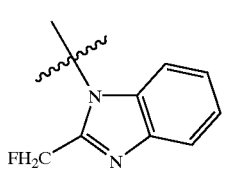 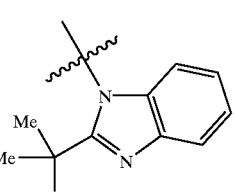

Z$^a$-11     Z$^a$-12

TABLE 1-continued

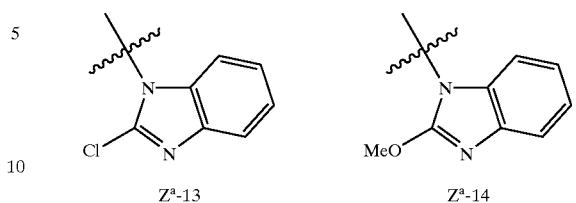

Z$^a$-13     Z$^a$-14

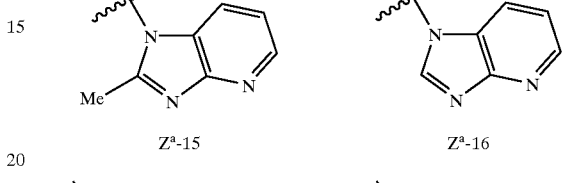

Z$^a$-15     Z$^a$-16

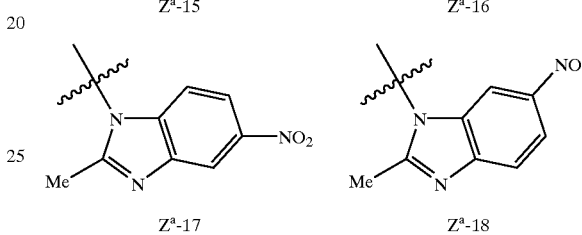

Z$^a$-17     Z$^a$-18

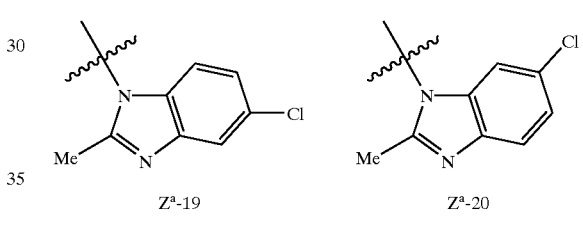

Z$^a$-19     Z$^a$-20

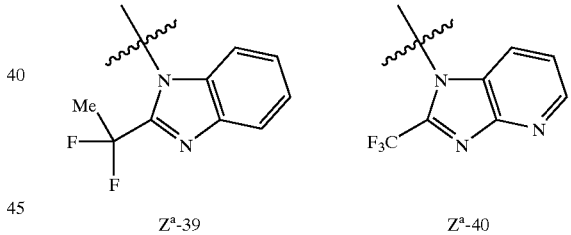

Z$^a$-39     Z$^a$-40

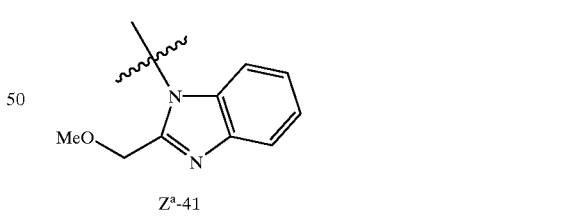

Z$^a$-41

| Ex | B | R$^1$ | Z$^a$ | MS [M + H] |
|---|---|---|---|---|
| 1 | B1 | t-butoxycarbonyl | Z$^a$-1 | 526 |
| 2 | B1 | H | Z$^a$-1 | 426 |
| 3 | B1 | methylsulfonyl | Z$^a$-1 | 504 |
| 4 | B1 | 2-propynyl | Z$^a$-1 | 464 |
| 5 | B1 | methyl | Z$^a$-1 | 440 |
| 6 | B1 | isopropyl | Z$^a$-1 | 468 |
| 7 | B1 | acetyl | Z$^a$-1 | 468 |
| 8 | B1 | propylsulfonyl | Z$^a$-1 | 532 |
| 9 | B1 | isopropylsulfonyl | Z$^a$-1 | 532 |
| 10 | B1 | t-butoxycarbonyl | Z$^a$-2 | 494 |
| 11 | B1 | H | Z$^a$-2 | 394 |
| 12 | B1 | 2-propynyl | Z$^a$-2 | 432 |

TABLE 1-continued

| | | | | |
|---|---|---|---|---|
| 13 | B1 | 2-butynyl | $Z^a$-2 | 446 |
| 14 | B1 | 3-butenyl | $Z^a$-2 | 449 |
| 15 | B2 | — | $Z^a$-2 | 393 |
| 16 | B1 | isopropyl | $Z^a$-2 | 436 |
| 17 | B1 | neopentyl | $Z^a$-2 | 464 |
| 18 | B1 | t-butoxycarbonyl | $Z^a$-3 | 522 |
| 19 | B1 | H | $Z^a$-3 | 422 |
| 20 | B1 | methyl | $Z^a$-3 | 436 |
| 21 | B1 | propyl | $Z^a$-3 | 464 |
| 22 | B1 | isopropyl | $Z^a$-3 | 464 |
| 23 | B1 | 2-propynyl | $Z^a$-3 | 460 |
| 24 | B1 | 3-butenyl | $Z^a$-3 | 476 |
| 25 | B1 | 2-butynyl | $Z^a$-3 | 475 |
| 26 | B1 | propylsulfonyl | $Z^a$-3 | 527 |
| 27 | B1 | butylsulfonyl | $Z^a$-3 | 542 |
| 28 | B1 | isopropylsulfonyl | $Z^a$-3 | 527 |
| 29 | B2 | — | $Z^a$-3 | 421 |
| 30 | B1 | isobutyl | $Z^a$-3 | 478 |
| 31 | B1 | neopentyl | $Z^a$-3 | 492 |
| 32 | B1 | t-butoxycarbonyl | $Z^a$-4 | 548 |
| 33 | B1 | H | $Z^a$-4 | 448 |
| 34 | B1 | isopropyl | $Z^a$-4 | 489 |
| 35 | B1 | 2-propynyl | $Z^a$-4 | 486 |
| 36 | B1 | 2-butynyl | $Z^a$-4 | 500 |
| 37 | B1 | 3-butenyl | $Z^a$-4 | 502 |
| 39 | B4 | — | $Z^a$-3 | 437 |
| 40 | B4 | — | $Z^a$-4 | 463 |
| 42 | B1 | propylsulfonyl | $Z^a$-4 | 554 |
| 43 | B1 | isopropylsulfonyl | $Z^a$-4 | 554 |
| 44 | B1 | butylsulfonyl | $Z^a$-4 | 567 |
| 45 | B1 | acetyl | $Z^a$-4 | 490 |
| 46 | B1 | 4-pentenoyl | $Z^a$-4 | [M] 529 |
| 47 | B1 | isobutyl | $Z^a$-4 | 504 |
| 48 | B1 | neopentyl | $Z^a$-4 | 518 |
| 49 | B2 | — | $Z^a$-4 | [M] 446 |
| 50 | B3 | — | $Z^a$-4 | 449 |
| 51 | B1 | t-butoxycarbonyl | $Z^a$-5 | 556 |
| 52 | B1 | H | $Z^a$-5 | 456 |
| 53 | B1 | t-butoxycarbonyl | $Z^a$-6 | 537 |
| 54 | B1 | H | $Z^a$-6 | 436 |
| 55 | B1 | 2-propynyl | $Z^a$-6 | 475 |
| 56 | B1 | 2-butynyl | $Z^a$-6 | 489 |
| 57 | B1 | isopropyl | $Z^a$-6 | 479 |
| 58 | B2 | — | $Z^a$-6 | [M] 435 |
| 59 | B4 | — | $Z^a$-6 | [M] 452 |
| 60 | B3 | — | $Z^a$-6 | [M] 437 |
| 61 | B1 | t-butoxycarbonyl | $Z^a$-7 | 530 |
| 62 | B1 | H | $Z^a$-7 | 430 |
| 63 | B1 | isopropyl | $Z^a$-7 | 472 |
| 64 | B1 | 2-propynyl | $Z^a$-7 | 468 |
| 65 | B1 | isobutyl | $Z^a$-7 | 486 |
| 66 | B1 | neopentyl | $Z^a$-7 | 500 |
| 67 | B2 | — | $Z^a$-7 | [M] 443 |
| 68 | B4 | — | $Z^a$-7 | [M] 452 |
| 69 | B3 | — | $Z^a$-7 | [M] 431 |
| 70 | B2 | — | $Z^a$-8 | 419 |
| 71 | B4 | — | $Z^a$-8 | [M] 435 |
| 72 | B3 | — | $Z^a$-8 | [M] 421 |
| 73 | B2 | — | $Z^a$-9 | [M] 434 |
| 74 | B4 | — | $Z^a$-9 | 449 |
| 75 | B4 | — | $Z^a$-10 | 449 |
| 76 | B2 | — | $Z^a$-10 | 433 |
| 79 | B4 | — | $Z^a$-11 | 427 |
| 80 | B2 | — | $Z^a$-11 | 411 |
| 81 | B4 | — | $Z^a$-12 | 455 |
| 82 | B2 | — | $Z^a$-12 | 439 |
| 83 | B4 | — | $Z^a$-3 | 437 |
| 84 | B4 | — | $Z^a$-3 | 437 |
| 85 | B1 | t-butoxycarbonyl | $Z^a$-13 | 514.3 |
| 86 | B1 | t-butoxycarbonyl | $Z^a$-14 | [M] 510 |
| 87 | B1 | t-butoxycarbonyl | $Z^a$-15 | 495 |
| 88 | B1 | t-butoxycarbonyl | $Z^a$-16 | 482 |
| 92 | B1 | H | $Z^a$-13 | 414 |
| 93 | B1 | H | $Z^a$-16 | 482 |
| 94 | B1 | H | $Z^a$-15 | 320 |
| 95 | B1 | t-butoxycarbonyl | $Z^a$-17 | 540 |
| 96 | B1 | t-butoxycarbonyl | $Z^a$-18 | 540 |
| 97 | B1 | t-butoxycarbonyl | $Z^a$-19 | 530 |
| 98 | B1 | t-butoxycarbonyl | $Z^a$-20 | 530 |
| 99 | B5 | — | $Z^a$-8 | 431 |
| 100 | B5 | — | $Z^a$-9 | 445 |
| 101 | B5 | — | $Z^a$-3 | 434 |
| 102 | B6 | — | $Z^a$-3 | 435 |
| 103 | B6 | — | $Z^a$-8 | [M + Na] 432 |
| 104 | B6 | — | $Z^a$-9 | 446 |
| 105 | B6 | — | $Z^a$-4 | 462 |
| 106 | B6 | — | $Z^a$-6 | 449 |
| 112 | B7 | t-butoxycarbonyl | $Z^a$-10 | 548 |
| 113 | B7 | H | $Z^a$-10 | 448 |
| 134 | B8 | t-butoxycarbonyl | $Z^a$-4 | [M + Na] 584 |
| 135 | B8 | H | $Z^a$-4 | 462 |
| 139 | B4 | — | $Z^a$-39 | 459 |
| 140 | B4 | — | $Z^a$-40 | 464 |
| 141 | B4 | — | $Z^a$-41 | 439 |

TABLE 2

$Z^a$:

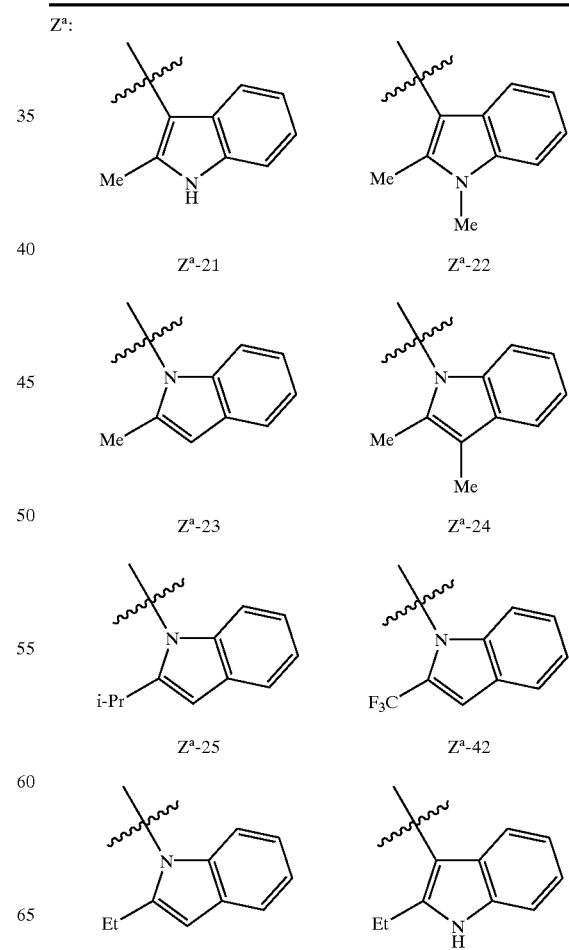

$Z^a$-21  $Z^a$-22

$Z^a$-23  $Z^a$-24

$Z^a$-25  $Z^a$-42

TABLE 2-continued

Z⁰-43, Z⁰-44, Z⁰-45, Z⁰-46, Z⁰-47, Z⁰-48

| Ex | B | R² | Zᵃ | MS [M + H] |
|---|---|---|---|---|
| 201 | B1 | t-butoxycarbonyl | Zᵃ-21 | 493 |
| 202 | B1 | t-butoxycarbonyl | Zᵃ-22 | 507 |
| 203 | B1 | H | Zᵃ-21 | 393 |
| 204 | B1 | H | Zᵃ-22 | 407 |
| 205 | B1 | isopropyl | Zᵃ-21 | 435 |
| 206 | B1 | 2-propynyl | Zᵃ-21 | 431 |
| 207 | B4 | — | Zᵃ-21 | 408 |
| 208 | B4 | — | Zᵃ-23 | 422 |
| 209 | B2 | — | Zᵃ-23 | 392 |
| 210 | B1 | t-butoxycarbonyl | Zᵃ-24 | 507 |
| 211 | B1 | t-butoxycarbonyl | Zᵃ-25 | 543 |
| 212 | B1 | H | Zᵃ-25 | 421 |
| 213 | B1 | H | Zᵃ-24 | 407 |
| 214 | B4 | — | Zᵃ-24 | 422 |
| 215 | B4 | — | Zᵃ-42 | 462 |
| 216 | B4 | — | Zᵃ-43 | 422 |
| 217 | B3 | — | Zᵃ-43 | 408 |
| 218 | B3 | — | Zᵃ-24 | 430 |
| 219 | B4 | — | Zᵃ-44 | 422 |
| 220 | B2 | — | Zᵃ-44 | 408 |
| 222 | B3 | — | Zᵃ-42 | 448 |
| 223 | B4 | — | Zᵃ-45 | 408 |
| 224 | B3 | — | Zᵃ-45 | 392 [M − H] |
| 225 | B4 | — | Zᵃ-22 | 422 |
| 226 | B2 | — | Zᵃ-45 | 392 |
| 227 | B3 | — | Zᵃ-22 | 408 |
| 228 | B3 | — | Zᵃ-46 | 422 |
| 229 | B4 | — | Zᵃ-46 | 437 |
| 501 | B4 | — | Zᵃ-47 | 407 [M − H] |
| 502 | B1 | t-butoxycarbonyl | Zᵃ-47 | 492 [M − H] |
| 503 | B1 | H | Zᵃ-47 | 394 |
| 504 | B4 | — | Zᵃ-47 | 437 |
| 505 | B1 | t-butoxycarbonyl | Zᵃ-48 | 544 |
| 506 | B1 | H | Zᵃ-48 | 422 |

TABLE 3

Zᵃ: Zᵃ-26, Zᵃ-27, Zᵃ-28, Zᵃ-29, Zᵃ-30, Zᵃ-31, Zᵃ-32, Zᵃ-33

| Ex | B | R² | Zᵃ | MS [M + H] |
|---|---|---|---|---|
| 301 | B1 | t-butoxycarbonyl | Zᵃ-26 | 513 |
| 302 | B1 | t-butoxycarbonyl | Zᵃ-27 | 529 |
| 303 | B1 | H | Zᵃ-26 | 413 |
| 304 | B1 | H | Zᵃ-27 | 429 |
| 305 | B1 | 2-propynyl | Zᵃ-27 | 467 |
| 306 | B1 | isopropyl | Zᵃ-27 | 471 |
| 307 | B1 | t-butoxycarbonyl | Zᵃ-28 | [M + TFA-1] 657 |
| 308 | B1 | H | Zᵃ-28 | 445 |
| 309 | B1 | 2-propynyl | Zᵃ-28 | 483 |
| 310 | B1 | isopropyl | Zᵃ-28 | 487 |
| 311 | B1 | 2-butynyl | Zᵃ-28 | 497 |
| 312 | B1 | isobutyl | Zᵃ-28 | 501 |
| 313 | B1 | methyl | Zᵃ-28 | 459 |
| 314 | B1 | isopropylsulfonyl | Zᵃ-28 | 551 |
| 315 | B1 | acetyl | Zᵃ-28 | 487 |
| 316 | B1 | t-butylcarbonyl | Zᵃ-28 | 529 |
| 317 | B1 | phenyl | Zᵃ-28 | 521 |
| 318 | B1 | 4-F-phenyl | Zᵃ-28 | 539 |
| 319 | B1 | 4-methoxy-phenyl | Zᵃ-28 | 551 |
| 320 | B1 | cyclopropylmethyl | Zᵃ-28 | 499 |
| 321 | B1 | cyclopentyl | Zᵃ-28 | 513 |
| 322 | B1 | tetrahydro-2H-pyran-4-yl | Zᵃ-28 | 529 |

TABLE 3-continued
| | | | | |
|---|---|---|---|---|
| 323 | B1 | neopentyl | $Z^a$-28 | 515 |
| 324 | B2 | — | $Z^a$-28 | 444 |
| 325 | B3 | — | $Z^a$-28 | 446 |
| 326 | B4 | — | $Z^a$-28 | 460 |
| 327 | B1 | t-butoxycarbonyl | $Z^a$-29 | [M + TFA-1] 653 |
| 328 | B1 | t-butoxycarbonyl | $Z^a$-30 | [M + TFA-1] 669 |
| 329 | B1 | t-butoxycarbonyl | $Z^a$-31 | [M + TFA-1] 685 |
| 330 | B1 | H | $Z^a$-31 | 473 |
| 331 | B1 | 2-propynyl | $Z^a$-31 | 511 |
| 332 | B1 | isopropyl | $Z^a$-31 | 515 |
| 333 | B1 | isobutyl | $Z^a$-31 | 529 |
| 334 | B1 | butyl | $Z^a$-31 | 529 |
| 335 | B1 | neopentyl | $Z^a$-31 | 543 |
| 336 | B4 | — | $Z^a$-31 | 488 |
| 337 | B3 | — | $Z^a$-31 | 474 |
| 338 | B2 | — | $Z^a$-31 | [M + Na] 494 |
| 339 | B1 | t-butoxycarbonyl | $Z^a$-32 | 497 |
| 340 | B1 | t-butoxycarbonyl | $Z^a$-33 | [M + TFA-1] 657 |
TABLE 4
$Z^a$:
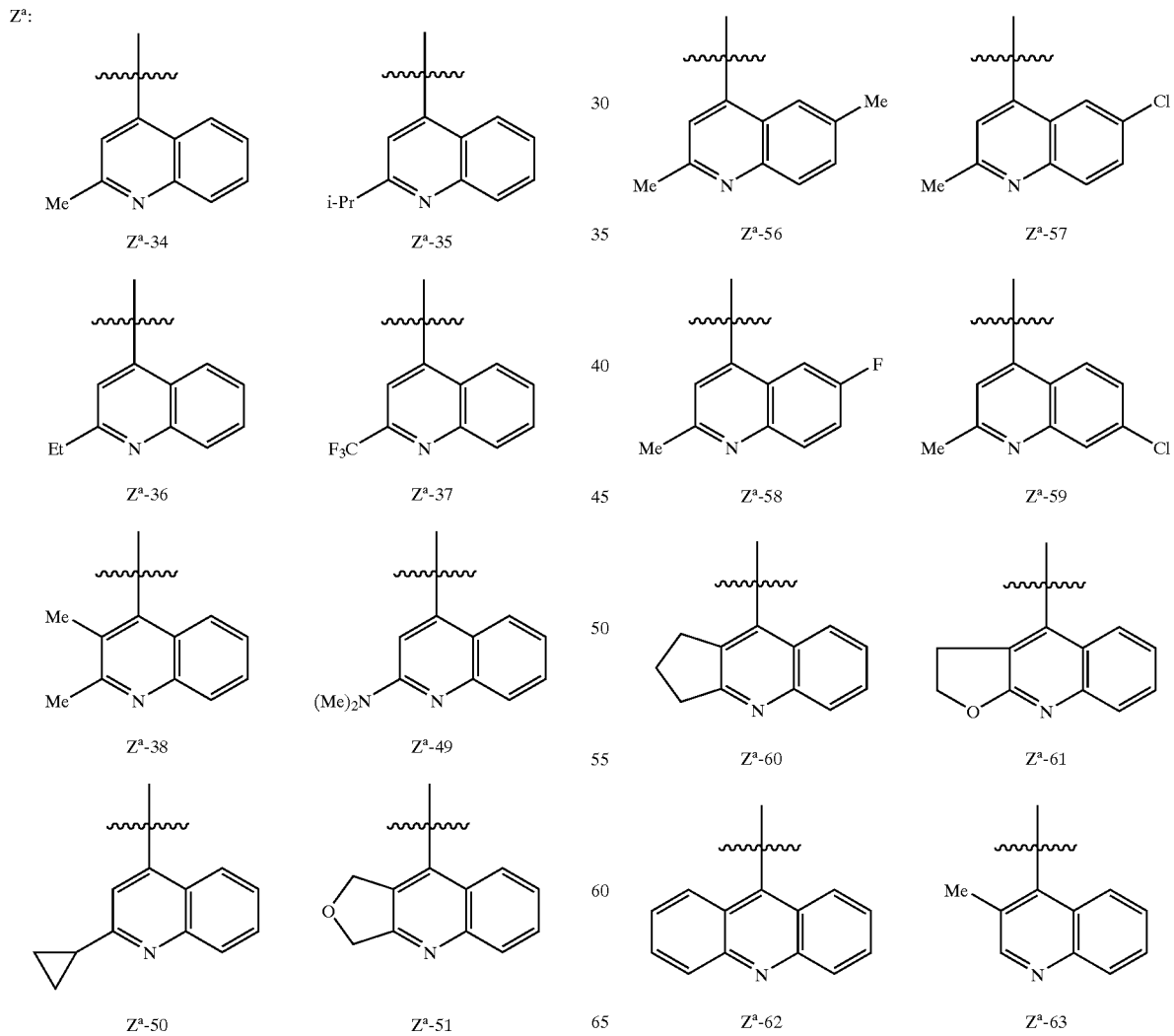

TABLE 4-continued

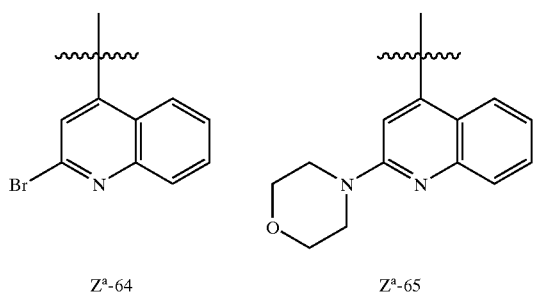

Zª-64    Zª-65

| Ex | B | R² | Zª | MS [M + H] |
|---|---|---|---|---|
| 401 | B1 | t-butoxycarbonyl | Zª-34 | 505 |
| 402 | B1 | H | Zª-34 | 405 |
| 403 | B1 | 2-propynyl | Zª-34 | 443 |
| 404 | B1 | isopropyl | Zª-34 | 447 |
| 405 | B1 | isobutyl | Zª-34 | 461 |
| 406 | B1 | butyl | Zª-34 | 461 |
| 407 | B1 | 2-butynyl | Zª-34 | 457 |
| 408 | B1 | methyl | Zª-34 | 419 |
| 409 | B1 | allyl | Zª-34 | 445 |
| 410 | B1 | cyclopropylmethyl | Zª-34 | 459 |
| 411 | B1 | cyclopentyl | Zª-34 | 473 |
| 412 | B1 | neopentyl | Zª-34 | 475 |
| 413 | B1 | tetrahydro-2H-pyran-4-yl | Zª-34 | 489 |
| 414 | B1 | phenyl | Zª-34 | 481 |
| 415 | B1 | 4-F-phenyl | Zª-34 | 499 |
| 416 | B1 | 4-methoxy-phenyl | Zª-34 | 511 |
| 417 | B1 | acetyl | Zª-34 | 447 |
| 418 | B1 | t-butylcarbonyl | Zª-34 | 489 |
| 419 | B1 | isopropylsulfonyl | Zª-34 | 511 |
| 420 | B1 | butylsulfonyl | Zª-34 | 525 |
| 421 | B1 | methoxycarbonyl | Zª-34 | 463 |
| 422 | B3 | — | Zª-34 | 406 |
| 423 | B4 | — | Zª-34 | 420 |
| 424 | B2 | — | Zª-34 | 404 |
| 425 | B1 | t-butoxycarbonyl | Zª-35 | 533 |
| 426 | B1 | H | Zª-35 | 433 |
| 427 | B1 | 2-propynyl | Zª-35 | 471 |
| 428 | B1 | isopropyl | Zª-35 | 475 |
| 429 | B1 | methyl | Zª-35 | 447 |
| 430 | B1 | cyclopentyl | Zª-35 | 473 |
| 431 | B4 | — | Zª-35 | 448 |
| 432 | B2 | — | Zª-35 | [M + TFA-1] 544 |
| 433 | B3 | — | Zª-35 | 434 |
| 434 | B1 | t-butoxycarbonyl | Zª-36 | 519 |
| 435 | B1 | H | Zª-36 | 419 |
| 436 | B1 | 2-propynyl | Zª-36 | 457 |
| 437 | B1 | 2-butynyl | Zª-36 | 471 |
| 438 | B4 | — | Zª-36 | 434 |
| 439 | B2 | — | Zª-36 | 418 |
| 440 | B3 | — | Zª-36 | 420 |
| 441 | B1 | t-butoxycarbonyl | Zª-37 | 559 |
| 442 | B4 | — | Zª-37 | 474 |
| 443 | B2 | — | Zª-37 | 458 |
| 444 | B1 | t-butoxycarbonyl | Zª-38 | 519 |
| 445 | B4 | — | Zª-38 | 434 |
| 446 | B2 | — | Zª-38 | 418 |
| 447 | B1 | 2-propynyl | Zª-37 | 497 |
| 448 | B3 | — | Zª-37 | 460 |
| 449 | B1 | 2-propynyl | Zª-38 | 457 |
| 450 | B3 | — | Zª-38 | 420 |
| 451 | B4 | — | Zª-49 | 449 |
| 452 | B3 | — | Zª-50 | 432 |
| 453 | B4 | — | Zª-50 | 446 |
| 454 | B3 | — | Zª-51 | 434 |
| 455 | B4 | — | Zª-51 | 448 |
| 456 | B1 | t-butoxycarbonyl | Zª-52 | 519 |
| 457 | B2 | — | Zª-52 | 418 |
| 458 | B4 | — | Zª-52 | 434 |
| 459 | B3 | — | Zª-52 | 420 |
| 460 | B4 | — | Zª-53 | 488 |
| 461 | B4 | — | Zª-54 | 454 |
| 462 | B3 | — | Zª-54 | 440 |
| 463 | B4 | — | Zª-55 | 448 |
| 464 | B3 | — | Zª-55 | 434 |
| 465 | B2 | — | Zª-55 | 432 |
| 466 | B3 | — | Zª-56 | 420 |
| 467 | B2 | — | Zª-56 | 418 |
| 468 | B4 | — | Zª-56 | 434 |
| 469 | B3 | — | Zª-57 | 440 |
| 470 | B4 | — | Zª-57 | 454 |
| 471 | B4 | — | Zª-58 | 438 |
| 472 | B4 | — | Zª-59 | 454 |
| 473 | B4 | — | Zª-60 | 446 |
| 474 | B4 | — | Zª-61 | 456 |
| 475 | B4 | — | Zª-62 | 448 |
| 476 | B4 | — | Zª-63 | 420 |
| 477 | B4 | — | Zª-64 | 484 |
| 478 | B4 | — | Zª-65 | 491 |

TABLE 5

Zª:

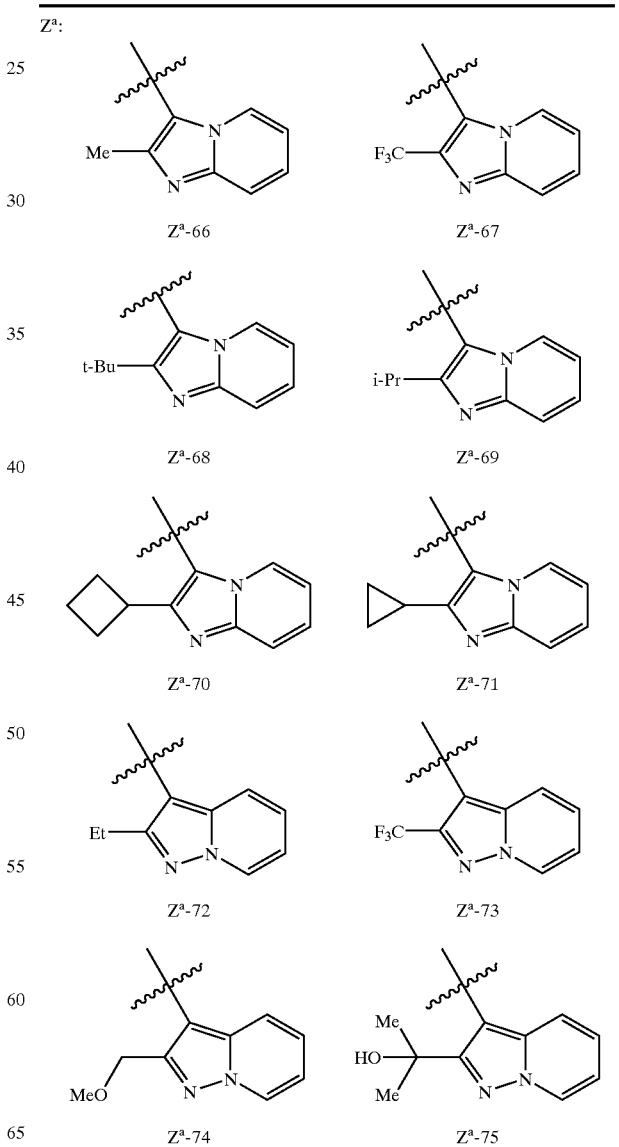

Zª-66    Zª-67

Zª-68    Zª-69

Zª-70    Zª-71

Zª-72    Zª-73

Zª-74    Zª-75

TABLE 5-continued

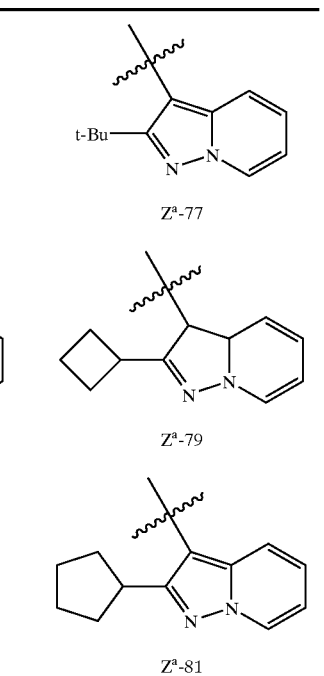

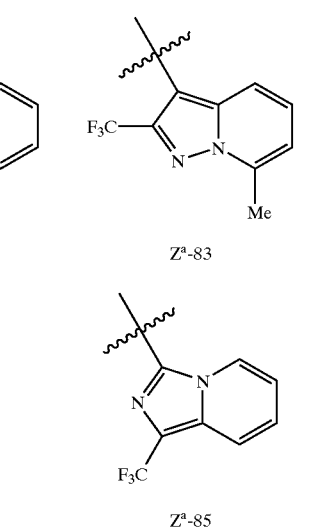

TABLE 5-continued

| Ex | B | R¹ | Zᵃ | MS [M + H] |
|---|---|---|---|---|
| 608 | B2 | — | Zᵃ-67 | 447 |
| 609 | B2 | — | Zᵃ-70 | 434 |
| 610 | B4 | — | Zᵃ-71 | 435 |
| 701 | B4 | — | Zᵃ-72 | 423 |
| 702 | B4 | — | Zᵃ-73 | 463 |
| 703 | B4 | — | Zᵃ-74 | 439 |
| 704 | B4 | — | Zᵃ-75 | 453 |
| 705 | B4 | — | Zᵃ-76 | 437 |
| 706 | B4 | — | Zᵃ-77 | 451 |
| 707 | B4 | — | Zᵃ-78 | 435 |
| 708 | B4 | — | Zᵃ-79 | 449 |
| 709 | B2 | — | Zᵃ-79 | 433 |
| 710 | B4 | — | Zᵃ-80 | 471 |
| 711 | B4 | — | Zᵃ-81 | 461 [M − H] |
| 712 | B4 | — | Zᵃ-82 | 479 |
| 713 | B2 | — | Zᵃ-73 | 469 [M + Na] |
| 714 | B1 | t-butoxycarbonyl | Zᵃ-73 | 570 [M + Na] |
| 715 | B1 | H | Zᵃ-73 | 448 |
| 716 | B4 | — | Zᵃ-83 | 475 [M − H] |
| 801 | B4 | — | Zᵃ-84 | 409 |
| 802 | B4 | — | Zᵃ-85 | 463 |
| 803 | B4 | — | Zᵃ-86 | 409 |
| 804 | B4 | — | Zᵃ-87 | 463 |

Utility

The compounds of formula I are expected to possess matrix metalloprotease and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, Cancer and Metastasis Reviews, 9, 289–303, 1990). The compounds of the present invention should be useful for the prevention and treatment of invasive tumors by inhibition of this aspect of metastasis.

The compounds of the present invention should also have utility for the prevention and treatment of osteopenia associated with matrix metalloprotease-mediated breakdown of cartilage and bone that occurs in osteoporosis patients.

Compounds that inhibit the production or action of TACE, aggrecanase, and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denotes agents that selectively inhibit COX-2 function. Such agents include, but are not limited to, celecoxib (Celebrex), rofecoxib (Vioxx), meloxicam (Movicox), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel), infliximab (Remicade), adalimumab (D2E7), CDP-571 (Humicade), and CDP-870.

Other anti-inflammatory agents that may be used in combination with the compounds of this invention, include, but are not limited to, methotrexate, interleukin-1 antagonists (e.g., anakinra (Kineret)), dihydroorotate synthase inhibitors (e.g., leflunomide (Arava)), and p38 MAP kinase inhibitors.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 $\mu$M for the inhibition of a desired MP. Preferred compounds of the present invention have $K_i$'s or $IC_{50}$'s of $\leq 1$ $\mu$M. More preferred compounds of the present invention have $K_i$'s or $IC_{50}$'s of $\leq 0.1$ $\mu$M. Even more preferred compounds of the present invention have $K_i$'s or $IC_{50}$'s of $\leq 0.01$ $\mu$M. Still more preferred compounds of the present invention have $K_i$'s or $IC_{50}$'s of $\leq 0.001$ $\mu$M.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. *Trans. Ortho. Res. Soc.* 1995, 20, 341). Therefore, in order to accumulate BNC aggrecanase in culture media, cartilage is first depleted of endogenous aggrecan by stimulation with 500 mg/ml human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, CE, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 μM for aggrecanase.

To evaluate inhibition of aggrecanase, compounds are prepared as 10 mM stocks in DMSO, water or other solvents and diluted to appropriate concentrations in water. Drug (50 μL) is added to 50 μL of aggrecanase-containing media and 50 μL of 2 mg/mL aggrecan substrate and brought to a final volume of 200 μL in 0.2 M Tris, pH 7.6, containing 0.4 M NaCl and 40 mM $CaCl_2$. The assay is run for 4 h at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 μg GAG) for 2 h at 37° C. and then with keratanase (0.1 units/10 μg GAG) and keratanase II (0.002 units/10 μg GAG) for 2 h at 37° C. in buffer containing 50 mM sodium acetate, 0.1 M Tris/HCl, pH 6.5. After digestion, aggrecan in the samples is precipitated with 5 volumes of acetone and resuspended in 30 μL of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 min to achieve optimal color development. Blots are quantitated by scanning densitometry and inhibition of aggrecanase determined by comparing the amount of product produced in the presence versus absence of compound.

TNF PBMC Assay

Human peripheral blood mononuclear cells (PBMC) were obtained from normal donor blood by leukophoresis and isolated by Ficoll-Paque density separation. PBMCs were suspended in 0.5 mL RPMI 1640 with no serum at $2 \times 10^6$ cells/mL in 96 well polystyrene plates. Cells were preincubated 10 min with compound, then stimulated with 1 μg/mL LPS (Lipopolysaccharide, *Salmonella typhimurium*) to induce TNF production. After an incubation of 5 h at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 mL. 225 μL of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 min before the addition of 100 mg/mL LPS. Plates are incubated for 5 h in an atmosphere of 5% $CO_2$ in air. At the end of 5 h, 750 μL of serum free media is added to each tube and the samples are spun at 1200 RPM for 10 min. The supernatant is collected off the top and assayed for TNF-alpha production by a standard sandwich ELISA. The ability of compounds to inhibit TNF-alpha production by 50% compared to DMSO treated cultures is given by the $IC_{50}$ value.

TNF Induction in Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med. Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-$NH_2$, was present at a final concentration of 10 μM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the IC50 values were converted to Ki values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of an inflammatory disorder (as defined previously). In another embodiment, the package insert states that the pharmaceutical composition can be used in combination (as defined previously) with a second therapeutic agent to treat an inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 mg to about 100 mg of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 mg of active ingredient, 100 mg of cellulose and 10 mg of magnesium stearate.

A large number of unit capsules may also prepared by filling standard two-piece hard gelatin capsules each with 100 mg of powdered active ingredient, 150 mg of lactose, 50 mg of cellulose, and 6 mg magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Semi-Solid Gel

| | Wt. % |
|---|---|
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

| | Wt. % |
|---|---|
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste

| | Wt. % |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 mg of the active ingredient. The capsules are washed and dried.

Tablets

Tablets may be prepared by conventional procedures so that the dosage unit is 500 mg of active ingredient, 150 mg of lactose, 50 mg of cellulose and 10 mg of magnesium stearate.

A large number of tablets may also be prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 min apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:
1. A compound of formula (I):

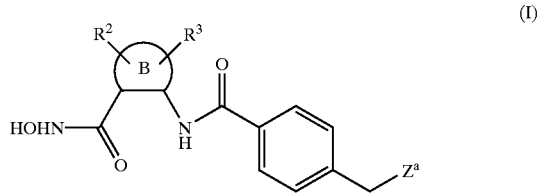

or a stereoisomer or pharmaceutically acceptable salt form thereof, wherein;

ring B is a 4–7 membered non-aromatic carbocyclic or heterocyclic ring consisting of:
carbon atoms, 0–3 carbonyl groups, 0–3 double bonds, and 0–2 ring heteroatoms selected from O, N, $NR_1$, and $S(O)_p$, provided that ring B contains other than a S—S, O—O, or S—O bond;

R1 is selected from Q, $C_{1-6}$alkylene-Q, $C_{2-6}$alkenylene-Q, $C_{2-6}$alkylene-Q, $(CR^aR^{a1})_qO(CR^aR^{a1})_s$-Q, $(CR^aR^{a1})_q NR^a(CR^aR^{a1})_s$-Q $(CR^aR^{a1})_rC(O)(CR^aR^{al})_s$-Q, $(CR_aR_{al})_rC(O)$-$C_{2-6}$ alkenylene-Q, $(CR^aR^{a1})_rC(O)O(CR^aR^{a1})_s$-Q, $(CR^aR^{al})_qOC(O)(CR^aR^{a1})$-$_sQ$, $(CR^aR^{a1})_q$ $OC(O)O(CR^aR^{a1})_s$-Q, $(CR^aR^{a1})_qOC(O)NR^a(CR^aR^{a1})_s$-Q, $(CR^aR^{a1})_rC(O)NR^aR^{al}$, $(CR^aR^{a1})_rC(O)NR^a(CR^aR^{a1})_s$-Q $(CR^aR^{a1})_qNR^aC(O)(CR^aR^{a1})_s$-Q, $(CR^aR^{a1})_qNR^aC(O)O((CR^aR^{a1})_s$-Q, $(CR^aR^{a1})_q NR^aC(O)NR^a(CR^aR^{a1})_s$-Q, $(CR^aR^{a1})_rS(O)_p(CR^aR^{a1})_s$- Q, $(CR^aR^{a1})_qNR^aSO_2(CR^aR^{a1})_s$-Q and $(CR^aR^{a1})_rS(O)_p(CR^aR^{a1})_sSO_2NR^a(CR^aR^{a1})_s$-Q;

$R^2$ is selected from Q, $C_{1-6}$alkylene-Q, $C_{2-6}$alkenylene-Q, $C_{2-6}$alkynylene-Q, $(CR^aR^{a1})_rO(CR^aR^{a1})_s$-Q, $(CR^aR^{a1})_r$ $NR^a(CR^aR^{a1})_s$-Q, $(CR^aR^{a1})_rC(O)$ $(CR^aR^{a1})_s$- Q, $(CR^aR^{a1})_rC(O)C_{2-6}$ alkenylene-Q, $(CR^aR^{a1})_rC(O)O(CR^aR^{a1})_s$-Q, $(CR^aR^{a1})_rC(O)NR^aR^{al}$, $(CR^aR^{a1})_r C(O)NR^a(CR^aR^{a1})_s$-Q, $(CR^aR^{a1})_rNR^aC(O)$ $(CR^aR^{a1})_s$ Q, $(CR^aR^{a1})_rNR^aC(O)O(CR^aR^{a1})_s$-Q, $(CR^aR^{a1})_r NR^aC(O)NR^a(CR^aR^{a1})_s$-Q, $(CR^aR^{a1})_rS(O)_p(CR^aR^{a1})_s$- Q, and $(CR^aR^{a1})_rSO_2NR^a_{(CR}{}^aR^{a1})_s$-Q;

Q is selected from H, a $C_{3-6}$ carbocycle substituted with 0–3 $R^{cl}$, and a 5–10 membered heterocycle consisting of: carbon atoms and 1–4 heteroatoms selected from the group consisting of N, O, and $S(O)_p$, and substituted with 0–3 $R^{cl}$;

R3 is selected from $Q^1$, Cl, F, $C_{1-6}$ alkylene-$Q_1$, $C_{2-6}$alkenylene-$Q^1$, $C_{2-6}$ alkynylene-$Q^1$, $(CR^aR^{a1})_rO(CR^aR^{a1})_s$-$Q^1$, $(CR^aR^{a1})_rNR^a(CR^aR^{a1})_s$-$Q^1$, $(CR^aR^{a1})_r$ $NR^aC(O)$ $(CR^aR^{a1})_s$-$Q^1$ $(CR^aR^{a1})_rC(O)NR^a_{(CR}{}^aR^{a1})_s$- $Q^1$, $(CR^aR^{a1})_rC(O)$ $(CR^aR^{a1})_s$-$Q^1$ $(CR^aR^{a1})_rC(O)O(CR^aR^{a1})_s$-$Q^1$, $(CR^aR^{a1})_rS(O)_p (CR^aR^{a1})_s$-$Q^1$ and $(CR^aR^{a1})SO_2NR^a(CR^aR^{a1})_s$-$Q^1$ $Q^1$ is selected from H, phenyl substituted with 0–3 $R^{cl}$, naphthyl substituted with 0–3 $R^{cl}$ and a 5–10 membered heterocycle consisting of: carbon atoms and 1–4 heteroatoms selected from the group consisting of N, O, and $S(O)_p$, and substituted with 0–3 $R^{cl}$;

$Z^a$ is selected from the group:

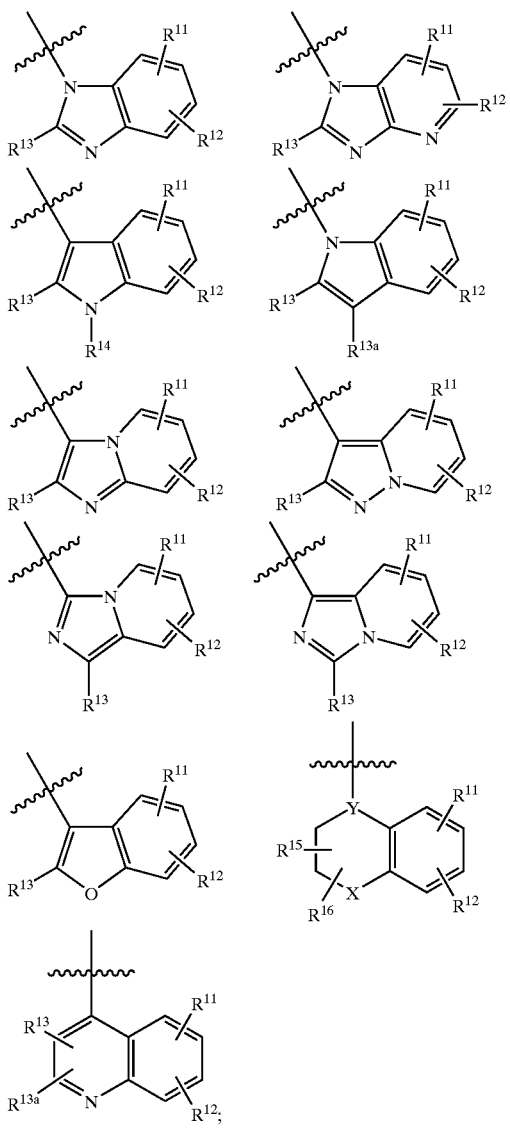

X is S, SO, SO$_2$, O, or NR$^{14}$;
Y is N or CR$^{17}$;
R$^{11}$ and R$^{12}$, at each occurrence, are independently selected from H, R$^C$, C$_{1-6}$ alkyl substituted with 0–3 R$^{cl}$, C$_{3-10}$ carbocycle substituted with 0–3 R$^{cl}$, and a 5–14 membered heterocycle consisting of: carbon atoms and 1–4 heteroatoms selected from the group consisting of N, O, and S(O)$_p$, and substituted with 0–3 R$^{cl}$;

R$^{13}$ and R$^{13a}$, at each occurrence, are independently selected from H, R$^C$, C$_{1-6}$ alkyl substituted with 0–3 R$^{cl}$, C$_{3-10}$ carbocycle substituted with 0–3 R$^{cl}$, and a 5–14 membered heterocycle consisting of: carbon atoms and 1–4 heteroatoms selected from the group consisting of N, O, and S(O)$_p$, and substituted with 0–3 R$^{cl}$;

alternatively, when R$^{13}$ and R$^{13a}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, and 0–2 heteroatoms selected from the group consisting of N, O, and S(O)$_p$, and substituted with 0–2 R$^{cl}$;

R$^{14}$, at each occurrence, is independently selected from H, C$_{1-4}$ alkyl, phenyl, and benzyl;

R$^{15}$ and R$^{16}$, at each occurrence, are independently selected from H, R$^{cl}$, C$_{1-6}$ alkyl substituted with 0–3 R$^{cl}$, C$_{3-10}$ carbocycle substituted with 0–3 R$^{cl}$, and a 5–14 membered heterocycle consisting of: carbon atoms and 1–4 heteroatoms selected from the group consisting of N, O, and S(O)$_p$, and substituted with 0–3 R$^{cl}$;

alternatively, when R$^{15}$ and R$^{16}$ are attached to adjacent carbon atoms, together with the carbon atoms to which they are attached, they form a 5–7 membered carbocyclic or heterocyclic ring consisting of: carbon atoms, 0–2 carbonyl groups, 0–3 double bonds, 0–2 heteroatoms selected from the group consisting of N, O, and S(O)$_p$, and substituted with 0–2 R$^{cl}$;

alternatively, when R$^{15}$ and R$^{16}$ are attached to the same carbon atom, together with the carbon atom to which they are attached, they form a 3–7 membered carbocyclic or heterocyclic ring consisting of: carbon atoms, 0–2 carbonyl groups, 0–3 double bonds, and 0–2 heteroatoms selected from the group consisting of N, O, and S(O)$_p$, and substituted with 0–2 R$^{cl}$;

R$^{17}$ is selected from H, Cl, F, and C$_{1-4}$ alkyl;

R$^a$, at each occurrence, is independently selected from H, C$_{1-4}$ alkyl, phenyl, and benzyl;

R$^{a1}$, at each occurrence, is independently selected from H and C$_{1-4}$alkyl;

R$^{a2}$, at each occurrence, is independently selected from C$_{1-4}$ alkyl, phenyl, and benzyl;

R$^C$, at each occurrence, is independently selected from C$_{1-6}$ alkyl, OR$^a$, Cl, F, Br, I, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, R$^a$NC(O)OR$^a$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, NR$^a$S(O)$_2$ R$^{a2}$, S(O)$_p$R$^{a2}$, CF$^3$, OCF$_3$, CF$_2$CF3, CH$_2$F, and CHF$_2$;

R$^{cl}$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)R$^a$, C(O)NR$^a$R$^{a1}$, R$^a$NC(O)NR$^a$R$^{a1}$, OC(O)NR$^a$R$^{a1}$, R$^a$NC(O)OR$^a$, S(O)$_2$NR$^a$R$^{a1}$, NR$^a$S(O)$_2$Ra$_2$, NR$^a$S(O)$_2$NR$^a$R$^{a1}$, OS(O)$_2$NR$^a$R$^{a1}$, NR$^a$S(O)$_2$ R$^{a2}$, S(O)$_p$R$^{a2}$, CF$_3$, OCF$_3$, CF$_2$CF$_3$, CH$_2$F, and CHF$_2$;

R$^d$, at each occurrence, is independently selected from C$_{1-6}$ alkyl, OR$^a$, Cl, F, Br, I, =O, —CN, NO$_2$, NR$^a$R$^{a1}$, C(O)R$^a$, C(O)R$^a$, C(O)NR$^a$R$^{a1}$, R$^a$NC(O)NR$^a$R$^{a1}$, OC(O)NR$^a$R$^{a1}$, R$^a$NC(O)O, S(O)$_2$NR$^a$R$^{a1}$, NR$^a$S(O)$_2$Ra$_2$, NR$^a$S(O)$_2$NR$^a$R$^{a1}$, OS(O)$_2$NR$^a$R$^{a1}$, NR$^a$S(O)$_2$R$^{a2}$, S(O)$_p$R$^{a2}$, CF$_3$, OCF$_3$, CF$_2$CF$_3$, C$_{3-10}$ carbocycle, and a 5–14 membered heterocycle consisting of: carbon atoms and 1–4 heteroatoms selected from the group consisting of N, O and S(O)$^p$;

p, at each occurrence, is selected from 0, 1, and 2;

q, at each occurrence, is selected from 1, 2, 3, and 4;

r, at each occurrence, is selected from 0, 1, 2, 3, and 4; and, s, at each occurrence, is selected from 0, 1, 2, 3, and 4.

2. A compound according to claim 1, wherein;

ring B is a 5–6 membered non-aromatic carbocyclic or heterocyclic ring consisting of:
carbon atoms, 0–1 carbonyl groups, 0–2 double bonds, and 0–2 ring heteroatoms selected from O, N, NR$_1$, provided that ring B contains other than a O—O bond;

R1 is selected from Q, $C_{1-6}$alkylene-Q, $C_{2-6}$alkenylene-Q, $C_{2-6}$alkylene-Q, $C(O)(CR^aR^{a1})_s$-Q, $C(O)$-$C_{2-6}$ alkenylene-Q, $C(O)O(CR^aR^{a1})_s$-Q, $C(O)NR^aR^{a1}$, $C(O)NR^a(CR^aR^{a1})_s$-Q, and $S(O)_p(CR^aR_{a1})_s$-Q;

$R^2$ is selected from Q, $C_{1-6}$alkylene-Q, $C_{2-6}$alkenylene-Q, $C_{2-6}$alkynylene-Q, $C(O)(CR^aR^{a1})_s$-Q, $C(O)$-$C_{2-6}$ alkenylene-Q, $C(O)O(CR^aR^{a1})_s$-Q, $C(O)NR^aR^{a1}$, $C(O)NR^a(CR^aR^{a1})_s$-Q, and $S(O)_p(CR^aR_{a1})_s$-Q;

Q is selected from H, cyclopropyl substituted with 0–1 $R^d$, cyclobutyl substituted with 0–1 $R^d$, cyclopentyl substituted with 0–1, cyclohexyl substituted with 0–1 $R^d$, phenyl substituted with 0–3 $R^d$, and a cyclohexyl substituted with 0–1 $R^d$, phenyl substituted with 0–3 $R^d$, and a heterocycle substituted with 0–2 $R^d$, wherein the heterocycle is selected from pyridyl, quinolinyl, thiazolyl, furanyl, tetrahydrofuranyl, imidazolyl, isoxazolyl, pyranyl, tetrahydro-2H-pyranyl, morpholinyl, piperidinyl, piperazinyl, and pyrrolidinyl;

R3 is selected from $Q^1$, Cl, F, $C_{1-6}$ alkylene-$Q_1$, $C_{2-4}$ alkenylene-$Q^1$;

$Q^1$ is selected from H and phenyl;

$R^{11}$ and $R^{12}$, at each occurrence, are independently selected from H, $R^C$, $C_{1-4}$ alkyl substituted with 0–3 $R^{cl}$, and phenyl substituted with 0–3 $R^{cl}$;

$R^{13}$ and $R^{13a}$, at each occurrence, are independently selected from H, $R^C$, $C_{1-4}$ alkyl substituted with 0–3 $R^{cl}$, $C_{3-6}$ carbocycle substituted with 0–3 $R^{cl}$, and a 5–6 membered heterocycle consisting of: carbon atoms and 1–4 heteroatoms selected from the group consisting of N, O, and $S(O)_p$, and substituted with 0–3 $R^{cl}$;

alternatively, when $R^{13}$ and $R^{13a}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{cl}$;

$R^{14}$, at each occurrence, is independently selected from H, $C_{1-4}$ alkyl, phenyl, and benzyl;

$R^{15}$ and $R^{16}$, at each occurrence, are independently selected from H, $R^{cl}$, $C_{1-4}$ alkyl substituted with 0–3 $R^{cl}$, and phenyl substituted with 0–3 $R^{cl}$;

alternatively, when $R^{15}$ and $R^{16}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, 0–2 heteroatoms selected from the group consisting of N, O, and $S(O)_p$, and substituted with 0–2 $R^{cl}$;

alternatively, when $R^{15}$ and $R^{16}$ are attached to the same carbon atom, together with the carbon atom to which they are attached, they form a 3–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{cl}$;

$R^a$, at each occurrence, is independently selected from H, $C_{1-4}$, and benzyl;

$R^{a2}$, at each occurrence, is independently selected from H and $C_{1-6}$ alkyl, and benzyl;

$R^C$, at each occurrence, is independently selected from $C_{1-6}$ alkyl, $OR^a$, Cl, F, Br, $NR^aR^{a1}$, $C(O)R^a$, $C(O)NR^aR^{a1}$, $S(O)_2NR^aR^{a1}$, $NR^aS(O)_2R^{a2}$, $NR^aS(O)_2NR^aR^{a1}$, $S(O)_2NR^aR^{a1}$, $S(O)_2NR^aR^{a1}$, $S(O)_pR^{a2}$, $CF^3$, $OCF_3$, $CF_2CF3$, $CH_2F$, and $CHF_2$;

$R^{cl}$, at each occurrence, at each occurrence, is independently selected from $C_{1-6}$ alkyl, $OR^a$, Cl, F, Br, $NR^aR^{a1}$, $C(O)R^a$, $C(O)NR^aR^{a1}$, $S(O)_2NR^aR^{a1}$, $NR^aS(O)_2R^{a2}$, $NR^aS(O)_2NR^aR^{a1}$, $S(O)_2NR^aR^{a1}$, $S(O)_2NR^aR^{a1}$, $S(O)_pR^{a2}$, $CF^3$, $OCF_3$, $CF_2CF3$, $CH_2F$, and $CHF_2$;

$R^d$, at each occurrence, is independently selected from $C_{1-6}$ alkyl, $OR^a$, Cl, F, Br, I, =O, $NR^aR^{a1}$, $C(O)R^a$, $C(O)R^a$, $C(O)NR^aR^{a1}$, $S(O)_2NR^aR^{a1}$, $S(O)_pRa^{a2}$, $CF_3$, and phenyl.

3. A compound according to claim 2, wherein;

ring B is a 5–6 membered non-aromatic carbocyclic or heterocyclic ring consisting of:
  carbon atoms, 0–1 carbonyl groups, 0–1 double bonds, and 0–1 ring heteroatoms selected from O, N, and $NR^1$;

$R^1$ is selected from Q, $C_{1-6}$ alkylene-Q, $C_{2-4}$ alkenylene-Q, $C(O)(CR^aR^{a1})_s$-Q, $C(O)$—$C_{2-6}$ alkenyl, $C(O)O(CR^aR^{a1})_s$-Q, $C(O)NR^a$-Q, and $S(O)_p(CR^aR^{a1})_s$-Q;

$R^2$ is selected from Q, $C_{1-4}$ alkylene-Q, $C_{2-4}$ alkenylene-Q, $C_{2-4}$ alkynylene-Q, $C(O)$-Q, $C(O)$—$C_{2-6}$ alkenyl, $C(O)O$-Q, $C(O)NR^a$-Q, and $S(O)_p$-Q;

Q is selected from H, cyclopropyl, cyclobutyl, cyclopentyl, cyclohexyl, tetrahydro-2H-pyran-4-yl, and phenyl substituted with 0–2 $R^d$;

$R^3$ is H;

X is S; SO, $SO_2$ or O;

Y is N;

$R^{11}$ and $R^{12}$, at each occurrence, are independently selected from H, $R^c$, and $C_{1-4}$ alkyl substituted with 0–3 $R^{c1}$;

$R^{13}$ and $R^{13a}$, at each occurrence, are independently selected from H, $R^c$, $C_{1-4}$ alkyl substituted with 0–3 $R^{c1}$, $C_{3-6}$, phenyl substituted with 0–3 $R^{c1}$, and a 5–6 membered heterocycle consisting of: carbon atoms and 1–2 heteroatoms selected from the group consisting of N, O, and $S(O)_p$;

alternatively, when $R^{13}$ and $R^{13a}$ are attached to adjacent carbon atoms, together with the carbon atoms to which they are attached, they form a 5–6 membered carbocyclic or heterocyclic ring consisting of: carbon atoms, 0–2 double bonds, and 0–1 heteroatom selected from the group consisting of N, O, and $S(O)_p$, and substituted with 0–2 $R^{c1}$;

$R^{15}$ and $R^{16}$, at each occurrence, are independently selected from H, $R^{c1}$, and $C_{1-4}$ alkyl substituted with 0–3 $R^{c1}$;

alternatively, when $R^{15}$ and $R^{16}$ are attached to adjacent carbon atoms, together with the carbon atoms to which they are attached, they form a 3–6 membered aromatic ring substituted with 0–2 $R^{c1}$;

alternatively, when $R^{15}$ and $R^{16}$ are attached to the same carbon atom, together with the carbon atom to which they are attached, they form a 3–6 membered cycloalkyl;

$R^a$, at each occurrence, is independently selected from H, $CH_3$, and $CH_2CH_3$;

$R^{a1}$, at each occurrence, is independently selected from H, $CH_3$, and $CH_2CH_3$; and, $R^{a2}$, at each occurrence, is independently selected from $CH_3$, and $CH_2CH_3$.

4. A compound according to claim 3, wherein the compound is of formula (II);

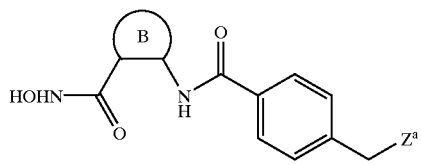

(II)

or a stereoisomer of pharmaceutically acceptable salt from thereof, wherein;

ring B is selected from the group:

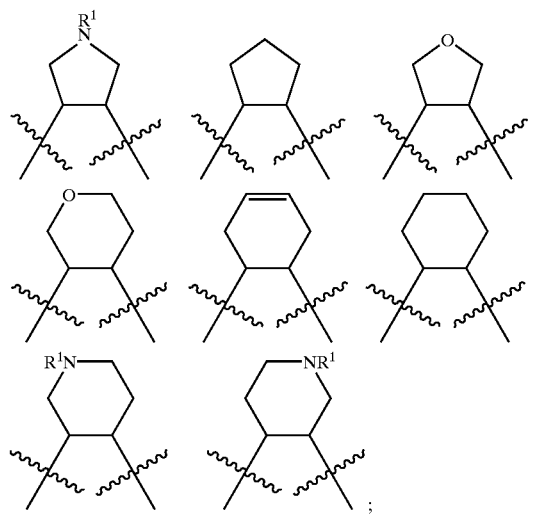

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

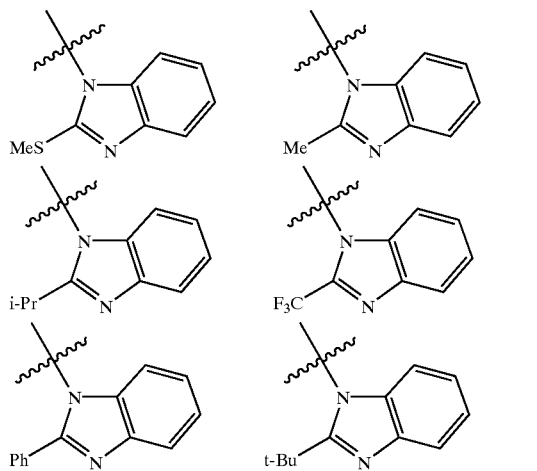

-continued

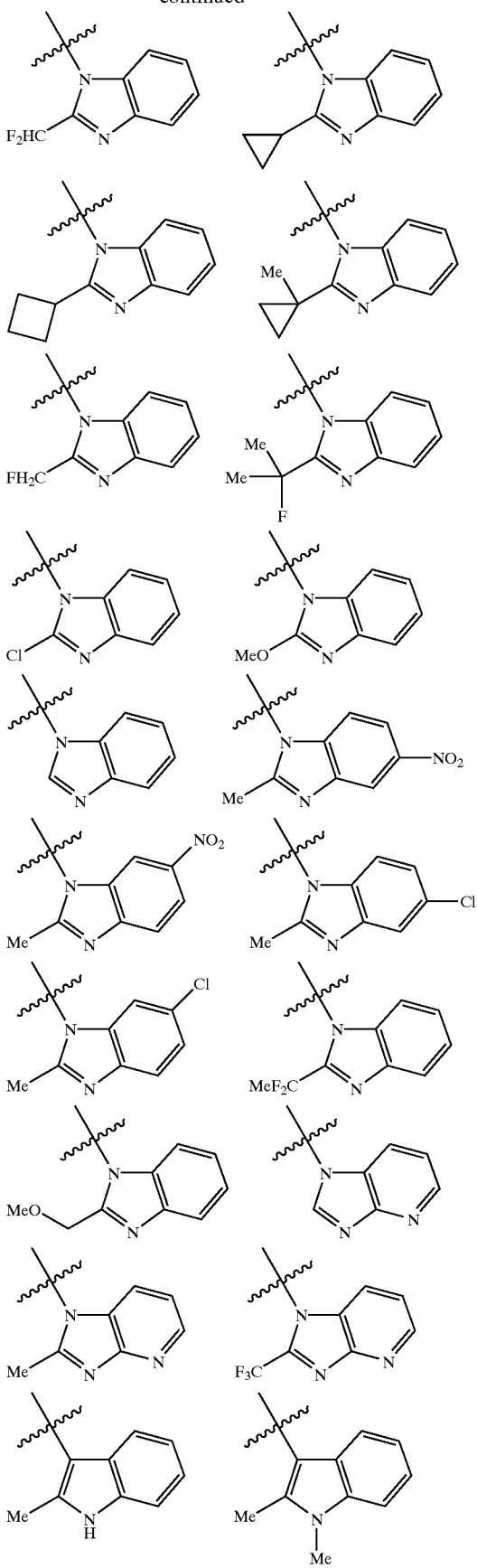

-continued
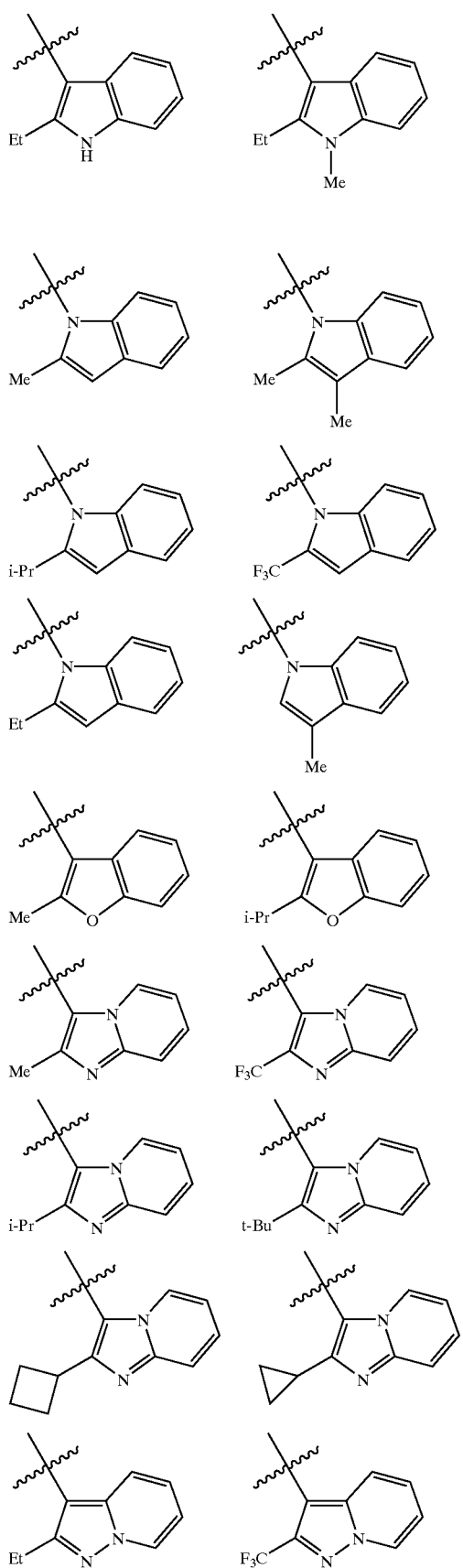
-continued
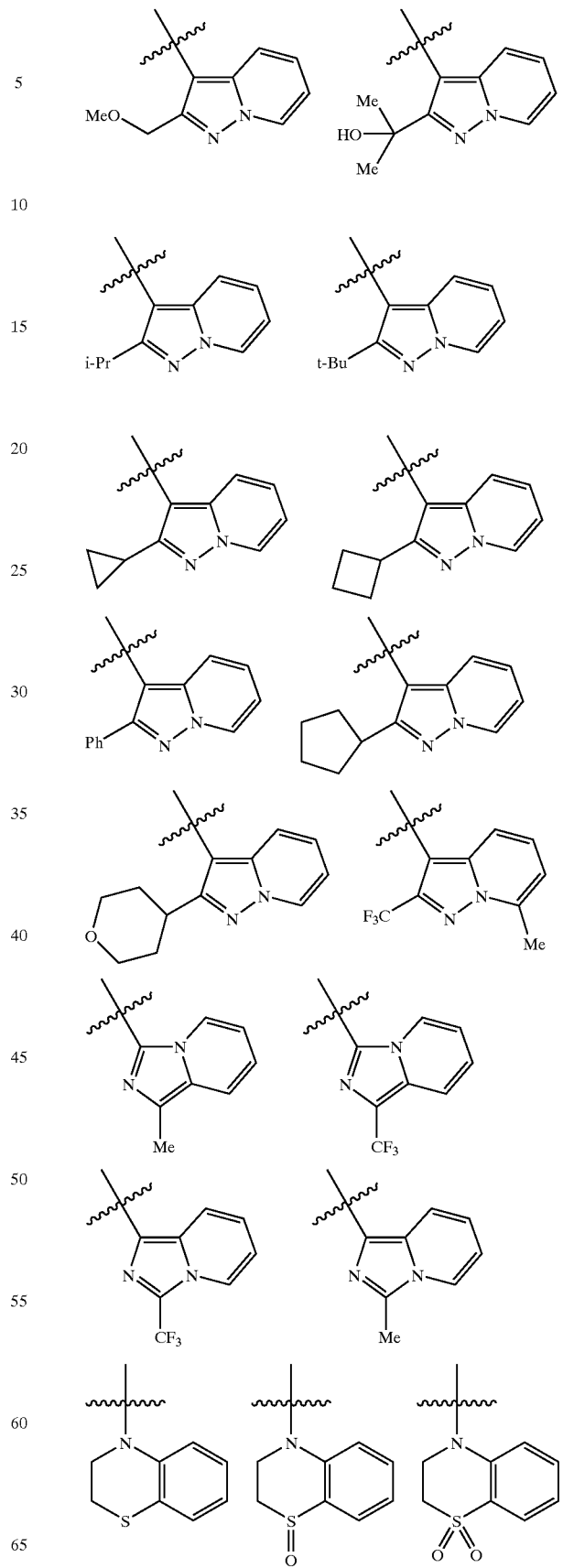

-continued
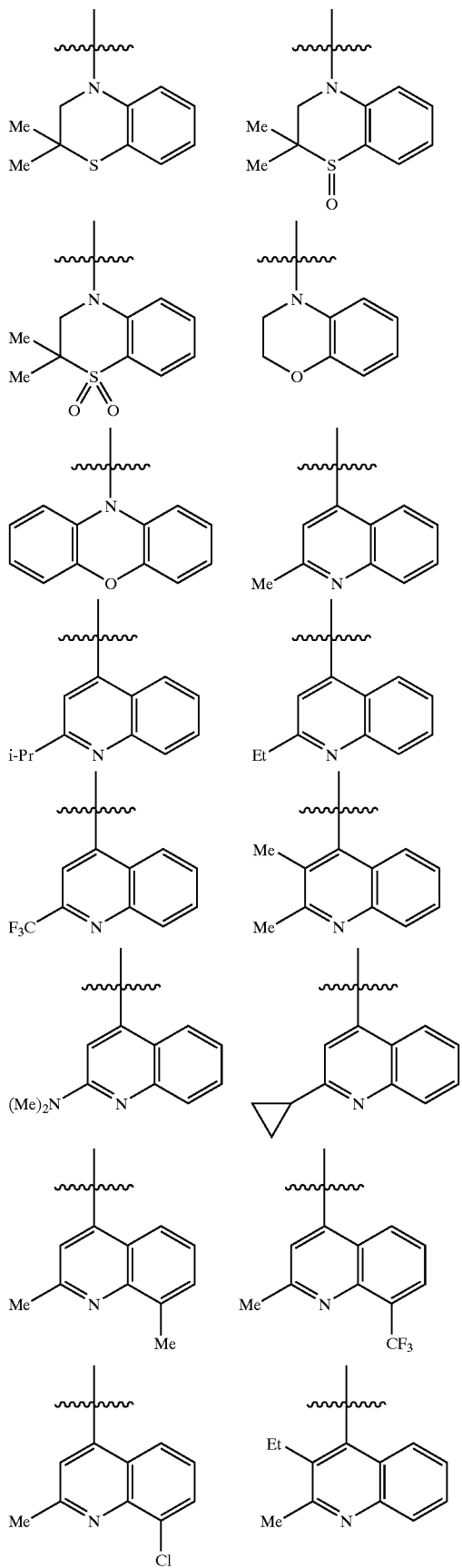
-continued
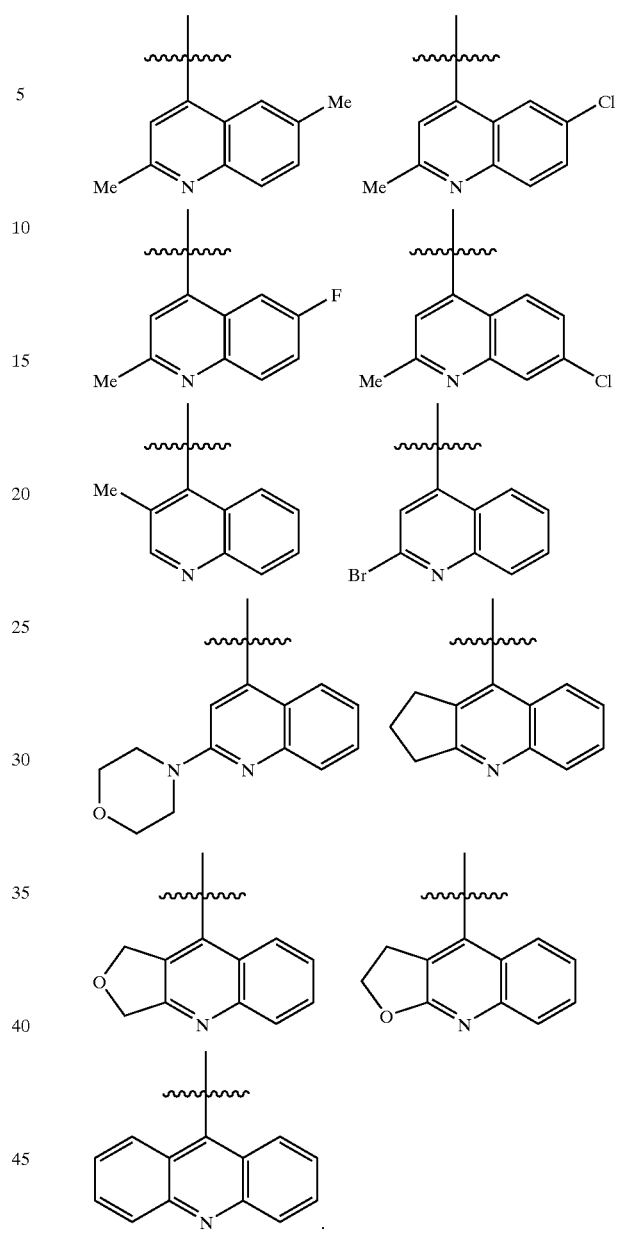
5. A compound according to claim 1, wherein;
$Z^a$ is selected from the group:
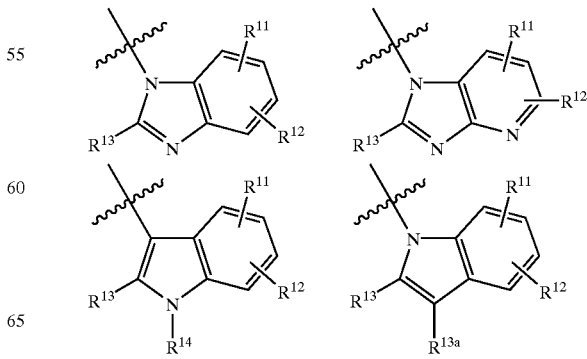

-continued

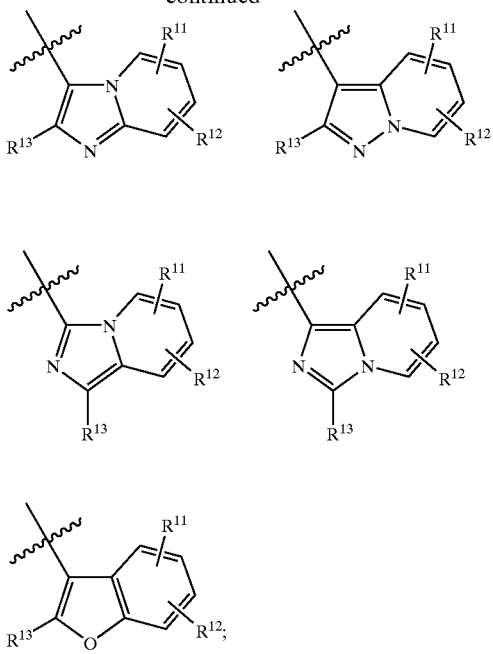

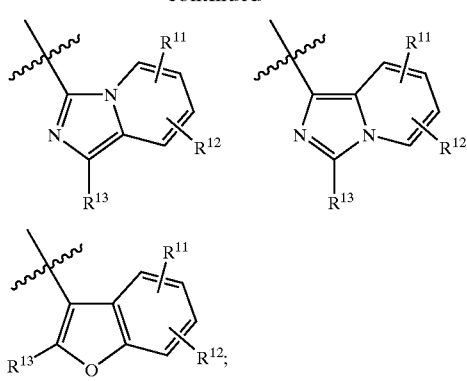

R¹¹ and R¹², at each occurrence, are independently selected from H, R$^c$, C$_{1-6}$ alkyl substituted with 0–3 R$^{c1}$, C$_{3-10}$ carbocycle substituted with 0–3 R$^{c1}$, and a 5–14 membered heterocycle consisting of: carbon atoms and 1–4 heteroatoms selected from the group consisting of N, O, and S(O)$_p$, and substituted with 0–3 R$^{c1}$;

R¹³ and R¹³$^a$, at each occurrence, are independently selected from H, R$^c$, C$_{1-6}$ alkyl substituted with 0–3 R$^{c1}$, C$_{3-10}$ carbocycle substituted with 0–3 R$^{c1}$, and a 5–14 membered heterocycle consisting of: carbon atoms and 1–4 heteroatoms selected from the group consisting of N, O, and S(O)$_p$, and substituted with 0–3 R$^{c1}$; and, R¹⁴, at each occurrence, is independently selected from H, C$_{1-4}$ alkyl, phenyl, and benzyl.

6. A compound according to claim 2, wherein;
Z$^a$ is selected from the group:

R¹¹ and R¹², at each occurrence, are independently selected from H, R$^c$, C$_{1-4}$ alkyl substituted with 0–3 R$^{c1}$, and phenyl substituted with 0–3 R$^{c1}$;

R¹³ and R¹³$^a$, at each occurrence, are independently selected from H, R$^c$, C$_{1-4}$ alkyl substituted with 0–3 R$^{c1}$, C$_{3-6}$ cycloalkyl substituted with 0–2 R$^{c1}$, phenyl substituted with 0–3 R$^{c1}$, and a 5–6 membered heterocycle consisting of: carbon atoms and 1–4 heteroatoms selected from the group consisting of N, O, and S(O)$_p$, and substituted with 0–3 R$^{c1}$; and, R¹⁴, at each occurrence, is independently selected from H, C$_{1-4}$ alkyl, and benzyl.

7. A compound according to claim 4, wherein;
ring B is selected from the group:

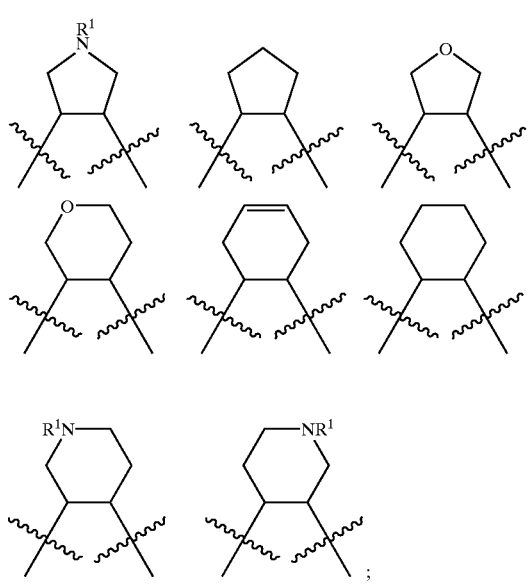

R¹ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:
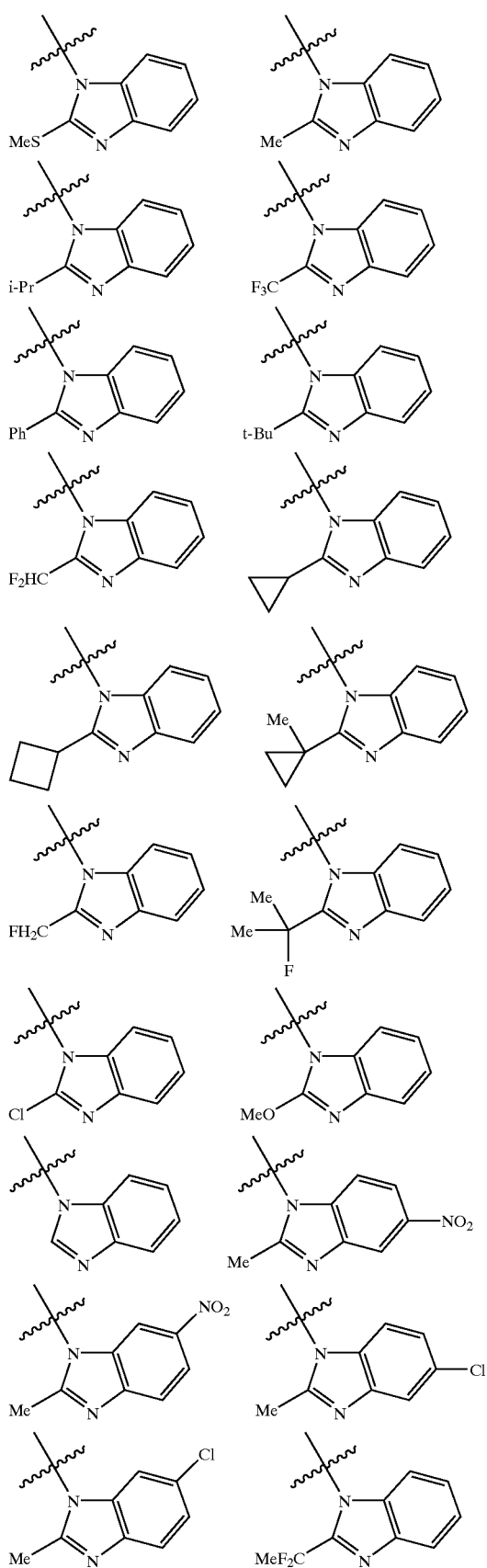
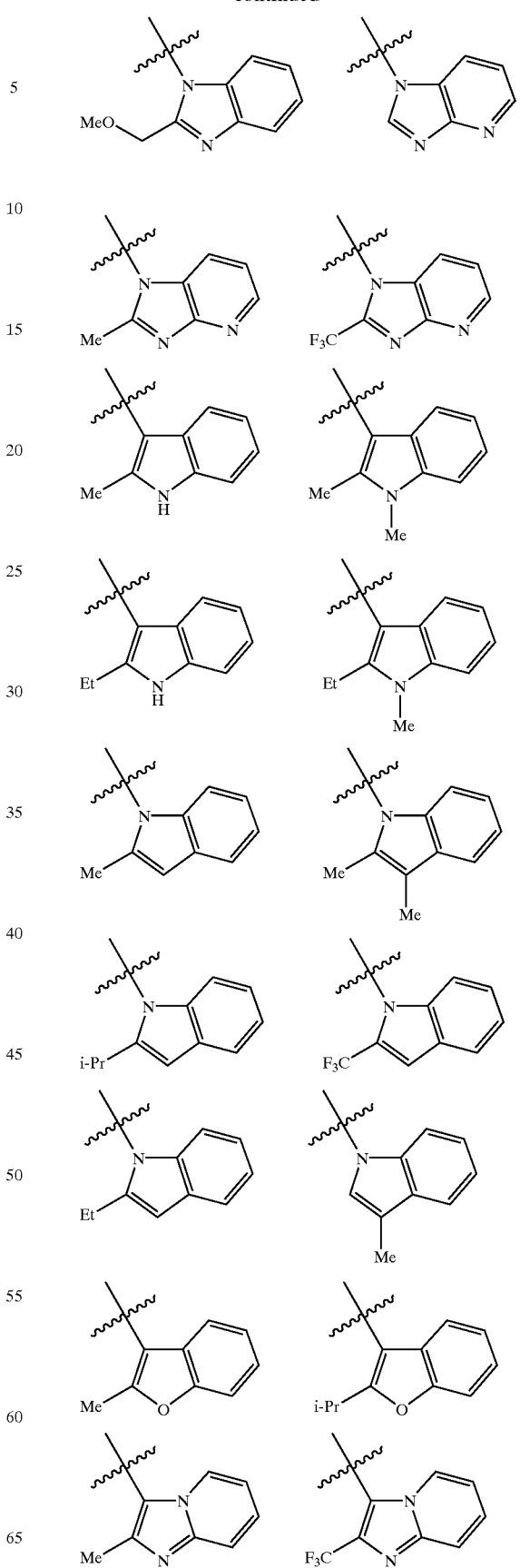

-continued

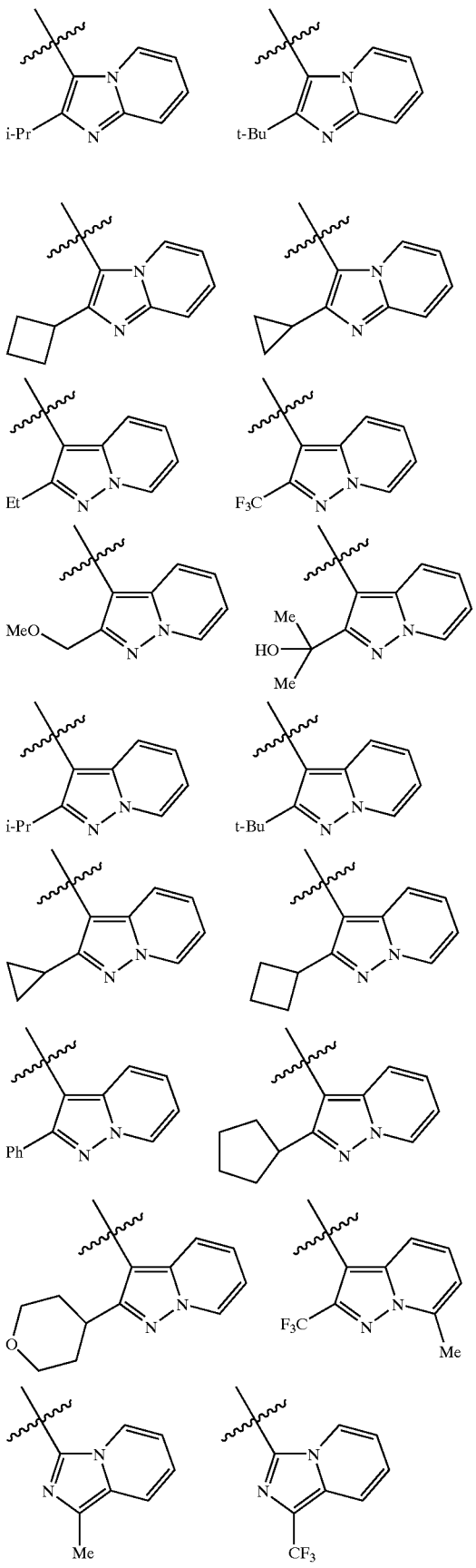
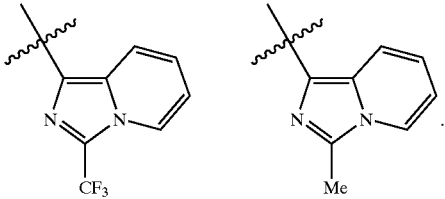

8. A compound according to claim 1, wherein the compound is selected from the group:

tert-butyl (3S,4S)-3-[(hydroxyamino)carbonyl]-4-[(4-{[2-(methylthio)-1H-benzimidazol-1-yl]methyl}benzoyl)amino]-1-pyrrolidinecarboxylate;

(3S,4S)-N-hydroxy-4-[(4-{[2-(methylthio)-1H-benzimidazol-1-yl]methyl}benzoyl)amino]-3-pyrrolidinecarboxamide;

(3S,4S)-N-hydroxy-1-(methylsulfonyl)-4-[(4-{[2-(methylthio)-1H-benzimidazol-1-yl]methyl}benzoyl)amino]-3-pyrrolidinecarboxamide;

(3S,4S)-N-hydroxy-4-[(4-{[2-(methylthio)-1H-benzimidazol-1-yl]methyl}benzoyl)amino]-1-(2-propynyl)-3-pyrroli dinecarboxamide;

(3S,4S)-N-hydroxy-1-methyl-4-[(4-{[2-(methylthio)-1H-benzimidazol-1-yl]methyl}benzoyl)amino]-3-pyrrolidinecarboxamide;

(3S,4S)-N-hydroxy-1-isopropyl-4-[(4-{[2-(methylthio)-1H-benzimidazol-1-yl]methyl}benzoyl)amino]-3-pyrrolidinecarboxamide;

(3S,4S)-1-acetyl-N-hydroxy-4-[(4-{[2-(methylthio)-1H-benzimidazol-1-yl]methyl}benzoyl)amino]-3-pyrrolidinecarboxamide;

(3S,4S)-N-hydroxy-4-[(4-{[2-(methylthio)-1H-benzimidazol-1-yl]methyl}benzoyl)amino]-1-(propylsulfonyl)-3-pyrrolidinecarboxamide;

(3S,4S)-N-hydroxy-1-(isopropylsulfonyl)-,4-[(4-{[2-(methylthio)-1H-benzimidazol-1-yl]methyl}benzoyl)amino]-3-pyrrolidinecarboxamide;

tert-butyl (3S,4S)-3-[(hydroxyamino)carbonyl]-4-({4-[(2-methyl-1H-benzimidazol-1-yl)methyl]benzoyl}amino)-1-pyrrolidinecarboxylate;

(3S,4S)-N-hydroxy-4-({4-[(2-methyl-1H-benzimidazol-1-yl)methyl]benzoyl}amino)-3-pyrrolidinecarboxamide (3S,4S)-N-hydroxy-4-({4-[(2-methyl-1H-benzimidazol-1-yl)methyl]benzoyl}amino)-1-(2-propynyl)-3-pyrrolidinecarboxamide;

(3S,4S)-1-(2-butynyl)-N-hydroxy-4-({4-[(2-methyl-1H-benzimidazol-1-yl)methyl]benzoyl}amino)-3-pyrrolidinecarboxamide;

(3S,4S)-1-(3-butenyl)-N-hydroxy-4-({4-[(2-methyl-1H-benzimidazol-1-yl)methyl]benzoyl}amino)-3-pyrrolidinecarboxamide;

N-{(1R,2S)-2-[(hydroxyamino)carbonyl]cyclopentyl}-4-[(2-methyl-1H-benzimidazol-1-yl)methyl]benzamide;

(3S,4S)-N-hydroxy-1-isopropyl-4-({4-[(2-methyl-1H-benzimidazol-1-yl)methyl]benzoyl}amino)-3-pyrrolidinecarboxamide;

(3S,4S)-N-hydroxy-4-({4-[(2-methyl-1H-benzimidazol-1-yl)methyl]benzoyl}amino)-1-neopentyl-3-pyrrolidinecarboxamide;

tert-butyl (3S,4S)-3-[(hydroxyamino)carbonyl]-4-({4-[(2-isopropyl-1H-benzimidazol-1-yl)methyl]benzoyl}amino)-1-pyrrolidinecarboxylate;

(3S,4S)-N-hydroxy-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-methyl-3-pyrrolidinecarboxamide;

(3S,4S)-N-hydroxy-4-({4-[(2-isopropyl-1H-benzimidazol-1-yl)methyl]benzoyl}amino)-1-propyl-3-pyrrolidinecarboxamide;

(3S,4S)-N-hydroxy-1-isopropyl-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-(2-propynyl)-3-pyrrolidinecarboxamide;

(3S,4S)-1-(3-butenyl)-N-hydroxy-4-({4-[(2-isopropyl-1H-benzimidazol-1-yl)methyl]benzoyl}amino)-3-pyrrolidinecarboxamide;

(3S,4S)-1-(2-butynyl)-N-hydroxy-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-(propylsulfonyl)-3-pyrrolidinecarboxamide;

(3S,4S)-1-(butylsulfonyl)-N-hydroxy-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-(isopropylsulfonyl)-3-pyrrolidinecarboxamide;

N-{(1R,2S)-2-[(hydroxyamino)carbonyl]cyclopentyl}-4-[(2-isopropyl-1H-benzimidazol-1-yl)methyl]benzamide;

(3S,4S)-N-hydroxy-1-isobutyl-4-({4-[(2-isopropyl-1H-benzimidazol-1-yl)methyl]benzoyl}amino)-3-pyrrolidinecarboxamide;

(3S,4S)-N-hydroxy-4-({4-[(2-isopropyl-1H-benzimidazol-1-yl)methyl]benzoyl}amino)-1-neopentyl-3-pyrrolidinecarboxamide;

tert-butyl (3S,4S)-3-[(hydroxyamino)carbonyl]-4-[(4-{[2-, (trifluoromethyl)-1H-benzimidazol-1-yl]methyl}benzoyl)amino]-1-pyrrolidinecarboxylate;

(3S,4S)-N-hydroxy-4-[(4-{[2-(trifluoromethyl)-1H-benzimidazol-1-yl]methyl}benzoyl)amino]-3-pyrrolidinecarboxamide;

(3S,4S)-N-hydroxy-1-isopropyl-4-[(4-{[2-(trifluoromethyl)-1H-benzimidazol-1-yl]methyl}benzoyl)amino]-3-pyrrolidinecarboxamide;

(3S,4S)-N-hydroxy-1-(2-propynyl)-4-[(4-{[2-(trifluoromethyl)-1H-benzimidazol-1-yl]methyl}benzoyl)amino]-3-pyrrolidinecarboxamide;

(3S,4S)-1-(2-butynyl)-N-hydroxy-4-[(4-{[2-(trifluoromethyl)-1H-benzimidazol-1-yl]methyl}benzoyl)amino]-3-pyrrolidinecarboxamide;

(3S,4S)-1-(3-butenyl)-N-hydroxy-4-[(4-{[2-(trifluoromethyl)-1H-benzimidazol-1-yl]methyl}benzoyl)amino]-3-pyrrolidinecarboxamide;

(3R,4R)-N-hydroxy-4-({4-[(2-isopropyl-1H-benzimidazol-1-yl)methyl]benzoyl}amino)tetrahydro-2H-pyran-3-carboxamide;

(3R,4R)-N-hydroxy-4-[(4-{[2-(trifluoromethyl)-1H-benzimidazol-1-yl]methyl}benzoyl)amino]tetrahydro-2H-pyran-3-carboxamide;

(3S,4S)-N-hydroxy-1-(propylsulfonyl)-4-[(4-{[2-(trifluoromethyl)-1H-benzimidazol-1-yl]methyl}benzoyl)amino]-3-pyrrolidinecarboxamide;

(3S,4S)-N-hydroxy-1-(isopropylsulfonyl)-4-[(4-{[2-(trifluoromethyl)-1H-benzimidazol-1-yl]methyl}benzoyl)amino]-3-pyrrolidinecarboxamide;

(3S,4S)-1-(butylsulfonyl)-N-hydroxy-4-[(4-{[2-(trifluoromethyl)-1H-benzimidazol-1-yl]methyl}benzoyl)amino]-3-pyrrolidinecarboxamide;

(3S,4S)-1-acetyl-N-hydroxy-4-[(4-{[2-(trifluoromethyl)-1H-benzimidazol-1-yl]methyl}benzoyl)amino]-3-pyrrolidinecarboxamide;

(3S,4S)-N-hydroxy-1-(4-pentenoyl)-4-[(4-{[2-(trifluoromethyl)-1H-benzimidazol-1-yl]methyl}benzoyl)amino]-3-pyrrolidinecarboxamide;

(3S,4S)-N-hydroxy-1-isobutyl-4-[(4-{[2-(trifluoromethyl)-1H-benzimidazol-1-yl]methyl}benzoyl)amino]-3-pyrrolidinecarboxamide;

(3S,4S)-N-hydroxy-1-neopentyl-4-[(4-{[2-(trifluoromethyl)-1H-benzimidazol-1-yl]methyl}benzoyl)amino]-3-pyrrolidinecarboxamide;

cis-N-{-2-[(hydroxyamino)carbonyl]cyclopentyl}-4-{[2-(trifluoromethyl)-1H-benzimidazol-1-yl]methyl}benzamide;

(3R,4S)-N-hydroxy-4-[(4-{[2-(trifluoromethyl)-1H-benzimidazol-1-yl]methyl}benzoyl)amino]tetrahydro-3-furancarboxamide;

tert-butyl (3S,4S)-3-[(hydroxyamino)carbonyl]-4-({4-[(2-phenyl-1H-benzimidazol-1-yl)methyl]benzoyl}amino)-1-pyrrolidinecarboxylate;

(3S,4S)-N-hydroxy-4-({4-[(2-phenyl-1H-benzimidazol-1-yl)methyl]benzoyl}amino)-3-pyrrolidinecarboxamide;

tert-butyl (3S,4S)-3-({4-[(2-tert-butyl-1H-benzimidazol-1-yl)methyl]benzoyl}amino)-4-[(hydroxyamino)carbonyl]-1-pyrrolidinecarboxylate;

(3S,4S)-4-({4-[(2-tert-butyl-1H-benzimidazol-1-yl)methyl]benzoyl}amino)-N-hydroxy-3-pyrrolidinecarboxamide;

(3S,4S)-4-({4-[(2-tert-butyl-1H-benzimidazol-1-yl)methyl]benzoyl}amino)-N-hydroxy-1-(2-propynyl)-3-pyrrolidinecarboxamide;

(3S,4S)-4-({4-[(2-tert-butyl-1H-benzimidazol-1-yl)methyl]benzoyl}amino)-1-(2-butynyl)-N-hydroxy-3-pyrrolidinecarboxamide;

(3S,4S)-4-({4-[(2-tert-butyl-1H-benzimidazol-1-yl)methyl]benzoyl}amino)-N-hydroxy-1-isopropyl-3-pyrrolidinecarboxamide;

cis-4-[(2-tert-butyl-1H-benzimidazol-1-yl)methyl]-N-{2-[(hydroxyamino)carbonyl]cyclopentyl}benzamide;

(3R,4R)-4-({4-[(2-tert-butyl-1H-benzimidazol-1-yl)methyl]benzoyl}amino)-N-hydroxytetrahydro-2H-pyran-3-carboxamide;

(3R,4S)-4-({4-[(2-tert-butyl-1H-benzimidazol-1-yl)methyl]benzoyl}amino)-N-hydroxytetrahydro-3-furancarboxamide;

tert-butyl (3S,4S)-3-[(4-{[2-(difluoromethyl)-1H-benzimidazol-1-yl]methyl}benzoyl)amino]-4-[(hydroxyamino)carbonyl]-1-pyrrolidinecarboxylate;

(3S,4S)-4-[(4-{[2-(difluoromethyl)-1H-benzimidazol-1-yl]methyl}benzoyl)amino]-N-hydroxy-3-pyrrolidinecarboxamide;

(3S,4S)-4-[(4-{[2-(difluoromethyl)-1H-benzimidazol-1-yl]methyl}benzoyl)amino]-N-hydroxy-1-isopropyl-3-pyrrolidinecarboxamide;

(3S,4S)-4-[(4-{[2-(difluoromethyl)-1H-benzimidazol-1-yl]methyl}benzoyl)amino]-N-hydroxy-1-(2-propynyl)-3-pyrrolidinecarboxamide;

(3S,4S)-4-[(4-{[2-(difluoromethyl)-1H-benzimidazol-1-yl]methyl}benzoyl)amino]-N-hydroxy-1-isobutyl-3-pyrrolidinecarboxamide;

(3S,4S)-4-[(4-{[2-(difluoromethyl)-1H-benzimidazol-1-yl]methyl}benzoyl)amino]-N-hydroxy-1-neopentyl-3-pyrrolidinecarboxamide;

4-{[2-(difluoromethyl)-1H-benzimidazol-1-yl]methyl}-N-cis-2-[(hydroxyamino)carbonyl]cyclopentyl}benzamide;

(3R,4R)-4-[(4-{[2-(difluoromethyl)-1H-benzimidazol-1-yl]methyl}benzoyl)amino]-N-hydroxytetrahydro-2H-pyran-3-carboxamide;

(3R,4S)-4-[(4-{[2-(difluoromethyl)-1H-benzimidazol-1-yl]methyl}benzoyl)amino]-N-hydroxytetrahydro-3-furancarboxamide;

4-[(2-cyclopropyl-1H-benzimidazol-1-yl)methyl]-N-{(1R,2S)-2-[(hydroxyamino)carbonyl]cyclopentyl}benzamide;

(3R,4R)-4-({4-[(2-cyclopropyl-1H-benzimidazol-1-yl)methyl]benzoyl}amino)-N-hydroxytetrahydro-2H-pyran-3-carboxamide;

(3R,4S)-4-({4-[(2-cyclopropyl-1H-benzimidazol-1-yl)methyl]benzoyl}amino)-N-hydroxytetrahydro-3-furancarboxamide;

4-[(2-cyclobutyl-1H-benzimidazol-1-yl)methyl]-N-{(1R,2S)-2-[(hydroxyamino)carbonyl]cyclopentyl}benzamide;

(3R,4R)-4-({4-[(2-cyclobutyl-1H-benzimidazol-1-yl)methyl]benzoyl}amino)-N-hydroxytetrahydro-2H-pyran-3-carboxamide;

(3R,4R)-N-hydroxy-4-[(4-{[2-(1-methylcyclopropyl)-1H-benzimidazol-1-yl]methyl}benzoyl)amino]tetrahydro-2H-pyran-3-carboxamide;

N-{(1R,2S)-2-[(hydroxyamino)carbonyl]cyclopentyl}-4-{[2-(1-methylcyclopropyl)-1H-benzimidazol-1-yl]methyl}benzamide;

(3R,4R)-4-[(4-{[2-(fluoromethyl)-1H-benzimidazol-1-yl]methyl}benzoyl)amino]-N-hydroxytetrahydro-2H-pyran-3-carboxamide;

4-{[2-(fluoromethyl)-1H-benzimidazol-1-yl]methyl}-N-{(1R,2S)-2-[(hydroxyamino)carbonyl]cyclopentyl}benzamide;

(3R,4R)-4-[(4-{[2-(1-fluoro-1-methylethyl)-1H-benzimidazol-1-yl]methyl}benzoyl)amino]-N-hydroxytetrahydro-2H-pyran-3-carboxamide;

4-{[2-(1-fluoro-1-methylethyl)-1H-benzimidazol-1-yl]methyl}-N-{(1R,2S)-2-[(hydroxyamino)carbonyl]cyclopentyl}benzamide;

(3S,4R)-N-hydroxy-4-({4-[(2-isopropyl-1H-benzimidazol-1-yl)methyl]benzoyl}amino)tetrahydro-2H-pyran-3-carboxamide;

(3R,4S)-N-hydroxy-4-({4-[(2-isopropyl-1H-benzimidazol-1-yl)methyl]benzoyl}amino)tetrahydro-2H-pyran-3-carboxamide;

tert-butyl (3S,4S)-3-({4-[(2-chloro-1H-benzimidazol-1-yl)methyl]benzoyl}amino)-4-[(hydroxyamino)carbonyl]-1-pyrrolidinecarboxylate;

tert-butyl (3S,4S)-3-[(hydroxyamino)carbonyl]-4-({4-[(2-methoxy-1H-benzimidazol-1-yl)methyl]benzoyl}amino)-1-pyrrolidinecarboxylate;

tert-butyl (3S,4S)-3-[(hydroxyamino)carbonyl]-4-({4-[(2-methyl-1H-imidazo[4,5-b]pyridin-1-yl)methyl]benzoyl}amino)-1-pyrrolidinecarboxylate;

tert-butyl (3S,4S)-3-[(hydroxyamino)carbonyl]-4-{[4-(1H-imidazo[4,5-b]pyridin-1-ylmethyl)benzoyl]amino}-1-pyrrolidinecarboxylate;

(3R,4R)-4-({4-[(2-chloro-1H-benzimidazol-1-yl)methyl]benzoyl}amino)-N-hydroxy-3-pyrrolidinecarboxamide;

(3S,4S)-N-hydroxy-4-{[4-(1H-imidazo[4,5-b]pyridin-1-ylmethyl)benzoyl]amino}-3-pyrrolidinecarboxamide;

(3S,4S)-N-hydroxy-4-({4-[(2-methyl-1H-imidazo[4,5-b]pyridin-1-yl)methyl]benzoyl}amino)-3-pyrrolidinecarboxamide;

tert-butyl (3S,4S)-3-[(hydroxyamino)carbonyl]-4-({4-[(2-methyl-5-nitro-1H-benzimidazol-1-yl)methyl]benzoyl}amino)-1-pyrrolidinecarboxylate;

tert-butyl (3S,4S)-3-[(hydroxyamino)carbonyl]-4-({4-[(2-methyl-6-nitro-1H-benzimidazol-1-yl)methyl]benzoyl}amino)-1-pyrrolidinecarboxylate;

tert-butyl (3S,4S)-3-({4-[(5-chloro-2-methyl-1H-benzimidazol-1-yl)methyl]benzoyl}amino)-4-[(hydroxyamino)carbonyl]-1-pyrrolidinecarboxylate;

tert-butyl (3S,4S)-3-({4-[(6-chloro-2-methyl-1H-benzimidazol-1-yl)methyl]benzoyl}amino)-4-[(hydroxyamino)carbonyl]-1-pyrrolidinecarboxylate;

4-[(2-cyclopropyl-1H-benzimidazol-1-yl)methyl]-N-{(1R,6S)-6-[(hydroxyamino)carbonyl]-3-cyclohexen-1-yl}benzamide;

4-[(2-cyclobutyl-1H-benzimidazol-1-yl)methyl]-N-{(1R,6S)-6-[(hydroxyamino)carbonyl]-3-cyclohexen-1-yl)benzamide;

N-{(1R,6S)-6-[(hydroxyamino)carbonyl]-3-cyclohexen-1-yl}-4-[(2-isopropyl-1H-benzimidazol-1-yl)methyl]benzamide;

N-{(1R,2S)-2-[(hydroxyamino)carbonyl]cyclohexyl}-4-[(2-isopropyl-1H-benzimidazol-1-yl)methyl]benzamide;

4-[(2-cyclopropyl-1H-benzimidazol-1-yl)methyl]-N-{(1R,2S)-2-[(hydroxyamino)carbonyl]cyclohexyl}benzamide;

4-[(2-cyclobutyl-1H-benzimidazol-1-yl)methyl]-N-{(1R,2S)-2-[(hydroxyamino)carbonyl]cyclohexyl}benzamide;

N-{(1R,2S)-2-[(hydroxyamino)carbonyl]cyclohexyl}-4-{[2-(trifluoromethyl)-1H-benzimidazol-1-yl]methyl}benzamide;

4-[(2-tert-butyl-1H-benzimidazol-1-yl)methyl]-N-{(1R,2S)-2-[(hydroxyamino)carbonyl]cyclohexyl}benzamide;

tert-butyl (3S,4R)-3-[(hydroxyamino)carbonyl]-4-[(4-{[2-(1-methylcyclopropyl)-1H-benzimidazol-1-yl]methyl}benzoyl)amino]-1-piperidinecarboxylate;

(3S,4R)-N-hydroxy-4-[(4-{[2-(1-methylcyclopropyl)-1H-benzimidazol-1-yl]methyl}benzoyl)amino]-3-piperidinecarboxamide;

tert-butyl (3S,4S)-4-[(hydroxyamino)carbonyl]-3-[(4-{[2-(trifluoromethyl)-1H-benzimidazol-1-yl]methyl}benzoyl)amino]-1-piperidinecarboxylate;

(3S,4S)-N-hydroxy-3-[(4-{[2-(trifluoromethyl)-1H-benzimidazol-1-yl]methyl}benzoyl)amino]-4-piperidinecarboxamide;

(3R,4R)-4-({4-[(2-(1,1-difluoro-ethyl)-1H-benzimidazol-1-yl)methyl]benzoyl}amino)-N-hydroxytetrahydro-2H-pyran-3-carboxamide;

(3R,4R)-N-hydroxy-4-[(4-{[2-(trifluoromethyl)-1H-imidazo[4,5-b]pyridin-1-yl]methyl}benzoyl)amino]-tetrahydro-2H-pyran-3-carboxamide;

(3R,4R)-N-hydroxy-4-[(4-{[2-(methoxymethyl)-1H-benzimidazol-1-yl]methyl}benzoyl)amino]tetrahydro-2H-pyran-3-carboxamide;

tert-butyl (3S,4S)-3-[(hydroxyamino)carbonyl]-4-({4-[(2-methyl-1H-indol-3-yl)methyl]benzoyl}amino)-1-pyrrolidinecarboxylate;

tert-butyl (3S,4S)-3-({4-[(1,2-dimethyl-1H-1indol-3-yl)methyl]benzoyl}amino)-4-[(hydroxyamino)carbonyl]-1-pyrrolidinecarboxylate;

(3S,4S)-N-hydroxy-4-({4-[(2-methyl-1H-indol-3-yl)methyl]benzoyl}amino)-3-pyrrolidinecarboxamide;

(3S,4S)-4-({4-[(1,2-dimethyl-1H-indol-3-yl)methyl]benzoyl}amino)-N-hydroxy-3-pyrrolidinecarboxamide;

(3S,4S)-N-hydroxy-1-isopropyl-4-({4-[(2-methyl-1H-indol-3-yl)methyl]benzoyl}amino)-3-pyrrolidinecarboxamide;

(3S,4S)-N-hydroxy-4-({4-[(2-methyl-1H-indol-3-yl)methyl]benzoyl}amino)-1-(2-propynyl)-3-pyrrolidinecarboxamide;

(3R,4R)-N-hydroxy-4-({4-[(2-methyl-1H-indol-3-yl)methyl]benzoyl}amino)tetrahydro-2H-pyran-3-carboxamide;

(3R,4R)-N-hydroxy-4-({4-[(2-methyl-1H-indol-1-yl)methyl]benzoyl}amino)tetrahydro-2H-pyran-3-carboxamide;

N-{(1R,2S)-2-[(hydroxyamino)carbonyl]cyclopentyl}-4-[(2-methyl-1H-indol-1-yl)methyl]benzamide;

tert-butyl (3S,4S)-3-({4-[(2,3-dimethyl-1H-indol-1-yl)methyl]benzoyl}amino)-4-[(hydroxyamino)carbonyl]-1-pyrrolidinecarboxylate;

tert-butyl (3S,4S)-3-[(hydroxyamino)carbonyl]-4-({4-[(2-isopropyl-1H-indol-1-yl)methyl]benzoyl}amino)-1-pyrrolidinecarboxylate;

(3S,4S)-N-hydroxy-4-({4-[(2-isopropyl-1H-indol-1-yl)methyl]benzoyl}amino)-3-pyrrolidinecarboxamide;

(3S,4S)-4-({4-[(2,3-dimethyl-1H-indol-1-yl)methyl]benzoyl}amino)-N-hydroxy-3-pyrrolidinecarboxamide;

(3R,4R)-4-({4-[(2,3-dimethyl-1H-indol-1-yl)methyl]benzoyl}amino)-N-hydroxytetrahydro-2H-pyran-3-carboxamide;

(3R,4R)-N-hydroxy-4-[(4-{[2-(trifluoromethyl)-1H-indol-1-yl]methyl}benzoyl)amino]tetrahydro-2H-pyran-3-carboxamide;

(3R,4R)-4-({4-[(2-ethyl-1H-indol-1-yl)methyl]benzoyl}amino)-N-hydroxytetrahydro-2H-pyran-3-carboxamide;

(3R,4S)-4-({4-[(2-ethyl-1H-indol-1-yl)methyl]benzoyl}amino)-N-hydroxytetrahydrofuran-3-carboxamide;

(3R,4S)-4-({4-[(2,3-dimethyl-1H-indol-1-yl)methyl]benzoyl}amino)-N-hydroxytetrahydrofuran-3-carboxamide;

(3R,4R)-4-({4-[(2-ethyl-1H-indol-3-yl)methyl]benzoyl}amino)-N-hydroxytetrahydro-2H-pyran-3-carboxamide;

(3R,4S)-4-({4-[(2-ethyl-1H-indol-3-yl)methyl]benzoyl}amino)-N-hydroxytetrahydrofuran-3-carboxamide;

(3R,4S)-N-hydroxy-4-[(4-{[2-(trifluoromethyl)-1H-indol-1-yl]methyl}benzoyl)amino]tetrahydrofuran-3-carboxamide;

(3R,4R)-N-hydroxy-4-({4-[(3-methyl-1H-indol-1-yl)methyl]benzoyl}amino)tetrahydro-2H-pyran-3-carboxamide;

(3R,4S)-N-hydroxy-4-({4-[(3-methyl-1H-indol-1-yl)methyl]benzoyl}amino)tetrahydrofuran-3-carboxamide;

(3R,4R)-4-({4-[(1,2-dimethyl-1H-indol-3-yl)methyl]benzoyl}amino)-N-hydroxytetrahydro-2H-pyran-3-carboxamide;

N-cis-2-[(hydroxyamino)carbonyl]cyclopentyl}-4-[(3-methyl-1H-indol-1-yl)methyl]benzamide;

(3R,4S)-4-({4-[(1,2-dimethyl-1H-indol-3-yl)methyl]benzoyl}amino)-N-hydroxytetrahydrofuran-3-carboxamide;

(3R,4S)-4-({4-[(2-ethyl-1-methyl-1H-indol-3-yl)methyl]benzoyl}amino)-N-hydroxytetrahydrofuran-3-carboxamide;

(3R,4R)-4-({4-[(2-ethyl-1-methyl-1H-indol-3-yl)methyl]benzoyl}amino)-N-hydroxytetrahydro-2H-pyran-3-carboxamide;

(3R,4R)-N-hydroxy-4-({4-[(2-methyl-1-benzofuran-3-yl)methyl]benzoyl}amino)tetrahydro-2H-pyran-3-carboxamide;

tert-butyl (3S,4S)-3-[(hydroxyamino)carbonyl]-4-({4-[(2-methyl-1-benzofuran-3-yl)methyl]benzoyl}amino)pyrrolidine-1-carboxylate;

(3S,4S)-N-hydroxy-4-({4-[(2-methyl-1-benzofuran-3-yl)methyl]benzoyl}amino)pyrrolidine-3-carboxamide;

(3R,4R)-N-hydroxy-4-({4-[(2-isopropyl-1-benzofuran-3-yl)methyl]benzoyl}amino)tetrahydro-2H-pyran-3-carboxamide;

tert-butyl (3S,4S)-3-[(hydroxyamino)carbonyl]-4-({4-[(2-isopropyl-1-benzofuran-3-yl)methyl]benzoyl}amino)pyrrolidine-1-carboxylate;

(3S,4S)-N-hydroxy-4-({4-[(2-isopropyl-1-benzofuran-3-yl)methyl]benzoyl}amino)pyrrolidine-3-carboxamide;

(3R,4R)-N-hydroxy-4-({4-[(2-methylimidazo[1,2-a]pyridin-3-yl)methyl]benzoyl}amino)tetrahydro-2H-pyran-3-carboxamide;

(3R,4R)-N-hydroxy-4-[(4-{[2-(trifluoromethyl)imidazo[1,2-a]pyridin-3-yl]methyl}benzoyl)amino]tetrahydro-2H-pyran-3-carboxamide;

(3R,4R)-4-({4-[(2-tert-butylimidazo[1,2-a]pyridin-3-yl)methyl]benzoyl}amino)-N-hydroxytetrahydro-2H-pyran-3-carboxamide;

N-{(1R,2S)-2-[(hydroxyamino)carbonyl]cyclopentyl}-4-[(2-isopropylimidazo[1,2-a]pyridin-3-yl)methyl]benzamide;

(3R,4R)-N-hydroxy-4-({4-[(2-isopropylimidazo[1,2-a]pyridin-3-yl)methyl]benzoyl}amino)tetrahydro-2H-pyran-3-carboxamide;

4-[(2-tert-butylimidazo[1,2-a]pyridin-3-yl)methyl]-N-{(1R,2S)-2-[(hydroxyamino)carbonyl]cyclopentyl}benzamide;

(3R,4R)-4-({4-[(2-cyclobutylimidazo[1,2-a]pyridin-3-yl)methyl]benzoyl}amino)-N-hydroxytetrahydro-2H-pyran-3-carboxamide;

N-{(1R,2S)-2-[(hydroxyamino)carbonyl]cyclopentyl}-4-{[2-(trifluoromethyl)imidazo[1,2-a]pyridin-3-yl]methyl}benzamide;

4-[(2-cyclobutylimidazo[1,2-a]pyridin-3-yl)methyl]-N-{(1R,2S)-2-[(hydroxyamino)carbonyl]cyclopentyl}benzamide;

(3R,4R)-4-({4-[(2-cyclopropylimidazo[1,2-a]pyridin-3-yl)methyl]benzoyl}amino)-N-hydroxytetrahydro-2H-pyran-3-carboxamide;

(3R,4R)-4-({4-[(2-ethylpyrazolo[1,5-a]pyridin-3-yl)methyl]benzoyl}amino)-N-hydroxytetrahydro-2H-pyran-3-carboxamide;

(3R,4R)-N-hydroxy-4-[(4-{[2-(trifluoromethyl)pyrazolo[1,5-a]pyridin-3-yl]methyl}benzoyl)amino]tetrahydro-2H-pyran-3-carboxamide;

(3R,4R)-N-hydroxy-4-[(4-{[2-(methoxymethyl)pyrazolo[1,5-a]pyridin-3-yl]methyl}benzoyl)amino]tetrahydro-2H-pyran-3-carboxamide;

(3R,4R)-N-hydroxy-4-[(4-{[2-(1-hydroxy-1-methylethyl)pyrazolo[1,5-a]pyridin-3-yl]methyl}benzoyl)amino]tetrahydro-2H-pyran-3-carboxamide;

(3R,4R)-N-hydroxy-4-({4-[(2-isopropylpyrazolo[1,5-a]pyridin-3-yl)methyl]benzoyl}amino)tetrahydro-2H-pyran-3-carboxamide;

(3R,4R)-4-({4-[(2-tert-butylpyrazolo[1,5-a]pyridin-3-yl)methyl]benzoyl}amino)-N-hydroxytetrahydro-2H-pyran-3-carboxamide;

(3R,4R)-4-({4-[(2-cyclopropylpyrazolo[1,5-a]pyridin-3-yl)methyl]benzoyl}amino)-N-hydroxytetrahydro-2H-pyran-3-carboxamide;

(3R,4R)-4-({4-[(2-cyclobutylpyrazolo[1,5-a]pyridin-3-yl)methyl]benzoyl}amino)-N-hydroxytetrahydro-2H-pyran-3-carboxamide;

4-[(2-cyclobutylpyrazolo[1,5-a]pyridin-3-yl)methyl]-N-{(1R,2S)-2-[(hydroxyamino)carbonyl]cyclopentyl}benzamide;

(3R,4R)-N-hydroxy-4-({4-[(2-phenylpyrazolo[1,5-a]pyridin-3-yl)methyl]benzoyl}amino)tetrahydro-2H-pyran-3-carboxamide;

(3R,4R)-4-({4-[(2-cyclopentylpyrazolo[1,5-a]pyridin-3-yl)methyl]benzoyl}amino)-N-hydroxytetrahydro-2H-pyran-3-carboxamide;

(3R,4R)-N-hydroxy-4-({4-[(2-tetrahydro-2H-pyran-4-ylpyrazolo[1,5-a]pyridin-3-yl)methyl]benzoyl}amino)tetrahydro-2H-pyran-3-carboxamide;

N-{(1R,2S)-2-[(hydroxyamino)carbonyl]cyclopentyl}-4-{[2-(trifluoromethyl)pyrazolo[1,5-a]pyridin-3-yl]methyl}benzamide;

tert-butyl (3S,4S)-3-[(hydroxyamino)carbonyl]-4-[(4-{[2-(trifluoromethyl)pyrazolo[1,5-a]pyridin-3-yl]methyl}benzoyl)amino]pyrrolidine-1-carboxylate;

(3S,4S)-N-hydroxy-4-[(4-{[2-(trifluoromethyl)pyrazolo[1,5-a]pyridin-3-yl]methyl}benzoyl)amino]pyrrolidine-3-carboxamide;

(3R,4R)-N-hydroxy-4-[(4-{([7-methyl-2-(trifluoromethyl)pyrazolo[1,5-a]pyridin-3-yl]methyl}benzoyl)amino]tetrahydro-2H-pyran-3-carboxamide;

(3R,4R)-N-hydroxy-4-({4-[(1-methylimidazo[1,5-a]pyridin-3-yl)methyl]benzoyl}amino)tetrahydro-2H-pyran-3-carboxamide;

(3R,4R)-N-hydroxy-4-[(4-{[1-(trifluoromethyl)imidazo[1,5-a]pyridin-3-yl]methyl}benzoyl)amino]tetrahydro-2H-pyran-3-carboxamide;

(3R,4R)-N-hydroxy-4-[(4-{[3-(trifluoromethyl)imidazo[1,5-a]pyridin-1-yl]methyl}benzoyl)amino]tetrahydro-2H-pyran-3-carboxamide; and, (3R,4R)-N-hydroxy-4-({4-[(3-methylimidazo[1,5-a]pyridin-1-yl)methyl]benzoyl}amino)tetrahydro-2H-pyran-3-carboxamide;

or a pharmaceutically acceptable salt form thereof.

9. A compound according to claim 1, wherein;
$Z^a$ is

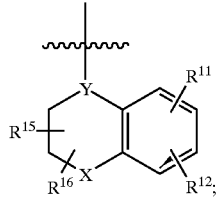

X is S, SO, $SO_2$, O, or $NR^{14}$;
Y is N or $CR^{17}$;
$R^{11}$ and $R^{12}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$;
$R^{14}$, at each occurrence, is independently selected from H, $C_{1-4}$ alkyl, phenyl, and benzyl;
$R^{15}$ and $R^{16}$, at each occurrence, are independently selected from H, $R^{c1}$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$;
alternatively, when $R^{15}$ and $R^{16}$ are attached to adjacent carbon atoms, together with the carbon atoms to which they are attached, they form a 5–7 membered carbocyclic or heterocyclic ring consisting of: carbon atoms, 0–2 carbonyl groups, —O–3 double bonds, 0–2 heteroatoms selected from the group consisting of N, O, and $S(O)_p$, and substituted with 0–2 $R^{c1}$;
alternatively, when $R^{15}$ and $R^{16}$ are attached to the same carbon atom, together with the carbon atom to which they are attached, they form a 3–7 membered carbocyclic or heterocyclic ring consisting of: carbon atoms, 0–2 carbonyl groups, 0–3 double bonds, and 0–2 heteroatoms selected from the group consisting of N, O, and $S(O)_p$; this ring is substituted with 0–2 $R^{c1}$; and,
$R^{17}$ is selected from H, Cl, F, and $C_{1-4}$ alkyl.

10. A compound according to claim 2, wherein;
$Z^a$ is

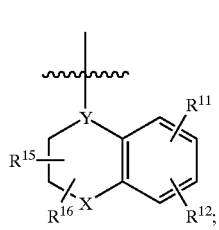

X is S, SO, $SO_2$, O, or $NR^{14}$;
Y is N or $CR^{17}$;
$R^{11}$ and $R^{12}$, at each occurrence, are independently selected from H, $R^c$, $C_{1-4}$ alkyl substituted with 0–3 $R^{c1}$, and phenyl substituted with 0–3 $R^{c1}$;

R[14], at each occurrence, is independently selected from H, $C_{1-4}$ alkyl, and benzyl;

R[15] and R[16], at each occurrence, are independently selected from H, $R^{c1}$, $C_{1-4}$ alkyl substituted with 0–3 $R^{c1}$, and phenyl;

alternatively, when R[15] and R[16] are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$;

alternatively, when R[15] and R[16] are attached to the same carbon atom, together with the carbon atom to which they are attached they form a 3–6 membered carbocyclic or heterocyclic ring consisting of: carbon atoms, 0–1 carbonyl groups, 0–2 double bonds, and 0–2 heteroatoms selected from the group consisting of N, O, and $S(O)_p$; this ring is substituted with 0–1 $R^{c1}$; and, R[17] is selected from H, Cl, F, and $C_{1-4}$ alkyl.

11. A compound according to claim 4, wherein;
ring B is selected from the group:

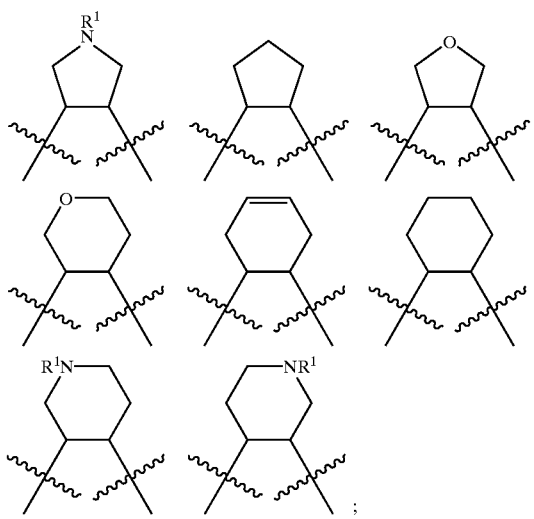

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

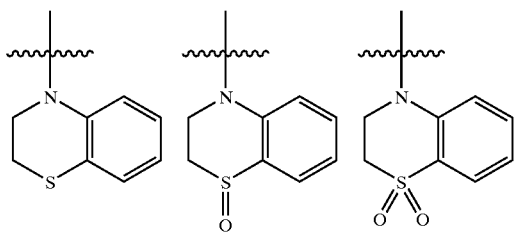

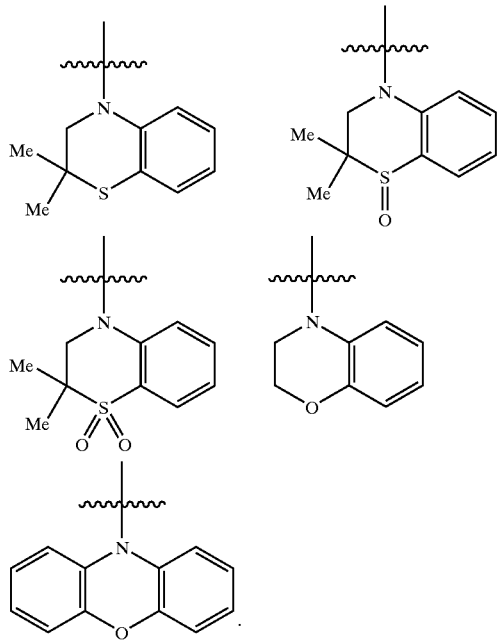

12. A compound according to claim 1, wherein the compound is selected from the group:

tert-butyl (3S,4S)-3-{[4-(2,3-dihydro-4H-1,4-benzothiazin-4-ylmethyl)benzoyl]amino}-4-[(hydroxyamino)carbonyl]-1-pyrrolidinecarboxylate;

tert-butyl (3S,4S)-3-[(hydroxyamino)carbonyl]-4-({4-[(1-oxido-2,3-dihydro-4H-1,4-benzothiazin-4-yl)methyl]benzoyl}amino)-1-pyrrolidinecarboxylate;

(3S,4S)-4-{[4-(2,3-dihydro-4H-1,4-benzothiazin-4-ylmethyl)benzoyl]amino}-N-hydroxy-3-pyrrolidinecarboxamide;

(3S,4S)-N-hydroxy-4-({4-[(1-oxido-2,3-dihydro-4H-1,4-benzothiazin-4-yl)methyl]benzoyl}amino)-3-pyrrolidinecarboxamide;

(3S,4S)-N-hydroxy-4-({4-[(1-oxido-2,3-dihydro-4H-1,4-benzothiazin-4-yl)methyl]benzoyl}amino)-1-(2-propynyl)-3-pyrrolidinecarboxamide;

(3S,4S)-N-hydroxy-1-isopropyl-4-({4-[(1-oxido-2,3-dihydro-4H-1,4-benzothiazin-4-yl)methyl]benzoyl}amino)-3-pyrrolidinecarboxamide;

tert-butyl (3S,4S)-3-({4-[(1,1-dioxido-2,3-dihydro-4H-1,4-benzothiazin-4-yl)methyl]benzoyl}amino)-4-[(hydroxyamino)carbonyl]-1-pyrrolidinecarboxylate;

(3S,4S)-4-({4-[(1,1-dioxido-2,3-dihydro-4H-1,4-benzothiazin-4-yl)methyl]benzoyl}amino)-N-hydroxy-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-(2-propynyl)-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-isopropyl-3-pyrrolidinecarboxamide;

(3S,4S)-1-(2-butynyl)-4-({4-[(1,1-dioxido-2,3-dihydro-4H-1,4-benzothiazin-4-yl)methyl]benzoyl}amino)-N-hydroxy-1-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-isobutyl-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-methyl-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-(isopropylsulfonyl)-3-pyrrolidinecarboxamide;

(3S,4S)-1-acetyl-4-({4-[(1,1-dioxido-2,3-dihydro-4H-1,4-benzothiazin-4-yl)methyl]benzoyl}amino)-N-hydroxy-3-pyrrolidinecarboxamide;

(3S,4S)-1-(2,2-dimethylpropanoyl)-4-({4-[(1,1-dioxido-2,3-dihydro-4H-1,4-benzothiazin-4-yl)methyl]benzoyl}amino)-N-hydroxy-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-phenyl-3-pyrrolidinecarboxamide;

(3S,4S)-4-({4-[(1,1-dioxido-2,3-dihydro-4H-1,4-benzothiazin-4-yl)methyl]benzoyl}amino)-1-(4-fluorophenyl)-N-hydroxy-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-(4-methoxyphenyl)-3-pyrrolidinecarboxamide;

(3S,4S)-1-(cyclopropylmethyl)-4-({4-[(1,1-dioxido-2,3-dihydro-4H-1,4-benzothiazin-4-yl)methyl]benzoyl}amino)-N-hydroxy-3-pyrrolidinecarboxamide;

(3S,4S)-1-cyclopentyl-4-({4-[(1,1-dioxido-2,3-dihydro-4H-1,4-benzothiazin-4-yl)methyl]benzoyl}amino)-N-hydroxy-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-tetrahydro-2H-pyran-4-yl-3-pyrrolidinecarboxamide;

(3S,4S)-4-({4-[(1,1-dioxido-2,3-dihydro-4H-1,4-benzothiazin-4-yl)methyl]benzoyl}amino)-N-hydroxy-1-neopentyl-3-pyrrolidinecarboxamide;

4-[(1,1-dioxido-2,3-dihydro-4H-1,4-benzothiazin-4-yl)methyl]-N-cis-{2-[(hydroxyamino)carbonyl]cyclopentyl}benzamide;

(3R,4S)-4-({4-[(1,1-dioxido-2,3-dihydro-4H-1,4-benzothiazin-4-yl)methyl]benzoyl}amino)-N-hydroxytetrahydro-3-furancarboxamide;

(3R,4R)-4-({4-[(1,1-dioxido-2,3-dihydro-4H-1,4-benzothiazin-4-yl)methyl]benzoyl}amino)-N-hydroxytetrahydro-2H-pyran-3-carboxamide;

tert-butyl (3S,4S)-3-({4-[(2,2-dimethyl-2,3-dihydro-4H-1,4-benzothiazin-4-yl)methyl]benzoyl}amino)-4-[(hydroxyamino)carbonyl]-1-pyrrolidinecarboxylate;

tert-butyl (3S,4S)-3-({4-[(2,2-dimethyl-1-oxido-2,3-dihydro-4H-1,4-benzothiazin-4-yl)methyl]benzoyl}amino)-4-[(hydroxyamino)carbonyl]-1-pyrrolidinecarboxylate;

tert-butyl (3S,4S)-3-({4-[(2,2-dimethyl-1,1-dioxido-2,3-dihydro-4H-1,4-benzothiazin-4-yl)methyl]benzoyl}amino)-4-[(hydroxyamino)carbonyl]-1-pyrrolidinecarboxylate;

(3S,4S)-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide;

(3S,4S)-4-({4-[(2,2-dimethyl-1,1-dioxido-2,3-dihydro-4H-1,4-benzothiazin-4-yl)methyl]benzoyl}amino)-N-hydroxy-1-(2-propynyl)-3-pyrrolidinecarboxamide;

(3S,4S)-4-({4-[(2,2-dimethyl-1,1-dioxido-2,3-dihydro-4H-1,4-benzothiazin-4-yl)methyl]benzoyl}amino)-N-hydroxy-1-isopropyl-3-pyrrolidinecarboxamide;

(3S,4S)-4-({4-[(2,2-dimethyl-1,1-dioxido-2,3-dihydro-4H-1,4-benzothiazin-4-yl)methyl]benzoyl}amino)-N-hydroxy-1-isobutyl-3-pyrrolidinecarboxamide;

(3S,4S)-1-butyl-4-({4-[(2,2-dimethyl-1,1-dioxido-2,3-dihydro-4H-1,4-benzothiazin-4-yl)methyl]benzoyl}amino)-N-hydroxy-3-pyrrolidinecarboxamide;

(3S,4S)-4-({4-[(2,2-dimethyl-1,1-dioxido-2,3-dihydro-4H-1,4-benzothiazin-4-yl)methyl]benzoyl}amino)-N-hydroxy-1-neopentyl-3-pyrrolidinecarboxamide;

(3R,4R)-4-({4-[(2,2-dimethyl-1,1-dioxido-2,3-dihydro-4H-1,4-benzothiazin-4-yl)methyl]benzoyl}amino)-N-hydroxytetrahydro-2H-pyran-3-carboxamide;

(3R,4S)-4-({4-[(2,2-dimethyl-1,1-dioxido-2,3-dihydro-4H-1,4-benzothiazin-4-yl)methyl]benzoyl}amino)-N-hydroxytetrahydro-3-furancarboxamide;

4-[(2,2-dimethyl-1,1-dioxido-2,3-dihydro-4H-1,4-benzothiazin-4-yl)methyl]-N-cis-{2-[(hydroxyamino)carbonyl]cyclopentyl}benzamide;

tert-butyl (3S,4S)-3-{[4-(2,3-dihydro-4H-1,4-benzoxazin-4-ylmethyl)benzoyl]amino}-4-[(hydroxyamino)carbonyl]-1-pyrrolidinecarboxylate; and, tert-butyl (3S,4S)-3-[(hydroxyamino)carbonyl]-4-{[4-(10H-phenoxazin-10-ylmethyl)benzoyl]amino}-1-pyrrolidinecarboxylate;

or a pharmaceutically acceptable salt form thereof.

13. A compound according to claim 1, wherein;

$Z^a$ is

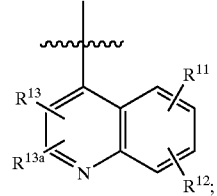

$R^{11}$ and $R^{12}$, at each occurrence, are independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$; and $R^{13}$ and $R^{13a}$, at each occurrence, is independently selected from H, $R^c$, $C_{1-6}$ alkyl substituted with 0–3 $R^{c1}$, $C_{3-10}$ carbocycle substituted with 0–3 $R^{c1}$, and a 5–14 membered heterocycle consisting of: carbon atoms and 1–4 heteroatoms selected from the group consisting of N, O, and $S(O)_p$, and substituted with 0–3 $R^{c1}$; and, alternatively, when $R^{13}$ and $R^{13a}$ are attached to adjacent carbon atoms, together with the carbon atoms to which they are attached, they-form a 5–7 membered carbocyclic or heterocyclic ring consisting of: carbon atoms, 0–2 carbonyl groups, 0–3 double bonds, and 0–2 heteroatoms selected from the group consisting of N, O, and $S(O)_p$, and substituted with 0–2 $R^{c1}$.

14. A compound according to claim 2, wherein;

$Z^a$ is

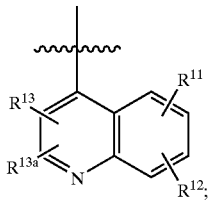

$R^{13}$ and $R^{13a}$, at each occurrence, are independently selected from H, $R^c$, $C_{1-4}$ alkyl substituted with 0–3 $R^{c1}$, $C_{3-6}$ cycloalkyl substituted with 0–2 $R^{c1}$, phenyl substituted with 0–3 $R^{c1}$, and a 5–6 membered heterocycle consisting of: carbon atoms and 1–4 heteroatoms selected from the group consisting of N, O, and $S(O)_p$, and substituted with 0–3 $R^{c1}$; and, alternatively, when $R^{13}$ and $R^{13a}$ are attached to adjacent carbon atoms, together with the carbon atoms to which they are attached, they form a 5–6 membered carbocyclic or heterocyclic ring consisting of: carbon atoms, 0–1 carbonyl groups, 0–2 double bonds, and 0–2 heteroatoms selected from the group consisting of N, O, and $S(O)_p$, and substituted with 0–2 $R^{c1}$.

15. A compound according to claim 4, wherein;

ring B is selected from the group:

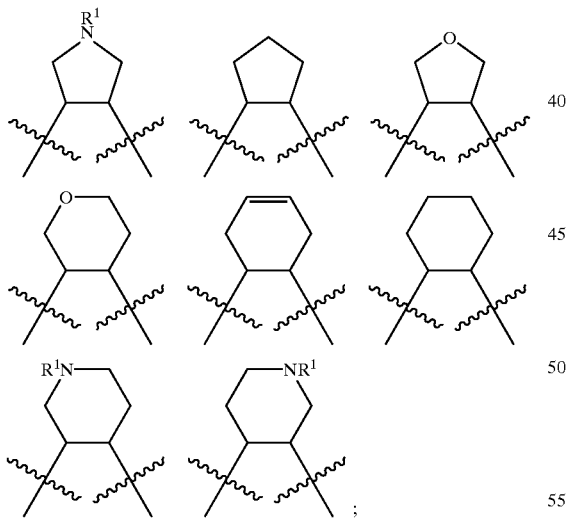

$R^1$ is selected from H, methyl, isopropyl, butyl, isobutyl, neopentyl, allyl, 3-butenyl, 2-propynyl, 2-butynyl, 3-butynyl, acetyl, t-butylcarbonyl, 4-pentenoyl, t-butoxycarbonyl, methoxycarbonyl, methylsulfonyl, propylsulfonyl, isopropylsulfonyl, butylsulfonyl, phenyl, 4-F-phenyl, 4-methoxy-phenyl, cyclopropylmethyl, cyclopentyl, and tetrahydro-2H-pyran-4-yl; and, $Z^a$ is selected from the group:

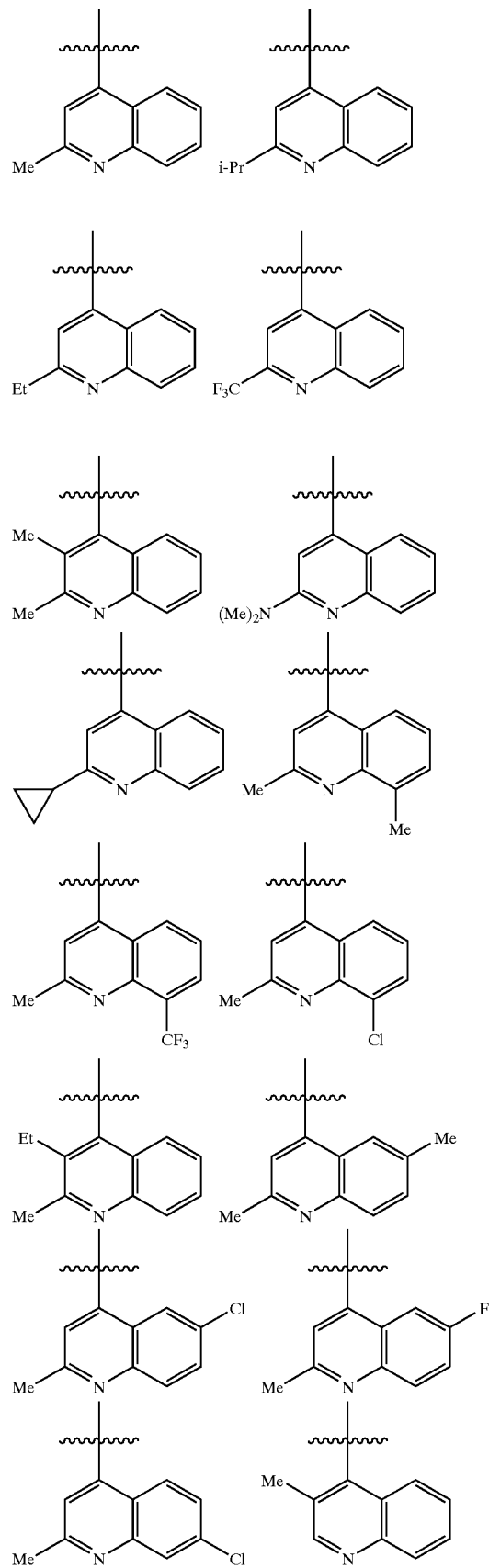

-continued

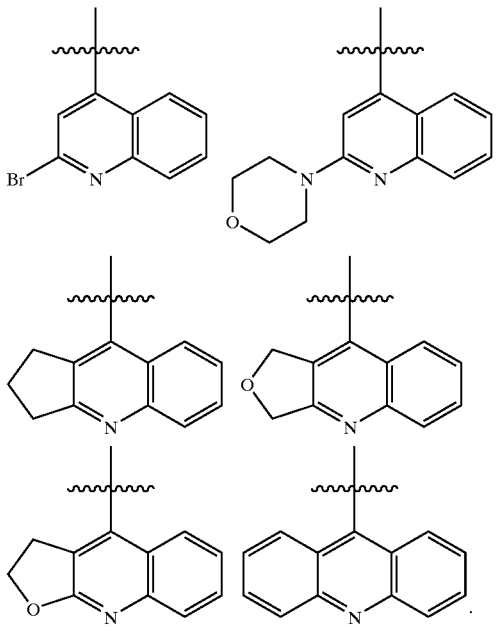

16. A compound according to claim 1, wherein the compound is selected from the group:

tert-butyl (3S,4S)-3-[(hydroxyamino)carbonyl]-4-({4-[(2-methyl-4-quinolinyl)methyl]benzoyl}amino)-1-pyrrolidinecarboxylate;

(3S,4S)-N-hydroxy-4-({4-[(2-methyl-4-quinolinyl)methyl]benzoyl}amino)-3-pyrrolidinecarboxamide;

(3S,4S)-N-hydroxy-4-({4-[(2-methyl-4-quinolinyl)methyl]benzoyl}amino)-1-(2-propynyl)-3-pyrrolidinecarboxamide;

(3S,4S)-N-hydroxy-1-isopropyl-4-({4-[(2-methyl-4-quinolinyl)methyl]benzoyl}amino)-3-pyrrolidinecarboxamide;

(3S,4S)-N-hydroxy-1-isobutyl-4-({4-[(2-methyl-4-quinolinyl)methyl]benzoyl}amino)-3-pyrrolidinecarboxamide;

(3S,4S)-1-butyl-N-hydroxy-4-({4-[(2-methyl-4-quinolinyl)methyl]benzoyl}amino)-3-pyrrolidinecarboxamide;

(3S,4S)-1-(2-butynyl)-N-hydroxy-4-({4-[(2-methyl-4-quinolinyl)methyl]benzoyl}amino)-3-pyrrolidinecarboxamide;

(3S,4S)-N-hydroxy-1-methyl-4-({4-[(2-methyl-4-quinolinyl)methyl]benzoyl}amino)-3-pyrrolidinecarboxamide;

(3S,4S)-1-allyl-N-hydroxy-4-({4-[(2-methyl-4-quinolinyl)methyl]benzoyl}amino)-3-pyrrolidinecarboxamide;

(3S,4S)-1-(cyclopropylmethyl)-N-hydroxy-4-({4-[(2-methyl-4-quinolinyl)methyl]benzoyl}amino)-3-pyrrolidinecarboxamide;

(3S,4S)-1-cyclopentyl-N-hydroxy-4-({4-[(2-methyl-4-quinolinyl)methyl]benzoyl}amino)-3-pyrrolidinecarboxamide;

(3S,4S)-N-hydroxy-4-({4-[(2-methyl-4-quinolinyl)methyl]benzoyl}amino)-1-neopentyl-3-pyrrolidinecarboxamide;

(3S,4S)-N-hydroxy-4-({4-[(2-methyl-4-quinolinyl)methyl]benzoyl}amino)-1-tetrahydro-2H-pyran-4-yl-3-pyrrolidinecarboxamide;

(3S,4S)-N-hydroxy-4-({4-[(2-methyl-4-quinolinyl)methyl]benzoyl}amino)-1-phenyl-3-pyrrolidinecarboxamide;

(3S,4S)-1-(4-fluorophenyl)-N-hydroxy-4-({4-[(2-methyl-4-quinolinyl)methyl]benzoyl}amino)-3-pyrrolidinecarboxamide;

(3S,4S)-N-hydroxy-1-(methoxyphenyl)-4-({4-[(2-methyl-4-quinolinyl)methyl]benzoyl}amino)-3-pyrrolidinecarboxamide;

(3S,4S)-1-acetyl-N-hydroxy-4-({4-[(2-methyl-4-quinolinyl)methyl]benzoyl}amino)-3-pyrrolidinecarboxamide;

(3S,4S)-1-(2,2-dimethylpropanoyl)-N-hydroxy-4-({4-[(2-methyl-4-quinolinyl)methyl]benzoyl}amino)-3-pyrrolidinecarboxamide;

(3S,4S)-N-hydroxy-1-(isopropylsulfonyl)-4-({4-[(2-methyl-4-quinolinyl)methyl]benzoyl}amino)-3-pyrrolidinecarboxamide;

(3S,4S)-1-(butylsulfonyl)-N-hydroxy-4-({4-[(2-methyl-4-quinolinyl)methyl]benzoyl}amino)-3-pyrrolidinecarboxamide;

methyl (3S,4S)-3-[(hydroxyamino)carbonyl]-4-({4-[(2-methyl-4-quinolinyl)methyl]benzoyl}amino)-1-pyrrolidinecarboxylate;

(3R,4S)-N-hydroxy-4-({4-[(2-methyl-4-quinolinyl)methyl]benzoyl}amino)tetrtahydro-3-furancarboxamide;

(3R,4R)-N-hydroxy-4-({4-[(2-methyl-4-quinolinyl)methyl]benzoyl}amino)tetrahydro-2H-pyran-3-carboxamide;

N-cis-{2-[(hydroxyamino)carbonyl]cyclopentyl}-4-[(2-methyl-4-quinolinyl)methyl]benzamide;

tert-butyl (3S,4S)-3-[(hydroxyamino)carbonyl]-4-({4-[(2-isopropyl-4-quinolinyl)methyl]benzoyl}amino)-1-pyrrolidinecarboxylate;

(3S,4S)-N-hydroxy-4-({4-[(2-isopropyl-4-quinolinyl)methyl]benzoyl}amino)-3-pyrrolidinecarboxamide;

(3S,4S)-N-hydroxy-4-({4-[(2-isopropyl-4-quinolinyl)methyl]benzoyl}amino)-1-(2-propynyl)-3-pyrrolidinecarboxamide;

(3S,4S)-N-hydroxy-1-isopropyl-4-({4-[(2-isopropyl-4-quinolinyl)methyl]benzoyl}amino)-3-pyrrolidinecarboxamide;

(3S,4S)-N-hydroxy-4-({4-[(2-isopropyl-4-quinolinyl)methyl]benzoyl}amino)-1-methyl-3-pyrrolidinecarboxamide;

(3S,4S)-1-cyclopentyl-N-hydroxy-4-({4-[(2-isopropyl-4-quinolinyl)methyl]benzoyl}amino)-3-pyrrolidinecarboxamide;

(3R,4R)-N-hydroxy-4-({4-[(2-isopropyl-4-quinolinyl)methyl]benzoyl}amino)tetrahydro-2H-pyran-3-carboxamide;

N-cis-{2-[(hydroxyamino)carbonyl]cyclopentyl}-4-[(2-isopropyl-4-quinolinyl)methyl]benzamide;

(3R,4S)-N-hydroxy-4-({4-[(2-isopropyl-4-quinolinyl)methyl]benzoyl}amino)tetrtahydro-3-furancarboxamide;

tert-butyl (3S,4S)-3-({4-[(2-ethyl-4-quinolinyl)methyl]benzoyl}amino)-4-[(hydroxyamino)carbonyl]-1-pyrrolidinecarboxylate;

(3S,4S)-4-({4-[(2-ethyl-4-quinolinyl)methyl]benzoyl}amino)-N-hydroxy-3-pyrrolidinecarboxamide;

(3S,4S)-4-({4-[(2-ethyl-4-quinolinyl)methyl]benzoyl}amino)-N-hydroxy-1-(2-propynyl)-3-pyrrolidinecarboxamide;

(3S,4S)-1-(2-butynyl)-4-({4-[(2-ethyl-4-quinolinyl)methyl]benzoyl}amino)-N-hydroxy-3-pyrrolidinecarboxamide;

(3R,4R)-4-({4-[(2-ethyl-4-quinolinyl)methyl]benzoyl}amino)-N-hydroxytetrahydro-2H-pyran-3-carboxamide;

4-[(2-ethyl-4-quinolinyl)methyl]-N-{cis-2-[(hydroxyamino)carbonyl]cyclopentyl}-benzamide;

(3R,4S)-4-({4-[(2-ethyl-4-quinolinyl)methyl]benzoyl}amino)-N-hydroxytetrtahydro-3-furancarboxamide;

tert-butyl (3S,4S)-3-[(hydroxyamino)carbonyl]-4-({4-[(2-(trifluoromethyl)-4-quinolinyl)methyl]benzoyl}amino)-1-pyrrolidinecarboxylate;

(3R,4R)-N-hydroxy-4-[(4-{[2-(trifluoromethyl)-4-quinolinyl]methyl}benzoyl)amino]tetrahydro-2H-pyran-3-carboxamide;

N-{cis-2-[(hydroxyamino)carbonyl]cyclopentyl}-4-{[2-(trifluoromethyl)-4-quinolinyl]methyl}benzamide;

tert-butyl (3S,4S)-3-[(hydroxyamino)carbonyl]-4-({4-[(2,3-dimethyl-4-quinolinyl)methyl]benzoyl}amino)-1-pyrrolidinecarboxylate;

(3R,4R)-4-({4-[(2,3-dimethyl-4-quinolinyl)methyl]benzoyl}amino)-N-hydroxytetrahydro-2H-pyran-3-carboxamide;

4-[(2,3-dimethyl-4-quinolinyl)methyl]-N-{cis-2-[(hydroxyamino)carbonyl]cyclopentyl}benzamide;

(3S,4S)-N-hydroxy-4-[(4-{[2-(trifluoromethyl)-4-quinolinyl]methyl}benzoyl)amino]-1-(2-propynyl)-3-pyrrolidinecarboxamide;

(3R,4S)-N-hydroxy-4-[(4-{[2-(trifluoromethyl)-4-quinolinyl]methyl}benzoyl)amino]-tetrahydro-3-furancarboxamide;

(3S,4S)-4-({4-[(2,3-dimethyl-4-quinolinyl)methyl]benzoyl}amino)-N-hydroxy-1-(2-propynyl)-3-pyrrolidinecarboxamide;

(3R,4S)-N-hydroxy-4-({4-[(2,3-dimethyl-4-quinolinyl)methyl]benzoyl}amino)-tetrahydro-3-furancarboxamide;

(3R,4R)-4-[(4-{[2-(dimethylamino)-4-quinolinyl]methyl}benzoyl)amino]-N-hydroxytetrahydro-2H-pyran-3-carboxamide;

(3R,4S)-4-({4-[(2-cyclopropyl-4-quinolinyl)methyl]benzoyl}amino)-N-hydroxytetrahydro-3-furancarboxamide;

(3R,4R)-4-({4-[(2-cyclopropyl-4-quinolinyl)methyl]benzoyl}amino)-N-hydroxytetrahydro-2H-pyran-3-carboxamide;

(3R,4S)-4-{[4-(1,3-dihydrofuro[3,4-b]quinolin-9-ylmethyl)benzoyl]amino}-N-hydroxytetrahydro-3-furancarboxamide;

(3R,4R)-4-{[4-(1,3-dihydrofuro[3,4-b]quinolin-9-ylmethyl)benzoyl]amino}-N-hydroxytetrahydro-2H-pyran-3-carboxamide;

tert-butyl (3S,4S)-4-({4-[(2,8-dimethyl-4-quinolinyl)methyl]benzoyl}amino)-3-[(hydroxyamino)carbonyl]-1-pyrrolidinecarboxylate;

4-[(2,8-dimethyl-4-quinolinyl)methyl]-N-{cis-2-[(hydroxyamino)carbonyl]cyclopentyl}benzamide;

(3R,4R)-4-({4-[(2,8-dimethyl-4-quinolinyl)methyl]benzoyl}amino)-N-hydroxytetrahydro-2H-pyran-3-carboxamide;

(3R,4S)-4-({4-[(2,8-dimethyl-4-quinolinyl)methyl]benzoyl}amino)-N-hydroxytetrahydro-3-furancarboxamide;

(3R,4R)-N-hydroxy-4-[(4-{[2-methyl-8-(trifluoromethyl)-4-quinolinyl]methyl}benzoyl)amino]tetrahydro-2H-pyran-3-carboxamide;

(3R,4R)-4-({4-[(8-chloro-2-methyl-4-quinolinyl)methyl]benzoyl}amino)-N-hydroxytetrahydro-2H-pyran-3-carboxamide;

(3R,4S)-4-({4-[(8-chloro-2-methyl-4-quinolinyl)methyl]benzoyl}amino)-N-hydroxytetrahydro-3-furancarboxamide;

(3R,4R)-4-({4-[(3-ethyl-2-methyl-4-quinolinyl)methyl]benzoyl}amino)-N-hydroxytetrahydro-2H-pyran-3-carboxamide;

(3R,4S)-4-({4-[(3-ethyl-2-methyl-4-quinolinyl)methyl]benzoyl}amino)-N-hydroxytetrahydro-3-furancarboxamide;

4-[(3-ethyl-2-methyl-4-quinolinyl)methyl]-N-{cis-2-[(hydroxyamino)carbonyl]cyclopentyl}benzamide;

(3R,4S)-4-({4-[(2,6-dimethyl-4-quinolinyl)methyl]benzoyl}amino)-N-hydroxytetrahydro-3-furancarboxamide;

4-[(2,6-dimethyl-4-quinolinyl)methyl]-N-{cis-2-[(hydroxyamino)carbonyl]cyclopentyl}benzamide;

(3R,4R)-N-hydroxy-4-({4-[(2,6-dimethyl-4-quinolinyl)methyl]benzoyl}amino) tetrahydro-2H-pyran-3-carboxamide;

(3R,4S)-4-({4-[(6-chloro-2-methyl-4-quinolinyl)methyl]benzoyl}amino)-N-hydroxytetrahydro-3-furancarboxamide;

(3R,4R)-4-({4-[(6-chloro-2-methyl-4-quinolinyl)methyl]benzoyl}amino)-N-hydroxytetrahydro-2H-pyran-3-carboxamide;

(3R,4R)-4-({4-[(6-fluoro-2-methyl-4-quinolinyl)methyl]benzoyl}amino)-N-hydroxytetrahydro-2H-pyran-3-carboxamide;

(3R,4R)-4-({4-[(7-chloro-2-methyl-4-quinolinyl)methyl]benzoyl}amino)-N-hydroxytetrahydro-2H-pyran-3-carboxamide;

(3R,4R)-4-{[4-(2,3-dihydro-1H-cyclopenta[b]quinolin-9-ylmethyl)benzoyl]amino}-N-hydroxytetrahydro-2H-pyran-3-carboxamide;

(3R,4R)-4-{[4-(2,3-dihydrofuro[2,3-b]quinolin-4-ylmethyl)benzoyl]amino}-N-hydroxytetrahydro-2H-pyran-3-carboxamide;

(3R,4R)-4-{[4-(acridin-9-ylmethyl)benzoyl]amino}-N-hydroxytetrahydro-2H-pyran-3-carboxamide;

(3R,4R)-4-({4-[(3-methyl-4-quinolinyl)methyl]benzoyl}amino)-N-hydroxytetrahydro-2H-pyran-3-carboxamide;

(3R,4R)-4-({4-[(2-bromoquinolin-4-yl)methyl]benzoyl}amino)-N-hydroxytetrahydro-2H-pyran-3-carboxamide; and, (3R,4R)-N-hydroxy-4-({4-[(2-morpholin-4-ylquinolin-4-yl)methyl]benzoyl}amino)tetrahydro-2H-pyran-3-carboxamide;

or a pharmaceutically acceptable salt form thereof.

17. A pharmaceutical composition, comprising: a pharmaceutically acceptable carrier and a therapeutically effective amount of a compound according to claim 1 or a pharmaceutically acceptable salt form thereof.

18. A method for treating an inflammatory disorder, comprising: administering to a patient in need thereof a therapeutically effective amount of a compound of claim 1 or a pharmaceutically acceptable salt form thereof.

19. A method of treating a condition or disease mediated by MMPs, TACE, aggrecanase, or a combination thereof in a mammal, comprising: administering to the mammal in need of such treatment a therapeutically effective amount of a compound according to claim 1.

20. A method of treating according to claims 19, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Siogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

21. A method for treating inflammatory disorders, comprising: administering, to a host in need of such treatment, a therapeutically effective amount of a compound of claim 1 in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

22. An article of manufacture, comprising:
    (a) a first container;
    (b) a pharmaceutical composition located within the first container, wherein the composition, comprises: a first therapeutic agent, comprising: a compound according to claim 1 or a pharmaceutically acceptable salt form thereof; and,
    (c) a package insert stating that the pharmaceutical composition can be used for the treatment of a thromboembolic disorder.

23. An article of manufacture according to claim 22, further comprising:
    (d) a second container; wherein components (a) and (b) are located within the second container and component (c) is located within or outside of the second container.

24. An article of manufacture, comprising:
    (a) a first container;
    (b) a pharmaceutical composition located within the first container, wherein the composition, comprises: a first therapeutic agent, comprising: a compound according to claim 1 or a pharmaceutically acceptable salt form thereof; and,
    (c) a package insert stating that the pharmaceutical composition can be used in combination with a second therapeutic agent to treat a thromboembolic disorder.

25. An article of manufacture according to claim 24, further comprising:
    (d) a second container;
    wherein components (a) and (b) are located within the second container and component
    (c) is located within or outside of the second container.

26. A pharmaceutical composition, comprising: a pharmaceutically acceptable carrier and a therapeutically effective amount of a compound according to claim 2 or a pharmaceutically acceptable salt form thereof.

27. A method for treating an inflammatory disorder, comprising: administering to a patient in need thereof a therapeutically effective amount of a compound of claim 2 or a pharmaceutically acceptable salt form thereof.

28. A method of treating a condition or disease mediated by MMPs, TACE, aggrecanase, or a combination thereof in a mammal, comprising: administering to the mammal in need of such treatment a therapeutically effective amount of a compound according to claim 2.

29. A method of treating according to claim 28, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

30. A pharmaceutical composition, comprising: a pharmaceutically acceptable carrier and a therapeutically effective amount of a compound according to claim 3 or a pharmaceutically acceptable salt form thereof.

31. A method for treating an inflammatory disorder, comprising: administering to a patient in need thereof a therapeutically effective amount of a compound of claim 3 or a pharmaceutically acceptable salt form thereof.

32. A method of treating a condition or disease mediated by MMPs, TACE, aggrecanase, or a combination thereof in a mammal, comprising: administering to the mammal in need of such treatment a therapeutically effective amount of a compound according to claim 3.

33. A method of treating according to claim 32, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

34. A pharmaceutical composition, comprising: a pharmaceutically acceptable carrier and a therapeutically effective amount of a compound according to claim 4 or a pharmaceutically acceptable salt form thereof.

35. A method for treating an inflammatory disorder, comprising: administering to a patient in need thereof a therapeutically effective amount of a compound of claim 4 or a pharmaceutically acceptable salt form thereof.

36. A method of treating a condition or disease mediated by MMPs, TACE, aggrecanase, or a combination thereof in a mammal, comprising: administering to the mammal in need of such treatment a therapeutically effective amount of a compound according to claim 4.

37. A method of treating according to claim 36, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

38. A pharmaceutical composition, comprising: a pharmaceutically acceptable carrier and a therapeutically effective amount of a compound according to claim 5 or a pharmaceutically acceptable salt form thereof.

39. A method for treating an inflammatory disorder, comprising: administering to a patient in need thereof a therapeutically effective amount of a compound of claim 5 or a pharmaceutically acceptable salt form thereof.

40. A method of treating a condition or disease mediated by MMPs, TACE, aggrecanase, or a combination thereof in a mammal, comprising: administering to the mammal in need of such treatment a therapeutically effective amount of a compound according to claim 5.

41. A method of treating according to claim 40 wherein the disease or condition is selected from to as acute infection, acute phase response, age related macular degeneration, alcoholic liver disease, allergy, allergic asthma, anorexia, aneurism; aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

42. A pharmaceutical composition, comprising: a pharmaceutically acceptable carrier and a therapeutically effective amount of a compound according to claim 6 or a pharmaceutically acceptable salt form thereof.

43. A method for treating an inflammatory disorder, comprising: administering to a patient in need thereof a therapeutically effective amount of a compound of claim 6 or a pharmaceutically acceptable salt form thereof.

44. A method of treating a condition or disease mediated by MMPs, TACE, aggrecanase, or a combination thereof in a mammal, comprising: administering to the mammal in need of such treatment a therapeutically effective amount of a compound according to claim 6.

45. A method of treating according to claim 44, wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

46. A pharmaceutical composition, comprising: a pharmaceutically acceptable carrier and a therapeutically effective amount of a compound according to claim 7 or a pharmaceutically acceptable salt form thereof.

47. A method for treating an inflammatory disorder, comprising: administering to a patient in need thereof a therapeutically effective amount of a compound of claim 7 or a pharmaceutically acceptable salt form thereof.

48. A method of treating a condition or disease mediated by MMPs, TACE, aggrecanase, or a combination thereof in a mammal, comprising: administering to the mammal in need of such treatment a therapeutically effective amount of a compound according to claim 7.

49. A method of treating according to claim 48 wherein the disease or condition is selected from to as acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

* * * * *